(12) United States Patent
Suzaki

(10) Patent No.: US 12,402,530 B2
(45) Date of Patent: Aug. 26, 2025

(54) ORGANIC ELECTROLUMINESCENCE DEVICE AND FUSED POLYCYCLIC COMPOUND FOR ORGANIC ELECTROLUMINESCENCE DEVICE

(71) Applicant: Samsung Display Co., Ltd., Yongin-si (KR)

(72) Inventor: Yuji Suzaki, Yokohama (JP)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 941 days.

(21) Appl. No.: 17/392,762

(22) Filed: Aug. 3, 2021

(65) Prior Publication Data

US 2022/0093875 A1    Mar. 24, 2022

(30) Foreign Application Priority Data

Sep. 18, 2020 (KR) .................. 10-2020-0120268

(51) Int. Cl.
*H10K 85/60* (2023.01)
*C07D 471/06* (2006.01)
(Continued)

(52) U.S. Cl.
CPC ....... *H10K 85/6572* (2023.02); *C07D 471/06* (2013.01); *C09K 11/06* (2013.01);
(Continued)

(58) Field of Classification Search
CPC ............. H10K 85/6572; H10K 85/636; H10K 85/322; H10K 85/151; H10K 85/111;
(Continued)

(56) References Cited

U.S. PATENT DOCUMENTS

| | | |
|---|---|---|
| 8,932,731 B2 | 1/2015 | Parham et al. |
| 9,133,119 B2 | 9/2015 | Parham et al. |

(Continued)

FOREIGN PATENT DOCUMENTS

| | | |
|---|---|---|
| CN | 109456326 | 3/2019 |
| CN | 110526931 | 12/2019 |

(Continued)

OTHER PUBLICATIONS

Yi Yuan et al., "The Design of Fused Amine/Carbonyl System for Efficient Thermally Activated Delayed Fluorescence: Novel Multiple Resonance Core and Electron Acceptor", Advanced Optical Materials, 2019, pp. 1-6, 1801536.

(Continued)

*Primary Examiner* — Shane Fang
(74) *Attorney, Agent, or Firm* — KILE PARK REED & HOUTTEMAN PLLC

(57) ABSTRACT

A fused polycyclic compound of an embodiment is represented by Formula 1, which is defined in the disclosure. An organic electroluminescence device is also provided. The organic electroluminescence device includes a first electrode, a second electrode facing the first electrode, and organic layers disposed between the first electrode and the second electrode. At least one of the organic layers includes the fused polycyclic compound represented by Formula 1, thereby providing improved luminous efficiency to the organic electroluminescence device.

$$A\text{-}L\text{-}(B)_n \qquad \text{[Formula 1]}$$

20 Claims, 6 Drawing Sheets

(51) Int. Cl.
*C09K 11/06* (2006.01)
*H10K 50/11* (2023.01)
*H10K 101/10* (2023.01)

(52) U.S. Cl.
CPC ...... *C09K 2211/1018* (2013.01); *H10K 50/11* (2023.02); *H10K 2101/10* (2023.02)

(58) Field of Classification Search
CPC .. H10K 50/11; H10K 50/121; H10K 2101/10; H10K 2101/40; C07F 5/027; C08G 61/10; C08G 61/122; C08G 2261/124; C08G 2261/1412; C08G 2261/1414; C08G 2261/148; C08G 2261/18; C08G 2261/228; C08G 2261/312; C08G 2261/3142; C08G 2261/3162; C08G 2261/3221; C08G 2261/95; C09K 11/06; C09K 2211/1018
See application file for complete search history.

(56) References Cited

U.S. PATENT DOCUMENTS

2008/0220286 A1* 9/2008 Qiu ................. C07D 471/06
546/41
2014/0058099 A1 2/2014 Wakamiya et al.

FOREIGN PATENT DOCUMENTS

| DE | 198 08 088 | 8/1999 |
| JP | 11-339868 | 12/1999 |
| JP | 2009-512628 | 3/2009 |
| JP | 5591996 | 9/2014 |
| KR | 10-2014-0013001 | 2/2014 |
| KR | 10-1490069 | 2/2015 |
| KR | 10-2017-0077781 | 7/2017 |
| KR | 10-1928714 | 12/2018 |
| WO | 2010/050778 | 5/2010 |
| WO | 2015/102118 | 7/2015 |

OTHER PUBLICATIONS

Dieter Hellwinkel et al., "8.12-Dihydro-4H-benzo[1.9]chinolizino[3.4.5.6.7-defg]acridin-trion-(4.8.12) und 5.9-Dihydro-chino[3.2.1-de]acridin-dion-(5.9)", Chem. Ber., 1971, pp. 1001-1016, vol. 104.
David Hall et al., "Improving Processability and Efficiency of Resonant TADF Emitters: A Design Strategy", Advanced Optical Materials, 2020, pp. 1 of 10, vol. 8, 1901627.
Xing Li et al., "Thermally Activated Delayed Fluorescence Carbonyl Derivatives for Organic Light-Emitting Diodes with Extremely Narrow Full Width at Half-Maximum", ACS Applied Materials & Interfaces, Mar. 20, 2019, pp. 13472-13480, vol. 11.
Sravan K. Surampudi et al., "Apical Functionalization of Chiral Heterohelicenes", The Journal of Organic Chemistry, Jan. 19, 2012, pp. 2074-2079, vol. 77.
Shinobu Arikawa et al. "Azoniadibenzo[a,j]phenalenide: A Polycyclic Zwitterion with Singlet Biradical Character", Angewandte Chemie International Edition, 2019, pp. 6415-6419, vol. 58.
Jason E. Field et al., "Bridged Triarylamines: A New Class of Heterohelicenes", J. Org. Chem. Mar. 13, 2003, pp. 6071-6078, vol. 68, No. 16.
Dianming Sun et al., "The design of an extended multiple resonance TADF emitter based on a polycyclic amine/carbonyl system", The Royal Society of Chemistry and the Chinese Chemical Society 2020, 4, pp. 2018-2022.

* cited by examiner

ORGANIC ELECTROLUMINESCENCE DEVICE AND FUSED POLYCYCLIC COMPOUND FOR ORGANIC ELECTROLUMINESCENCE DEVICE

CROSS-REFERENCE TO RELATED APPLICATION(S)

This application claims priority to and benefits of Korean Patent Application No. 10-2020-0120268 under 35 U.S.C. § 119, filed on Sep. 18, 2020 in the Korean Intellectual Property Office, the entire contents of which are incorporated herein by reference.

BACKGROUND

1. Technical Field

The disclosure relates to a fused polycyclic compound used as a luminescent material and an organic electroluminescence device including the same.

2. Description of the Related Art

Active development continues for an organic electroluminescence display as an image display. In contrast to a liquid crystal display, the organic electroluminescence display is a so-called self-luminescent display in which holes and electrons respectively injected from a first electrode and a second electrode recombine in an emission layer, and a light-emitting material including an organic compound in the emission layer emits light to achieve display.

In the application of an organic electroluminescence device to a display apparatus, there is a demand for an organic electroluminescence device having a low driving voltage, high luminous efficiency, and a long service life, and continuous development is required for materials in an organic electroluminescence device which stably achieves such characteristics.

To accomplish the production of an organic electroluminescence device with high efficiency, techniques on phosphorescence emission which uses energy in a triplet state or delayed fluorescence emission which uses the generating phenomenon of singlet excitons by the collision of triplet excitons (triplet-triplet annihilation, TTA) are being developed, and development is being conducted on a material for thermally activated delayed fluorescence (TADF) using delayed fluorescence phenomenon.

SUMMARY

The disclosure provides an organic electroluminescence device with improved luminous efficiency.

The disclosure also provides a fused polycyclic compound which may improve luminous efficiency of an organic electroluminescence device.

An embodiment provides an organic electroluminescence device that may include a first electrode, a second electrode facing the first electrode, and organic layers disposed between the first electrode and the second electrode. At least one of the organic layers may include a fused polycyclic compound represented by Formula 1 below:

$$A\text{-}L\text{-}(B)_n \qquad \text{[Formula 1]}$$

In Formula 1 above, L may be a direct linkage, O, S, S=O, $Si(R_a)(R_b)$, $N(R_c)$, $P(R_d)$, $B(R_e)$, N=N, CC, C=O, C(=O)O, OC(=O)O, C=S, P=O, P=S, N, P, B, a substituted or unsubstituted alkyl linking group having 1 to 30 carbon atoms, a substituted or unsubstituted alkenyl linking group having 2 to 30 carbon atoms, a substituted or unsubstituted alkynyl linking group having 3 to 30 carbon atoms, a substituted or unsubstituted aryl linking group having 6 to 60 ring-forming carbon atoms, or a substituted or unsubstituted heteroaryl linking group having 2 to 60 ring-forming carbon atoms, and $R_a$ to $R_e$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring. In Formula 1, n may be an integer from 1 to 3, A may be a group represented by Formula 2 below, and B may be a group represented by Formula 3 below:

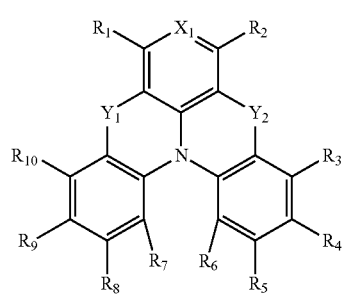

[Formula 2]

In Formula 2 above, $X_1$ may be N or $C(R_{11})$, $Y_1$ and $Y_2$ may each independently be C=O, C=S, S=O, $SO_2$, C≡C, $(R_f)(R_g)$, P=O, or P=S, and $R_1$ to $R_{11}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, except that any one of $R_1$ to $R_{10}$ is a binding site to L in Formula 1 above. In Formula 2, $R_f$ and $R_g$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring.

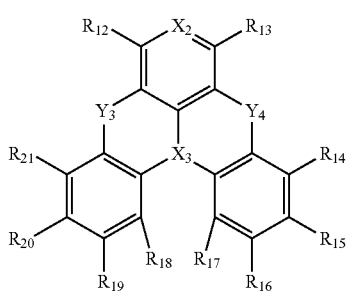

[Formula 3]

In Formula 3 above, $X_2$ may be N or $C(R_{22})$, $X_3$ may be N, B, or P, $Y_3$ and $Y_4$ may each independently be C=O, C=S, S=O, $SO_2$, C=C($R_h$)($R_i$), P=O, P=S, N($R_j$), or B($R_k$), and $R_{12}$ to $R_{22}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, except that one of $R_{12}$ to $R_{22}$ is a binding site to L of Formula 1 above. In Formula 3, $R_h$ to $R_k$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring.

In an embodiment, the organic layers may include a hole transport region disposed on the first electrode, an emission layer disposed on the hole transport region, and an electron transport region disposed on the emission layer. The emission layer may include the fused polycyclic compound.

In an embodiment, the emission layer may emit delayed fluorescence.

In an embodiment, the emission layer may be a delayed fluorescence emission layer including a host and a dopant, and the dopant may include the fused polycyclic compound.

In an embodiment, in Formula 1 above, A and B may have a same structure.

In an embodiment, in Formula 1 above, n may be 2 or 3, and multiple B(s) may have a same structure as each other.

In an embodiment, the fused polycyclic compound represented by Formula 1 above may be represented by Formula 4 below:

[Formula 4]

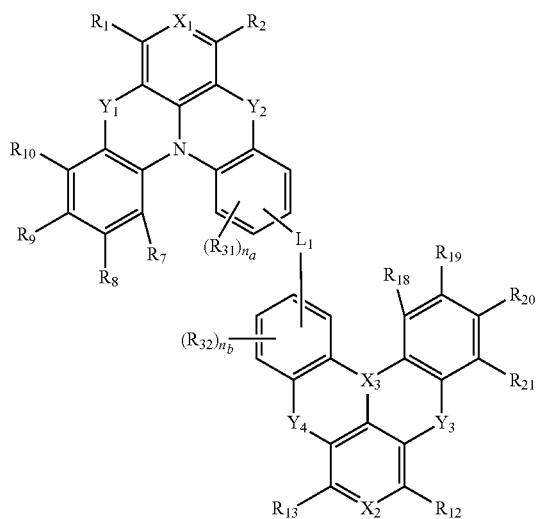

In Formula 4 above, L may be a direct linkage, O, S, S=O, Si($R_a$)($R_b$), N($R_c$), P($R_d$), B($R_e$), N=N, CC, C=O, C(=O)O, OC(=O)O, C=S, P=O, P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 3 to 30 carbon atoms, a substituted or unsubstituted arylene group having 6 to 60 ring-forming carbon atoms, or a substituted or unsubstituted heteroarylene group having 2 to 60 ring-forming carbon atoms, $R_{31}$ and $R_{32}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or are bonded to an adjacent group to form a ring, and $n_a$ and $n_b$ may each independently be an integer from 0 to 3.

In Formula 4 above, $X_1$, $X_2$, $X_3$, $Y_1$, $Y_2$, $Y_3$, $Y_4$, $R_1$, $R_2$, $R_7$ to $R_{13}$, $R_{18}$ to $R_{22}$, and $R_a$ to $R_k$ may be the same as defined in connection with Formula 2 and Formula 3 above.

In an embodiment, the fused polycyclic compound represented by Formula 4 above may be represented by any one of Formula 4-1 to Formula 4-3 below:

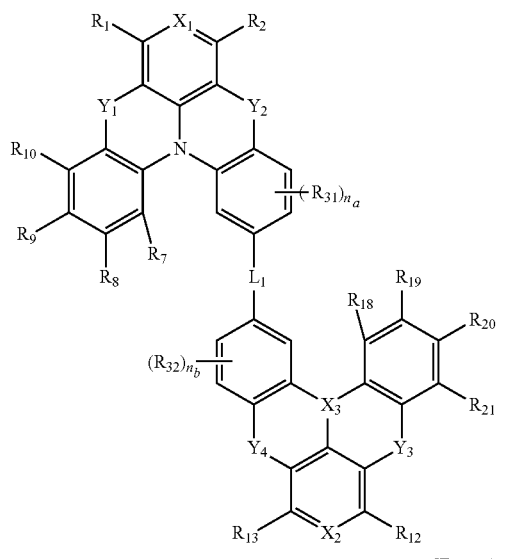

[Formula 4-1]

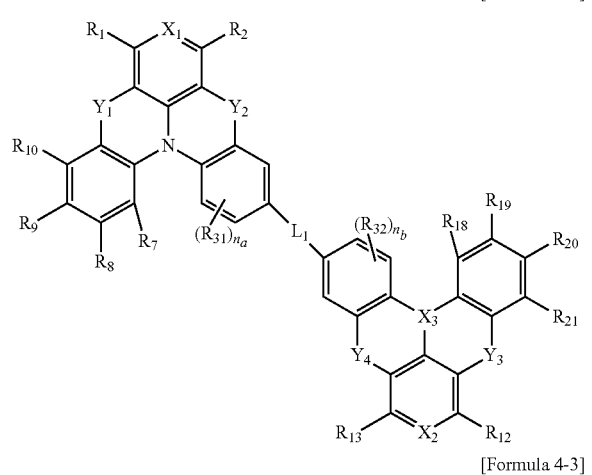

[Formula 4-2]

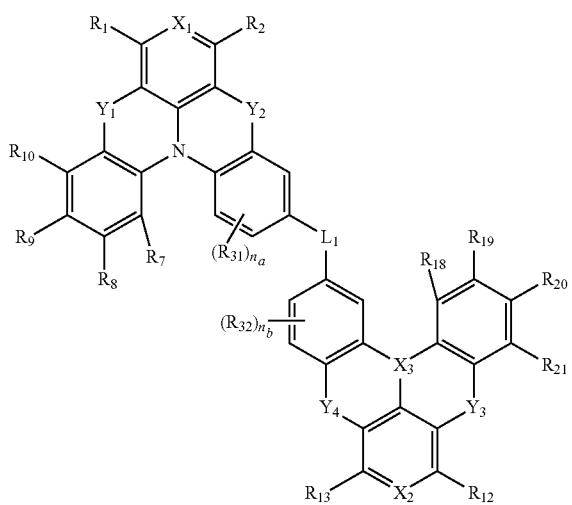

[Formula 4-3]

In Formula 4-1 to Formula 4-3 above, $X_1$, $X_2$, $X_3$, $Y_1$, $Y_2$, $Y_3$, $Y_4$, $R_1$, $R_2$, $R_7$ to $R_{13}$, $R_{18}$ to $R_{22}$, $R_a$ to $R_k$, $L_1$, $R_{31}$, $R_{32}$, $n_a$ and $n_b$ may be the same as defined in connection with Formula 2, Formula 3, and Formula 4 above.

In an embodiment, the fused polycyclic compound represented by Formula 1 above may be represented by Formula 5 below:

[Formula 5]

In Formula 5 above, $L_2$ may be a direct linkage, O, S, S=O, Si($R_a$)($R_b$), N($R_c$), P($R_d$), B($R_e$), N=N, CC, C=O, C(=O)O, OC(=O)O, C=S, P=O, P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 3 to 30 carbon atoms, a substituted or unsubstituted arylene group having 6 to 60 ring-forming carbon atoms, or a substituted or unsubstituted heteroarylene group having 2 to 60 ring-forming carbon atoms, $R_{31}$ and $R_{33}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, $n_a$ may be an integer from 0 to 3, and $n_c$ may be an integer from 0 to 2.

In Formula 5 above, $X_1$, $X_2$, $X_3$, $Y_1$, $Y_2$, $Y_3$, $Y_4$, $R_1$, $R_2$, $R_7$ to $R_{11}$, $R_{14}$ to $R_{21}$, and $R_a$ to $R_k$ may be the same as defined in connection with Formula 2 and Formula 3 above.

In an embodiment, the fused polycyclic compound represented by Formula 5 above may be represented by any one of Formula 5-1 to Formula 5-3 below:

[Formula 5-1]

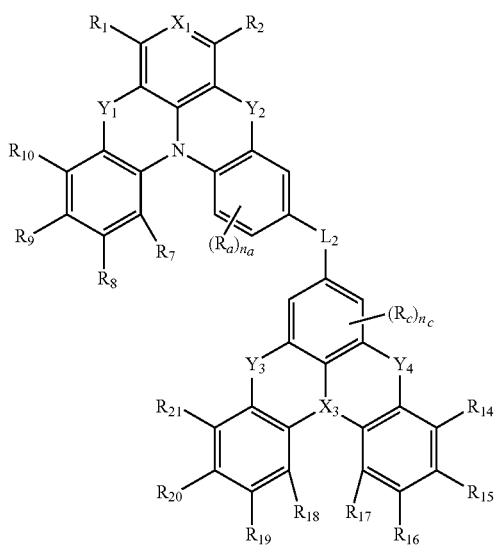

[Formula 5-3]

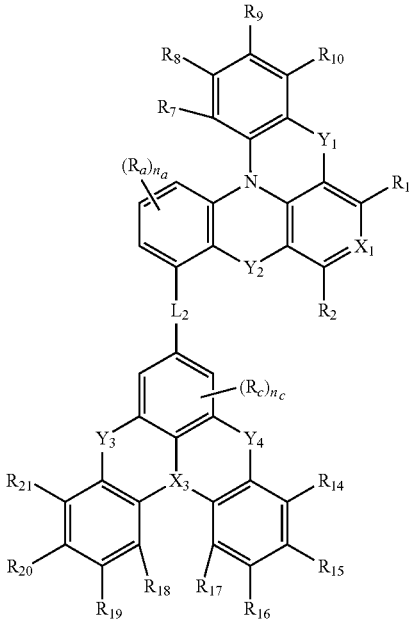

In Formula 5-1 to Formula 5-3 above, $X_1$, $X_2$, $X_3$, $Y_1$, $Y_2$, $Y_3$, $Y_4$, $R_1$, $R_2$, $R_7$ to $R_{11}$, $R_{14}$ to $R_{21}$, $R_a$ to $R_f$, $L_2$, $R_{31}$, $R_{33}$, $n_a$ and $n_c$ may be the same as defined in connection with Formula 2, Formula 3, and Formula 5 above.

In an embodiment, the fused polycyclic compound represented by Formula 1 above may be represented by Formula 6 below:

[Formula 5-2]

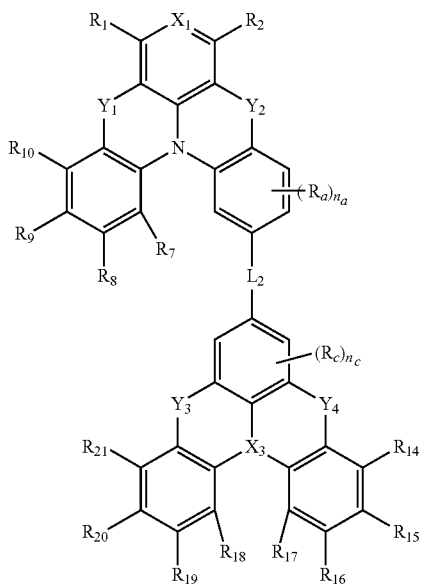

[Formula 6]

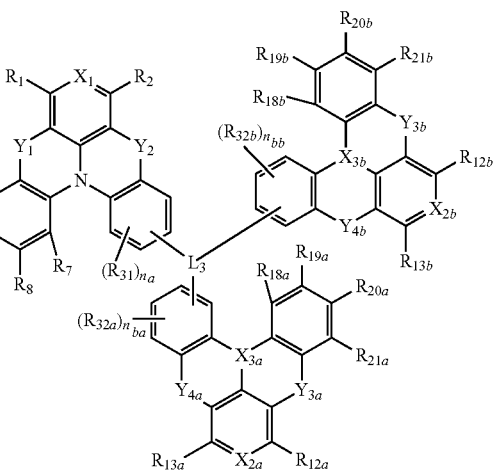

In Formula 6 above, $L_3$ may be N, P, B, a substituted or unsubstituted trivalent alkyl group having 1 to 30 carbon atoms, a substituted or unsubstituted trivalent alkenyl group having 2 to 30 carbon atoms, a substituted or unsubstituted trivalent alkynyl group having 3 to 30 carbon atoms, a substituted or unsubstituted trivalent aryl group having 6 to 60 ring-forming carbon atoms, or a substituted or unsubstituted trivalent heteroaryl group having 2 to 60 ring-forming carbon atoms, $X_{2a}$ and $X_{2b}$ may each independently be N or $C(R_{22})$, $X_{3a}$ and $X_{3b}$ may each independently be N, B, or P, $Y_{3a}$, $Y_{3b}$, $Y_{4a}$ and $Y_{4b}$ may each independently be C=O, C=S, S=O, $SO_2$, C≡C($R_h$)($R_i$), P=O, P=S, N($R_j$), or B($R_k$), $R_{12a}$, $R_{13a}$, $R_{18a}$ to $R_{21a}$, $R_{12b}$, $R_{13b}$, $R_{18b}$ to $R_{21b}$, $R_{31}$, $R_{32a}$, and $R_{32b}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, and $n_a$, $n_{ba}$, and $n_{bb}$ may each independently be an integer from 0 to 3.

In Formula 6 above, $X_1$, $Y_1$, $Y_2$, $R_1$, $R_2$, $R_7$ to $R_{11}$, Rn, and $R_a$ to $R_k$ may be the same as defined in connection with Formula 2 and Formula 3.

In an embodiment, the fused polycyclic compound represented by Formula 6 above may be represented by Formula 6-1 below:

[Formula 6-1]

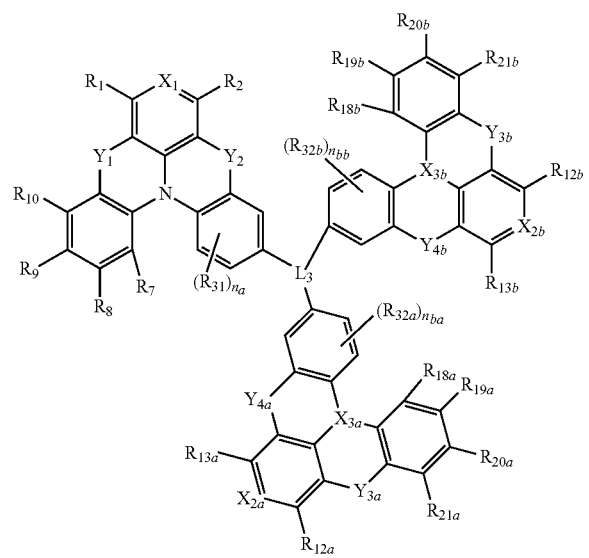

In Formula 6-1 above, $X_1$, $Y_1$, $Y_2$, $R_1$, $R_2$, $R_7$ to $R_{11}$, Rn, $R_a$ to $R_k$, $L_3$, $X_{2a}$, $X_{2b}$, $X_{3a}$, $X_{3b}$, $Y_{3a}$, $Y_{3b}$, $Y_{4a}$, $Y_{4b}$, $R_{12a}$, $R_{13a}$, $R_{18a}$ to $R_{21a}$, $R_{12b}$, $R_{13b}$, $R_{18b}$ to $R_{21b}$, $R_{31}$, $R_{32a}$, $R_{32b}$, $n_a$, $n_{ba}$, and $n_{bb}$ may be the same as defined in connection with Formula 2, Formula 3, and Formula 6.

In an embodiment, the fused polycyclic compound represented by Formula 1 above may be represented by Formula 7:

[Formula 7]

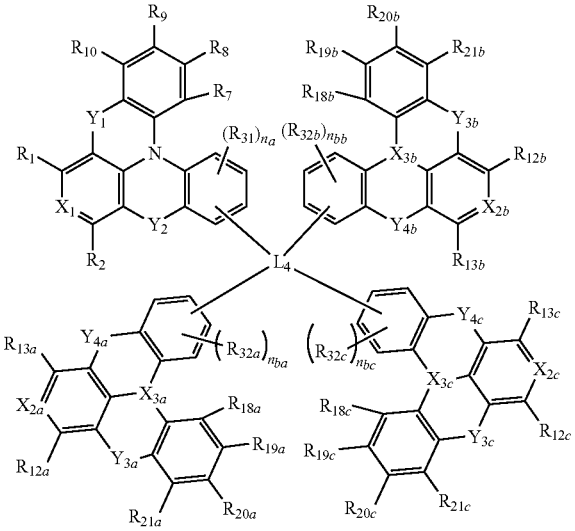

In Formula 7 above, $L_4$ may be a substituted or unsubstituted tetravalent alkyl group having 1 to 30 carbon atoms, a substituted or unsubstituted tetravalent alkenyl group having 3 to 30 carbon atoms, a substituted or unsubstituted tetravalent alkynyl group having 3 to 30 carbon atoms, a substituted or unsubstituted tetravalent aryl group having 6 to 60 ring-forming carbon atoms, or a substituted or unsubstituted tetravalent heteroaryl group having 2 to 60 ring-forming carbon atoms, $X_{2a}$ to $X_{2c}$ may each independently be N or C($R_{22}$), $X_{3a}$ and $X_{3c}$ may each independently be N, B, or P, $Y_{3a}$ to $Y_{3c}$ and $Y_{4a}$ to $Y_{4c}$ may each independently be C=O, C=S, S=O, $SO_2$, C≡C($R_h$)($R_i$), P=O, P=S, N($R_j$), or B($R_k$), $R_{12a}$, $R_{13a}$, $R_{18a}$ to $R_{21a}$, $R_{12b}$, $R_{13b}$, $R_{18b}$ to $R_{21b}$, $R_{12c}$, $R_{13c}$, $R_{18c}$ to $R_{21c}$, $R_{31}$, $R_{32a}$ to $R_{32c}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, and $n_a$ and $n_{ba}$ to $n_{bc}$ may each independently be an integer from 0 to 3.

In Formula 7 above, $X_1$, $Y_1$, $Y_2$, $R_1$, $R_2$, $R_7$ to $R_{11}$, $R_{22}$, and $R_a$ to $R_k$ may be the same as defined in connection with Formula 2 and Formula 3.

In an embodiment, a fused polycyclic compound represented by Formula 7 may be represented by Formula 7-1 below:

[Formula 7-1]

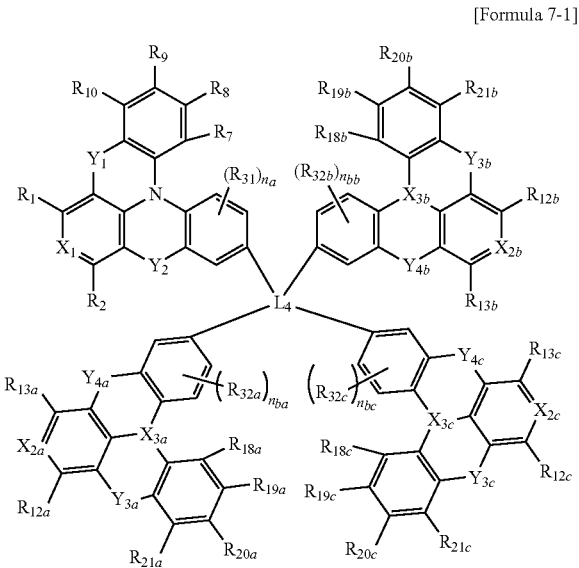

In Formula 7-1 above, $X_1$, $Y_1$, $Y_2$, $R_1$, $R_2$, $R_7$ to $R_{11}$, $R_{22}$, $R_a$ to $R_k$, $L_4$, $X_{2a}$ to $X_{2c}$, $X_{3a}$ to $X_{3c}$, $Y_{3a}$ to $Y_{3c}$, $Y_{4a}$ to $Y_{4c}$, $R_{12a}$, $R_{13a}$, $R_{18a}$ to $R_{21a}$, $R_{12b}$, $R_{13b}$, $R_{18b}$ to $R_{21b}$, $R_{12c}$, $R_{13c}$, $R_{18c}$ to $R_{21c}$, $R_{31}$, $R_{32a}$ to $R_{32c}$, $n_a$, and $n_{ba}$ to $n_{bc}$ may be the same as defined in connection with Formula 2, Formula 3, and Formula 7.

In an embodiment, in Formula 2 above, $Y_1$ and $Y_2$ may each independently be C=O or C=S.

In an embodiment, in Formula 3 above, $X_3$ may be N, and in Formula 2 and Formula 3, $X_1$ may be the same as $X_2$, $Y_1$ may be the same as $Y_3$, and $Y_2$ may be the same as $Y_4$.

In an embodiment, the organic electroluminescence device may further include a capping layer disposed on the second electrode. The capping layer may have a refractive index equal to or greater than about 1.6.

In an embodiment, the host may include a compound represented by Formula E-2a or Formula E-2b below:

[Formula E-2a]

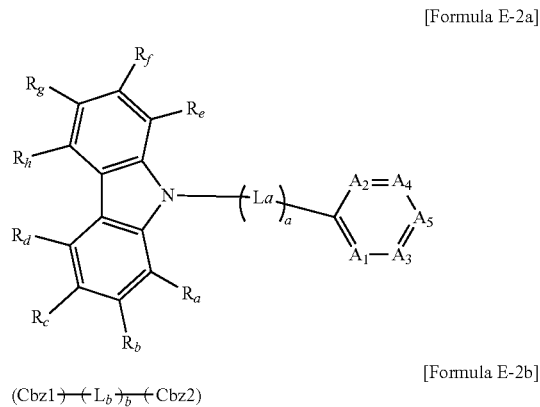

[Formula E-2b]

(Cbz1)─(L_b)_b─(Cbz2)

In Formula E-2a above, a may be an integer from 0 to 10, $L_a$ may be a direct linkage, a substituted or unsubstituted arylene group having 6 to 30 ring-forming carbon atoms, or a substituted or unsubstituted heteroarylene group having 2 to 30 ring-forming carbon atoms, $A_1$ to $A_5$ may each independently be N or $C(R_i)$, $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or bonded to an adjacent group to form a ring, and two or three of $A_1$ to $A_5$ may be N, and the remainder of $A_1$ to $A_5$ may be $C(R_i)$. In Formula E-2b above, Cbz1 and Cbz2 may each independently be an unsubstituted carbazole group, or a carbazole group substituted with an aryl group having 6 to 30 ring-forming carbon atoms, $L_b$ may be a direct linkage, a substituted or unsubstituted arylene group having 6 to 30 ring-forming carbon atoms, or a substituted or unsubstituted heteroarylene group having 2 to 30 ring-forming carbon atoms, and b may be an integer from 0 to 10.

The fused polycyclic compound according to an embodiment may be represented by Formula 1 above.

BRIEF DESCRIPTION OF THE DRAWINGS

The accompanying drawings are included to provide a further understanding of the disclosure, and are incorporated in and constitute a part of this specification. The drawings illustrate embodiments of the disclosure, together with the description. The above and other aspects and features of the disclosure will become more apparent by describing in detail embodiments thereof with reference to the attached drawings, in which.

DETAILED DESCRIPTION OF THE EMBODIMENTS

Figure 1:
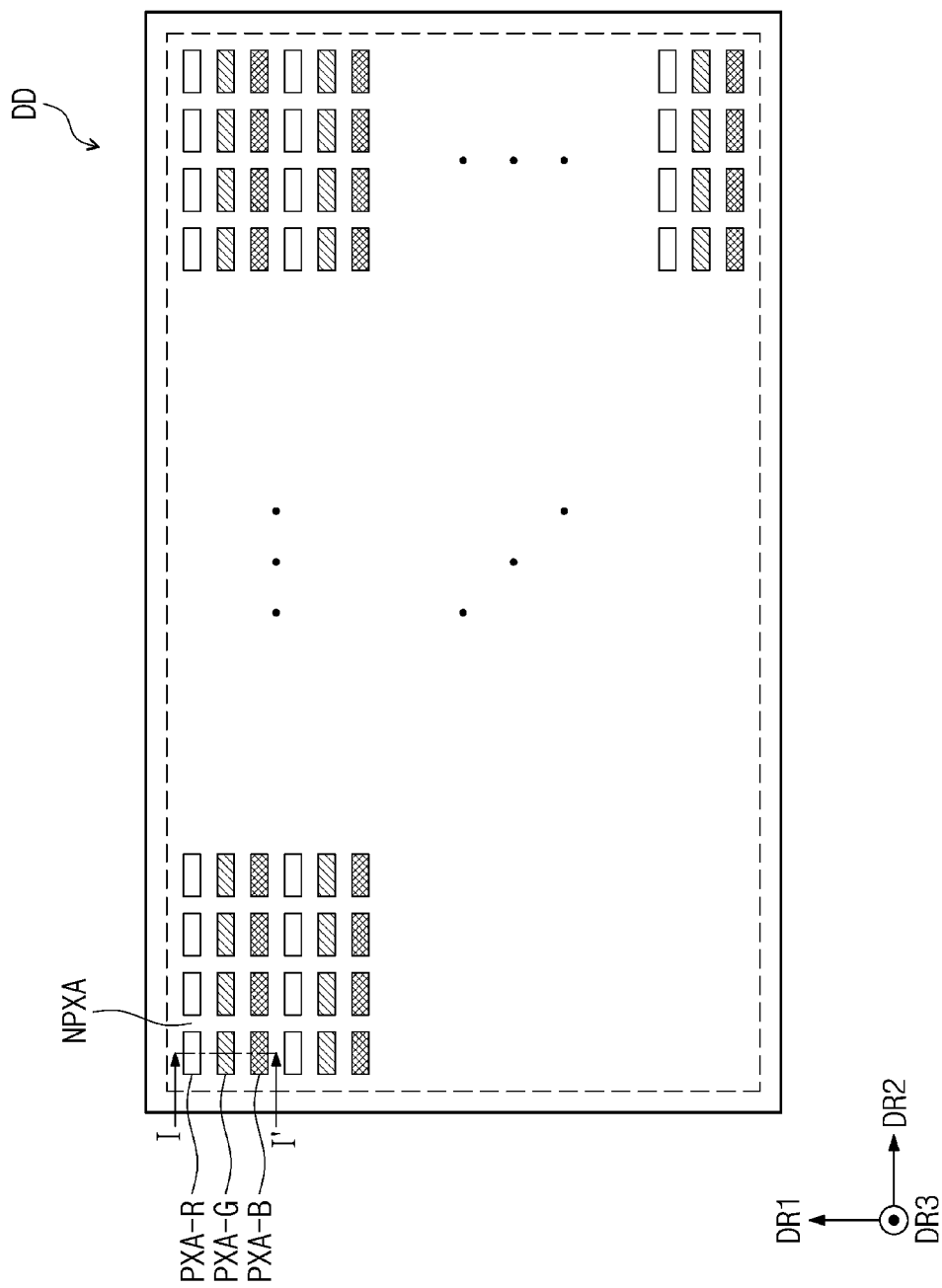
FIG. 1 is a plan view of a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

Like reference numerals refer to like elements throughout the specification. In the drawings, the thicknesses, the ratios, and the dimensions of structures and constituent elements may be exaggerated for effective explanation of their technical contents. Therefore, as the sizes and thicknesses of components in the drawings may be arbitrarily illustrated for convenience of explanation, such embodiments of the disclosure are not limited thereto.

As used herein, the expressions used in the singular such as "a," "an," and "the" are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the disclosure.

It should be understood that the terms "comprises," "comprising," "includes," "including," "have," "having," "contains," "containing," and the like are intended to specify the presence of stated features, numerals, steps, operations, elements, parts, or combinations thereof, but do not preclude the presence or addition of one or more other features, numerals, steps, operations, elements, parts, or combinations thereof.

It will be understood that when an element such as a layer, film, region, or substrate is referred to as being "on," "connected to," or "coupled to" another element, it can be directly on, connected to, or coupled to the other element, or one or more intervening elements may also be present. When an element is referred to as being "directly on", "directly connected to," or "directly coupled to" another element, there are no intervening elements present. Throughout the specification, the word "on" a target element will be understood to be positioned above or below the target element, and will not necessarily be understood to be positioned "at an upper side" based on an opposite to gravity direction.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "overlap" or "overlapped" mean that a first object may be above or below or to a side of a second object, and vice versa. Additionally, the term "overlap" may include layer, stack, face or facing, extending over, covering, or partly covering or any other suitable term as would be appreciated and understood by those of ordinary skill in the art.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, 10%, or 5% of the stated value.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the specification, the term "substituted or unsubstituted" may mean being substituted or unsubstituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine group, a phosphine oxide group, a phosphine sulfide group, an alkyl group, an alkenyl group, an alkynyl group, an alkoxy group, a hydrocarbon ring group, an aryl group, and a heterocyclic group. Each of the substituents above may be substituted or unsubstituted. For example, a biphenyl group may be interpreted as an aryl group or a phenyl group substituted with a phenyl group.

In the specification, the phrase "bonded to an adjacent group to form a ring" may mean that one is bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. The rings formed by being bonded to each other may be connected to another ring to form a spiro structure.

In the specification, the term "adjacent group" may mean a substituent substituted at an atom which is directly connected to an atom substituted with a corresponding substituent, another substituent substituted at an atom which is substituted with a corresponding substituent, or a substituent sterically positioned at the nearest position to a corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other. For example, two methyl groups in 4,5-dimethylphenanthrene may be interpreted as "adjacent groups" to each other. For example, in 1,13-dimethylquinolino[3,2,1-de]acridine-5,9-dione, two methyl groups connected to the 1-position carbon and the 13-position carbon, respectively, may be interpreted as "adjacent groups" to each other.

In the specification, examples of the halogen atom may include a fluorine atom, a chlorine atom, a bromine atom, or an iodine atom.

In the specification, an alkyl group may be a linear, branched, or cyclic type. The number of carbon atoms in the alkyl group is 1 to 50, 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but embodiments are not limited thereto.

In the specification, a hydrocarbon ring group may be any functional group or substituent derived from an aliphatic hydrocarbon ring. The hydrocarbon ring group may be a saturated hydrocarbon ring group having 5 to 30 or 5 to 20 ring-forming carbon atoms.

In the specification, an aryl group" may be any functional group or substituent derived from an aromatic hydrocarbon ring. The aryl group may be a monocyclic aryl group or a polycyclic aryl group. The number of ring-forming carbon atoms in the aryl group may be 6 to 60, 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but embodiments are not limited thereto.

In the specification, a fluorenyl group may be substituted, and two substituents may be combined with each other to form a spiro structure. Examples of cases where the fluorenyl group is substituted are as follows. However, embodiments are not limited thereto.

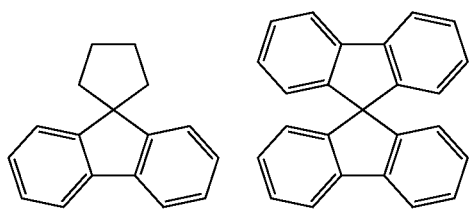

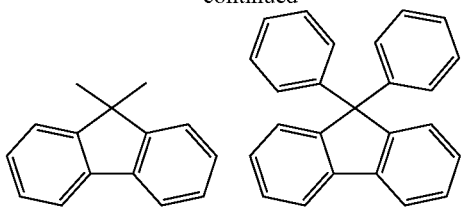

In the specification, a heterocyclic group may be any functional group or substituent derived from a ring including at least one of B, O, N, P, Si, and Se as a heteroatom. The heterocyclic group includes an aliphatic heterocyclic group and an aromatic heterocyclic group. The aromatic heterocyclic group may be a heteroaryl group. The aliphatic heterocycle and the aromatic heterocycle may be monocyclic or polycyclic.

In the specification, a heterocyclic group may include at least one of B, O, N, P, Si, and S as a heteroatom. If the heterocyclic group includes two or more heteroatoms, the two or more heteroatoms may be the same or different. The heterocyclic group may be a monocyclic heterocyclic group or a polycyclic heterocyclic group and may be understood to include a heteroaryl group. The number of ring-forming carbon atoms in the heterocyclic group may be 2 to 60, 2 to 30, 2 to 20, or 2 to 10.

In the specification, an aliphatic heterocyclic group may include at least one of B, O, N, P, Si, and S as a heteroatom. The number of ring-forming carbon atoms of the aliphatic heterocyclic group may be 2 to 60, 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but embodiments are not limited thereto.

In the specification, a heteroaryl group herein may include at least one of B, O, N, P, Si, and S as a heteroatom. When the heteroaryl group contains two or more heteroatoms, the two or more heteroatoms may be the same as or different from each other. The heteroaryl group may be a monocyclic heteroaryl group or polycyclic heteroaryl group. The number of ring-forming carbon atoms of the heteroaryl group may be 2 to 60, 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazolyl group, a thiadiazole group, a phenothiazine group, a dibenzosilole group, a dibenzofuran group, etc., but embodiments are not limited thereto.

In the specification, the above description with respect to the aryl group may be applied to an arylene group except that the arylene group is a divalent group. The above description with respect to the heteroaryl group may be applied to a heteroarylene group except that the heteroarylene group is a divalent group.

In the specification, an alkenyl group may be linear or branched. The number of carbon atoms in the alkenyl group is not specifically limited, but is 2 to 30, 2 to 20, or 2 to 10. Examples of the alkenyl group include a vinyl group, a 1-butenyl group, a 1-pentenyl group, a 1,3-butadienyl aryl group, a styrenyl group, a styryl vinyl group, etc., but embodiments are not limited thereto.

In the specification, the number of carbon atoms in the alkynyl group is not specifically limited, but may range from 2 to 30, 2 to 20, or 2 to 10. Examples of the alkynyl group include a vinyl group, a 2-butynyl group, a 2-pentynyl group, a 1,3-pentadiynyl aryl group, etc., but embodiments are not limited thereto.

In the specification, the description of the alkyl group, the alkenyl group, the alkynyl group, the aryl group, and the heteroaryl group as described above may be applied to an alkyl linking group, an alkenyl linking group, an alkynyl linking group, an aryl group, and a heteroaryl group, respectively, except that the alkyl linking group, the alkenyl linking group, the alkynyl linking group, the aryl group, and the heteroaryl group are a divalent group, a trivalent group, or a tetravalent group.

In the specification, a silyl group may include an alkyl silyl group and an aryl silyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., but embodiments are not limited thereto.

In the specification, the number of ring-forming carbon atoms in the carbonyl group may be 1 to 40, 1 to 30, or 1 to 20. For example, the carbonyl group may have the following structures, but embodiments are not limited thereto.

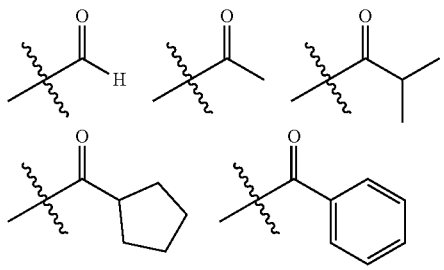

In the specification, the number of carbon atoms in the sulfinyl group and the sulfonyl group is not particularly limited, but may be 1 to 30. The sulfinyl group may include an alkyl sulfinyl group and an aryl sulfinyl group. The sulfonyl group may include an alkyl sulfonyl group and an aryl sulfonyl group.

In the specification, a thio group may include an alkylthio group and an arylthio group. The thio group may mean that a sulfur atom is bonded to the alkyl group or the aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, but embodiments are not limited thereto.

In the specification, a oxy group may be an oxygen atom that is bonded to the alkyl group or the aryl group as defined above. The oxy group may include an alkoxy group and an aryl oxy group. The alkoxy group may be a linear chain, a branched chain, or a ring chain. The number of carbon atoms in the alkoxy group is not specifically limited, but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc., without limitation.

In the specification, a boron group may be a boron atom that is bonded to the alkyl group or the aryl group as defined above. The boron group includes an alkyl boron group and an aryl boron group. Examples of the boron group may include a trimethylboron group, a triethylboron group, a t-butyldimethylboron group, a triphenylboron group, a diphenylboron group, a phenylboron group, etc., but embodiments are not limited thereto.

In the specification, the number of carbon atoms in an amine group is not specifically limited, but may be 1 to 30. The amine group may include an alkyl amine group and an aryl amine group. Examples of the amine group may include a methylamine group, a dimethylamine group, a phenylamine group, a diphenylamine group, a naphthylamine group, a 9-methyl-anthracenylamine group, a triphenylamine group, etc., but embodiments are not limited thereto.

In the specification, an alkyl group included in an alkylthio group, an alkyl sulfoxy group, an alkyl aryl group, an alkyl amine group, an alkyl boron group, or an alkyl silyl group may be the same as the examples of the alkyl group described above.

In the specification, an aryl group included an aryloxy group, an arylthio group, an aryl sulfoxy group, an aryl amine group, an aryl boron group, or an aryl silyl group may be the same as the examples of the aryl group described above.

In the specification, a direct linkage may be a single bond.

In the specification, "―⁀―" and "―•" each indicate a binding site to a neighboring atom.

Hereinafter, embodiments will be described with reference to the accompanying drawings.

Figure 2:
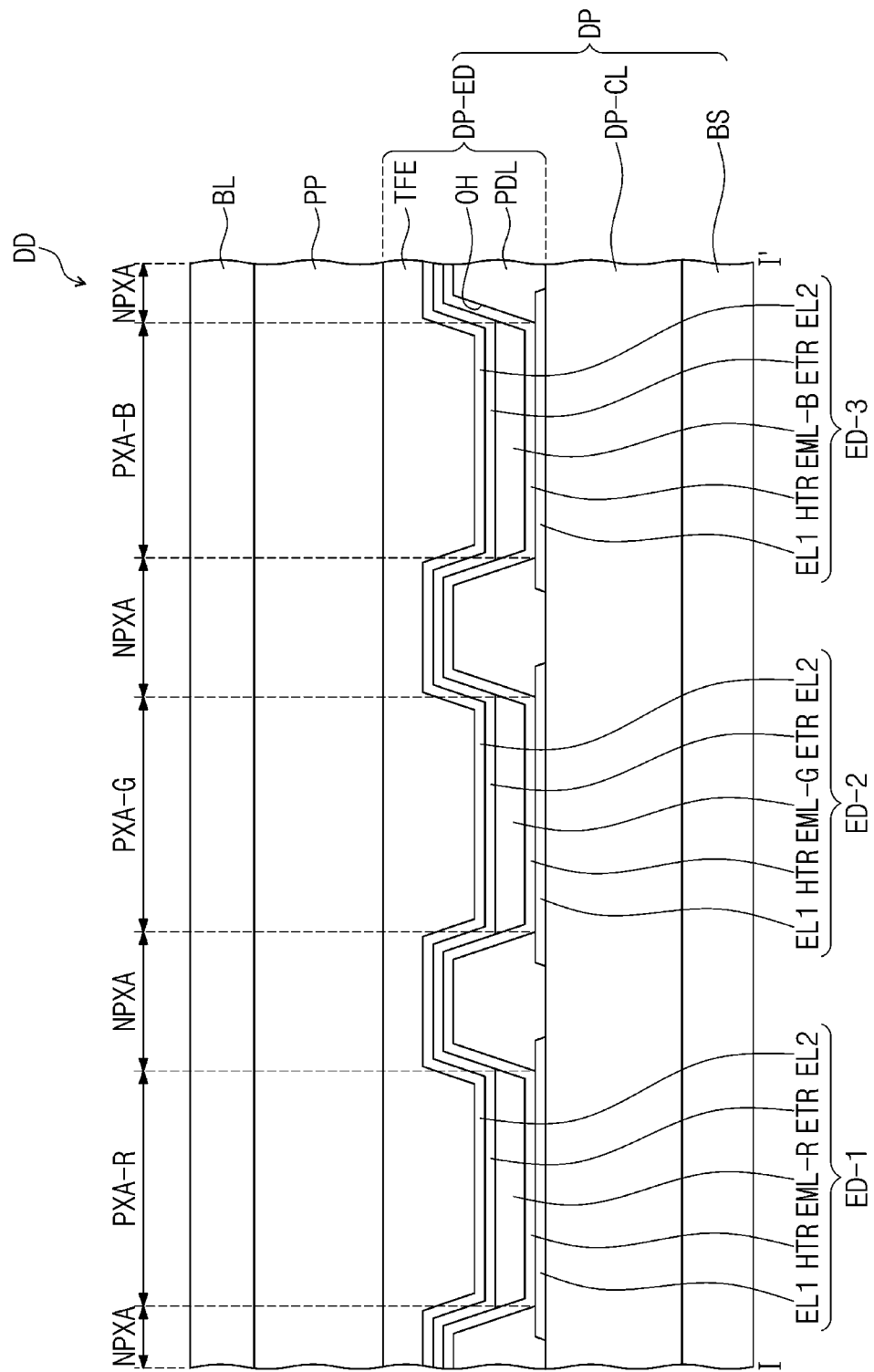
FIG. 2 is a schematic cross-sectional view of a display apparatus according to an embodiment.

FIG. 1 is a plan view illustrating an embodiment of a display apparatus DD. FIG. 2 is a schematic cross-sectional view of the display apparatus DD of the embodiment. FIG. 2 is a schematic cross-sectional view illustrating a part taken along line I-F of FIG. 1.

The display apparatus DD may include a display panel DP and an optical layer PP disposed on the display panel DP. The display panel DP includes light emitting devices ED-1, ED-2, and ED-3. The display apparatus DD may include multiple light emitting devices ED-1, ED-2, and ED-3. The optical layer PP may be disposed on the display panel DP and control light reflected from an external light at the display panel DP. The optical layer PP may include, for example, a polarization layer or a color filter layer. While not illustrated in the drawing, in another embodiment, the optical layer PP may be omitted from the display apparatus DD.

An upper base layer BL may be disposed on the optical layer PP. The upper base layer BL may be a member which provides a base surface on which the optical layer PP disposed. The upper base layer BL may be a glass substrate, a metal substrate, a plastic substrate, etc. However, embodiments are not limited thereto, and the upper base layer BL may be an inorganic layer, an organic layer, or a composite material layer. While not shown, in an embodiment, the upper base layer BL may be omitted.

The display apparatus DD according to an embodiment may further include a filling layer (not shown). The filling layer (not shown) may be disposed between a display device layer DP-ED and the upper base layer BL. The filling layer (not shown) may be an organic material layer. The filling layer (not shown) may include at least one of an acrylic-based resin, a silicone-based resin, and an epoxy-based resin.

The display panel DP may include a base layer BS, a circuit layer DP-CL provided on the base layer BS, and a display device layer DP-ED. The display device layer DP-ED may include a pixel defining film PDL, the light emitting devices ED-1, ED-2, and ED-3 disposed between portions of the pixel defining film PDL, and an encapsulation layer TFE disposed on the light emitting devices ED-1, ED-2, and ED-3.

The base layer BS may be a member which provides a base surface on which the display device layer DP-ED is disposed. The base layer BS may be a glass substrate, a metal substrate, a plastic substrate, etc. However, embodiments are not limited thereto, and the base layer BS may be an inorganic layer, an organic layer, or a composite material layer.

In an embodiment, the circuit layer DP-CL is disposed on the base layer BS, and the circuit layer DP-CL may include transistors (not shown). Each of the transistors (not shown) may include a control electrode, an input electrode, and an output electrode. For example, the circuit layer DP-CL may include a switching transistor and a driving transistor in order to drive the light emitting devices ED-1, ED-2, and ED-3 of the display device layer DP-ED.

Each of the light emitting devices ED-1, ED-2, and ED-3 may have a structure of a light emitting device ED of an embodiment according to FIGS. 3 to 6, which will be described later. Each of the light emitting devices ED-1, ED-2, and ED-3 may include a first electrode EL1, a second electrode EL2 facing the first electrode EL1, and organic layers disposed between the first electrode EL1 and the second electrode EL2. At least one of the organic layers may include a fused polycyclic compound of an embodiment, which will be described later. For example, in an embodiment, each of the light emitting devices ED-1, ED-2, and ED-3 may include a first electrode EL1, a hole transport region HTR, emission layers EML-R, EML-G, and EML-B, an electron transport region ETR, and a second electrode EL2.

FIG. 2 illustrates an embodiment in which the emission layers EML-R, EML-G, and EML-B of the light emitting devices ED-1, ED-2, and ED-3 in the openings OH defined in the pixel defining film PDL, and the hole transport region HTR, the electron transport region ETR, and the second electrode EL2 are provided as common layers in the light emitting devices ED-1, ED-2, and ED-3. However, embodiments are not limited thereto, and unlike the feature illustrated in FIG. 2, the hole transport region HTR and the electron transport region ETR in an embodiment may be provided by being patterned inside the opening OH defined in the pixel defining film PDL. For example, the hole transport region HTR, the emission layers EML-R, EML-G, and EML-B, and the electron transport region ETR in an embodiment may be provided by being patterned in an inkjet printing method.

The encapsulation layer TFE may cover the light emitting devices ED-1, ED-2, and ED-3. The encapsulation layer TFE may seal the display device layer DP-ED. The encapsulation layer TFE may be a thin film encapsulation layer. The encapsulation layer TFE may be formed by laminating one layer or multiple layers. The encapsulation layer TFE may include at least one insulation layer. The encapsulation layer TFE according to an embodiment may include at least one inorganic film (hereinafter, an encapsulation-inorganic film). The encapsulation layer TFE according to an embodiment may also include at least one organic film (hereinafter, an encapsulation-organic film) and at least one encapsulation-inorganic film.

The encapsulation-inorganic film may protect the display device layer DP-ED from moisture and/or oxygen, and the encapsulation-organic film may protect the display device layer DP-ED from foreign substances such as dust particles. The encapsulation-inorganic film may include silicon nitride, silicon oxynitride, silicon oxide, titanium oxide, aluminum oxide, or the like, but embodiments are not limited thereto. The encapsulation-organic film may include an acrylic-based compound, an epoxy-based compound, or the like. The encapsulation-organic film may include a photopolymerizable organic material, but embodiments are not limited thereto.

The encapsulation layer TFE may be disposed on the second electrode EL2 and may be disposed to fill the opening hole OH.

Referring to FIGS. 1 and 2, the display apparatus DD may include a non-light emitting region NPXA and light emitting regions PXA-R, PXA-G, and PXA-B. The light emitting regions PXA-R, PXA-G, and PXA-B may each be a region which emits light generated from the light emitting devices ED-1, ED-2, and ED-3, respectively. The light emitting regions PXA-R, PXA-G, and PXA-B may be spaced apart from each other in a plane.

Each of the light emitting regions PXA-R, PXA-G, and PXA-B may be a region divided by pixel defining film PDL. The non-light emitting regions NPXA may be regions between the adjacent light emitting regions PXA-R, PXA-G, and PXA-B, which correspond to portions of the pixel defining film PDL. In the specification, each of the light emitting regions PXA-R, PXA-G, and PXA-B may correspond to a pixel. The pixel defining film PDL may separate the light emitting devices ED-1, ED-2, and ED-3. The emission layers EML-R, EML-G, and EML-B of the light emitting devices ED-1, ED-2, and ED-3 may be disposed in openings OH defined by the pixel defining film PDL and separated from each other.

The light emitting regions PXA-R, PXA-G, and PXA-B may be divided into groups according to the color of light generated from the light emitting devices ED-1, ED-2, and ED-3. In the display apparatus DD of an embodiment shown in FIGS. 1 and 2, three light emitting regions PXA-R, PXA-G, and PXA-B which emit red light, green light, and blue light, respectively are illustrated. For example, the display apparatus DD of an embodiment may include the red light emitting region PXA-R, the green light emitting region PXA-G, and the blue light emitting region PXA-B which are different.

In the display apparatus DD according to an embodiment, the light emitting devices ED-1, ED-2, and ED-3 may emit light in different wavelength regions. For example, in an embodiment, the display apparatus DD may include a first light emitting device ED-1 that emits red light, a second light emitting device ED-2 that emits green light, and a third light emitting device ED-3 that emits blue light. For example, the red light emitting region PXA-R, the green light emitting region PXA-G, and the blue light emitting region PXA-B of the display apparatus DD may correspond to the first light emitting device ED-1, the second light emitting device ED-2, and the third light emitting device ED-3, respectively.

However, embodiments are not limited thereto, and the first to the third light emitting devices ED-1, ED-2, and ED-3 may emit light in the same wavelength range or at least one light emitting device may emit light in a wavelength range different from the others. For example, the first to third light emitting devices ED-1, ED-2, and ED-3 may all emit blue light.

The light emitting regions PXA-R, PXA-G, and PXA-B in the display apparatus DD according to an embodiment may be arranged in a stripe form. Referring to FIG. 1, the red light emitting regions PXA-R, the green light emitting regions PXA-G, and the blue light emitting regions PXA-B each may be arranged along a second directional axis DR2. The red light emitting region PXA-R, the green light emitting region PXA-G, and the blue light emitting region PXA-B may be alternately arranged in this order along a first directional axis DR1.

FIGS. 1 and 2 illustrate that light emitting regions PXA-R, PXA-G, and PXA-B have a similar area, but embodiments are not limited thereto, and the light emitting regions PXA-R, PXA-G, and PXA-B may have different areas from each other according to a wavelength range of the emitted light. For example, the areas of the light emitting regions PXA-R, PXA-G, and PXA-B may be areas in a plan view that are defined by the first directional axis DR1 and the second directional axis DR2.

The arrangement of the light emitting regions PXA-R, PXA-G, and PXA-B is not limited to what is illustrated in FIG. 1, and the order in which the red light emitting region PXA-R, the green light emitting region PXA-G, and the blue light emitting region PXA-B are arranged may be variously combined and provided according to characteristics of a display quality required in the display apparatus DD. For example, the arrangement of the light emitting regions PXA-R, PXA-G, and PXA-B may be a PenTile® arrangement or a diamond arrangement.

The areas of the light emitting regions PXA-R, PXA-G, and PXA-B may be different from each other. For example, in an embodiment, the area of the green light emitting region PXA-G may be smaller than that of the blue light emitting region PXA-B, but embodiments are not limited thereto.

Hereinafter, FIGS. 3 to 6 are schematic cross-sectional views illustrating light emitting devices according to an embodiment. Each of the light emitting devices ED according to embodiments may include a first electrode EL1, a hole transport region HTR, an emission layer EML, an electron transport region ETR, and a second electrode EL2 that are sequentially stacked.

Figure 3:
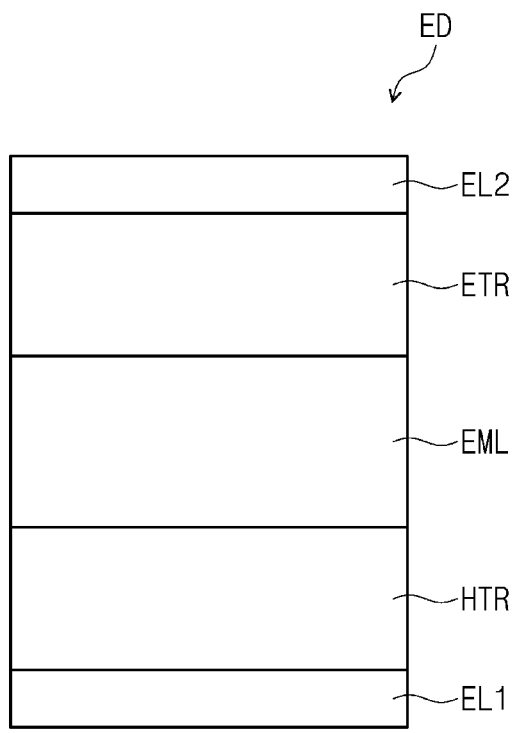
FIG. 3 is a schematic cross-sectional view illustrating an organic electroluminescence device according to an embodiment.
Figure 4:
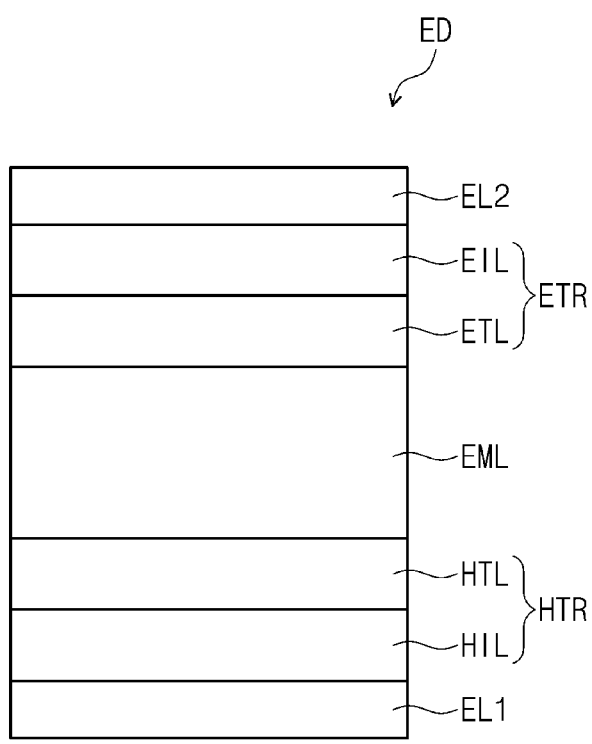
FIG. 4 is a schematic cross-sectional view illustrating an organic electroluminescence device according to an embodiment.
Figure 5:
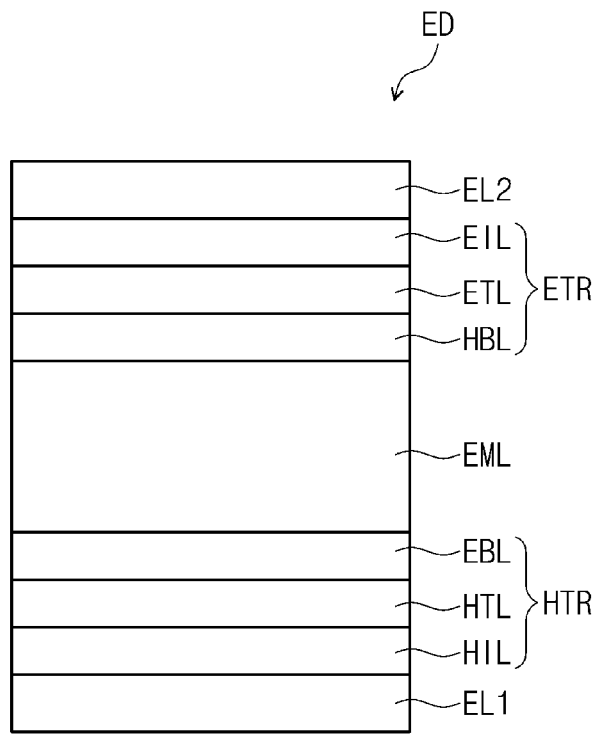
FIG. 5 is a schematic cross-sectional view illustrating an organic electroluminescence device according to an embodiment.
Figure 6:
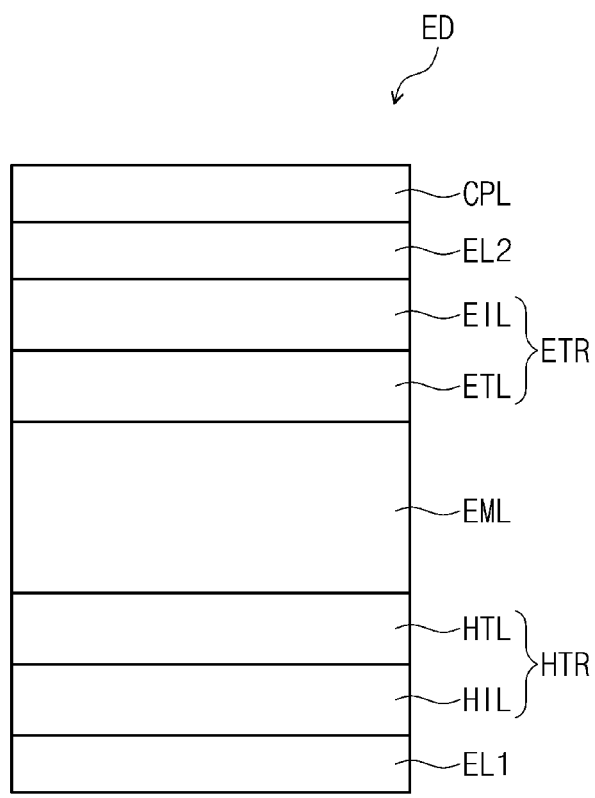
FIG. 6 is a schematic cross-sectional view illustrating an organic electroluminescence device according to an embodiment.

Compared to FIG. 3, FIG. 4 illustrates a schematic cross-sectional view of a light emitting device ED of an embodiment, in which a hole transport region HTR includes a hole injection layer HIL and a hole transport layer HTL, and an electron transport region ETR includes an electron injection layer EIL and an electron transport layer ETL. In comparison to FIG. 3, FIG. 5 illustrates a schematic cross-sectional view of a light emitting device ED of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 4, FIG. 6 illustrates a schematic cross-sectional view of a light emitting device ED of an embodiment including a capping layer CPL disposed on the second electrode EL2.

The first electrode EL1 has conductivity. The first electrode EL1 may be formed of a metal material, a metal alloy, or a conductive compound. The first electrode EL1 may be an anode or a cathode. However, embodiments are not limited thereto. The first electrode EL1 may be a pixel electrode. The first electrode EL1 may be a transmissive electrode, a transflective electrode, or a reflective electrode. If the first electrode EL1 is a transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, In, Zn, Sn, a compound thereof, or a mixture thereof (e.g., a mixture of Ag and Mg). In another embodiment, the first electrode EL1 may have a multilayer structure including a reflective film or a transflective film formed of the above-described materials, and a transparent conductive film formed of ITO, IZO, ZnO, ITZO, etc. For example, the first electrode EL1 may have a three-layer structure of ITO/Ag/ITO, but embodiments are not limited thereto. For example, the first electrode EL1 may include the above-described metal materials, combinations of at least two metal materials of the above-described metal materials, oxides of the above-described metal materials, or the like. A thickness of the first electrode EL1 may be in a range of about 700 Å to about 10,000 Å. For example, the thickness of the first electrode EL1 may be in a range of about 1,000 Å to about 3,000 Å.

The hole transport region HTR is provided on the first electrode EL1. The hole transport region HTR may include at least one of a hole injection layer HIL, a hole transport layer HTL, a buffer layer, an emission-auxiliary layer (not shown), and an electron blocking layer EBL. A thickness of the hole transport region HTR may be, for example, in a range of about 50 Å to about 15,000 Å.

The hole transport region HTR may have a single layer formed of a single material, a single layer formed of different materials, or a multilayer structure including multiple layers formed of different materials.

For example, the hole transport region HTR may have a single layer structure of the hole injection layer HIL or the hole transport layer HTL, and may have a single layer structure formed of a hole injection material and a hole transport material. The hole transport region HTR may have a single layer structure formed of different materials, or a structure in which a hole injection layer HIL/hole transport layer HTL, a hole injection layer HIL/hole transport layer HTL/buffer layer (not shown), a hole injection layer HIL/buffer layer (not shown), a hole transport layer HTL/buffer layer (not shown), or a hole injection layer HIL/hole transport layer HTL/electron blocking layer EBL are stacked in order from the first electrode EL1, but embodiments are not limited thereto.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include a compound represented by Formula H-1 below:

[Formula H-1]

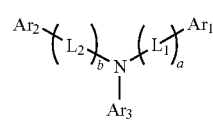

In Formula H-1 above, $L_1$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula H-1, a and b may each independently be an integer from 0 to 10. When a or b is an integer of 2 or greater, multiple $L_1$(s) and $L_2$(s) may each independently be a substituted or unsubstituted arylene group having 6 to 30 ring-forming carbon atoms, or a substituted or unsubstituted heteroarylene group having 2 to 30 ring-forming carbon atoms.

In Formula H-1, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. In Formula H-1, $Ar_3$ may be a substituted or unsubstituted aryl group having 6 to 30 ring-forming carbon atoms.

The compound represented by Formula H-1 above may be a monoamine compound. In another embodiment, the compound represented by Formula H-1 above may be a diamine compound in which at least one among $Ar_1$ to $Ar_3$ includes the amine group as a substituent. The compound represented by Formula H-1 above may be a carbazole-based compound including a substituted or unsubstituted carbazole group in at least one of $Ar_1$ or $Ar_2$, or a fluorene-based compound including a substituted or unsubstituted fluorene group in at least one of $Ar_1$ or $Ar_2$.

The compound represented by Formula H-1 may be represented by any one among the compounds of Compound Group H below. However, the compounds listed in Compound Group H below are examples, and the compounds represented by Formula H-1 are not limited to those represented by Compound Group H below:

[Compound Group H]

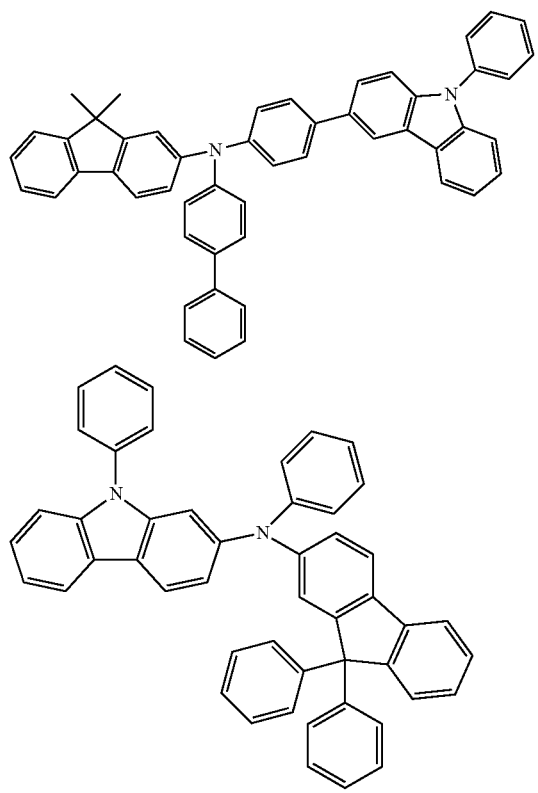

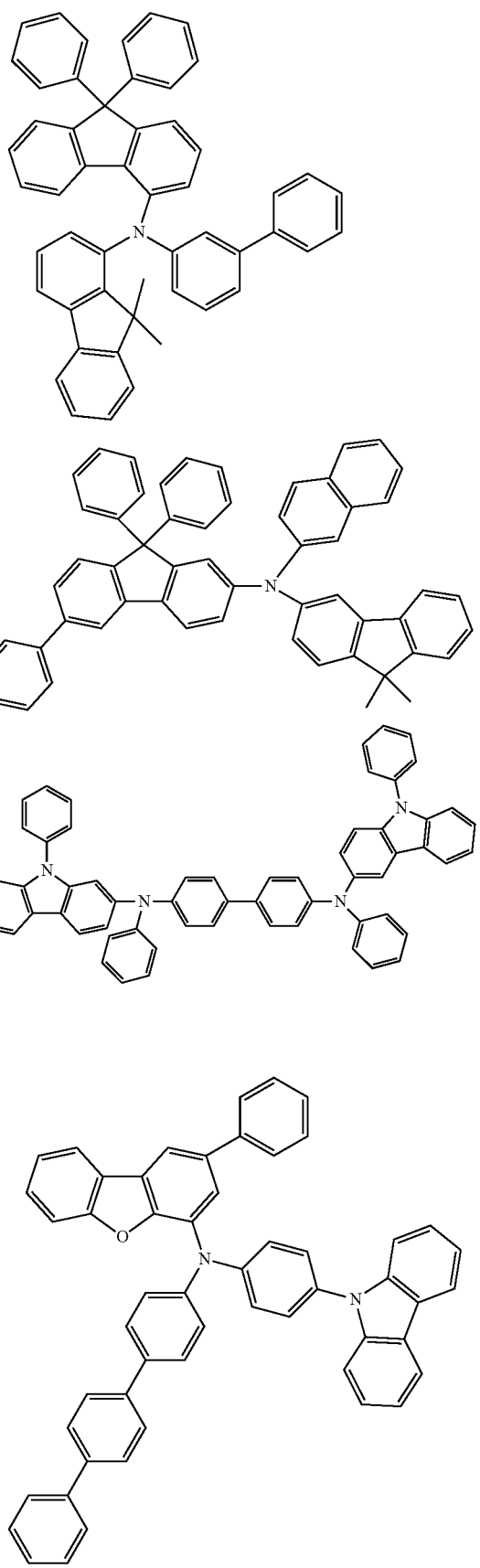

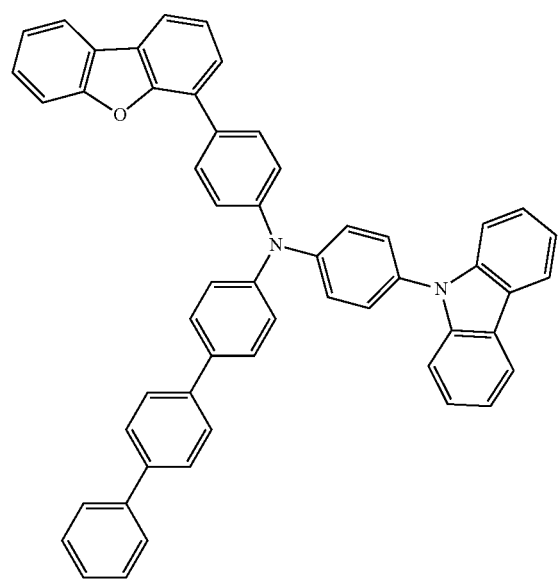
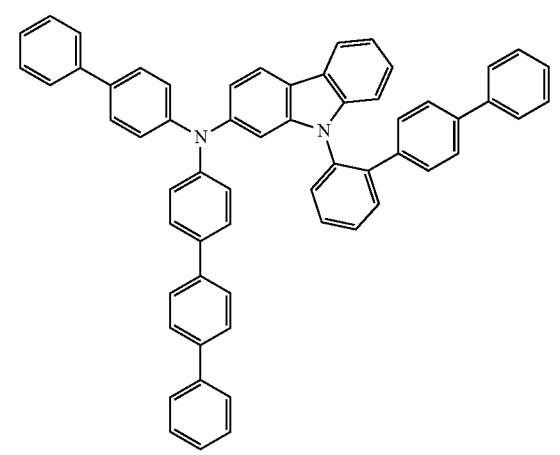
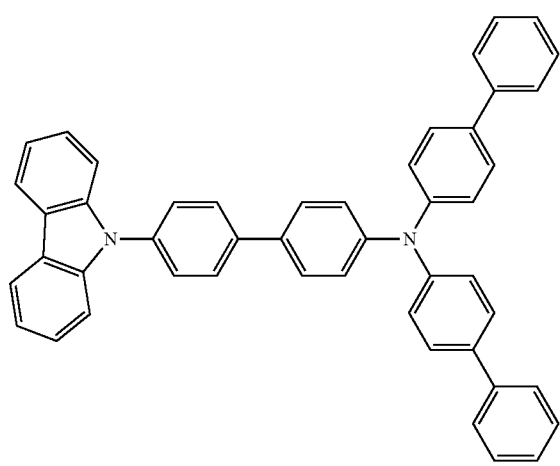
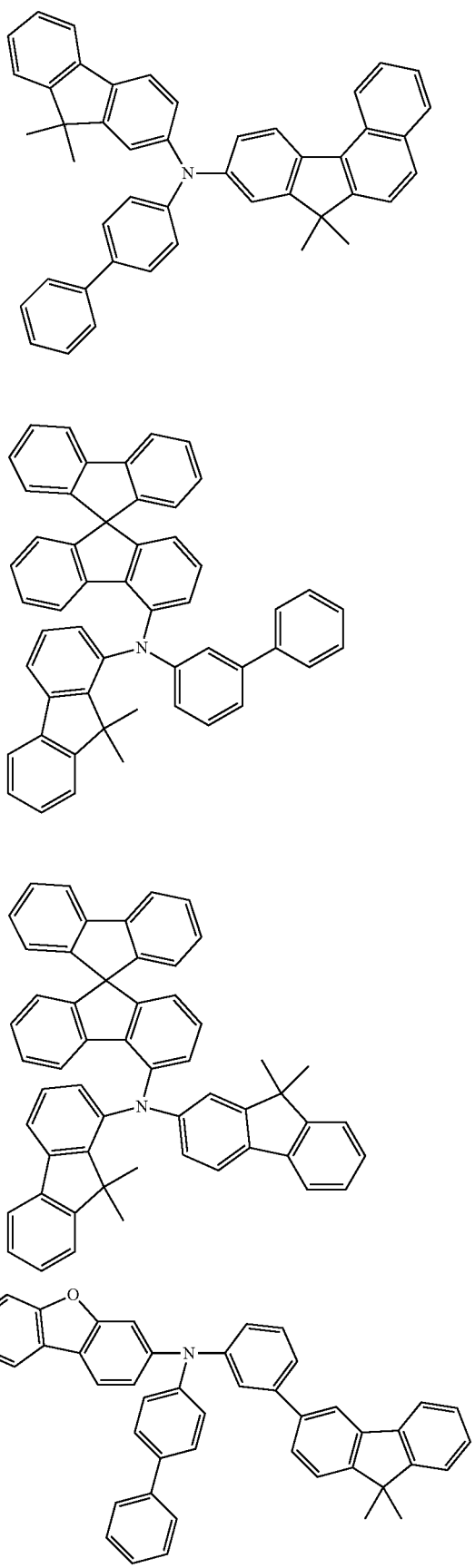

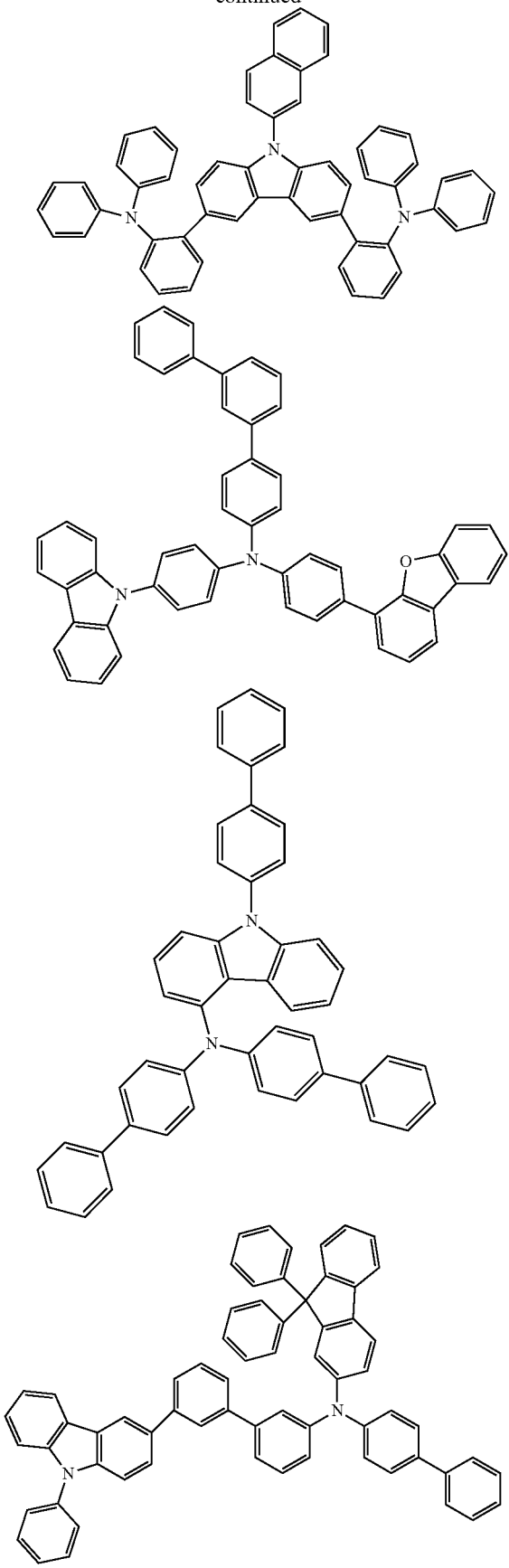

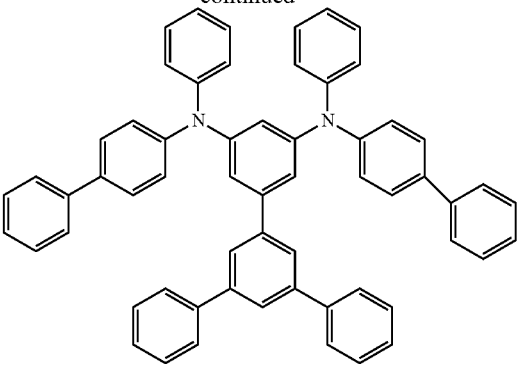

The hole transport region HTR may include a phthalocyanine compound such as copper phthalocyanine; $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4''-[tris(3-methylphenyl)phenylamino]triphenylamine] (m-MTDATA), 4,4',4''-tris(N,N-diphenylamino)triphenylamine (TDATA), 4,4',4''-tris(N,-(2-naphthyl) N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], dipyrazino[2,3-f: 2',3'-h]quinoxaline-2,3,6,7,10,11-hexacarbonitrile (HATCN), etc.

The hole transport region HTR may include carbazole derivatives such as N-phenyl carbazole and polyvinyl carbazole, fluorene derivatives, N,N-bis(3-methylphenyl)-N,N'-diphenyl-[1,1-biphenyl]-4,4'-diamine (TPD), triphenylamine derivatives such as 4,4',4''-tris(N-carbazolyl) triphenylamine (TCTA), N,N-di(naphthalene-1-yl)-N,N-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The hole transport region HTR may include carbazole derivatives such as N-phenyl carbazole and polyvinyl carbazole, fluorene derivatives, N,N-bis(3-methylphenyl)-N,N'-diphenyl-[1,1-biphenyl]-4,4'-diamine (TPD), triphenylamine derivatives such as 4,4',4''-tris(N-carbazolyl) triphenylamine (TCTA), N,N-di(naphthalene-1-yl)-N,N-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl) benzene (mCP), 1,3-bis(1,8-dimethyl-9H-carbazol-9-yl) benzene (mDCP), etc.

The hole transport region HTR may include the above-described compound of the hole transport region in at least one of a hole injection layer HIL, a hole transport layer HTL, and an electron blocking layer EBL.

A thickness of the hole transport region HTR may be in a range of about 100 Å to about 10,000 Å. For example, the thickness of the hole transport region HTR may be in a range of about 100 Å to about 5,000 Å. When the hole transport region HTR includes a hole injection layer HIL, the hole injection layer HIL may have, for example, a thickness in a range of about 30 Å to about 1,000 Å. When the hole transport region HTR includes a hole transport layer HTL, the hole transport layer HTL may have a thickness in a range of about 30 Å to about 1,000 Å. For example, when the hole transport region HTR includes an electron blocking layer EBL, the electron blocking layer EBL may have a thickness in a range of about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without a substantial increase in a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may include at least one of a halogenated metal compound, a quinone derivative, a metal oxide, and a cyano group-containing compound, but embodiments are not limited thereto. For example, the p-dopant may include metal halides such as CuI and RbI, quinone derivatives such as tetracyanoquinodimethane (TCNQ) and 2,3,5,6-tetrafluoro-7,7',8,8'-tetracyanoquinodimethane (F4-TCNQ), metal oxides such as tungsten oxide and molybdenum oxide, dipyrazino[2,3-f: 2',3'-h]quinoxaline-2,3,6,7,10,11-hexacarbonitrile (HATCN), 4-[[2,3-bis[cyano-(4-cyano-2,3,5,6-tetrafluorophenyl)methylidene]cyclopropylidene]-cyanomethyl]-2,3,5,6-tetrafluorobenzonitrile, etc., but embodiments are not limited thereto.

As described above, the hole transport region HTR may further include at least one of the buffer layer (not shown) and the electron blocking layer EBL in addition to the hole injection layer HIL and the hole transport layer HTL. The buffer layer (not shown) may compensate a resonance distance according to the wavelength of light emitted from the emission layer EML and may thus increase light emission efficiency. Materials which may be included in the hole transport region HTR may be used as materials to be included in the buffer layer (not shown). The electron blocking layer EBL is a layer that serves to prevent electrons from being injected from the electron transport region ETR to the hole transport region HTR.

The emission layer EML is provided on the hole transport region HTR. The emission layer EML may have a thickness in a range of about 100 Å to about 1,000 Å. For example, the thickness of the emission layer EML may be in a range of about 100 Å to about 300 Å. The emission layer EML may have a single layer formed of a single material, a single layer formed of different materials, or a multilayer structure having multiple layers formed of different materials.

The emission layer EML in the light emitting device ED according to an embodiment may include a fused polycyclic compound of an embodiment.

The fused polycyclic compound of an embodiment may include two or more quinolinoacridinediones or quinolinoacridinedione derivatives. The fused polycyclic compound of an embodiment includes two or more quinolinoacridinediones or quinolinoacridinedione derivatives, but does not include a structure in which dipole moments in a compound molecule cancel out to be 0.

The fused polycyclic compound of an embodiment may be represented by Formula 1 below:

$$A\text{-}L\text{-}(B)_n$$ [Formula 1]

In Formula 1, L may be a direct linkage, a divalent linking group such as O, S, S=O, Si(R$_a$)(R$_b$), N(R$_c$), P(R$_d$), B(R$_e$), N=N, CC, C=O, C(=O)O, OC(=O)O, C=S, P=O, or P=S, a trivalent linking group such as N, P, or B, a substituted or unsubstituted alkyl linking group having 1 to 30 carbon atoms, a substituted or unsubstituted alkenyl linking group having 2 to 30 carbon atoms, a substituted or unsubstituted alkynyl linking group having 3 to 30 carbon atoms, a substituted or unsubstituted aryl linking group having 6 to 60 ring-forming carbon atoms, or a substituted or unsubstituted heteroaryl linking group having 2 to 60 ring-forming carbon atoms. L may be, for example, a direct linkage, an ethyne linking group, a diazine linking group, an oxy group, a thio group, a substituted or unsubstituted silyl group, a substituted or unsubstituted phosphine group, a substituted or unsubstituted amine group, a substituted or unsubstituted boryl group, a substituted or unsubstituted methyl group, a substituted or unsubstituted carbonyl group, a substituted or unsubstituted vinyl group, a substituted or unsubstituted phenyl group, a substituted or unsubstituted biphenyl group, a substituted or unsubstituted naphthyl group, a substituted or unsubstituted anthracene group, a substituted or unsubstituted pyrenyl group, a substituted or unsubstituted pyridine group, a substituted or unsubstituted pyrimidine group, a substituted or unsubstituted pyrazinyl group, a substituted or unsubstituted triazine group, a substituted or unsubstituted furan group, a substituted or unsubstituted thiophene group, a substituted or unsubstituted benzothiophene group, or the like.

In Formula 1, n may be an integer from 1 to 3. In an embodiment, n may be 2 or 3, and multiple B(s) may be the same as or different from each other. For example, if n is 2 or 3, then the B(s) may have a same structure as each other.

L may be a divalent linking group, a trivalent linking group, or a tetravalent linking group depending on an n value. When n is 1, L may be a divalent linking group. When n is 2, L may be a trivalent linking group. When n is 3, L may be a tetravalent linking group. When n is 1, L may be a direct linkage, a divalent linking group such as O, S, S=O, Si(R$_a$)(R$_b$), N(R$_e$), P(R$_d$), B(R$_e$), N=N, CC, C=O, C(=O)O, OC(=O)O, C=S, P=O, or P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 3 to 30 carbon atoms, a substituted or unsubstituted arylene group having 6 to 60 ring-forming carbon atoms, or a substituted or unsubstituted heteroarylene linking group having 2 to 60 ring-forming carbon atoms. When n is 2, L may be N, P, B, a substituted or unsubstituted trivalent alkyl group having 1 to 30 carbon atoms, a substituted or unsubstituted trivalent alkenyl group having 2 to 30 carbon atoms, a substituted or unsubstituted trivalent alkynyl group having 3 to 30 carbon atoms, a substituted or unsubstituted trivalent aryl group having 6 to 60 ring-forming carbon atoms, or a substituted or unsubstituted trivalent heteroaryl group having 2 to 60 ring-forming carbon atoms. When n is 3, L may be a substituted or unsubstituted tetravalent alkyl group having 1 to 30 carbon atoms, a substituted or unsubstituted tetravalent alkenyl group having 2 to 30 carbon atoms, a substituted or unsubstituted tetravalent alkynyl group having 3 to 30 carbon atoms, a substituted or unsubstituted tetravalent aryl group having 6 to 60 ring-forming carbon atoms, or a substituted or unsubstituted tetravalent heteroaryl group having 2 to 60 ring-forming carbon atoms.

In Formula 1, R$_a$ to R$_e$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In another embodiment, $R_a$ to $R_e$ may each be bonded to an adjacent group to form a ring. For example, $R_a$ to $R_e$ may each independently be a substituted or unsubstituted phenyl group.

In Formula 1, A may be a group represented by Formula 2 below:

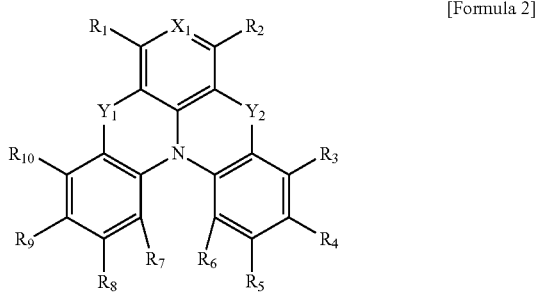

[Formula 2]

In Formula 2, $X_1$ may be N or $C(R_{11})$.

In Formula 2, $Y_1$ and $Y_2$ may each independently be C=O, C=S, S=O, $SO_2$, $C≡C(R_f)(R_g)$, P=O, or P=S. $Y_1$ and $Y_2$ may be the same as or different from each other. For example, in an embodiment, $Y_1$ and $Y_2$ may each independently be C=O or C=S. In another embodiment, $Y_1$ and $Y_2$ may each independently be S=O, $SO_2$, $C≡C(R_f)(R_g)$, or P=S.

In Formula 2, $R_1$ to $R_{11}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_1$ to $R_{11}$ each may be bonded to an adjacent group to form a ring. In an embodiment, $R_1$ to $R_{11}$ may each independently be a hydrogen atom, a deuterium atom, a substituted or unsubstituted methyl group, or a substituted or unsubstituted phenyl group. For example, in an embodiment, $R_1$ to $R_{11}$ may each independently be a hydrogen atom, a deuterium atom, an unsubstituted isopropyl group, an unsubstituted t-butyl group, or an unsubstituted phenyl group. In another embodiment, $R_6$ and $R_7$, which are adjacent to each other, may be bonded to each other to form a ring via an oxy group, a thio group, or a carbonyl group.

Any one of $R_1$ to $R_{10}$ may be a binding site to L in Formula 1. In Formula 2, $R_{11}$ is excluded from being a binding site to L in Formula 1. For example, $R_3$, $R_4$, or $R_5$ may be a binding site to L in Formula 1.

In Formula 2, $R_f$ and $R_g$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_f$ and $R_g$ each may be bonded to an adjacent group to form a ring. For example, $R_f$ and $R_g$ may be each independently a hydrogen atom or a substituted or unsubstituted phenyl group. For example, $R_f$ and $R_g$ may both be unsubstituted phenyl groups.

In Formula 1, B may be a group represented by Formula 3 below:

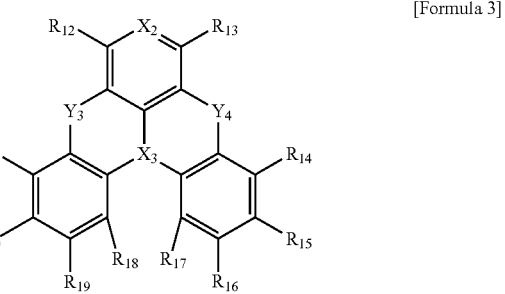

[Formula 3]

In Formula 3, $X_2$ may be N or $C(R_{22})$.

In Formula 3, $X_3$ may be N, B, or P.

In Formula 3, $Y_3$ and $Y_4$ may each independently be C=O, C=S, S=O, $SO_2$, $C≡C(R_h)(R_i)$, P=O, P=S, $N(R_j)$, or $B(R_k)$. In an embodiment, $Y_3$ and $Y_4$ may be the same as or different from each other. For example, $Y_3$ and $Y_4$ may each independently be C=O or C=S. In another embodiment, $Y_3$ and $Y_4$ may each independently be S=O, $SO_2$, $C≡C(R_h)(R_i)$, P=S, $N(R_j)$, or $B(R_k)$.

A substituent at $Y_3$ and $Y_4$ may be different from the substituent at $X_3$. For example, if $X_3$ is N, $Y_3$ and $Y_4$ may not be $N(R_i)$. If $X_3$ is B, $Y_3$ and $Y_4$ may not be $B(R_k)$. If $X_3$ is P, $Y_3$ and $Y_4$ may not be P=O or P=S.

In Formula 3, $R_{12}$ to $R_{22}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_{12}$ to $R_{22}$ each may be bonded to an adjacent group to form a ring. For example, $R_{12}$ to $R_{22}$ may each independently be a hydrogen atom, a deuterium atom, a substituted or unsubstituted methyl group, or a substituted or unsubstituted phenyl group. In an embodiment, $R_{12}$ to $R_{22}$ may each independently be a hydrogen atom, a deuterium atom, an unsubstituted isopropyl group, an unsubstituted t-butyl group, or an unsubstituted phenyl group. In another embodiment, $R_{17}$ and $R_{18}$, which are adjacent to each other, may be bonded to each other to form a ring via an oxy group, a thio group, an amine group, or a carbonyl group.

Any one of $R_{12}$ to $R_{22}$ may be a binding site to L in Formula 1. For example, $R_{15}$, $R_{16}$, or $R_{22}$ may be a binding site to L in Formula 1.

In Formula 3, $R_h$ to $R_k$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_h$ to $R_k$ each may be bonded to an adjacent group to form a ring. For example, $R_h$ to $R_k$ may be each independently a hydrogen atom or a substituted or unsubstituted phenyl group. In an embodiment, $R_f$ and $R_g$ may be each independently an unsubstituted phenyl group, or a phenyl group substituted with an isopropyl group or a phenyl group.

In Formula 1, A and B may have a same structure as each other. A and B may be a same moiety. For example, in Formula 3, $X_3$ may be N, and in Formula 2 and Formula 3, $X_1$ may be the same as $X_2$, $Y_1$ may be the same as $Y_3$, and $Y_2$ may be the same as $Y_4$. The substituent of a structure of A represented by Formula 2 may also be the same as the substituent of a structure of B represented by Formula 3. For example, $R_1$ and $R_{12}$ may be the same, $R_2$ and $R_{13}$ may be the same, $R_3$ and $R_{14}$ may be the same, $R_4$ and $R_{15}$ may be the same, $R_5$ and $R_{16}$ may be the same, $R_6$ and $R_{17}$ may be the same, $R_7$ and $R_{18}$ may be the same, $R_8$ and $R_{19}$ may be the same, $R_9$ and $R_{20}$ may be the same, and $R_{10}$ and $R_{21}$ may be the same. However, embodiment are not limited thereto, and A and B may be different.

The fused polycyclic compound of an embodiment includes a structure in which two or more quinolinoacridinediones or quinolinoacridinedione derivatives are connected via a linker or a direct linkage. The fused polycyclic compound of an embodiment includes two or more quinolinoacridinediones or derivatives thereof to form an expanded conjugation structure, thereby stabilizing the structure of the polycyclic aromatic ring. Thus, a wavelength range may be selected to be suitable for a blue luminescent material, and when the fused polycyclic compound of an embodiment is applied to a light emitting device, efficiency of the light emitting device may be improved.

The fused polycyclic compound represented by Formula 1 may be represented by Formula 4 below.

[Formula 4]

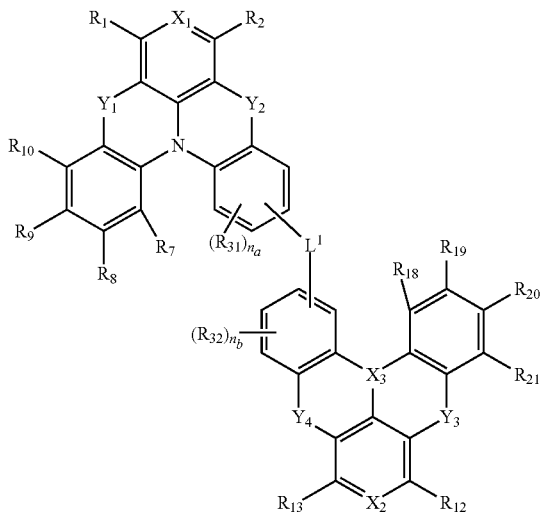

Formula 4 represents a case where in Formula 1, n is specified as 1, and the ring that is connected to L, in the structures of Formula 2 and Formula 3, is specified.

In Formula 4, $L_1$ may be a divalent linking group. $L_1$ may be a direct linkage, O, S, S=O, $Si(R_a)(R_b)$, $N(R_c)$, $P(R_d)$, $B(R_e)$, N=N, CC, C=O, C(=O)O, OC(=O)O, C=S, P=O, or P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 2 to 30 carbon atoms, a substituted or unsubstituted arylene group having 6 to 60 ring-forming carbon atoms, or a substituted or unsubstituted heteroarylene linking group having 2 to 60 ring-forming carbon atoms. $L_1$ may be, for example, a direct linkage, O, S, S=O, $Si(R_a)(R_b)$, $N(R_c)$, $P(R_d)$, $B(R_e)$, N=N, CC, C=O, C(=O)O, OC(=O)O, C=S, P=O, P=S, a substituted or unsubstituted vinyl group, a substituted or unsubstituted phenyl group, a substituted or unsubstituted biphenyl group, a substituted or unsubstituted naphthyl group, a substituted or unsubstituted anthracene group, a substituted or unsubstituted pyrenyl group, a substituted or unsubstituted pyridine group, a substituted or unsubstituted pyrimidine group, a substituted or unsubstituted pyrazinyl group, a substituted or unsubstituted triazine group, a substituted or unsubstituted furan group, a substituted or unsubstituted thiophene group, a substituted or unsubstituted benzothiophene group, or the like.

In Formula 4, $R_{31}$ and $R_{32}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_{31}$ and $R_{32}$ each may be bonded to an adjacent group to form a ring. For example, $R_{31}$ and $R_{32}$ may each independently be a hydrogen atom or a deuterium atom.

In Formula 4, $n_a$ and $n_b$ may each independently be an integer from 0 to 3. When $n_a$ and $n_b$ each are 0, the fused polycyclic compound according to an embodiment may not be substituted with $R_{31}$ and $R_{32}$. When $n_1$ and $n_2$ each are an integer of 2 or more, $R_{31}$ (s) and $R_{32}$ (s) each may be the same or at least one among multiple $R_{31}$ (s) and $R_{32}$ (s) may be different.

In Formula 4, $X_1$, $X_2$, $X_3$, $Y_1$, $Y_2$, $Y_3$, $Y_4$, $R_1$, $R_2$, $R_7$ to $R_{13}$, $R_{18}$ to $R_{22}$, and $R_a$ to $R_k$ may be the same as defined in connection with Formula 2 and Formula 3.

The fused polycyclic compound represented by Formula 4 may be represented by any one of Formula 4-1 to Formula 4-3 below:

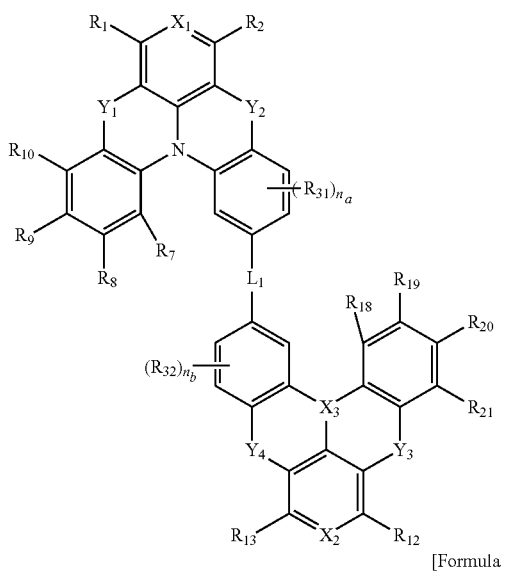

[Formula 4-1]

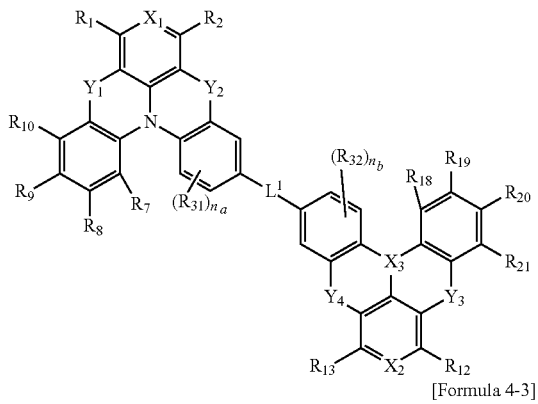

[Formula 4-2]

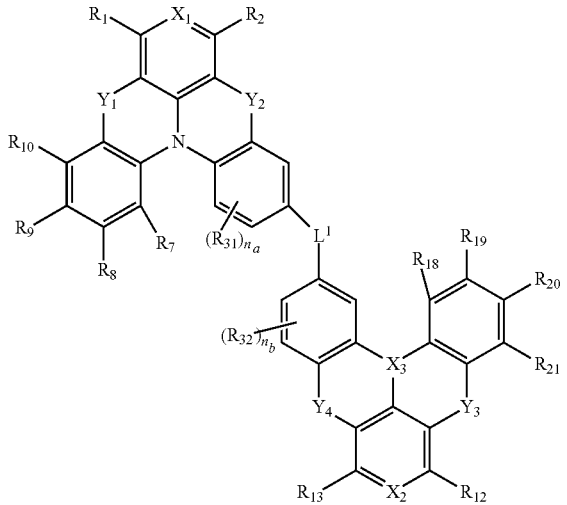

[Formula 4-3]

Formula 4-1 to Formula 4-3 each represent a case where in Formula 4, the carbon positions in which the structure of Formula 2 is connected to the structure of Formula 3 via $L_1$ are specified.

In Formula 4-1 to Formula 4-3 above, $X_1$, $X_2$, $X_3$, $Y_1$, $Y_2$, $Y_3$, $Y_4$, $R_1$, $R_2$, $R_7$ to $R_{13}$, $R_{18}$ to $R_{22}$, $R_a$ to $R_k$, $L_1$, $R_{31}$, $R_{32}$, $n_a$, and $n_b$ may be the same as defined in connection with Formula 2, Formula 3, and Formula 4.

The fused polycyclic compound represented by Formula 1 may be represented by Formula 5 below.

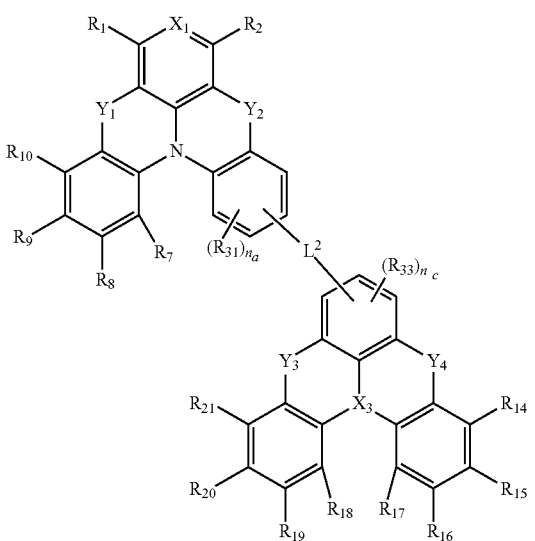

[Formula 5]

Formula 5 represents a case when in Formula 1, n is specified as 1, and the ring that is connected to L, in the structures of Formula 2 and Formula 3, is specified.

In Formula 5, $L_2$ may be a divalent linking group. $L_2$ may be a direct linkage, O, S, S=O, Si($R_a$)($R_b$), N($R_c$), P($R_d$), B($R_e$), N=N, CC, C=O, C(=O)O, OC(=O)O, C=S, P=O, P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 2 to 30 carbon atoms, a substituted or unsubstituted arylene group having 6 to 60 ring-forming carbon atoms, or a substituted or unsubstituted heteroarylene linking group having 2 to 60 ring-forming carbon atoms. The description of $L_1$ in Formula 4 may be applied to $L_2$.

In Formula 5, $R_{31}$ and $R_{33}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_{31}$ and $R_{33}$ each may be bonded to an adjacent group to form a ring. For example, $R_{31}$ and $R_{33}$ may each independently be a hydrogen atom or a deuterium atom.

In Formula 5, $n_a$ may be an integer from 0 to 3, and $n_c$ may be an integer from 0 to 2. When $n_a$ and $n_c$ each are 0, the fused polycyclic compound according to an embodiment may not be substituted with $R_{31}$ and $R_{33}$. When $n_a$ and $n_c$ each are an integer of 2 or more, $R_{31}$(s) and $R_{33}$(s) may each be the same or at least one among multiple $R_{31}$(s) and $R_{33}$(s) may be different.

In Formula 5, $X_1$, $X_2$, $X_3$, $Y_1$, $Y_2$, $Y_3$, $Y_4$, $R_1$, $R_2$, $R_7$ to $R_{11}$, $R_{14}$ to $R_{21}$, and $R_a$ to $R_k$ may be the same as defined in connection with Formula 2 and Formula 3.

The fused polycyclic compound represented by Formula 5 may be represented by any one of Formula 5-1 to Formula 5-3 below:

[Formula 5-1]

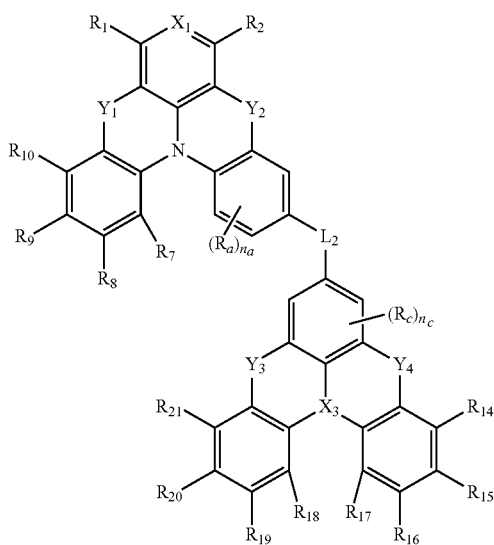

[Formula 5-2]

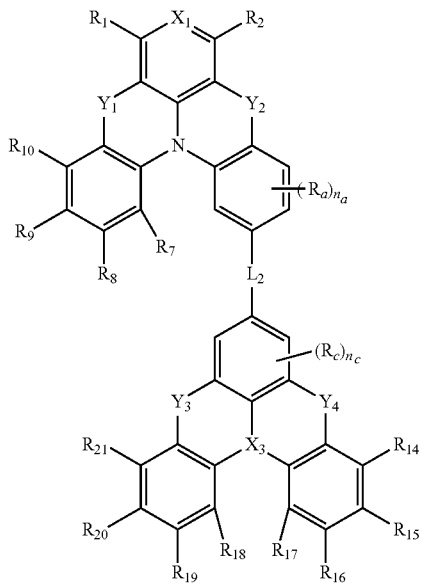

[Formula 5-3]

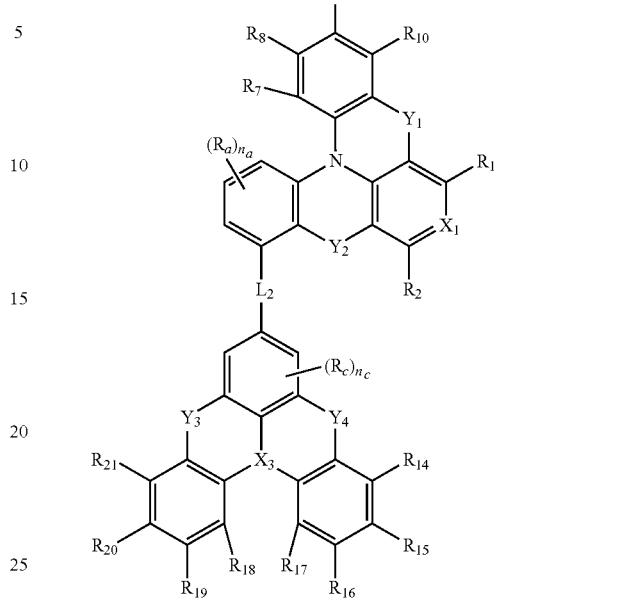

Formula 5-1 to Formula 5-3 each represent a case where in Formula 5, the carbon positions in which the structure of Formula 2 is connected to the structure of Formula 3 via $L_2$ are specified.

In Formula 5-1 to Formula 5-3, $X_1$, $X_2$, $X_3$, $Y_1$, $Y_2$, $Y_3$, $Y_4$, $R_1$, $R_2$, $R_7$ to $R_{11}$, $R_{14}$ to $R_{21}$, $R_4$ to $R_k$, $L_2$, $R_{31}$, $R_{33}$, $n_a$, and $n_c$ may be the same as defined in connection with Formula 2, Formula 3, and Formula 5.

The fused polycyclic compound represented by Formula 1 may be represented by Formula 6 below:

[Formula 6]

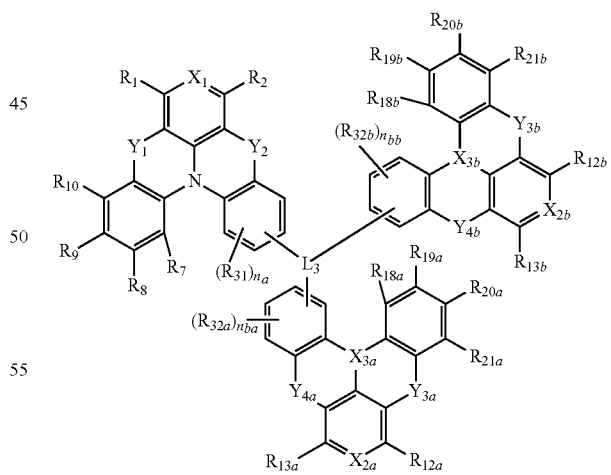

Formula 6 represents a case where in Formula 1, n is specified as 2, and the ring that is connected to L in the structures of Formula 2 and Formula 3 is specified.

In Formula 6, $L_3$ may be a trivalent linking group. $L_3$ may be N, P, B, a substituted or unsubstituted trivalent alkyl group having 1 to 30 carbon atoms, a substituted or unsubstituted trivalent alkenyl group having 2 to 30 carbon atoms, a substituted or unsubstituted trivalent alkynyl group having 3 to 30 carbon atoms, a substituted or unsubstituted trivalent aryl group having 6 to 60 ring-forming carbon atoms, or a substituted or unsubstituted trivalent heteroaryl group having 2 to 60 ring-forming carbon atoms. $L_3$ may be, for example, N, P, a substituted or unsubstituted phenyl group, a substituted or unsubstituted pyridine group, a substituted or unsubstituted pyrimidine group, or a substituted or unsubstituted triazine group.

In Formula 6, $X_{2a}$ and $X_{2b}$ may each independently be N or $C(R_{22})$. The description of $X_2$ in Formula 3 may be applied to $X_{2a}$ and $X_{2b}$.

In Formula 6, $X_{3a}$ and $X_{3b}$ may each independently be N, B, or P. The description of $X_3$ in Formula 3 may be applied to $X_{3a}$ and $X_{3b}$.

In Formula 6, $Y_{3a}$, $Y_{3b}$, $Y_{4a}$, and $Y_{4b}$ may each independently be C=O, C=S, S=O, $SO_2$, C=C($R_h$)($R_i$), P=O, P=S, N($R_j$), or B($R_k$). The descriptions of $Y_3$ in Formula 3 may be applied to $Y_{3a}$ and $Y_{3b}$, and the descriptions of $Y_4$ in Formula 3 may be applied to $Y_{4a}$, and $Y_{4b}$.

In Formula 6, $R_{12a}$, $R_{13a}$, $R_{18a}$ to $R_{21a}$, $R_{12b}$, $R_{13b}$, and $R_{18b}$ to $R_{21b}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. The descriptions of $R_{12}$, $R_{13}$, $R_{18}$ to $R_{21}$ in Formula 3 may be respectively applied to $R_{12a}$, $R_{13a}$, Rim to $R_{21a}$, and respectively applied to $R_{12b}$, $R_{13b}$, and $R_{18b}$ to $R_{21b}$.

In Formula 6, $R_{31}$, $R_{32a}$, and $R_{32b}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_{31}$, $R_{32a}$, and $R_{32b}$ each may be bonded to an adjacent group to form a ring. For example, $R_{31}$, $R_{32a}$, and $R_{32b}$ may each independently be a hydrogen atom or a deuterium atom.

In Formula 6, $n_a$, $n_{ba}$, and $n_{bb}$ may each independently be an integer from 0 to 3. When $n_a$, $n_{ba}$, and $n_{bb}$ each are 0, the fused polycyclic compound according to an embodiment may not be substituted with $R_{31}$, $R_{32a}$, and $R_{32b}$. When $n_a$, $n_{ba}$, and $n_{bb}$ each are an integer of 2 or more, $R_{31}(s)$, $R_{32a}(s)$, and $R_{32b}(s)$ may be the same, or at least one among multiple $R_{31}(s)$, $R_{32a}(s)$, and $R_{32b}(s)$ may be different.

In Formula 6, $X_1$, $Y_1$, $Y_2$, $R_1$, $R_2$, $R_7$ to $R_{11}$, $R_{22}$, and $R_a$ to $R_k$ may be the same as defined in connection with Formula 2 and Formula 3.

The fused polycyclic compound represented by Formula 6 may be represented by Formula 6-1 below:

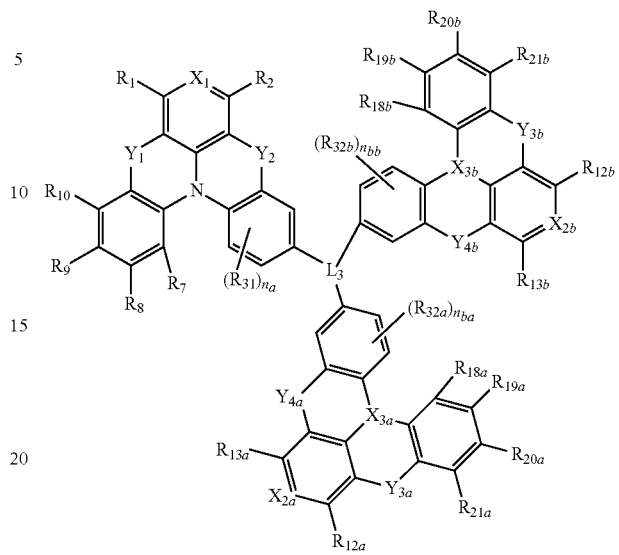

[Formula 6-1]

Formula 6-1 represents a case where in Formula 6, the carbon positions, in which the structure of Formula 2 is connected to the structure of Formula 3 via $L_3$, are specified.

In Formula 6-1, the same as those described in Formula 1 to Formula 3 and Formula 6 above may be applied to $X_1$, $Y_1$, $Y_2$, $R_1$, $R_2$, $R_7$ to $R_{11}$, $R_{22}$, $R_a$ to $R_k$, $L_3$, $X_{2a}$, $X_{2b}$, $X_{3a}$, $X_{3b}$, $Y_{3a}$, $Y_{3b}$, $Y_{4a}$, $Y_{4b}$, $R_{12a}$, $R_{13a}$, $R_{18a}$ to $R_{21a}$, $R_{12b}$, $R_{13b}$, $R_{18b}$ to $R_{21b}$, $R_{31}$, $R_{32a}$, $R_{32b}$, $n_a$, $n_{ba}$, and $n_{bb}$ may be the same as defined in connection with Formula 2, Formula 3, and Formula 6.

The fused polycyclic compound represented by Formula 1 may be represented by Formula 7 below.

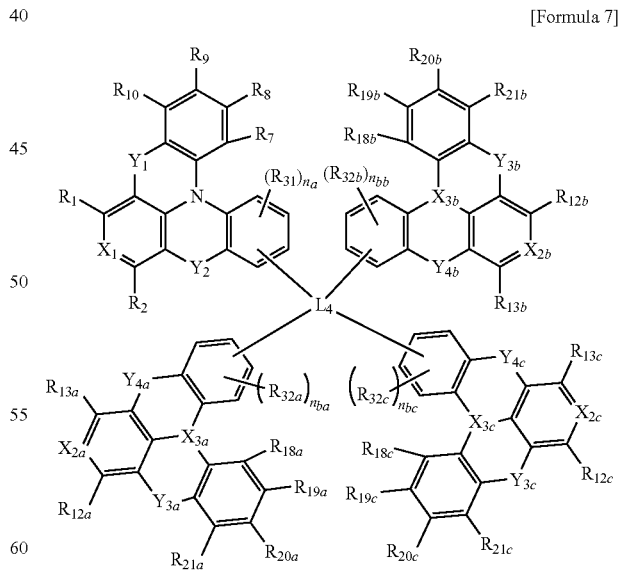

[Formula 7]

Formula 7 represents a case where in Formula 1, n is specified as 3, and the ring that is connected to L in the structures of Formula 2 and Formula 3 is specified.

In Formula 7, $L_4$ may be a tetravalent linking group. $L_4$ may be a substituted or unsubstituted tetravalent alkyl group having 1 to 30 carbon atoms, a substituted or unsubstituted tetravalent alkenyl group having 2 to 30 carbon atoms, a substituted or unsubstituted tetravalent alkynyl group having 3 to 30 carbon atoms, a substituted or unsubstituted tetravalent aryl group having 6 to 60 ring-forming carbon atoms, or a substituted or unsubstituted tetravalent heteroaryl group having 2 to 60 ring-forming carbon atoms. $L_4$ may be, for example, a substituted or unsubstituted phenyl group, or a substituted or unsubstituted biphenyl group.

In Formula 7, $X_{2a}$ to $X_{2c}$ may each independently be N or $C(R_{22})$. The description of $X_2$ in Formula 3 may be applied to $X_{2a}$ to $X_{2c}$.

In Formula 7, $X_{3a}$ to $X_{3c}$ may each independently be N, B, or P. The description of $X_3$ in Formula 3 may be applied to $X_{3a}$ to $X_{3c}$.

In Formula 7, $Y_{3a}$ to $Y_{3c}$ and $Y_{4a}$ to $Y_{4c}$ may each independently be C=O, C=S, S=O, $SO_2$, $C\equiv C(R_h)(R_i)$, P=O, P=S, $N(R_j)$, or $B(R_k)$. The descriptions of $Y_3$ in Formula 3 may be applied to $Y_{3a}$ to $Y_{3c}$, and the descriptions of $Y_4$ in Formula 3 may be applied to $Y_{4a}$ to $Y_{4c}$.

In Formula 7, $R_{12a}$, $R_{13a}$, $R_{18a}$ to $R_{21a}$, $R_{12b}$, $R_{13b}$, $R_{18b}$ to $R_{21b}$, $R_{12c}$, $R_{13c}$, and $R_{18c}$ to $R_{21c}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. The descriptions of $R_{12}$, $R_{13}$, $R_{18}$ to $R_{21}$ in Formula 3 may be respectively applied to $R_{12a}$, $R_{13a}$, and $R_{18a}$ to $R_{21a}$, and respectively applied to $R_{12b}$, $R_{13b}$, and $R_{18b}$ to $R_{21b}$, and respectively applied to $R_{12c}$, $R_{13c}$, and $R_{18c}$ to $R_{21c}$.

In Formula 7, $R_{31}$ and $R_{32a}$ to $R_{32c}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_{31}$ and $R_{32a}$ to $R_{32c}$ each may be bonded to an adjacent group to form a ring. For example, $R_{31}$ and $R_{32a}$ to $R_{32c}$ may be each independently a hydrogen atom or a deuterium atom.

In Formula 7, $n_a$ and $n_{ba}$ to $n_{bc}$ may each independently be an integer from 0 to 3. When $n_a$ and $n_{ba}$ to $n_{bc}$ each are 0, the fused polycyclic compound according to an embodiment may not be substituted with $R_{31}$ and $R_{32a}$ to $R_{32c}$. When $n_a$ and $n_{ba}$ to $n_{bc}$ each are an integer of 2 or more, $R_{31}$ (s) and $R_{32a}$(s) to $R_{32c}$(s) may each be the same, or at least one among multiple $R_{31}$ (s) and $R_{32a}$(s) to $R_{32c}$(s) may be different.

In Formula 7, $X_1$, $Y_1$, $Y_2$, $R_1$, $R_2$, $R_7$ to $R_{11}$, $R_{22}$, and $R_a$ to $R_k$ may be the same as defined in connection with Formula 2 and Formula 3.

The fused polycyclic compound represented by Formula 7 may be represented by Formula 7-1 below:

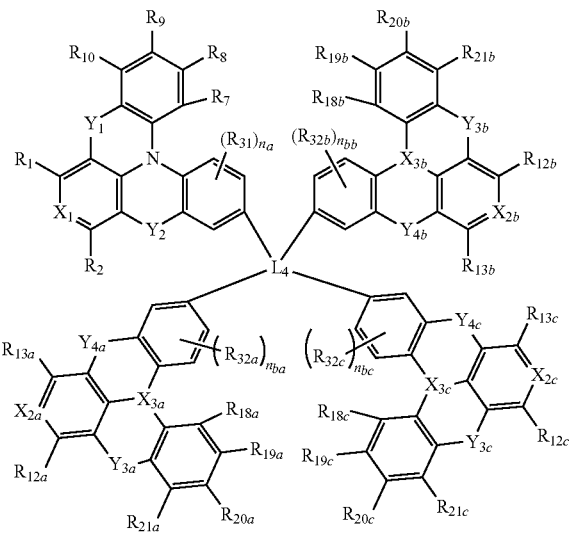

[Formula 7-1]

Formula 7-1 represents a case where in Formula 7, the carbon positions, in which the structure of Formula 2 is connected to the structure of Formula 3 via $L_4$, are specified.

In Formula 7-1, $X_1$, $Y_1$, $Y_2$, Ru, $R_2$, $R_7$ to $R_{11}$, $R_{22}$, $R_a$ to $R_k$, $L_4$, $X_{2a}$ to $X_{2c}$, $X_{3a}$ to $X_{3c}$, $Y_{3a}$ to $Y_{3c}$, $Y_{4a}$ to $Y_{4c}$, $R_{12a}$, $R_{13a}$, $R_{18a}$ to $R_{21a}$, $R_{12b}$, $R_{13b}$, $R_{18b}$ to $R_{21b}$, $R_{12c}$, $R_{13c}$, $R_{18c}$ to $R_{21c}$, $R_{31}$, $R_{32a}$ to $R_{32c}$, $n_a$, and $n_{ba}$ to $n_{bc}$ may be the same as defined in connection with Formula 2, Formula 3, and Formula 7.

The fused polycyclic compound of an embodiment may be any one of the compounds represented by Compound Group 1 below. The light emitting device ED of an embodiment may include at least one fused polycyclic compound selected from Compound Group 1 in the emission layer EML.

[Compound Group 1]

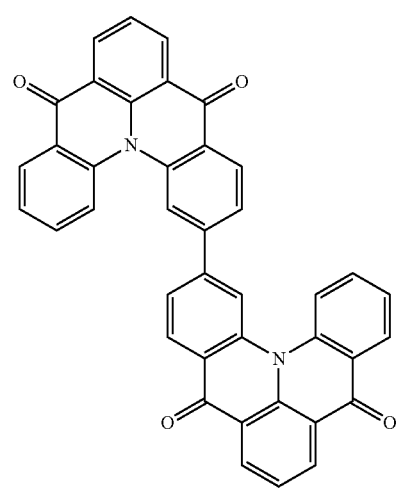

1

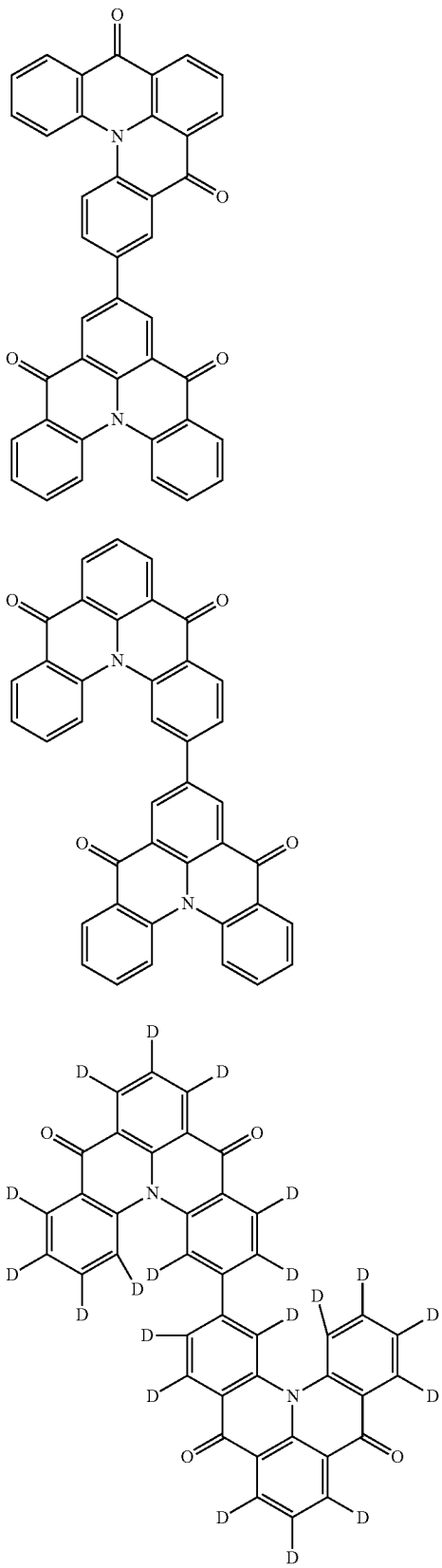
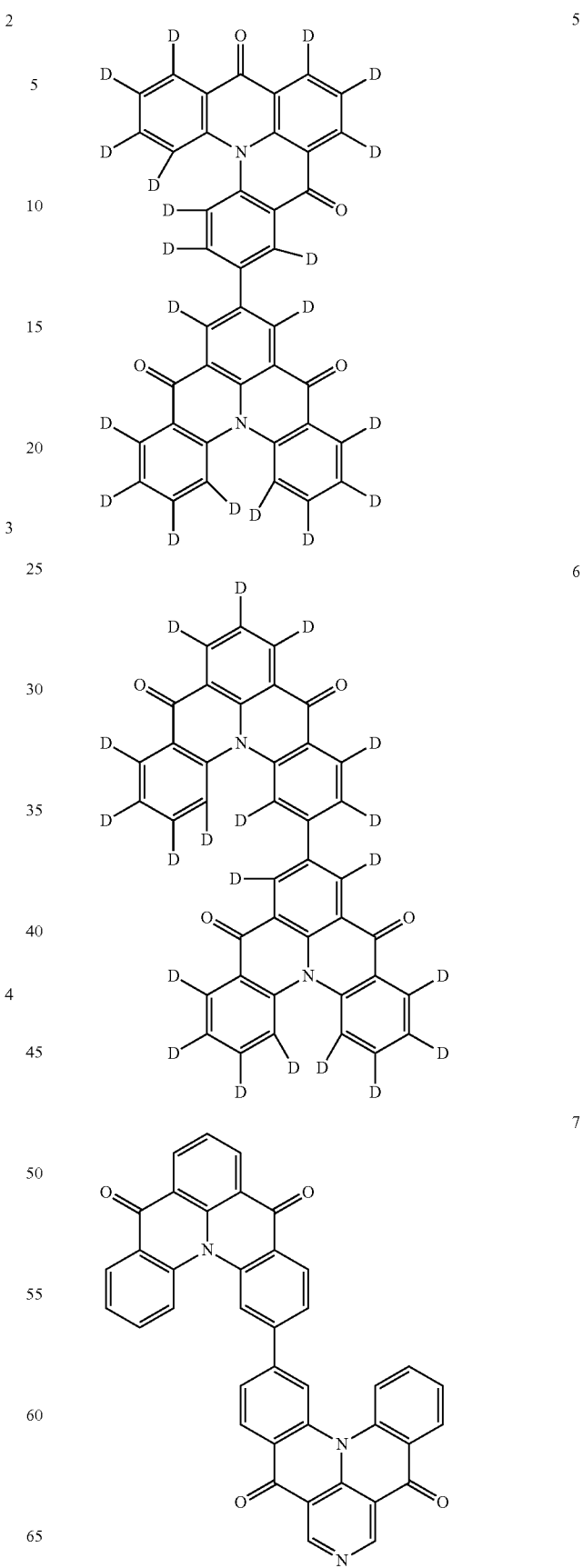

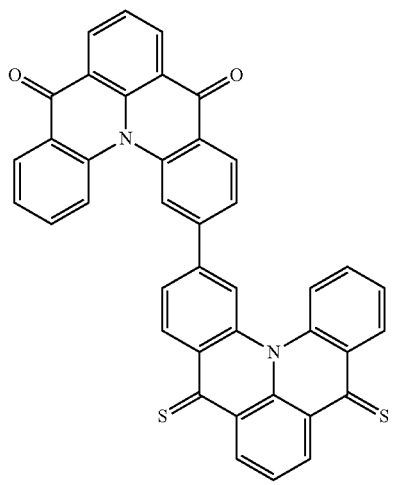
8
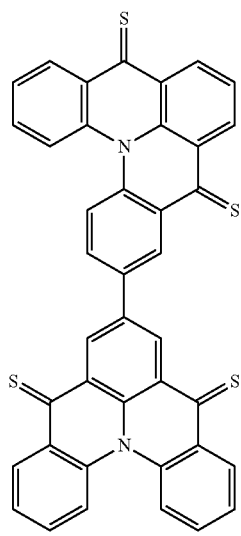
9
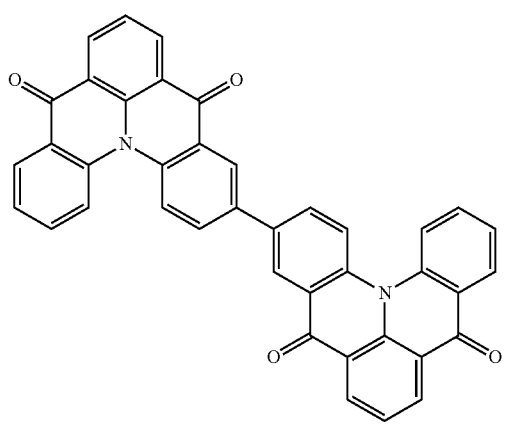
10
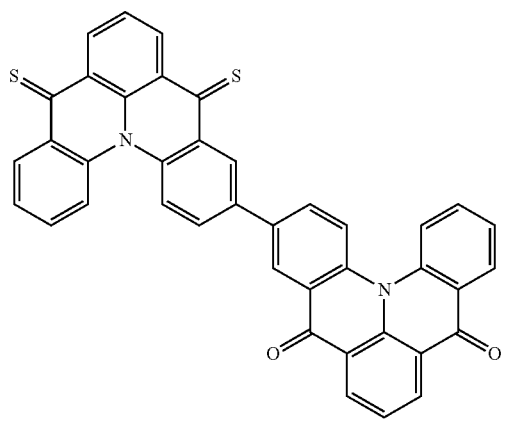
11
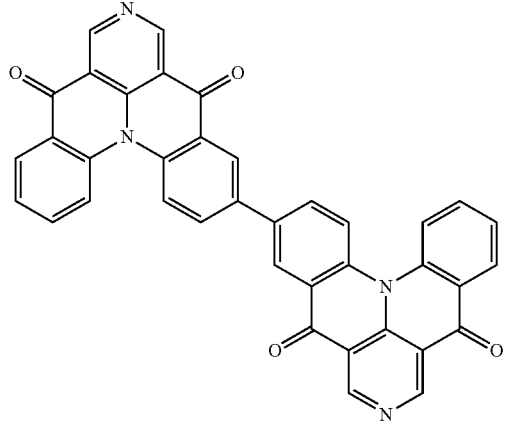
12
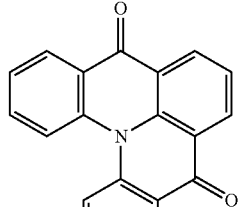
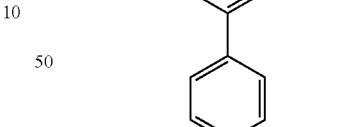
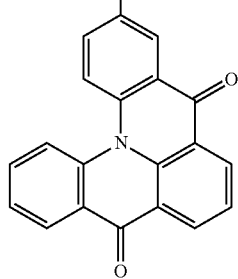
13

14
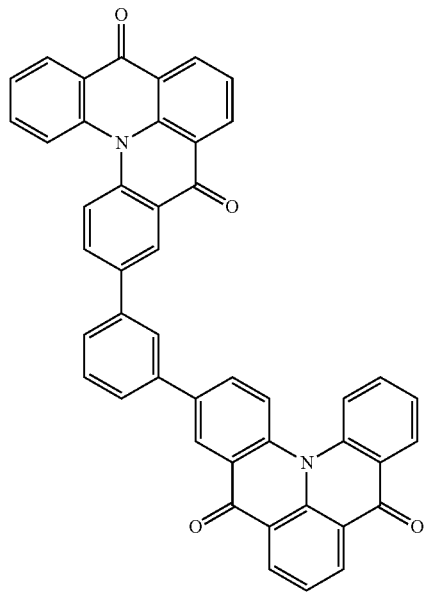
15
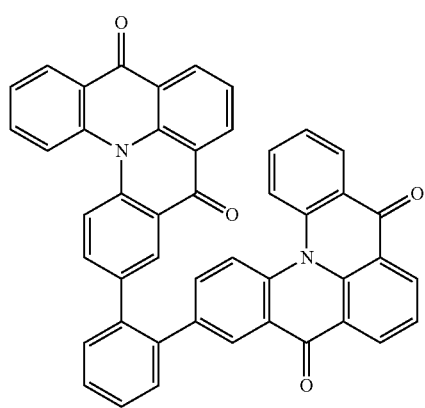
16
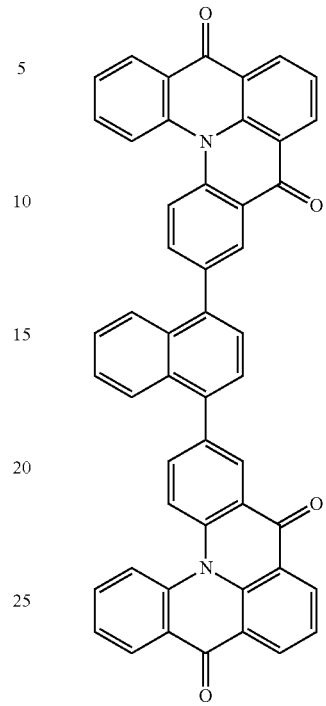
17
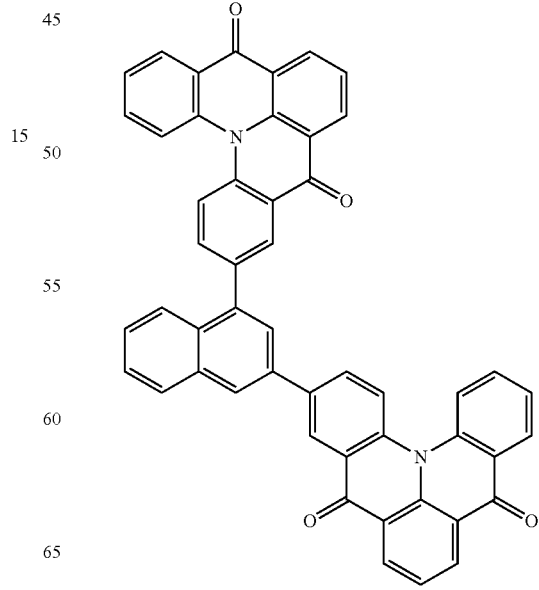

18
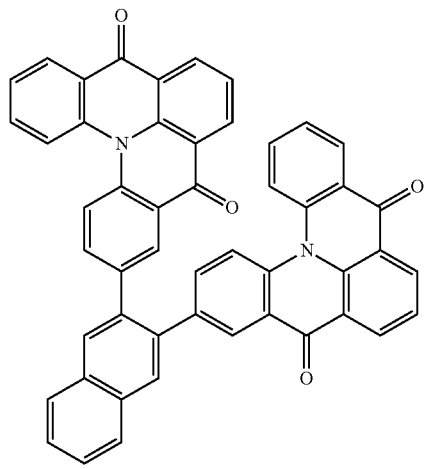
19
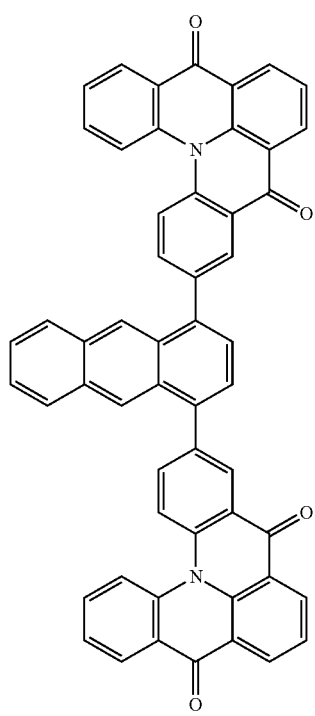
20
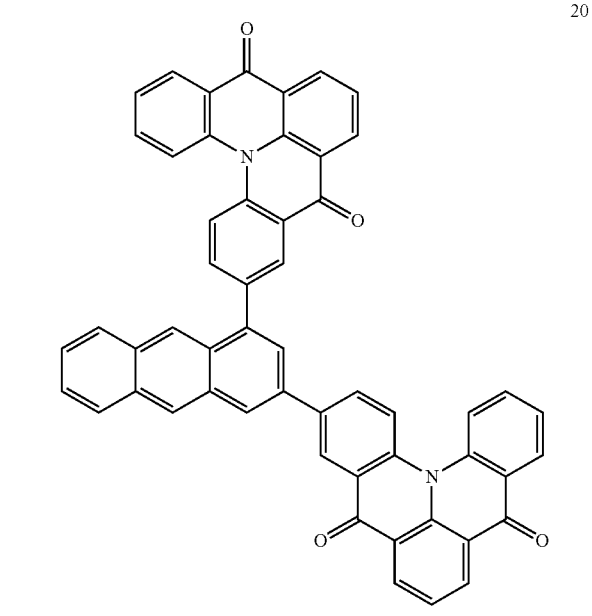
21
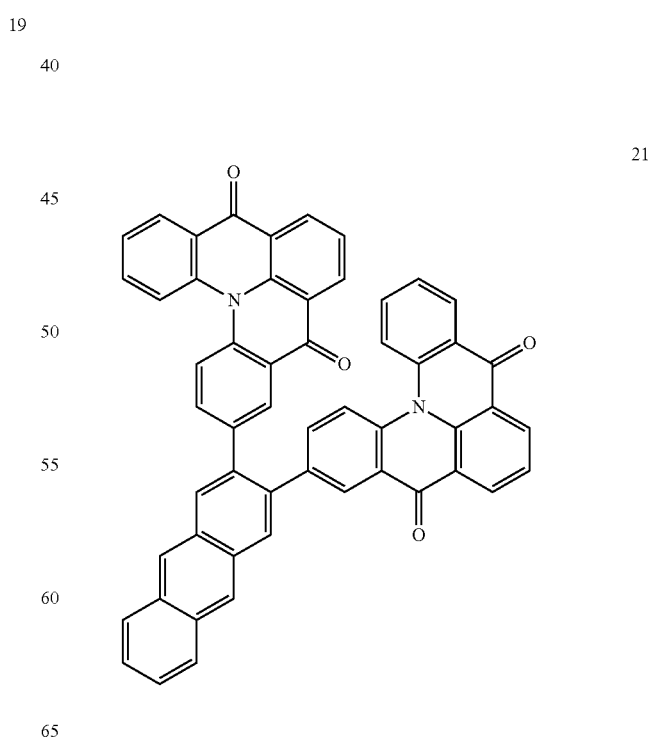

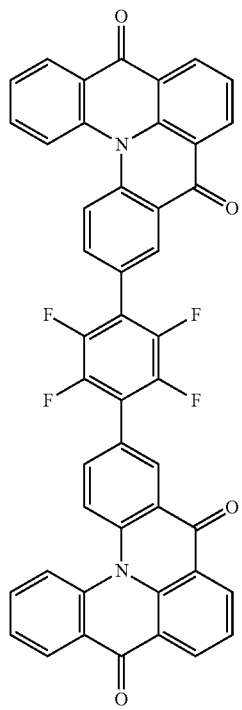
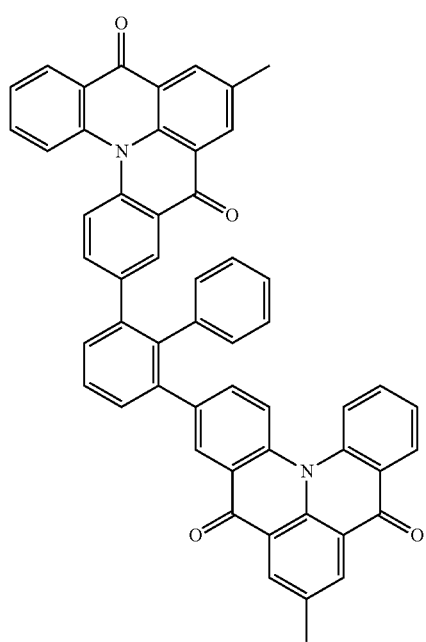
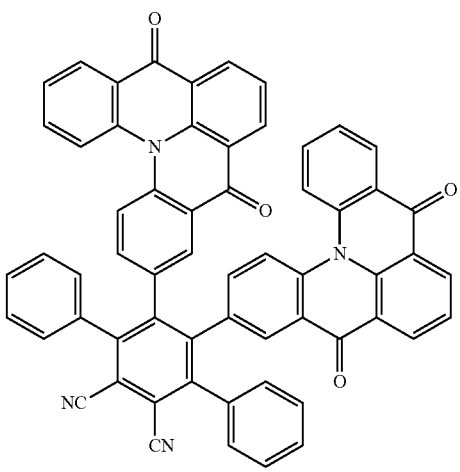
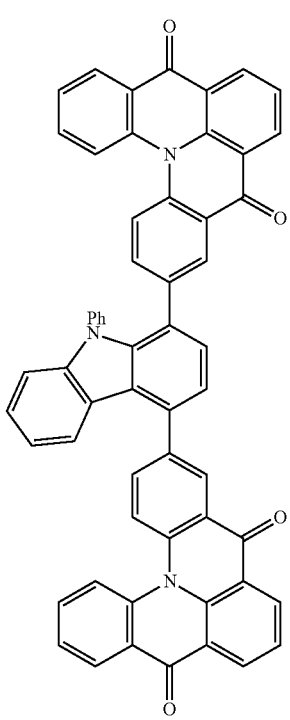

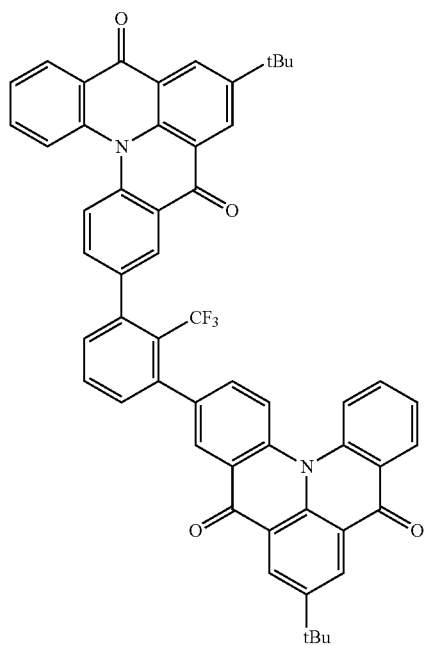
26
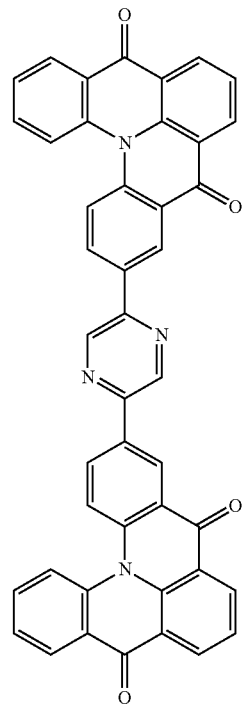
28
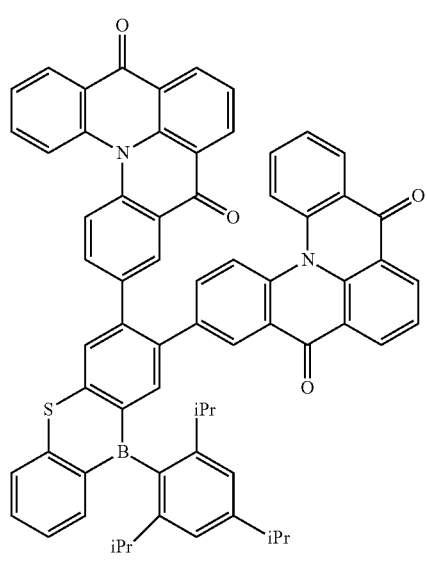
27
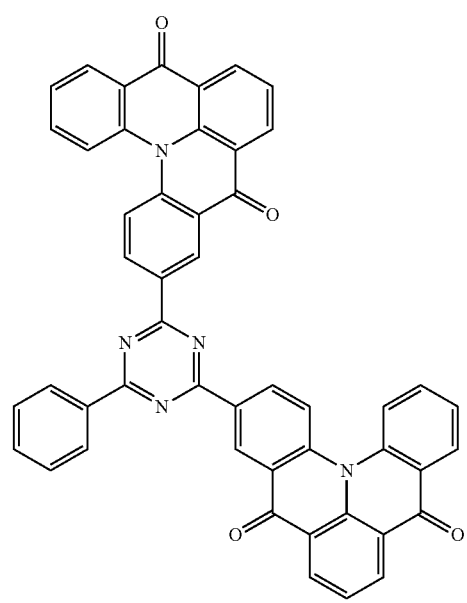
29

30
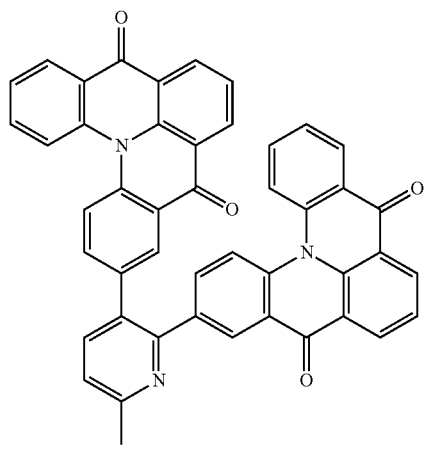
31
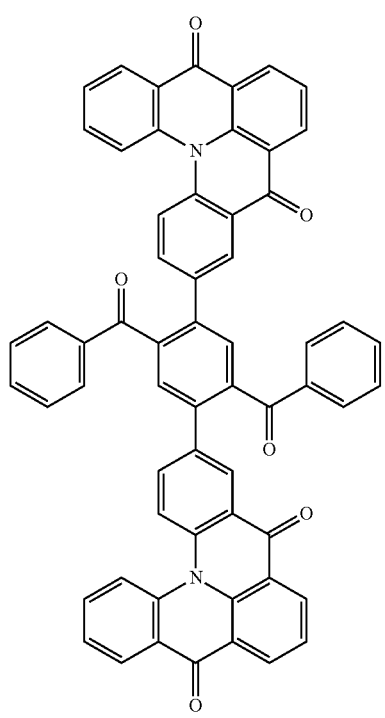
32
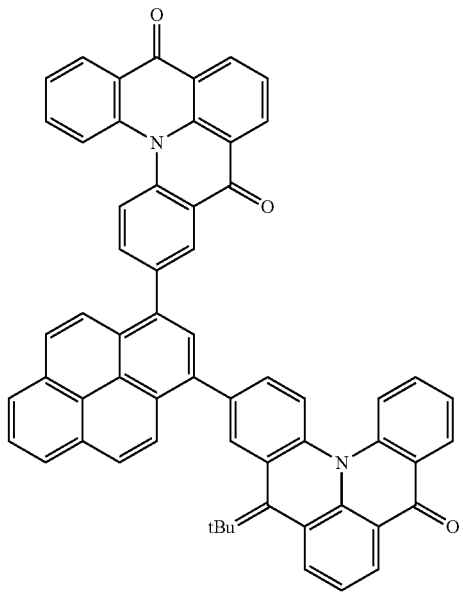
33
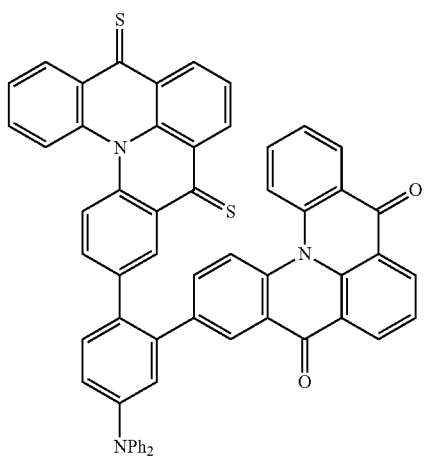

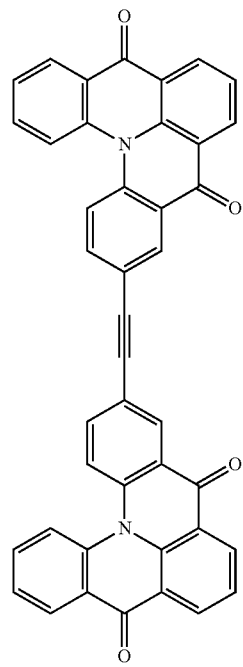
34
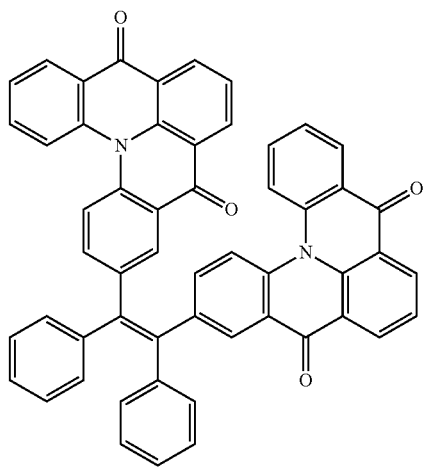
36
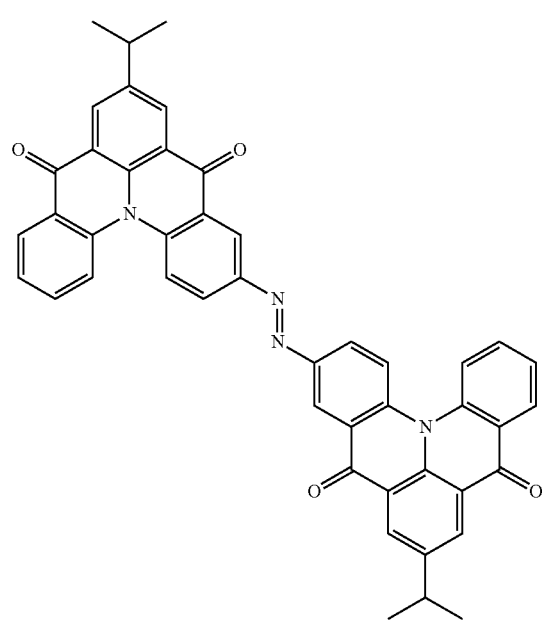
35
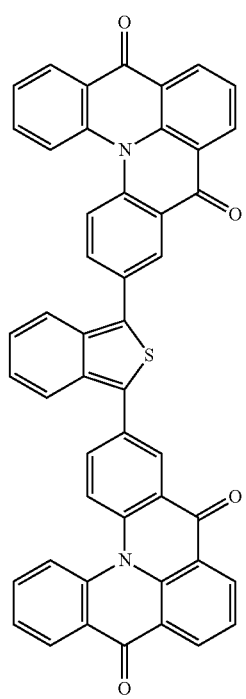
37

38
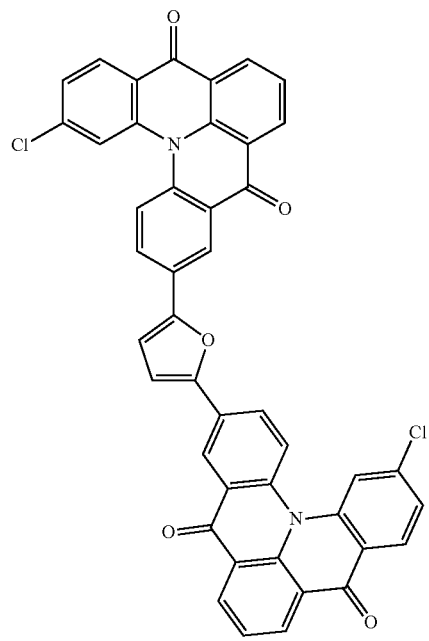
40
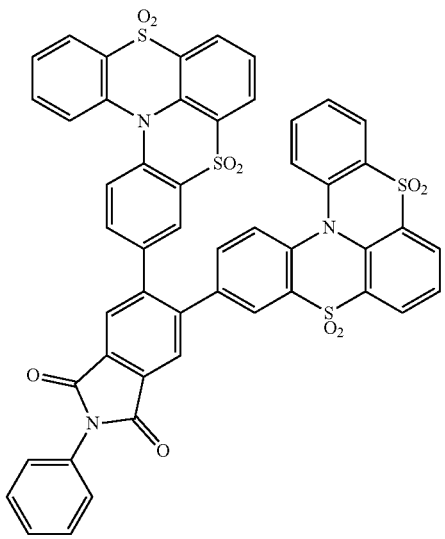
39
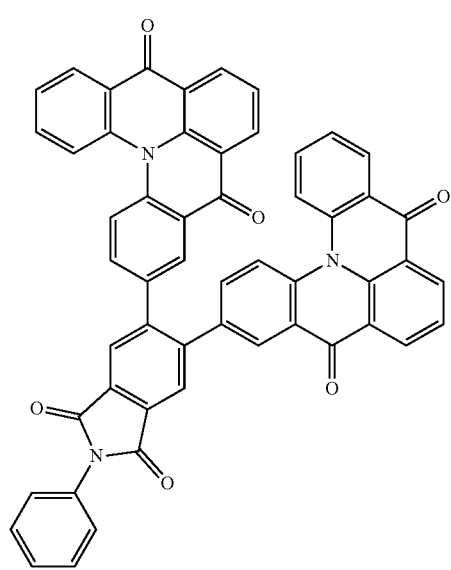
41
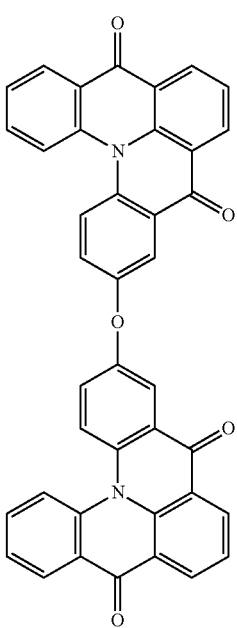

42
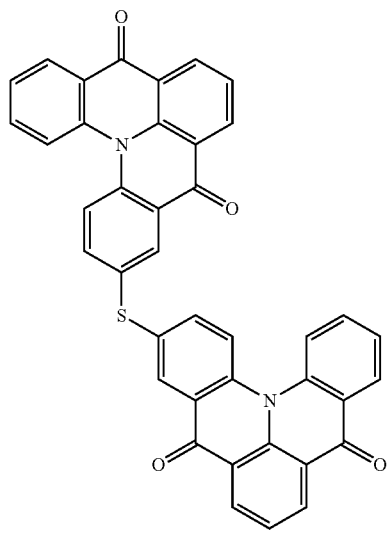
43
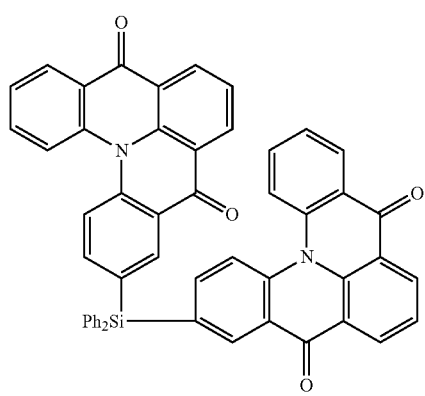
44
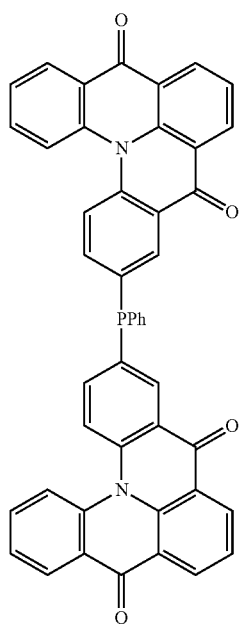
45
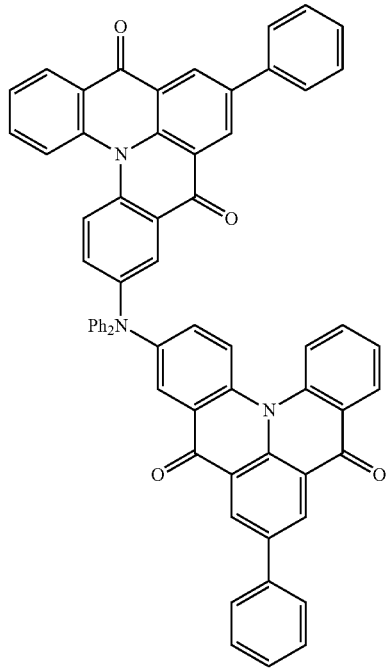
46
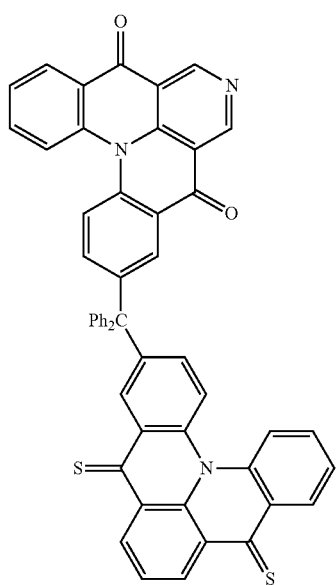

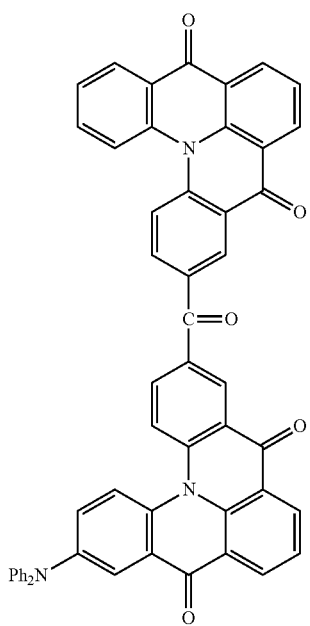
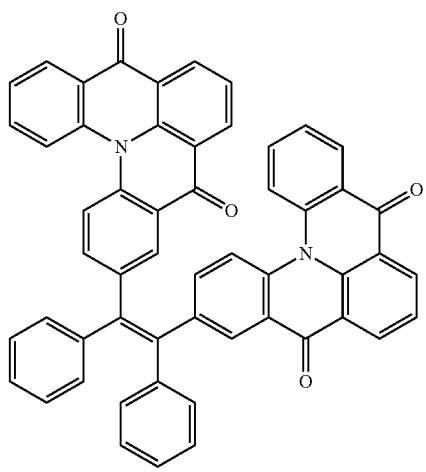
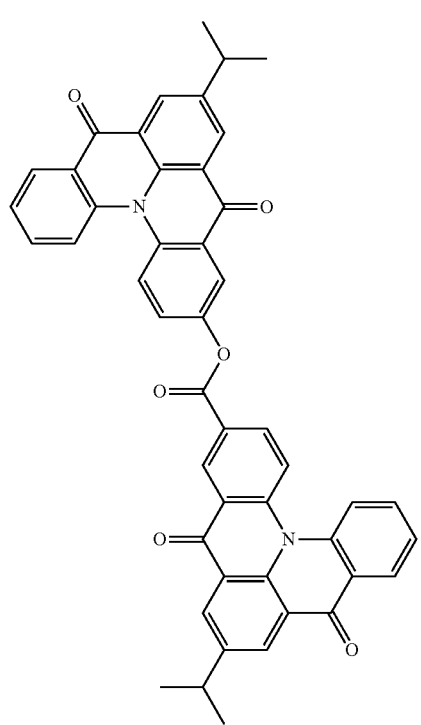
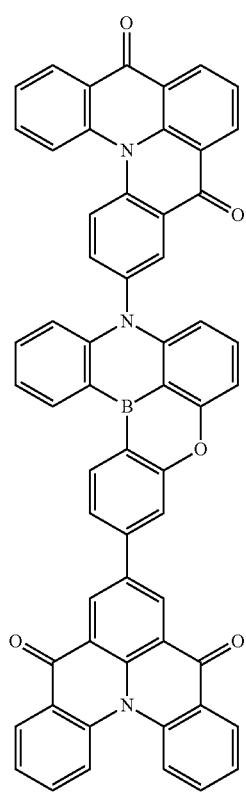

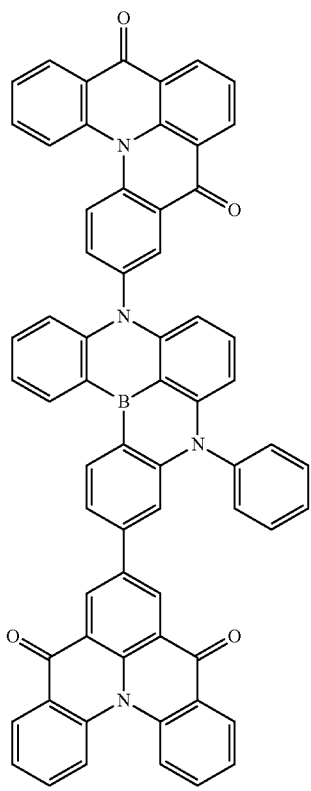
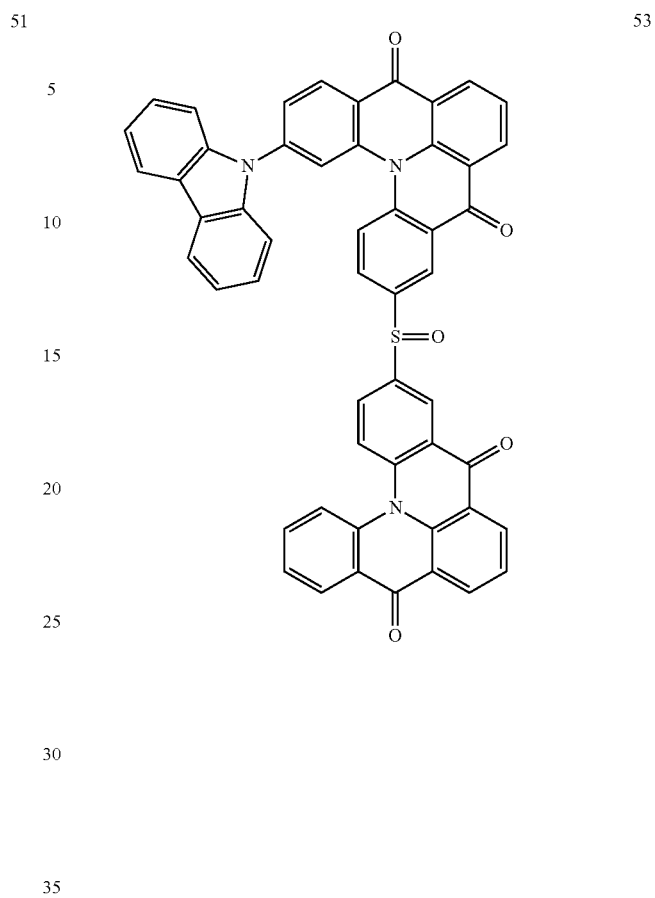
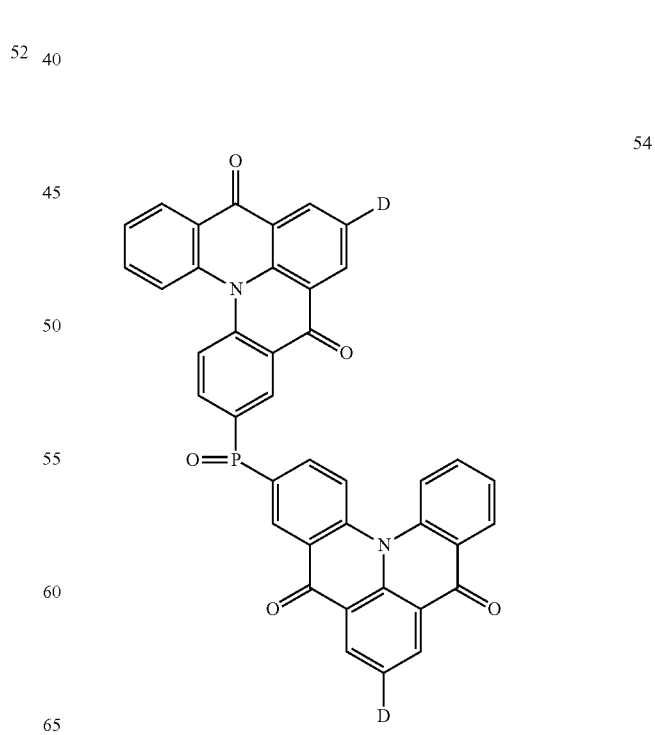

55
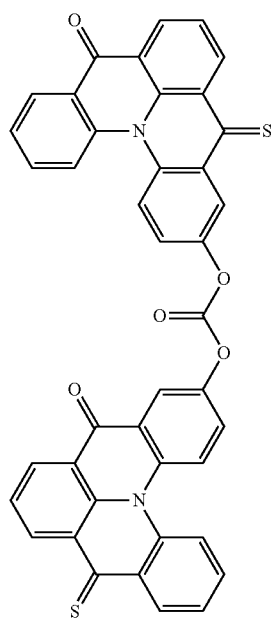
56
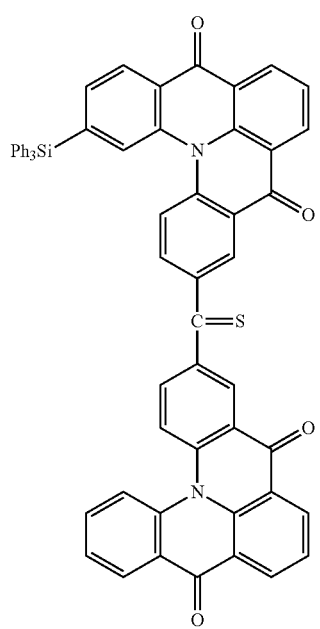
57
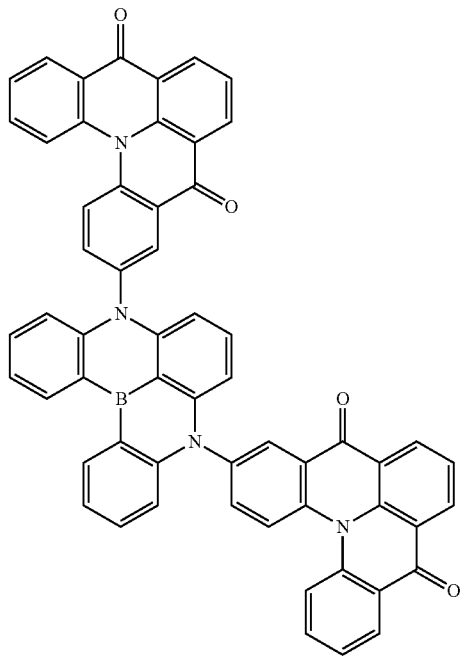
58
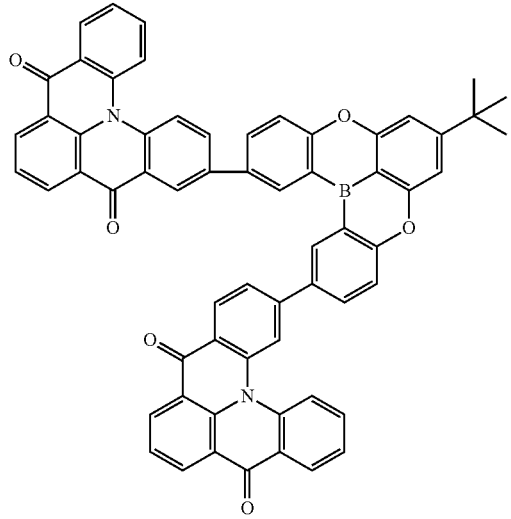

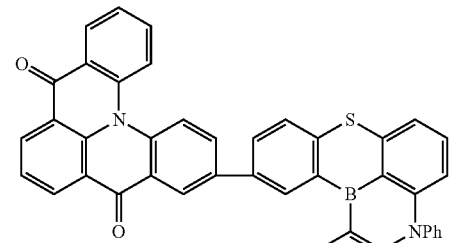
59
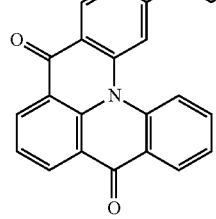
60
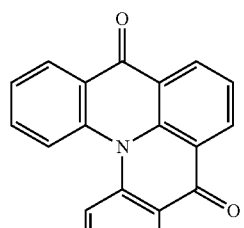
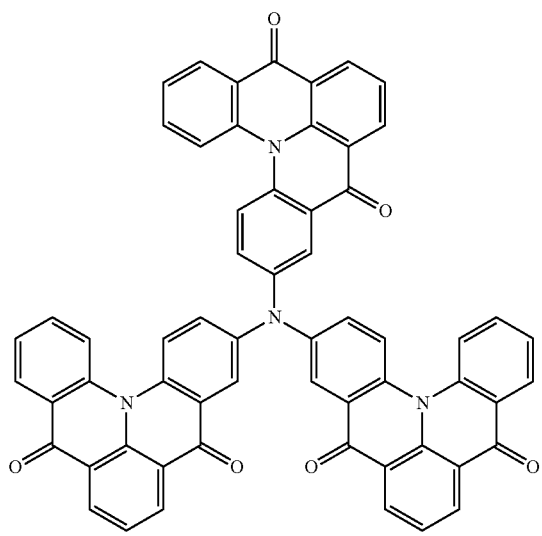
61
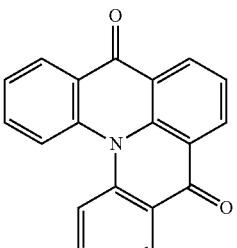
62
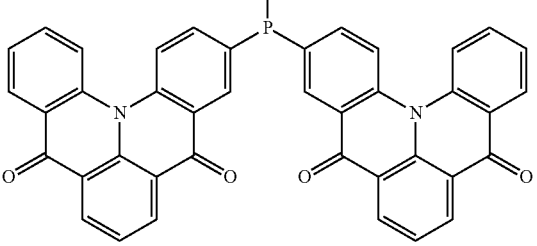
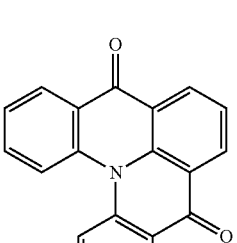
63
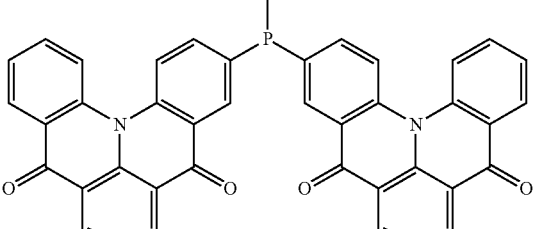
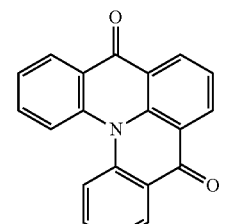
64
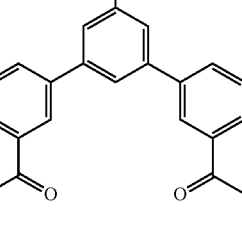

-continued
65
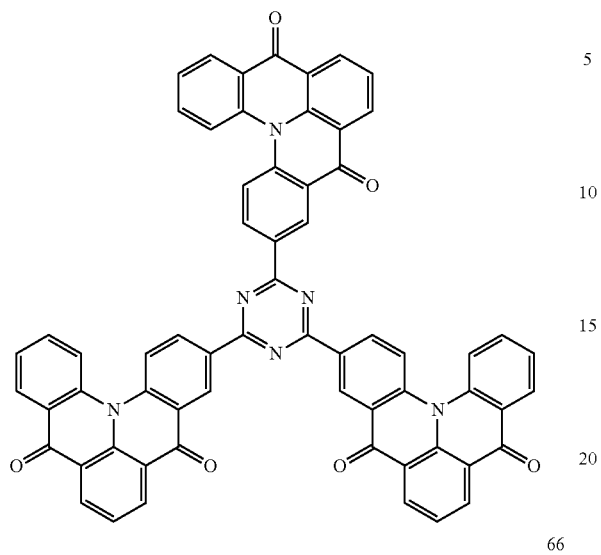
66
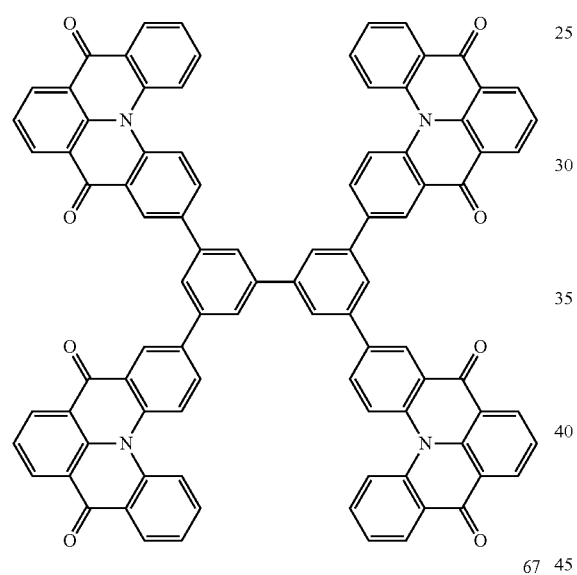
67
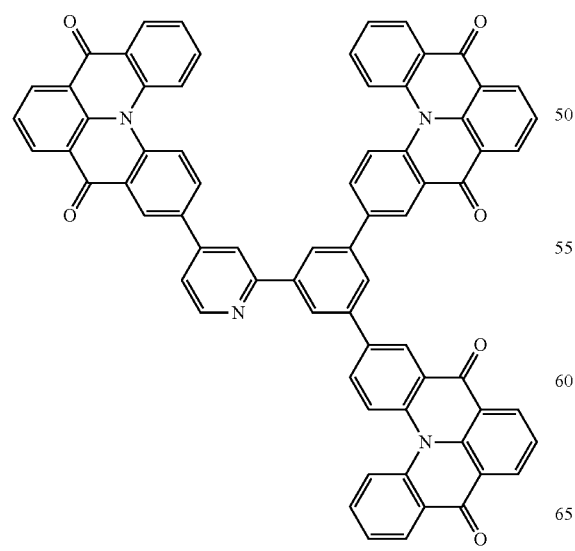
-continued
68
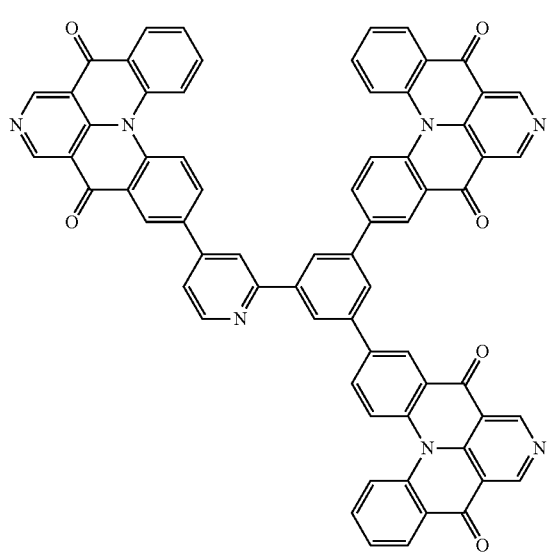
69
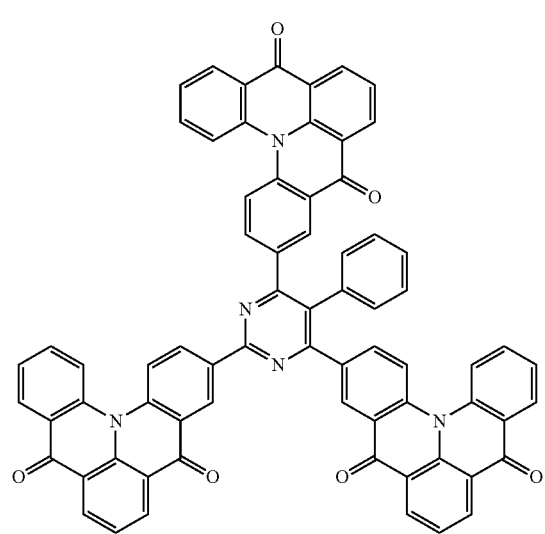
70
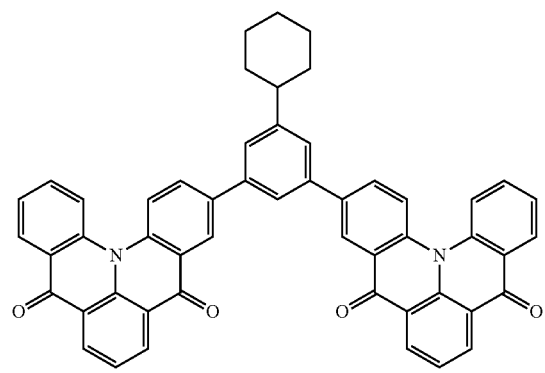

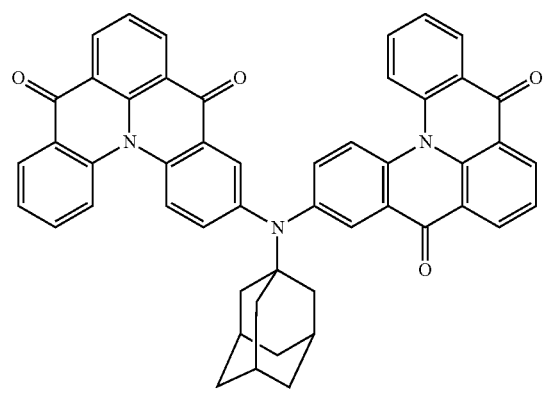
71
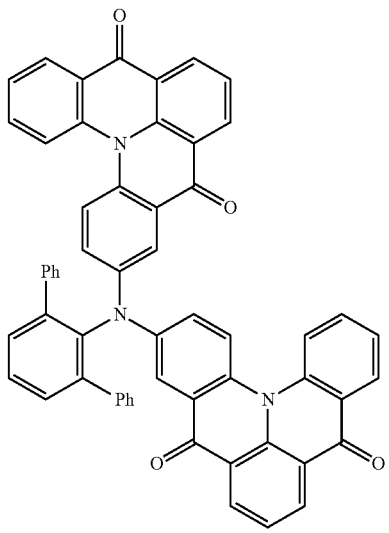
74
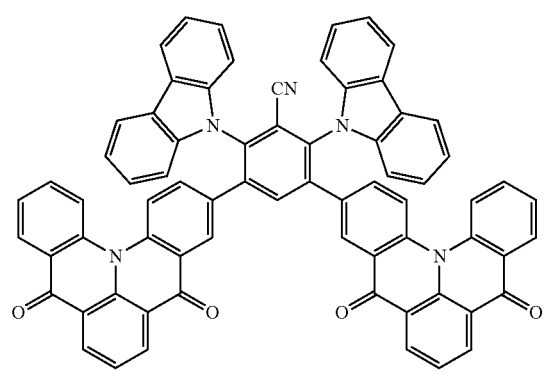
72
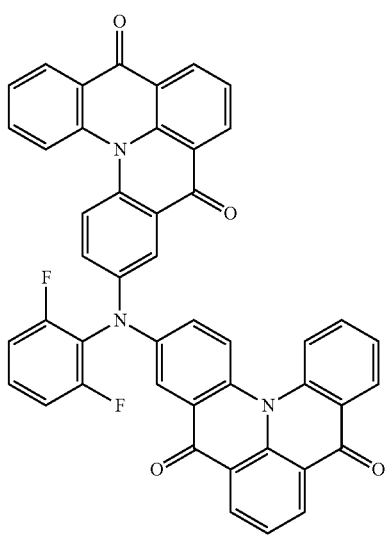
75
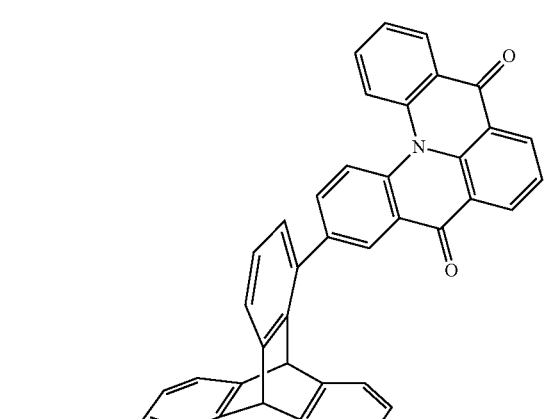
73
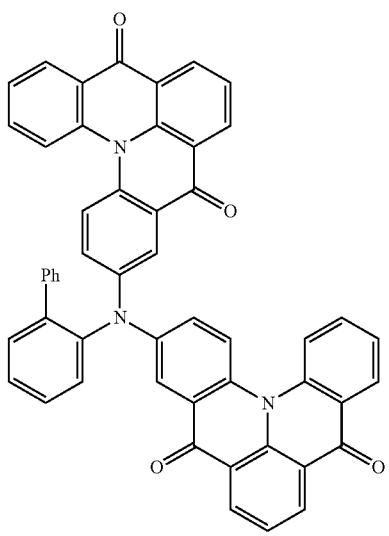
76

75
-continued
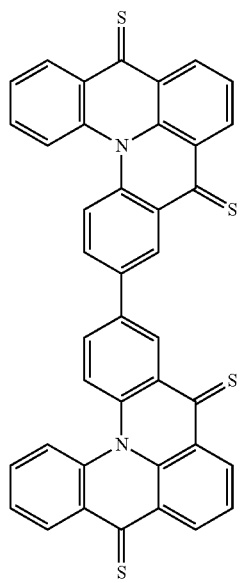
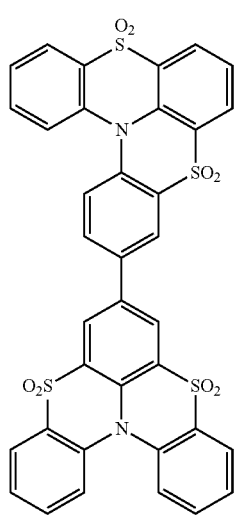
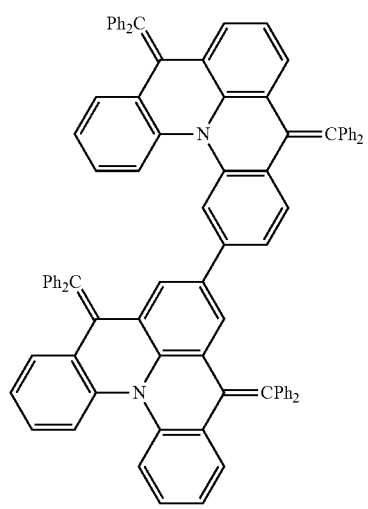
76
-continued
77
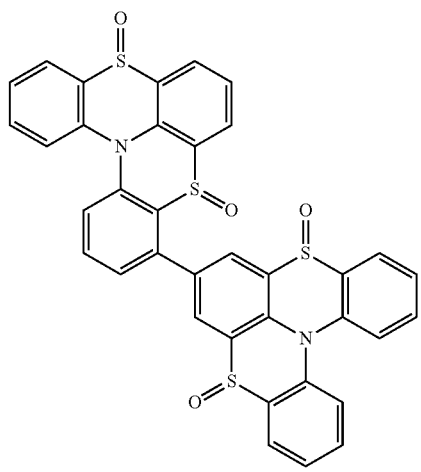
78
79
81
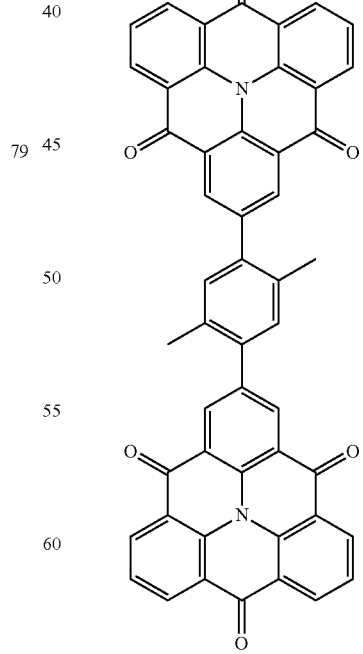

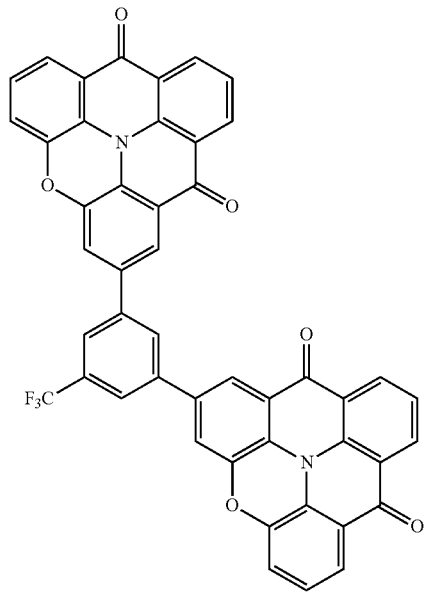
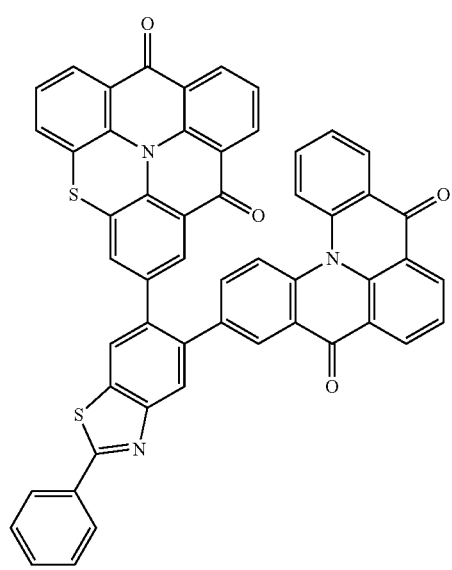
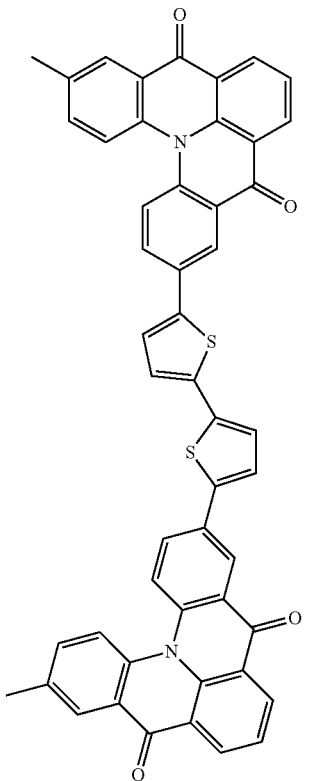

86
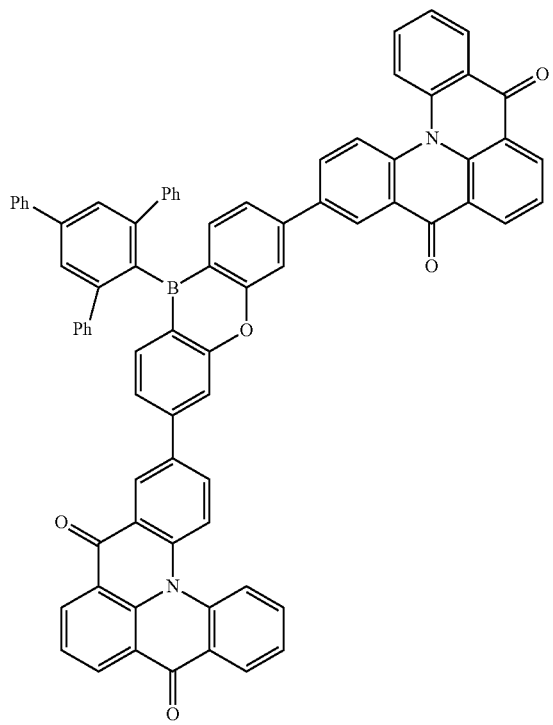
87
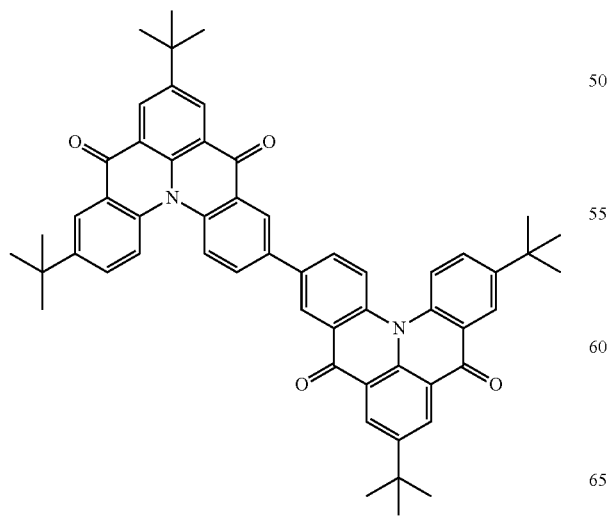
88
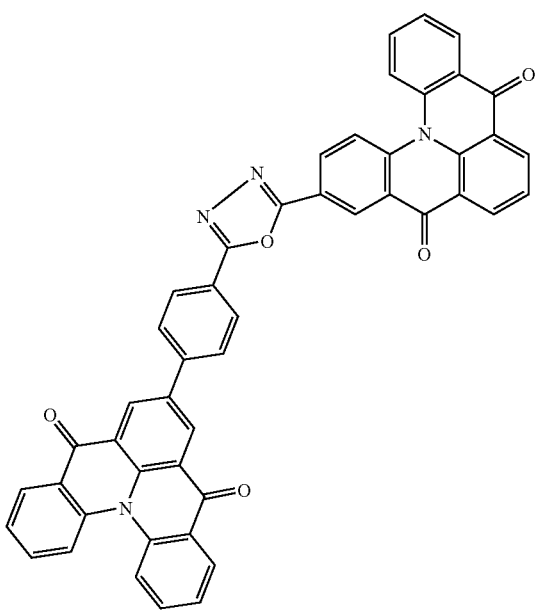
89
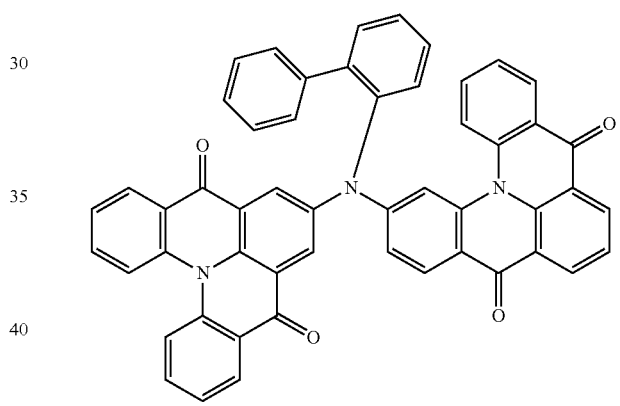
90
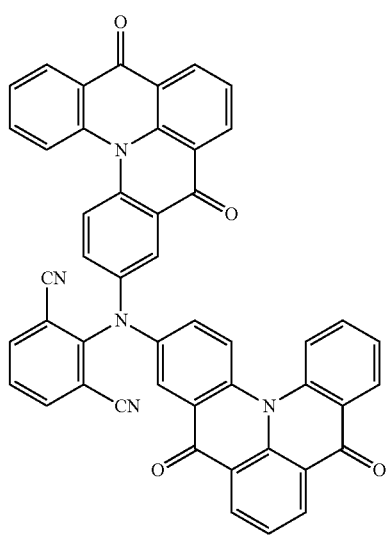

81
-continued
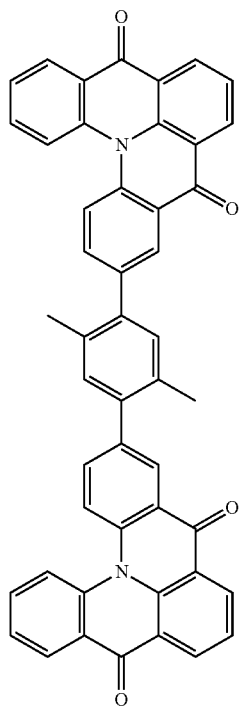
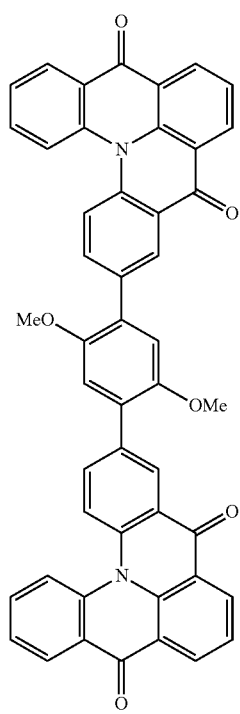
82
-continued
91
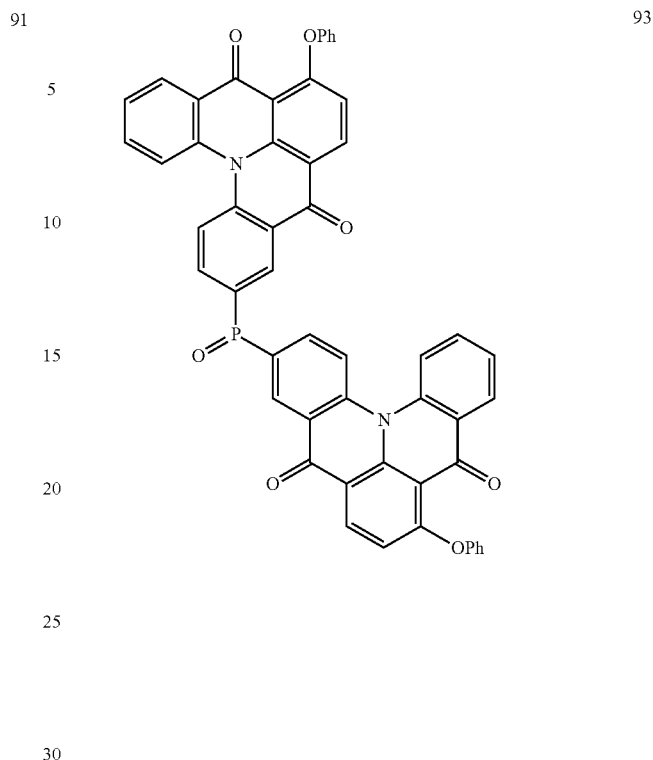
92
93
94
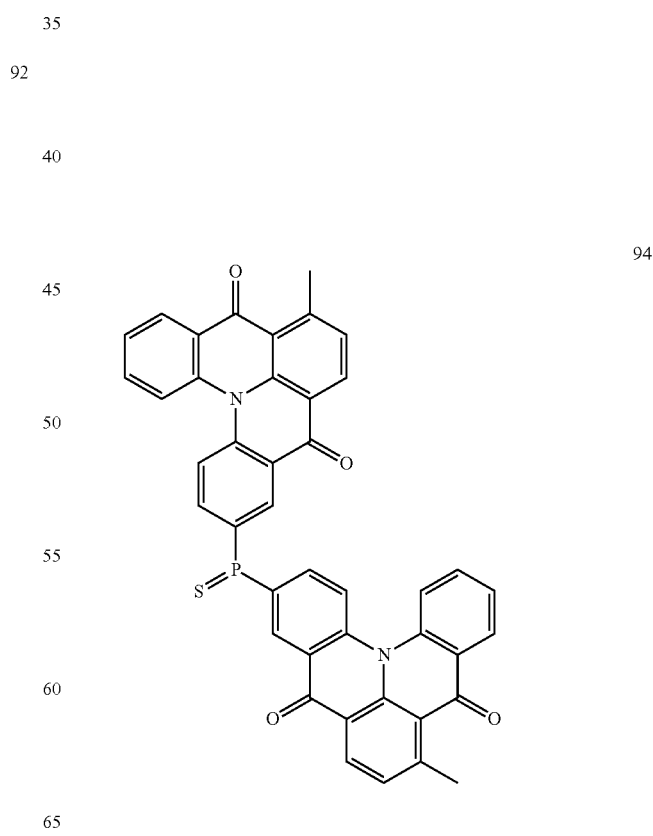

95
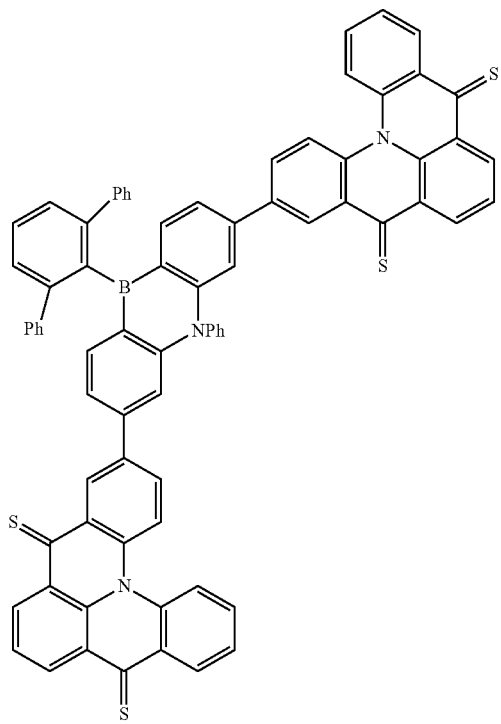
96
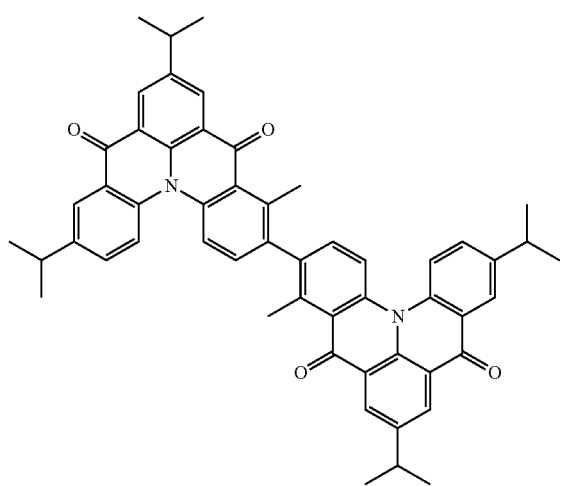
97
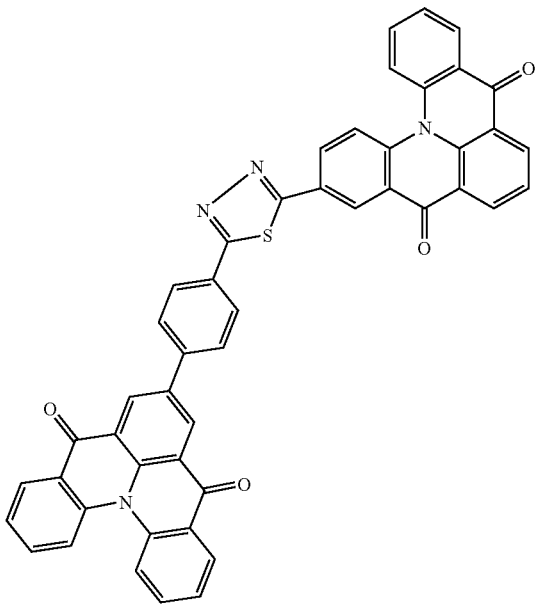
98
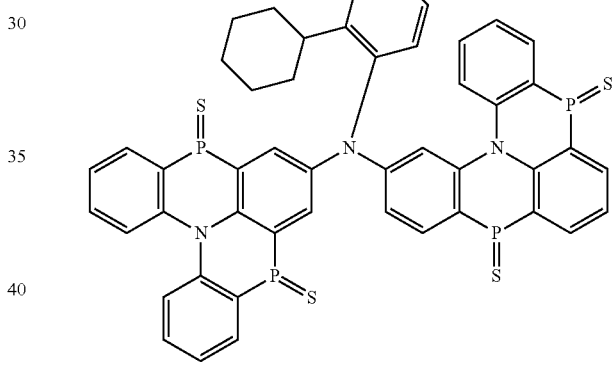
99
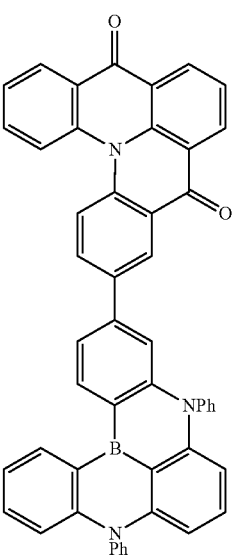

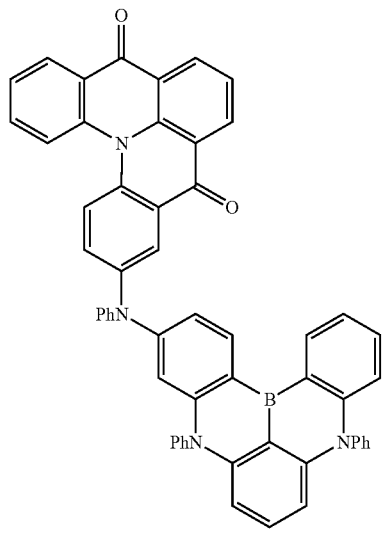
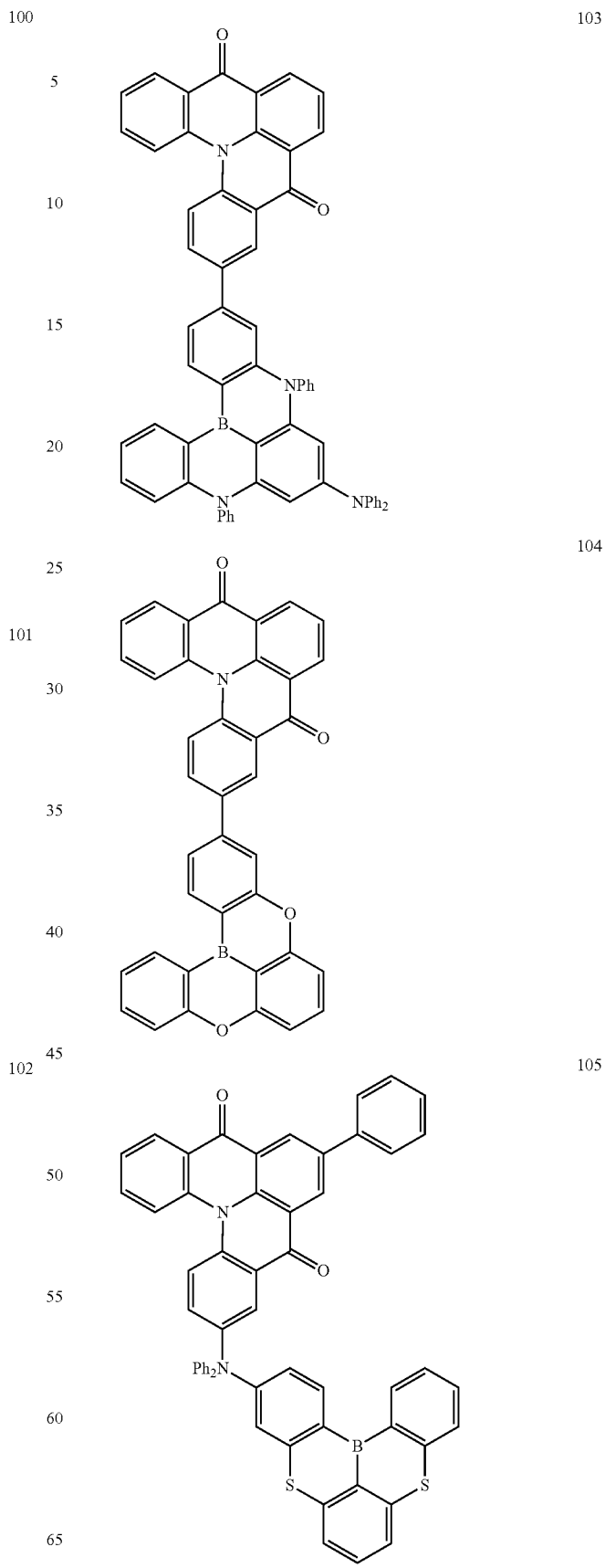

-continued
106
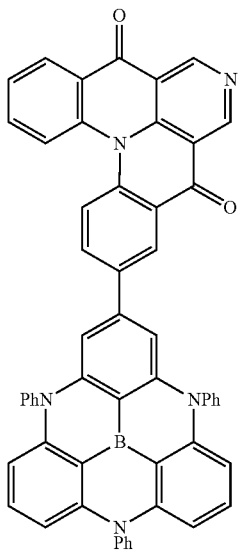
107
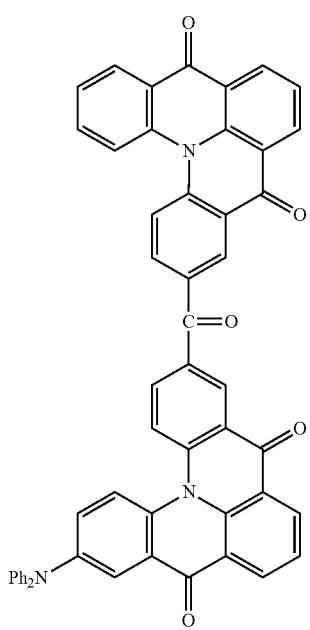
108
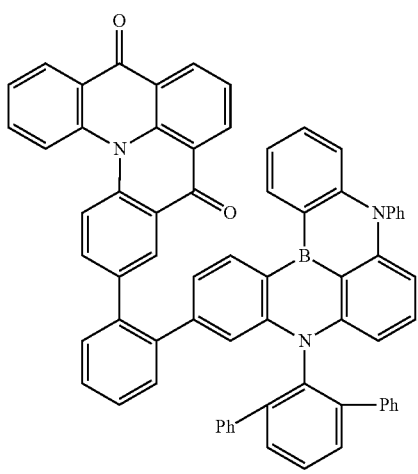
-continued
109
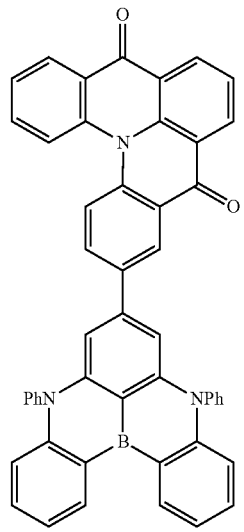
110
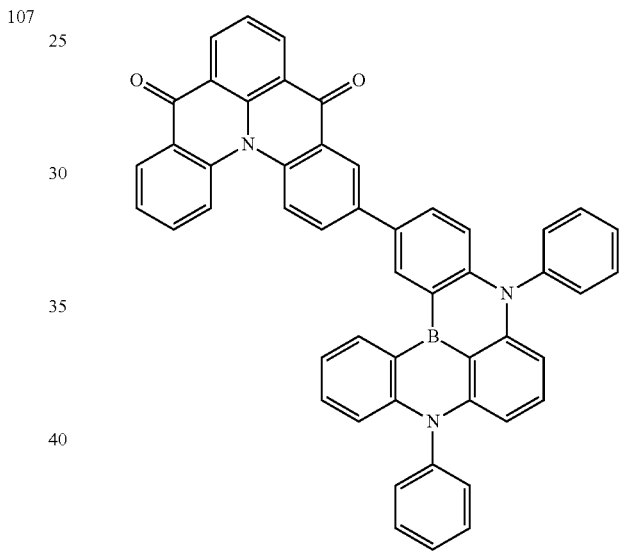
111
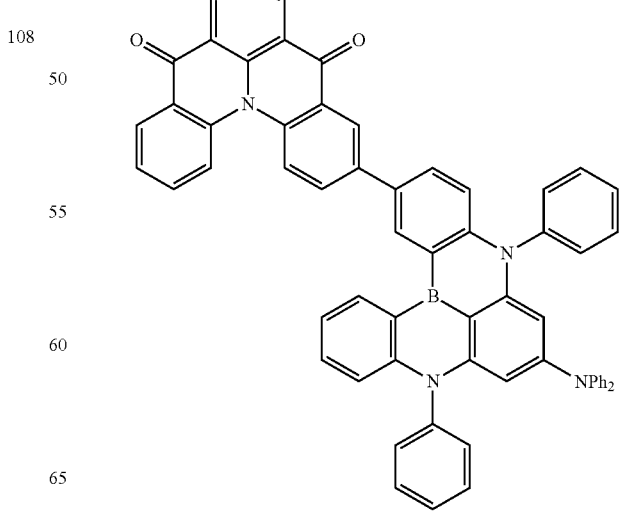

-continued

112

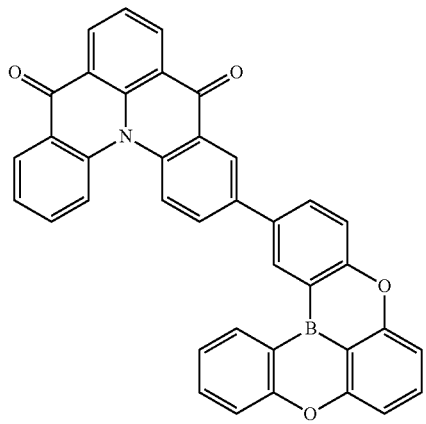

113

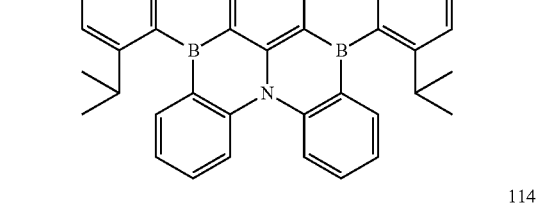

114

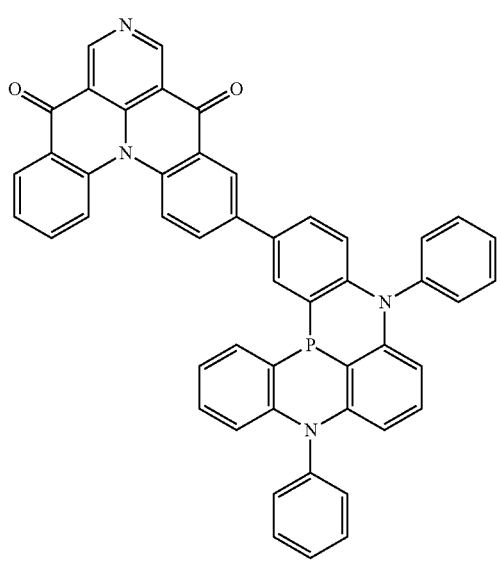

The emission spectrum of the fused polycyclic compound represented by Formula 1 of an embodiment may have a half-width in a range of about 10 nm to about 50 nm. For example, the emission spectrum of the fused polycyclic compound represented by Formula 1 of an embodiment may have a half-width in a range of about 20 nm to about 40 nm. The emission spectrum of the fused polycyclic compound represented by Formula 1 of an embodiment has the above range of half-width, thereby improving luminous efficiency when applied to a device. When the fused polycyclic compound of an embodiment is used as a blue light emitting device material for the luminescence device, the service life of the device may be improved.

The fused polycyclic compound represented by Formula 1 of an embodiment may be a thermally activated delayed fluorescence emitting material. Furthermore, the fused polycyclic compound represented by Formula 1 of an embodiment may be a thermally activated delayed fluorescence dopant having the difference ($\Delta E_{ST}$) between the lowest triplet exciton energy level (T1 level) and the lowest singlet exciton energy level (S1 level) of about 0.6 eV or less.

The fused polycyclic compound represented by Formula 1 of an embodiment may be a luminescence material having a luminescence center wavelength in a wavelength region in a range of about 430 nm to about 490 nm. For example, the fused polycyclic compound of an embodiment, represented by Formula 1 may be a blue thermally activated delayed fluorescence (TADF) dopant. However, embodiments are not limited thereto, and in case of using the fused polycyclic compound of an embodiment as the light-emitting material, the fused polycyclic compound may be used as a dopant material emitting light in various wavelength regions, such as a red emitting dopant and a green emitting dopant.

The emission layer EML in the light emitting device ED of an embodiment may emit delayed fluorescence. For example, the emission layer EML may emit thermally activated delayed fluorescence (TADF).

The emission layer EML of the light emitting device ED may emit blue light. For example, the emission layer EML of the organic electroluminescence device 10 of an embodiment may emit blue light at a wavelength equal to or less than about 490 nm. However, embodiments are not limited thereto, and the emission layer EML may emit green light or red light.

In an embodiment, the emission layer EML may include a host and a dopant, and may include the above-described fused polycyclic compound as a dopant. For example, the emission layer EML in the light emitting device ED of an embodiment may include a host for emitting delayed fluorescence and a dopant for emitting delayed fluorescence, and may include the above-described fused polycyclic compound as a dopant for emitting delayed fluorescence. The emission layer EML may include at least one among the fused polycyclic compounds represented by Compound Group 1 as described above as a thermally activated delayed fluorescence dopant.

In the light emitting device ED of an embodiment, the emission layer EML may further include anthracene derivatives, pyrene derivatives, fluoranthene derivatives, chrysene derivatives, dehydrobenzanthracene derivatives, or triphenylene derivatives. For example, the emission layer EML may include anthracene derivatives or pyrene derivatives.

In each light emitting device ED of embodiments illustrated in FIGS. 3 to 6, the emission layer EML may include a host and a dopant, and the emission layer EML may include a compound represented by Formula E-1 below. The compound represented by Formula E-1 below may be used as a fluorescence host material or a delayed fluorescence host material.

[Formula E-1]

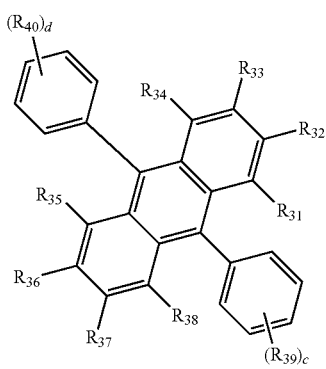

In Formula E-1, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula E-1, $R_{31}$ to $R_{40}$ may be bonded to an adjacent group to form a saturated hydrocarbon ring or an unsaturated hydrocarbon ring.

In Formula E-1, c and d may each independently be an integer from 0 to 5.

Formula E-1 may be represented by any one among Compound E1 to Compound E18 below:

E1

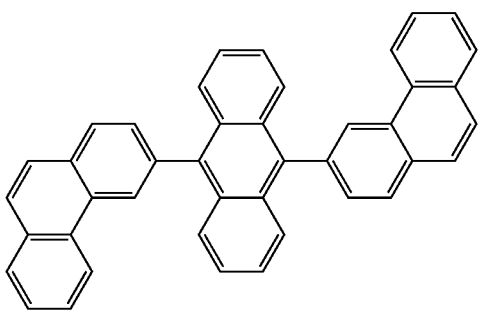

E2

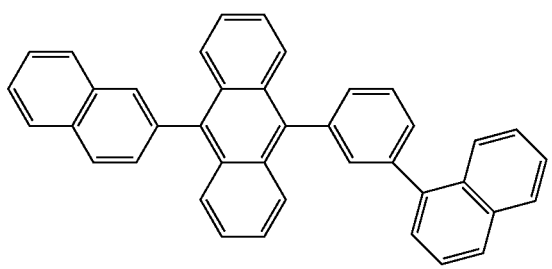

E3

E4

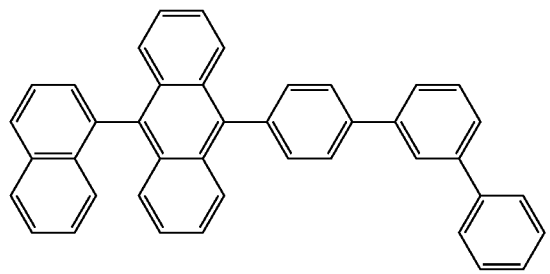

E5

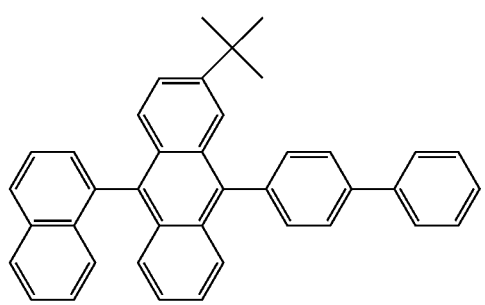

E6

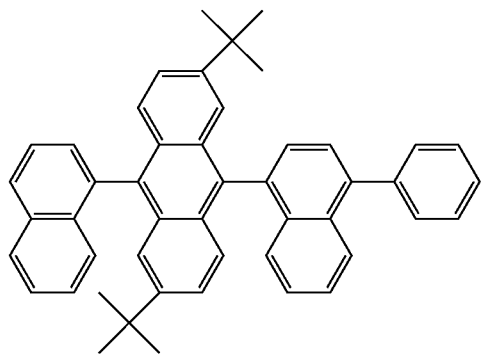

E7

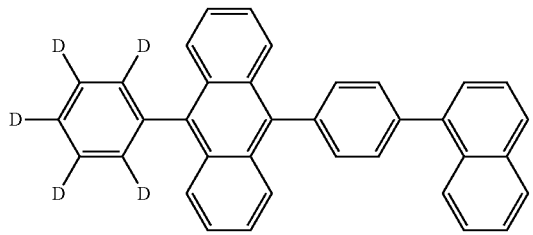

E8

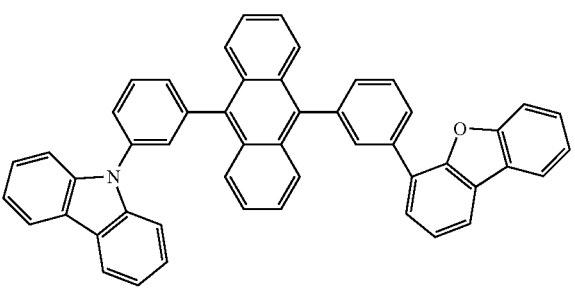

E9
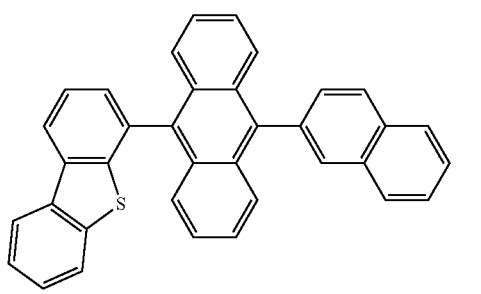
E10
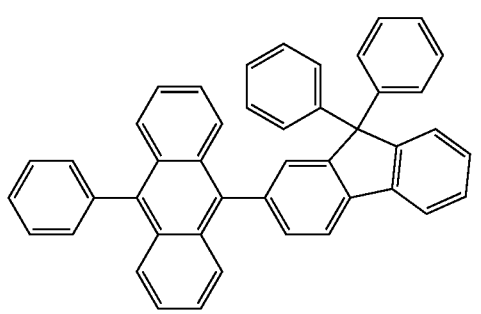
E11
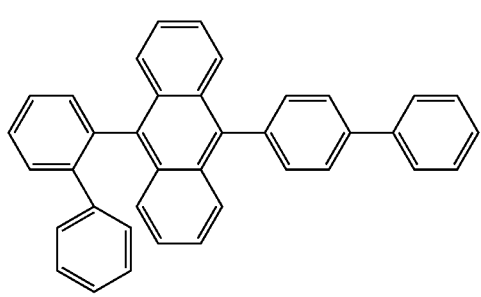
E12
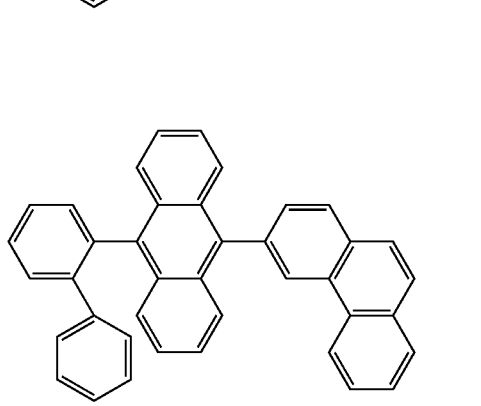
E13
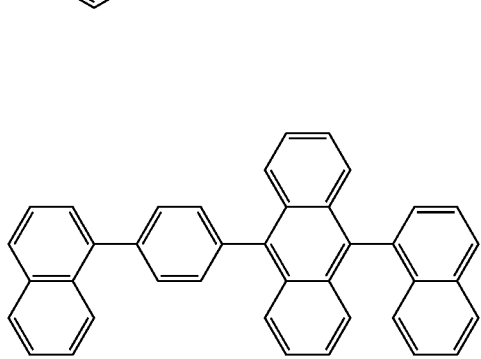
E14
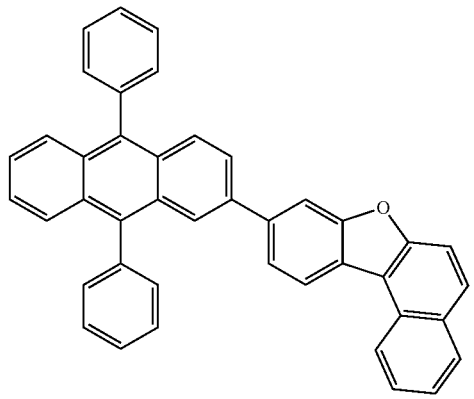
E15
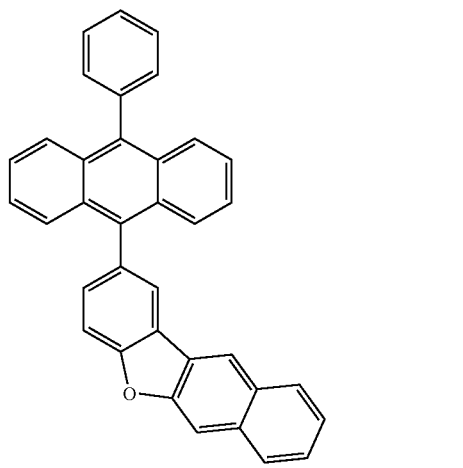
E16
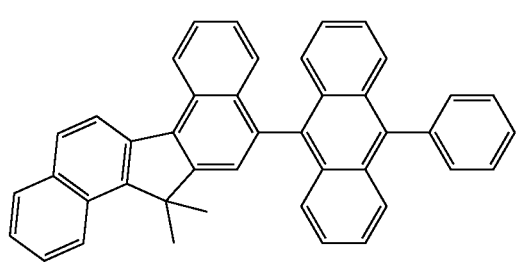
E17
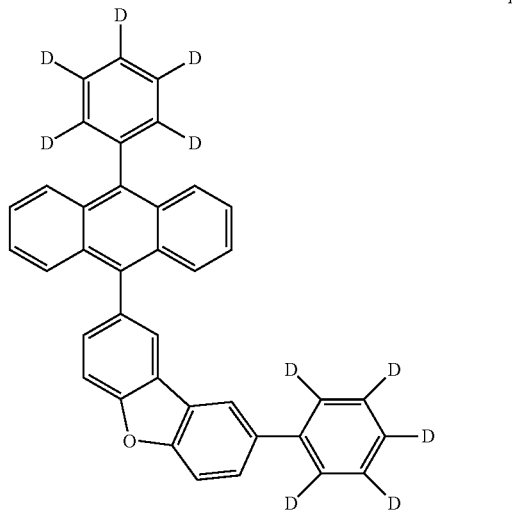

E18

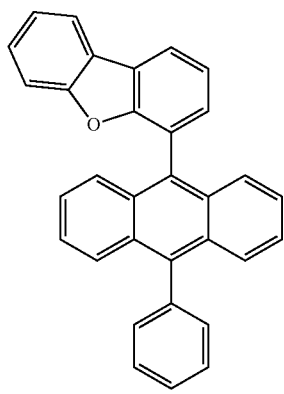

In an embodiment, the emission layer EML may include a compound represented by Formula E-2a or Formula E-2b below. The compound represented by Formula E-2a or Formula E-2b below may be used as a phosphorescence host material or a delayed fluorescence host material.

[Formula E-2a]

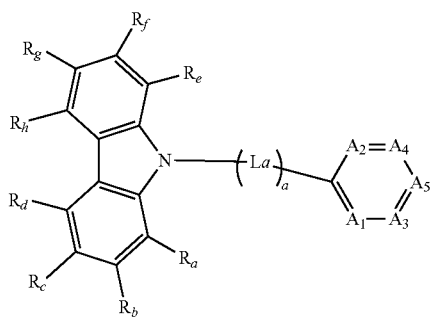

In Formula E-2a, a may be an integer from 0 to 10, and $L_a$ may be a direct linkage, a substituted or unsubstituted arylene group having 6 to 30 ring-forming carbon atoms, or a substituted or unsubstituted heteroarylene group having 2 to 30 ring-forming carbon atoms. When a is an integer of 2 or greater, multiple $L_a$(s) may be each independently a substituted or unsubstituted arylene group having 6 to 30 ring-forming carbon atoms, or a substituted or unsubstituted heteroarylene group having 2 to 30 ring-forming carbon atoms.

In Formula E-2a, $A_1$ to $A_5$ may each independently be N or $C(R_i)$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. $R_a$ to $R_i$ may be bonded to an adjacent group to form a hydrocarbon ring or a heterocycle containing N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

$$(\text{Cbz1})\!-\!(\text{L}_b)_b\!-\!(\text{Cbz2})$$

In Formula E-2b, Cbz1 and Cbz2 may each independently be an unsubstituted carbazole group, or a carbazole group substituted with an aryl group having 6 to 30 ring-forming carbon atoms. $L_b$ may be a direct linkage, a substituted or unsubstituted arylene group having 6 to 30 carbon atoms for forming a ring, or a substituted or unsubstituted heteroarylene group having 2 to 30 carbon atoms for forming a ring, In Formula E-2b, b may be an integer from 0 to 10, and when b is an integer of 2 or more, multiple $L_b$(s) may each independently be a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be represented by any one among the compounds of Compound Group E-2 below. However, the compounds listed in Compound Group E-2 below are examples, the compound represented by Formula E-2a or Formula E-2b is not limited to those represented by Compound Group E-2 below.

[Compound Group E-2]

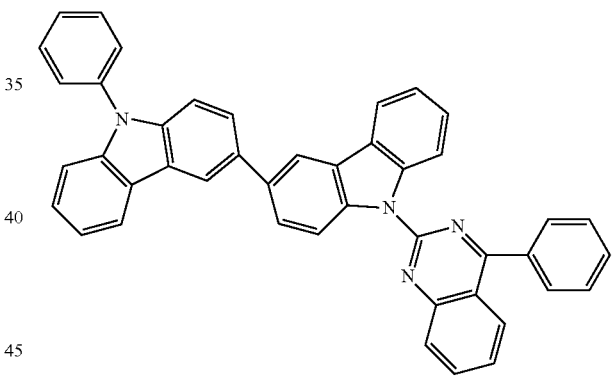

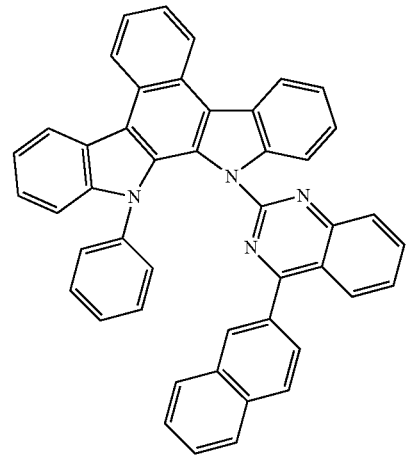

97
-continued
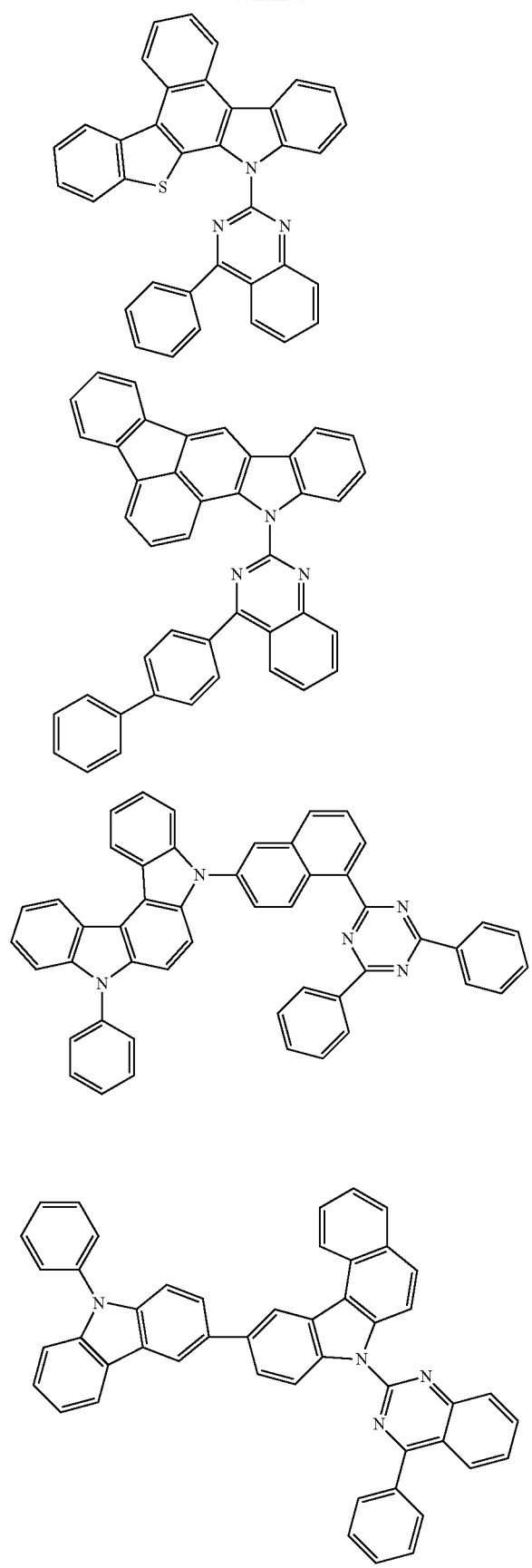
98
-continued
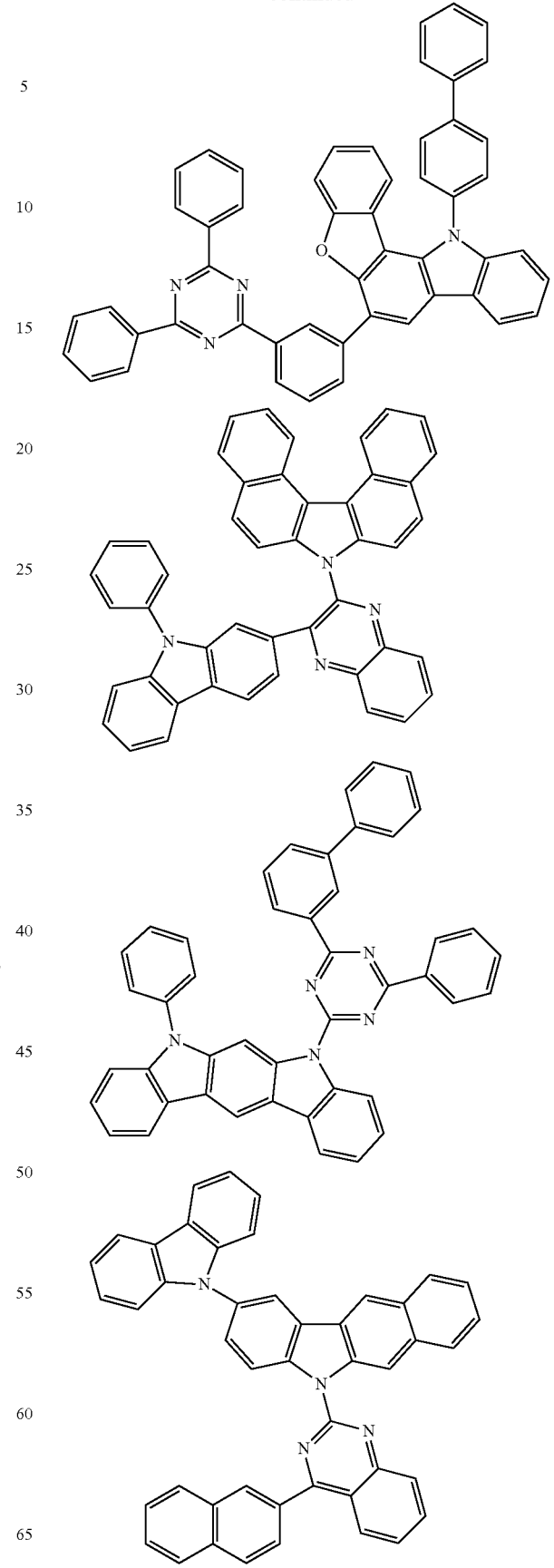

99
-continued
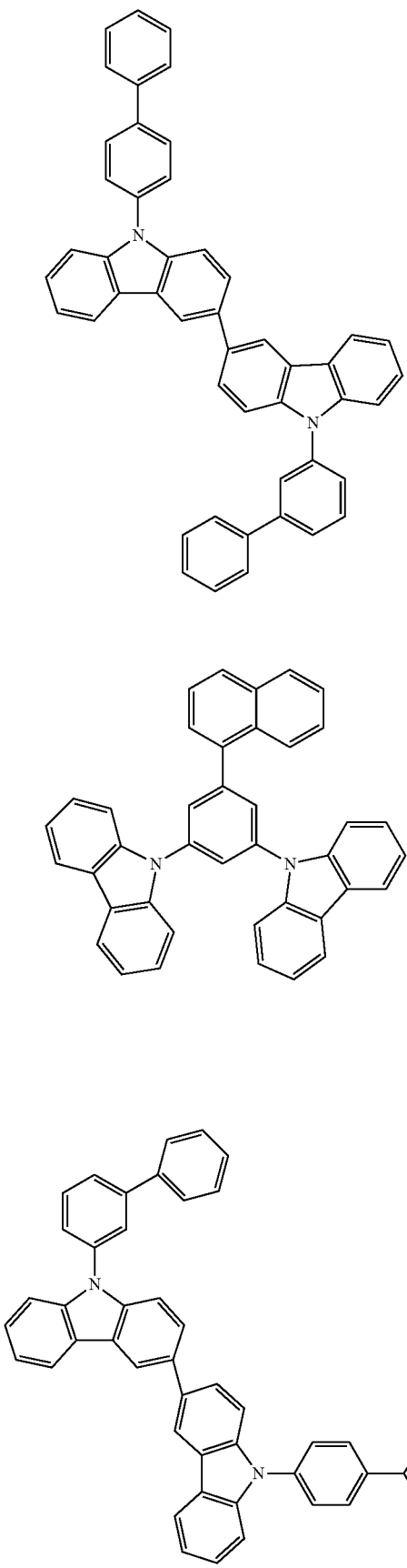
100
-continued
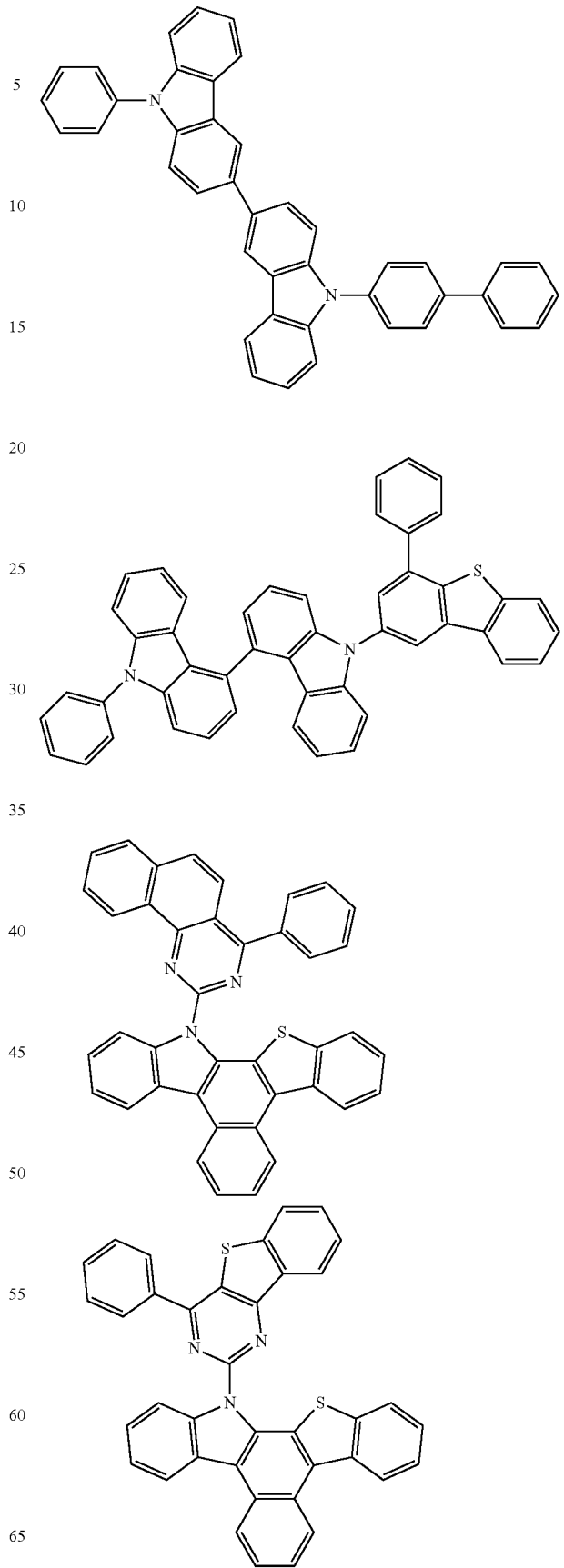

-continued

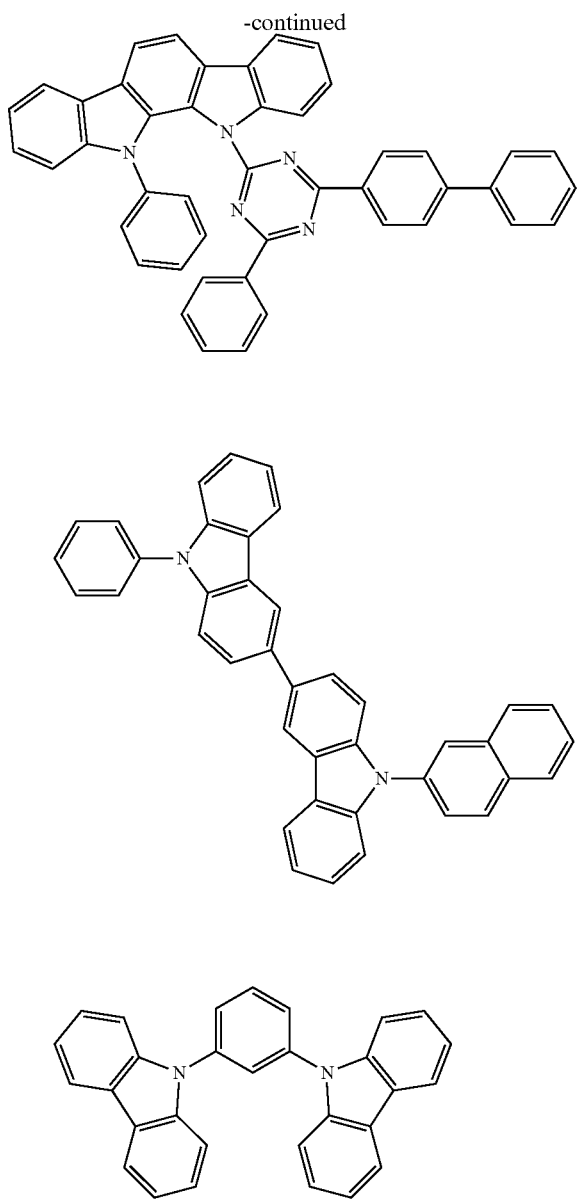

The emission layer EML may further include a general material in the art as a host material. For example, the emission layer EML may include, as a host material, at least one of bis[2-(diphenylphosphino)phenyl]ether oxide (DPEPO), 4,4'-bis(carbazol-9-yl)biphenyl (CBP), 1,3-bis (carbazol-9-yl)benzene (mCP), 2,8-bis(diphenylphosphoryl) dibenzo[b, d]furan (PPF), 4,4',4"-tris(carbazol-9-yl)-triphenylamine (TCTA), and 1,3,5-tris(1-phenyl-1H-benzo[d] imiclazole-2-yl)benzene (TPBi). However, embodiments are not limited thereto, and for example, tris(8-hydroxyquinolino)aluminum (Alq$_3$), 4,4'-bis(N-carbazolyl)-1,1'-biphenyl (CBP), poly(n-vinylcabazole) (PVK), 9,10-di(naphthalene-2-yl)anthracene (ADN), 4,4',4"-Tris(carbazol-9-yl)-triphenylamine (TCTA), 1,3,5-tris(N-phenylbenzimiclazole-2-yl)benzene (TPBi), 2-tert-butyl-9, 10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis (triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc. may be used as a host material.

The emission layer EML may include a compound represented by Formula M-a or Formula M-b below. The compound represented by Formula M-a or Formula M-b below may be used as a phosphorescence dopant material.

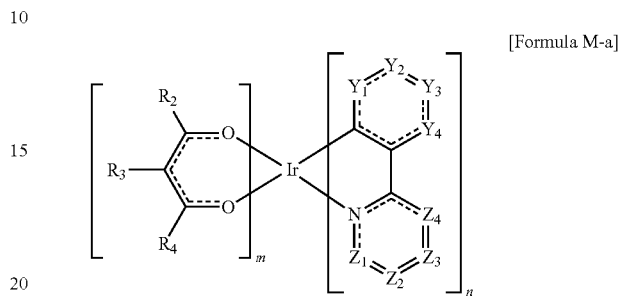

[Formula M-a]

In Formula M-a above, $Y_1$ to $Y_4$ and $Z_1$ to $Z_4$ may each independently be $C(R_1)$ or N, $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be used as a red phosphorescence dopant or a green phosphorescence dopant.

The compound represented by Formula M-a may be represented by any one among Compound M-a1 to Compound M-a5 below. However, Compounds M-a1 to M-a5 below are examples, and the compound represented by Formula M-a is not limited to those represented by Compounds M-a1 to M-a5 below.

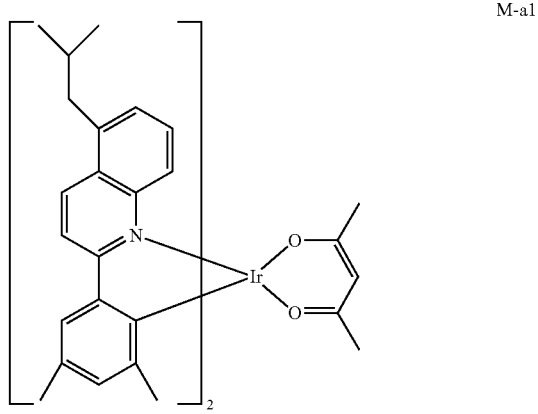

M-a1

M-a2

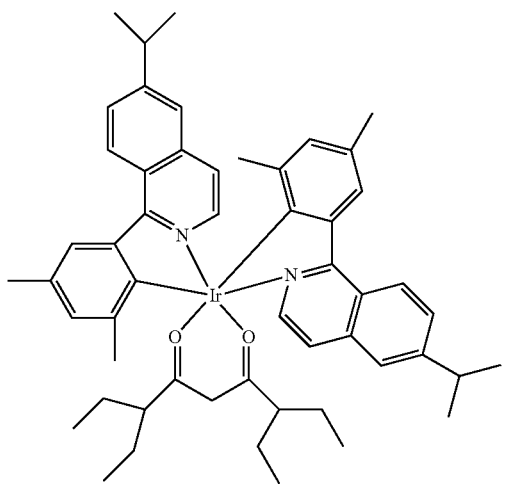

M-a3

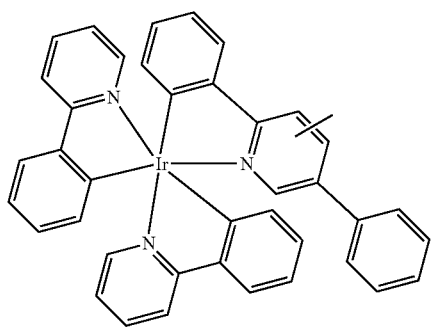

M-a4

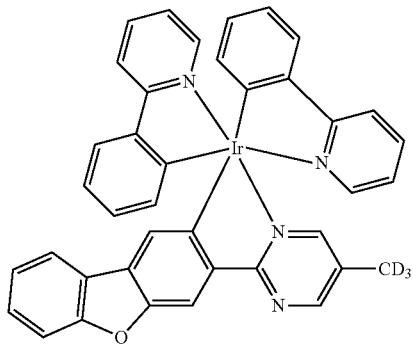

M-a5

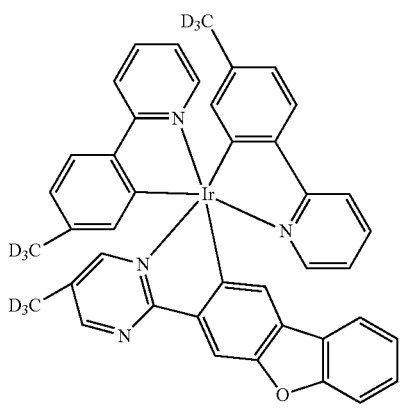

Compound M-a1 and Compound M-a2 may be used as a red dopant material, and Compound M-a3 to Compound M-a5 may be used as a green dopant material.

[Formula M-b]

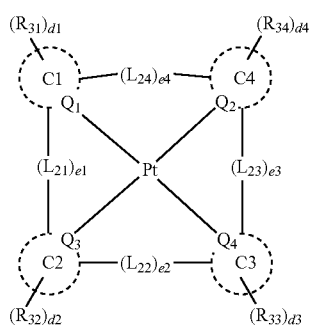

In Formula M-b, $Q_1$ to $Q_4$ may each independently be C or N, and $C_1$ to $C_4$ may each independently be a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may each independently be a direct linkage,

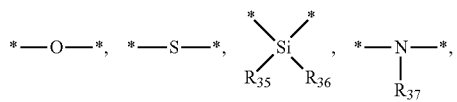

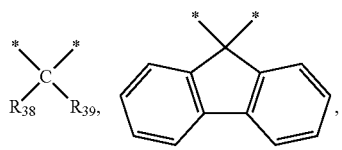

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. $R_{31}$ to $R_{39}$ may each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be represented by any one among the compounds below. However, the compounds below are examples, and the compound represented by Formula M-b is not limited to those represented by the compounds below.

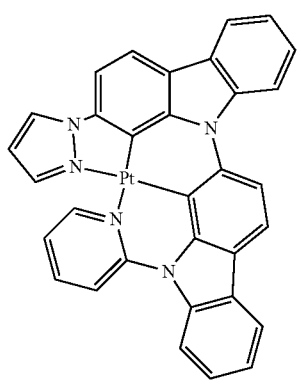
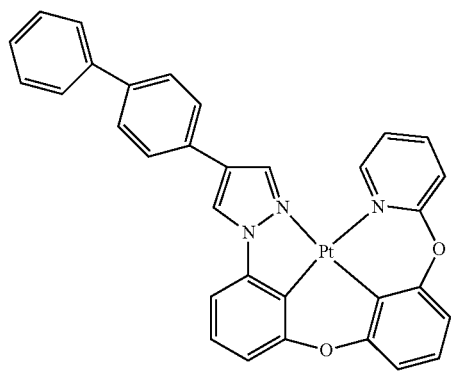
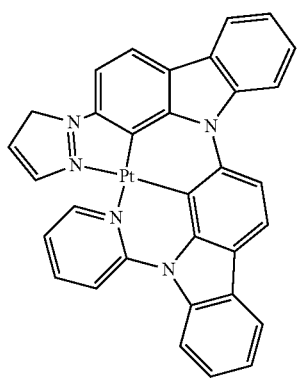
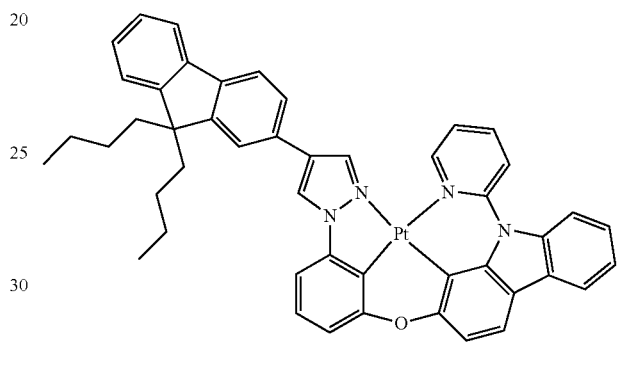
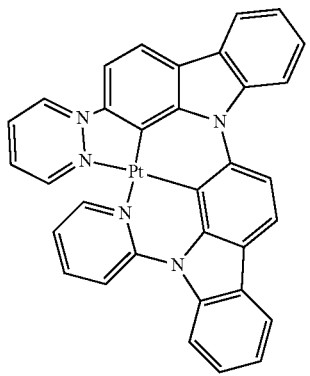
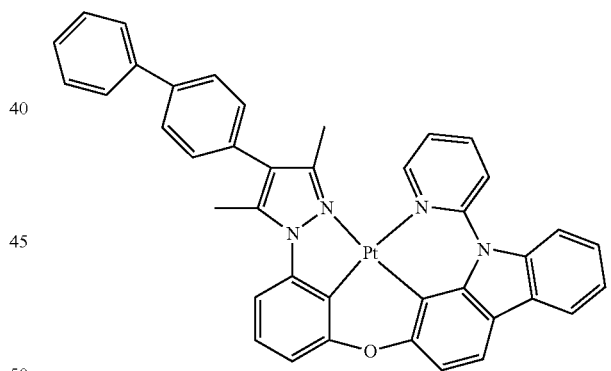
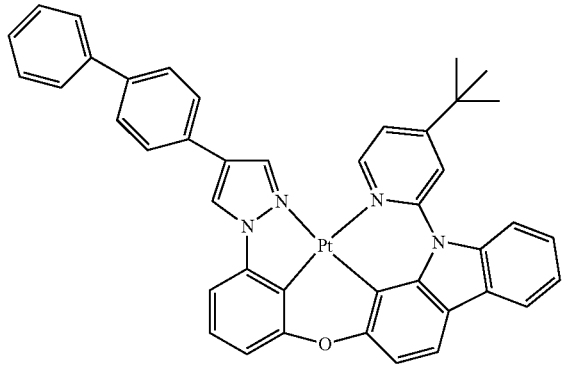
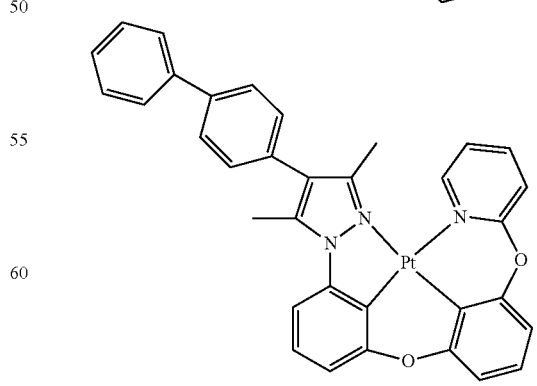

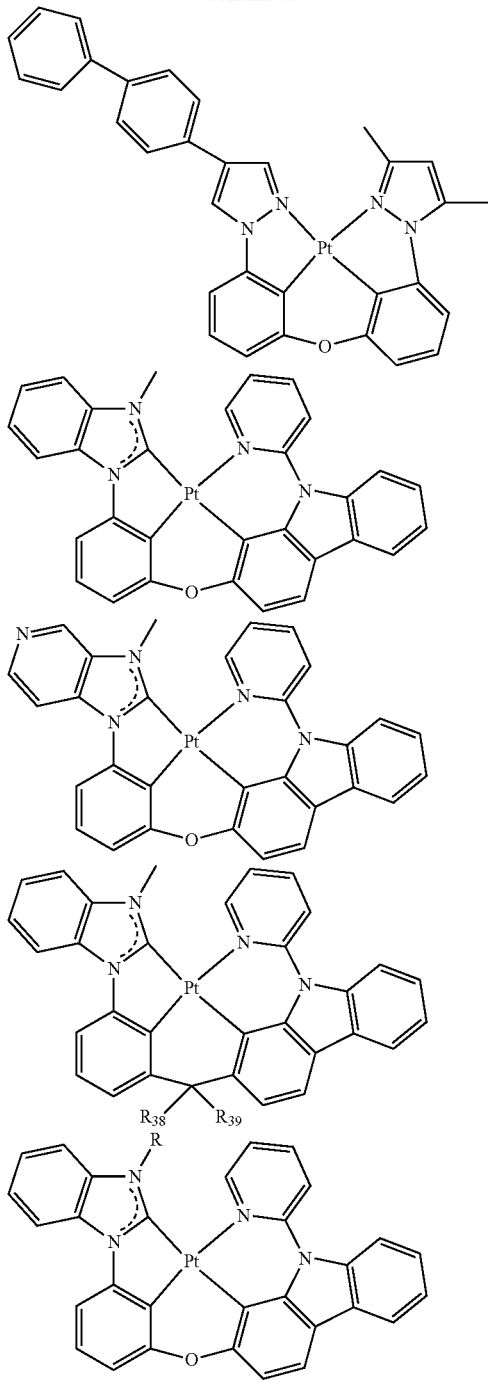

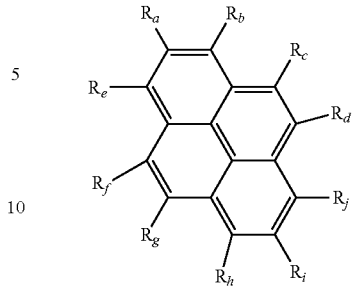
[Formula F-a]

In Formula F-a, any two of $R_a$ to $R_j$ may each independently be substituted with *•—$NAr_1Ar_2$. The remainder of $R_a$ to $R_j$, which are not substituted with *•—$NAr_1Ar_2$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In *•—$NAr_1Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

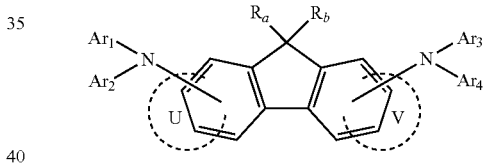
[Formula F-b]

In Formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-b, U and V may each independently be a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may each independently be 0 or 1. For example, in Formula F-b, when the number of U or V is 1, one ring may form a condensed ring at a part described as U or V, and when the number of U or V is 0, a ring described as U or V may not be present. For example, when the number of U is 0 and the number of V is 1, or when the number of U is 1 and the number of V is 0, the condensed ring having a fluorene core of Formula F-b may be a four-ring cyclic compound. When the number of U and V is each 0, the condensed ring of Formula F-b may be a three-ring cyclic compound. When the number of U and V is each 1, the condensed ring having a fluorene core of Formula F-b may be a five-ring cyclic compound.

In the compounds, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include a compound represented by any one of Formula F-a to Formula F-c below. The compound represented by Formula F-a or Formula F-c below may be used as a fluorescence dopant material.

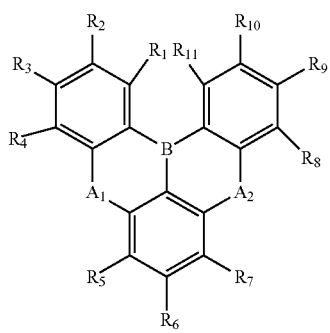

[Formula F-c]

In Formula F-c, $A_1$ and $A_2$ may each independently be O, S, Se, or $N(R_m)$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boron group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-c, $A_1$ and $A_2$ may each independently be bonded to substituents of an adjacent ring to form a condensed ring. For example, when $A_1$ and $A_2$ are each independently $N(R_m)$, $A_1$ may be bonded to $R_4$ or $R_5$ to form a ring. In an embodiment, $A_2$ may be bonded to $R_7$ or $R_8$ to form a ring.

In an embodiment, the emission layer EML may include, as a dopant material, styryl derivatives (e.g., 1,4-bis[2-(3-N-ethylcarbazoryl)vinyl]benzene (BCzVB), 4-(di-p-tolylamino)-4'-[(di-p-tolylamino) styryl]stilbene (DPAVB), and N-(4-((E)-2-(6-((E)-4-(diphenylamino)styryl)naphthalen-2-yl)vinyl)phenyl)-N-phenylbenzena mine (N-BDAVBi), 4,4'-bis[2-(4-(N,N-diphenylamino)phenyl)vinyl]biphenyl (DPAVBi), perylene and the derivatives thereof (e.g., 2,5,8, 11-tetra-t-butylperylene (TBP)), pyrene and the derivatives thereof (e.g., 1,1-dipyrene, 1,4-dipyrenylbenzene, 1,4-bis(N, N-diphenylamino)pyrene), etc.

The emission layer EML may include a phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), or thulium (Tm) may be used as a phosphorescence dopant. For example, iridium(III) bis(4,6-difluorophenylpyridinato-N,C2')picolinate (FIrpic), bis(2,4-difluorophenylpyridinato)-tetrakis(1-pyrazolyl)borate iridium(III) (FIr6), or platinum octaethyl porphyrin (PtOEP) may be used as a phosphorescence dopant. However, embodiments are not limited thereto.

The emission layer EML may include a quantum dot material. The core of the quantum dot may be selected from among a Group II-VI compound, a Group III-V compound, a Group IV-VI compound, a Group IV element, a Group IV compound, and a combination thereof.

A Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S_3$ and $In_2Se_3$, a ternary compound such as $InGaS_3$ and $InGaSe_3$, or any combination thereof.

A Group I-III-VI compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgA_1O_2$, and a mixture thereof, or a quaternary compound such as $AgInGaS_2$ and $CuInGaS_2$.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, MAINAs, InAlNSb, InAlPAs, InAlPSb, and a mixture thereof. The Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

For example, a binary compound, a ternary compound, or a quaternary compound may be present in particles in a uniform concentration distribution, or may be present in the same particle in a partially different concentration distribution. The quantum dot may have a core/shell structure in which one quantum dot surrounds another quantum dot. An interface between the core and the shell may have a concentration gradient in which the concentration of an element present in the shell becomes lower toward the center.

In embodiments, a quantum dot may have the above-described core-shell structure including a core having nanocrystals and a shell surrounding the core. The shell of the quantum dot may serve as a protection layer to prevent the chemical deformation of the core so as to maintain semiconductor properties, and/or a charging layer to impart electrophoresis properties to the quantum dot. The shell may be a single layer or a multilayer. An interface between the core and the shell may have a concentration gradient in which the concentration of an element present in the shell becomes lower toward the center. An example of the shell of the quantum dot may include a metal or non-metal oxide, a semiconductor compound, or a combination thereof.

For example, the metal or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, Or NiO, Or a ternary compound such as $MgAl_2O_4$, $CoFe_2O_4$, $NiFe_2O_4$, or $CoMn_2O_4$, but embodiments are not limited thereto.

Also, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of a light emission wavelength spectrum equal to or less than about 45 nm. For example, the quantum dot may have a FWHM of a light emission wavelength spectrum equal to or less than about 40 nm. For example, the quantum dot may have a FWHM of a light emission wavelength spectrum equal to or less than about 30 nm. Color purity or color reproducibility may be improved in the above-described ranges. Light emitted through such a quantum dot may be emitted in all directions, and thus a wide viewing angle may be improved.

The form of a quantum dot is not particularly limited. For example, a spherical, a pyramidal, a multi-arm, or a cubic quantum dot may be used, or a quantum dot in the form of nanoparticles, nanotubes, nanowires, nanofibers, nanoparticles, etc. may be used.

A quantum dot may control the color of emitted light according to the particle size thereof and thus the quantum dot may have various light emission colors such as green, red, etc.

In each light emitting device ED of embodiments illustrated in FIGS. 3 to 6, the electron transport region ETR is provided on the emission layer EML. The electron transport region ETR may include at least one of a hole blocking layer HBL, an electron transport layer ETL, and an electron injection layer EIL, but embodiments are not limited thereto.

The electron transport region ETR may have a single layer formed of a single material, a single layer formed of different materials, or a multilayer structure including multiple layers formed of different materials.

For example, the electron transport region ETR may have a single layer structure of the electron injection layer EIL or the electron transport layer ETL, and may have a single layer structure formed of an electron injection material and an electron transport material. The electron transport region ETR may have a single layer structure formed of different materials, or may have a structure in which an electron transport layer ETL/electron injection layer EIL and a hole blocking layer HBL/electron transport layer ETL/electron injection layer EIL are stacked in order from the emission layer EML, but embodiments are not limited thereto. A thickness of the electron transport region ETR may be, for example, in a range of about 1,000 Å to about 1,500 Å.

The electron transport region ETR may be formed by using various methods such as a vacuum deposition method, a spin coating method, a cast method, a Langmuir-Blodgett (LB) method, an inkjet printing method, a laser printing method, a laser induced thermal imaging (LITI) method, etc.

The electron transport region ETR may include a compound represented by Formula ET-1 below:

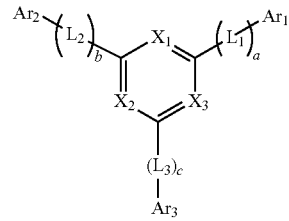

[Formula ET-1]

In Formula ET-1, at least one of $X_1$ to $X_3$ may be N, and the remainder of $X_1$ to $X_3$ may be $C(R_a)$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_3$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula ET-1, when a to c are an integer of 2 or greater, $L_1$ to $L_3$ may be each independently a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimiclazol-1-yl)phenyl)-9,10-dinaphthylanthracene, 1,3,5-tri(1-phenyl-1H-benzo[d]imiclazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq$_2$), 9,10-di(naphthalene-2-yl) anthracene (ADN), 1,3-Bis[3,5-di(pyridin-3-yl)phenyl] benzene (BmPyPhB), or a mixture thereof.

The electron transport regions ETR may include a metal halide such as LiF, NaCl, CsF, RbCl, RbI, CuI, or KI, a lanthanide metal such as Yb, and a co-deposited material of the metal halide and the lanthanide metal. For example, the electron transport region ETR may include KI:Yb, RbI:Yb, etc. as a co-deposited material. The electron transport region ETR may be formed using a metal oxide such as $Li_2O$ or BaO, or 8-hydroxyl-lithium quinolate (Liq), etc., but embodiments are not limited thereto. The electron transport region ETR may also be formed of a mixture material of an electron transport material and an insulating organometallic salt. The organometallic salt may be a material having an energy band gap equal to or greater than about 4 eV. For example, the organometallic salt may include metal acetates, metal benzoates, metal acetoacetates, metal acetylacetonates, or metal stearates.

The electron transport region ETR may further include at least one of 2,9-dimethyl-4,7-diphenyl-1,10-phenanthroline (BCP), and 4,7-diphenyl-1,10-phenanthroline (Bphen) in addition to the above-described materials, but embodiments are not limited thereto.

The electron transport region ETR may include the above-described compounds of the hole transport region in at least one of the electron injection layer EIL, the electron transport layer ETL, and the hole blocking layer HBL.

When the electron transport region ETR includes the electron transport layer ETL, the electron transport layer ETL may have a thickness in a range of about 100 Å to about 1,000 Å. For example, the electron transport layer ETL may have a thickness in a range of about 150 Å to about 500 Å. If the thickness of the electron transport layer ETL satisfies the aforementioned ranges, satisfactory electron transport characteristics may be obtained without a substantial increase in driving voltage. When the electron transport region ETR includes the electron injection layer EIL, the electron injection layer EIL may have a thickness in a range of about 1 Å to about 100 Å. For example, the electron injection layer EIL may have a thickness in a range of about 3 Å to about 90 Å. If the thickness of the electron injection layer EIL satisfies the above-described ranges, satisfactory electron injection characteristics may be obtained without a substantial increase in driving voltage.

The second electrode EL2 is provided on the electron transport region ETR. The second electrode EL2 may be a common electrode. The second electrode EL2 may be a cathode or an anode, but embodiments are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, In, Zn, Sn, a compound thereof, or a mixture thereof (e.g., AgMg, AgYb, or MgAg). In an embodiment, the second electrode EL2 may have a multilayer structure including a reflective film or a transflective film formed of the above-described materials, and a transparent conductive film formed of ITO, IZO, ZnO, ITZO, etc. For example, the second electrode EL2 may include the above-described metal materials, combinations of at least two metal materials of the above-described metal materials, oxides of the above-described metal materials, or the like.

Although not shown, the second electrode EL2 may be connected with an auxiliary electrode. If the second electrode EL2 is connected with an auxiliary electrode, the resistance of the second electrode EL2 may decrease.

A capping layer CPL may further be disposed on the second electrode EL2 of the light emitting device ED of an embodiment. The capping layer CPL may include a multi-layer or a single layer.

In an embodiment, the capping layer CPL may be an organic layer or an inorganic layer. For example, when the capping layer CPL includes an inorganic material, the inorganic material may include an alkaline metal compound such as LiF, an alkaline earth metal compound such as $MgF_2$, SiON, $SiN_x$, SiOy, etc.

For example, when the capping layer CPL includes an organic material, the organic material may include α-NPD, NPB, TPD, m-MTDATA, $Alq_3$, CuPc, N4,N4,N4',N4'-tetra (biphenyl-4-yl)biphenyl-4,4'-diamine (TPD15), 4,4',4"-tris (carbazol sol-9-yl)triphenylamine (TCTA), etc., or an epoxy resin, or acrylate such as methacrylate. However, embodiments are not limited thereto, and the capping layer CPL may include at least one among Compounds P1 to P5 below:

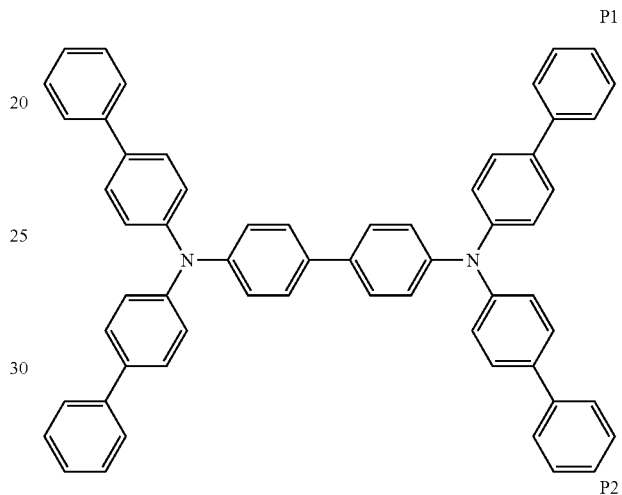

P1

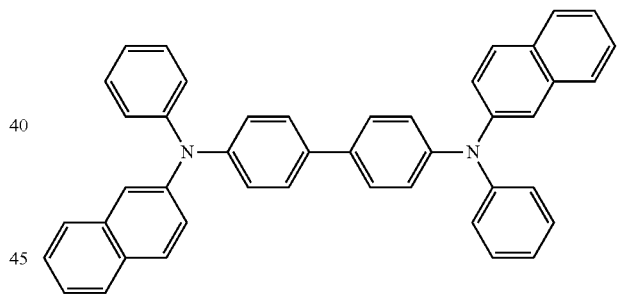

P2

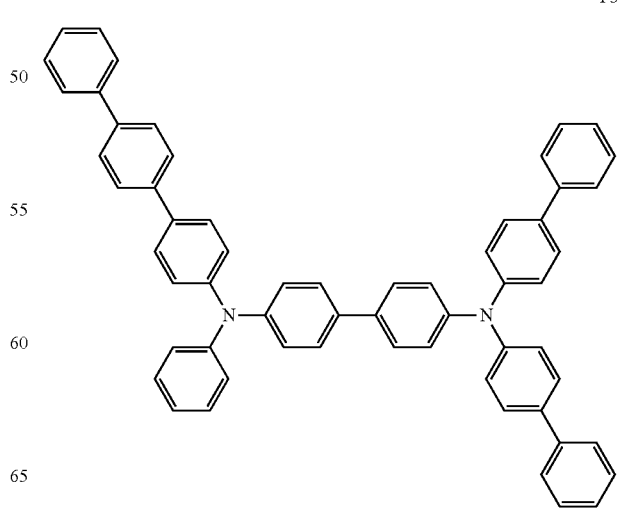

P3

-continued

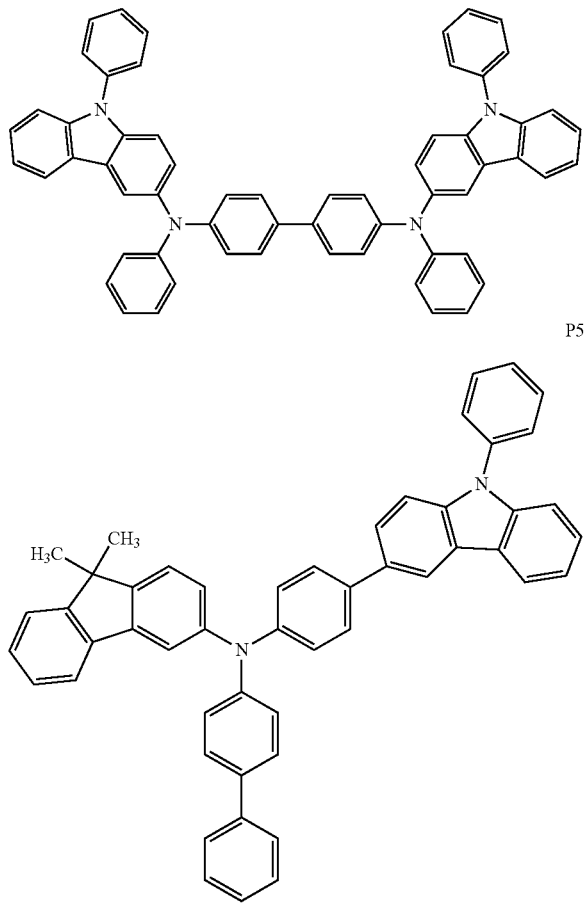

P4

P5

A refractive index of the capping layer CPL may be equal to or greater than about 1.6. For example, the refractive index of the capping layer CPL may be equal to or greater than about 1.6 with respect to light in a wavelength range of about 550 nm to about 660 nm.

Figure 7:
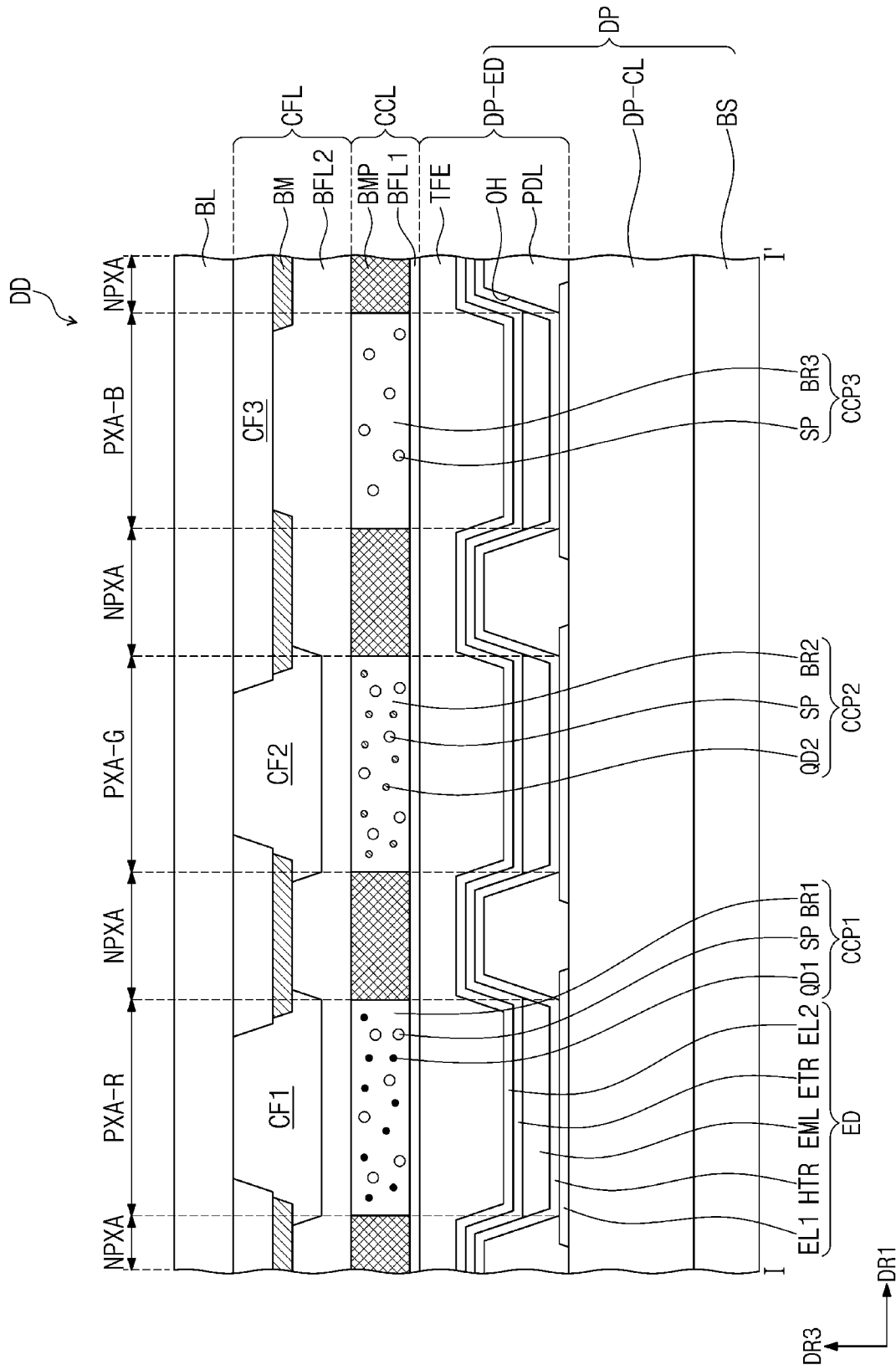
FIGS. 7 and 8 each are a schematic cross-sectional view of a display apparatus according to an embodiment.
Figure 8:
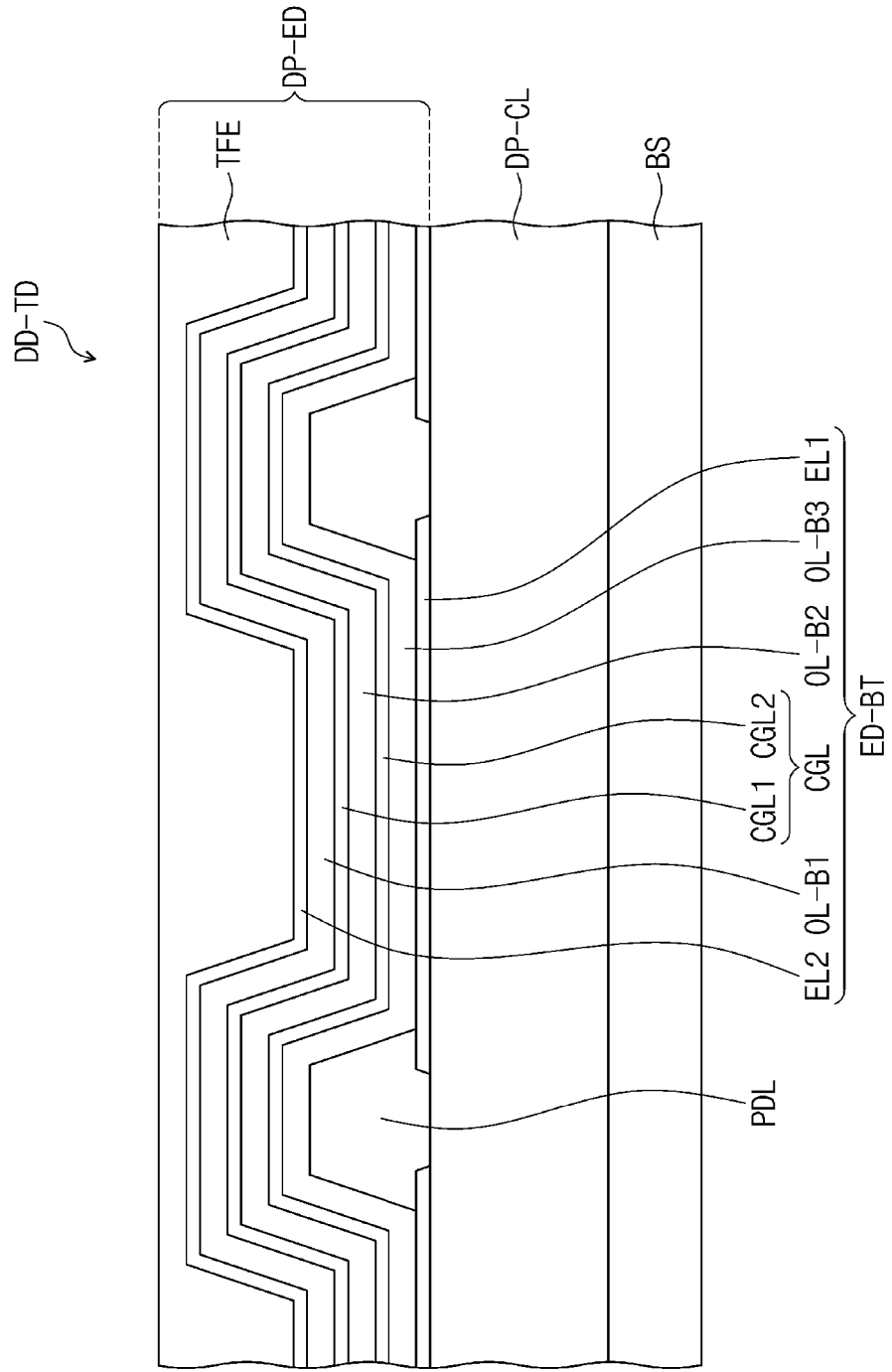

FIGS. 7 and 8 each are a schematic cross-sectional view of a display apparatus according to an embodiment. Hereinafter, in describing the display apparatus of an embodiment with reference to FIGS. 7 and 8, the duplicated features which have been described in FIGS. 1 to 6 are not described again, but their differences will be described.

Referring to FIG. 7, the display apparatus DD according to an embodiment may include a display panel DP including a display device layer DP-ED, a light control layer CCL disposed on the display panel DP, and a color filter layer CFL.

In an embodiment illustrated in FIG. 7, the display panel DP may include a base layer BS, a circuit layer DP-CL provided on the base layer BS, and the display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The structures of the light emitting devices of FIGS. 3 to 6 as described above may be applied to the structure of the light emitting device ED shown in FIG. 7.

Referring to FIG. 7, the emission layer EML may be disposed in an opening OH defined in a pixel defining film PDL. For example, the emission layer EML which is divided by the pixel defining film PDL and provided corresponding to each light emitting regions PXA-R, PXA-G, and PXA-B may emit light in a same wavelength range. In the display apparatus DD of an embodiment, the emission layer EML may emit blue light. While not shown, in an embodiment, the emission layer EML may be provided as a common layer in the light emitting regions PXA-R, PXA-G, and PXA-B.

The light control layer CCL may be disposed on the display panel DP. The light control layer CCL may include a light conversion body. The light conversion body may be a quantum dot, a phosphor, or the like. The light conversion body may emit provided light by converting the wavelength thereof. For example, the light control layer CCL may a layer containing the quantum dot or a layer containing the phosphor.

The light control layer CCL may include light control units CCP1, CCP2, and CCP3. The light control units CCP1, CCP2, and CCP3 may be spaced apart from one another.

Referring to FIG. 7, divided patterns BMP may be disposed between the light control units CCP1, CCP2, and CCP3 which are spaced apart from each other, but the embodiments are not limited thereto. FIG. 7 illustrates that the divided patterns BMP do not overlap the light control units CCP1, CCP2, and CCP3, but in an embodiment, at least a portion of the edges of the light control units CCP1, CCP2, and CCP3 may overlap the divided patterns BMP.

The light control layer CCL may include a first light control unit CCP1 containing a first quantum dot QD1 which converts first color light provided from the light emitting device ED into second color light, a second light control unit CCP2 containing a second quantum dot QD2 which converts the first color light into third color light, and a third light control unit CCP3 which transmits the first color light.

In an embodiment, the first light control unit CCP1 may provide red light that is the second color light, and the second light control unit CCP2 may provide green light that is the third color light. The third light control unit CCP3 may provide by transmitting blue light that is the first color light provided in the light-emitting element ED. For example, the first quantum dot QD1 may be a red quantum dot, and the second quantum dot QD2 may be a green quantum dot. The disclosure for the quantum dots described above may be applied with respect to the quantum dots QD1 and QD2.

The light control layer CCL may further include a scatterer SP. The first light control unit CCP1 may include the first quantum dot QD1 and the scatterer SP, the second light control unit CCP2 may include the second quantum dot QD2 and the scatterer SP, and the third light control unit CCP3 may not include any quantum dot but include the scatterer SP.

The scatterer SP may be inorganic particles. For example, the scatterer SP may include at least one of $TiO_2$, ZnO, $Al_2O_3$, $SiO_2$, and hollow silica. The scatterer SP may include any one of $TiO_2$, ZnO, $Al_2O_3$, $SiO_2$, and hollow silica, or may be a mixture of at least two materials selected from among $TiO_2$, ZnO, $Al_2O_3$, $SiO_2$, and hollow silica.

The first light control unit CCP1, the second light control unit CCP2, and the third light control unit CCP3 may respectively include base resins BR1, BR2, and BR3 in which the quantum dots QD1 and QD2 and the scatterer SP are dispersed. In an embodiment, the first light control unit CCP1 may include the first quantum dot QD1 and the scatterer SP dispersed in a first base resin BR1, the second light control unit CCP2 may include the second quantum dot QD2 and the scatterer SP dispersed in a second base resin BR2, and the third light control unit CCP3 may include the scatterer SP dispersed in a third base resin BR3. The base resins BR1, BR2, and BR3 are media in which the quantum dots QD1 and QD2 and the scatterer SP are dispersed, and may be formed of various resin compositions, which may be generally referred to as a binder. For example, the base resins BR1, BR2, and BR3 may be acrylic-based resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 each may be the same as or different from each other.

The light control layer CCL may include a barrier layer BFL1. The barrier layer BFL1 may serve to prevent the penetration of moisture and/or oxygen (hereinafter, referred to as 'moisture/oxygen'). The barrier layer BFL1 may be disposed on the light control units CCP1, CCP2, and CCP3 to block the light control units CCP1, CCP2, and CCP3 from being exposed to moisture/oxygen. The barrier layer BFL1 may cover the light control units CCP1, CCP2, and CCP3. The barrier layer BFL1 may be provided between the light control units CCP1, CCP2, and CCP3 and the color filter layer CFL.

The barrier layers BFL1 and BFL2 may include at least one inorganic layer. For example, the barrier layers BFL1 and BFL2 may include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. The barrier layers BFL1 and BFL2 may further include an organic film. The barrier layers BFL1 and BFL2 may be formed of a single layer or multiple layers.

In the display apparatus DD of an embodiment, the color filter layer CFL may be disposed on the light control layer CCL. For example, the color filter layer CFL may be directly disposed on the light control layer CCL. For example, the barrier layer BFL2 may be omitted.

The color filter layer CFL may include a light shielding unit BM and filters CF1, CF2, and CF3. The color filter layer CFL may include a first filter CF1 that transmits the second color light, a second filter CF2 that transmits the third color light, and a third filter CF3 that transmits the first color light. For example, the first filter CF1 may be a red filter, the second filter CF2 may be a green filter, and the third filter CF3 may be a blue filter. The filters CF1, CF2, and CF3 each may include a polymeric photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

Furthermore, in an embodiment, the first filter CF1 and the second filter CF2 may be a yellow filter. In another embodiment, the first filter CF1 and the second filter CF2 may not be separated but be provided as one filter.

The light shielding unit BM may be a black matrix. The light shielding unit BM may include an organic light shielding material or an inorganic light shielding material containing a black pigment or dye. The light shielding unit BM may prevent light leakage, and may separate boundaries between the adjacent filters CF1, CF2, and CF3. In an embodiment, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

An upper base layer BL may be disposed on the color filter layer CFL. The upper base layer BL may be a member which provides a base surface in which the color filter layer CFL, the light control layer CCL, and the like are disposed. The upper base layer BL may be a glass substrate, a metal substrate, a plastic substrate, etc. However, embodiments are not limited thereto, and the upper base layer BL may be an inorganic layer, an organic layer, or a composite material layer. While not shown, in an embodiment, the upper base layer BL may be omitted.

FIG. 8 is a schematic cross-sectional view illustrating a part of a display apparatus according to an embodiment. FIG. 8 illustrates a schematic cross-sectional view of a part corresponding to the display panel DP of FIG. 7. In the display apparatus DD-TD of an embodiment, the light emitting device ED-BT may include light emitting structures OL-B1, OL-B2, and OL-B3. The light emitting device ED-BT may include a first electrode EL1 and a second electrode EL2 which face each other, and the light emitting structures OL-B1, OL-B2, and OL-B3 sequentially stacked in the thickness direction between the first electrode EL1 and the second electrode EL2. The light emitting structures OL-B1, OL-B2, and OL-B3 each may include an emission layer EML (FIG. 7) and a hole transport region HTR and an electron transport region ETR disposed with the emission layer EML (FIG. 7) therebetween.

For example, the light emitting device ED-BT included in the display apparatus DD-TD of an embodiment may be a light emitting device having a tandem structure and including multiple emission layers.

In an embodiment illustrated in FIG. 8, light emitted from each of the light emitting structures OL-B1, OL-B2, and OL-B3 may be a blue light. However, embodiments are not limited thereto, and the light emitted from each of the light emitting structures OL-B1, OL-B2, and OL-B3 may be in a wavelength range different from each other. For example, the light emitting device ED-BT including the light emitting structures OL-B1, OL-B2, and OL-B3 which emit light in a wavelength range different from each other may emit white light.

A charge generation layer CGL may be disposed between neighboring light emitting structures OL-B1, OL-B2, and OL-B3. In an embodiment, the charge generating layer CGL may include charge generating layers CGL1 and CGL2. For example, charge generating layer CGL1 may be disposed between light emitting structures OL-B1 and OL-B2, and charge generating layer CGL2 may be disposed between light emitting structures OL-B2 and OL-B3. The charge generation layer CGL may include a p-type charge generation layer and/or an n-type charge generation layer.

The fused polycyclic compound of an embodiment as described above includes a structure in which two or more quinolinoacridinediones or quinolinoacridinedione derivatives are connected via a linker or a direct linkage. The fused polycyclic compound according to an embodiment has an expanded conjugation structure represented by Formula 1, thereby achieving high efficiency of the organic electroluminescence device when the fused polycyclic compound of an embodiment is used as a luminescent material of the organic electroluminescence device.

Hereinafter, with reference to Examples and Comparative Examples, a fused polycyclic according to an embodiment and an organic electroluminescence device of an embodiment will be described in detail. The Examples shown below are illustrated only for the understanding of the disclosure and the embodiments are not limited thereto.

EXAMPLES

1. Synthesis of Fused Polycyclic Compound

A synthesis method of the fused polycyclic compound according to an embodiment will be explained by illustrating the synthesis methods of Compounds 10, 13, 14, 15, 31, 64, and 91. In the following descriptions, the synthesis methods of the fused polycyclic compounds are provided as examples, but a synthesis method according to an embodiment is not limited to Examples below.

(1) Synthesis of Compound 10

Fused polycyclic compound 10 according to an example may be synthesized by, for example, the reaction below.

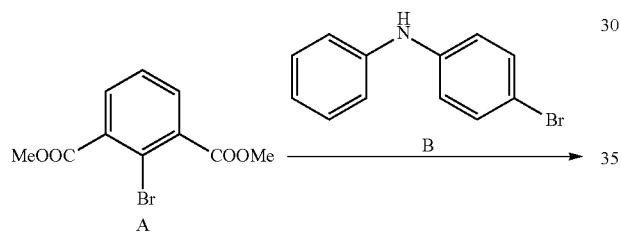

(Synthesis of Intermediate Compound C)

In an Ar atmosphere, in a 2000 mL three-neck flask, $C_6H_3$-1,3-$(COOMe)_2$-2-Br (Intermediate Compound A) (270 g) and H—NPh($C_6H_4$-4-Br) (Intermediate Compound B) (272 mmol) were dissolved in (n-Bu)$_2$O (500 mL), and potassium carbonate (100 g), copper powder (3.2 g), and CuI (6.5 g) were added thereto, and the mixture was heated and stirred at 170° C. for 60 hours. The reaction solution was cooled to room temperature and filtered to obtain a solution. The solvent was removed by distillation under reduced pressure from the obtained solution to obtain a crude product. The obtained crude product was purified by silica gel column chromatography (eluent: hexane/dichloromethane=4/1) to obtain Intermediate Compound C (amount: 124 g, yield: 56%) The objective was analyzed by Fast atom bombardment Mass Spectrometry (FAB-MS), and as a result, the mass number of Intermediate Compound C was 439.

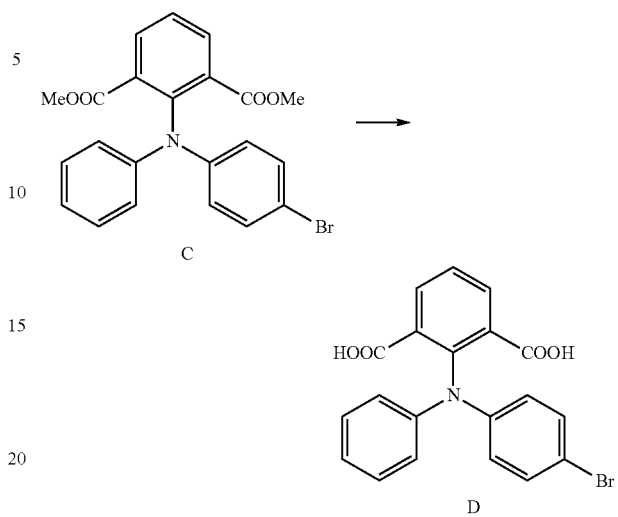

(Synthesis of Intermediate Compound D)

In a 2000 mL three-neck flask, Intermediate Compound C (104 g) and NaOH (51 g) were mixed in a solution of ethanol/water (800 mL/400 mL) and heated under reflux for 10 hours. The reaction solution was cooled to room temperature, and a hydrochloric acid aqueous solution (6 mol/L) was added thereto until the reaction solution became acidic, thereby extracting. Intermediate Compound D extracted was obtained by filtration (amount: 83 g, yield: 85%). The objective was analyzed by FAB-MS, and as a result, the mass number of Intermediate Compound D was 411.

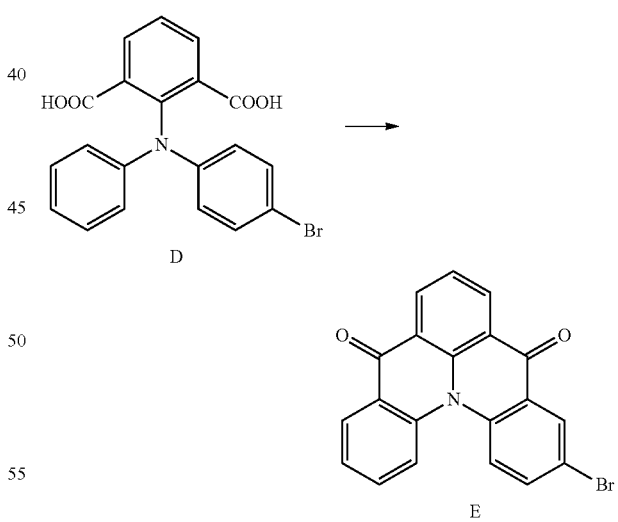

(Synthesis of Intermediate Compound E)

In an Ar atmosphere, in a 2000 mL three-neck flask, dichloromethane (1,000 mL), N,N-dimethylformamide (1.5 mL), and oxalyl chloride (150 mL) were added to Intermediate Compound D (81 g) and heated under reflux for 30 minutes, and tin(IV) chloride (200 mL) was added thereto and heated under reflux for 4 hours further. The obtained reaction solution was dropped to a NaOH solution (1 mol/L, 3000 mL), and an organic layer was extracted with $CH_2Cl_2$. The obtained dichloromethane solution was dried over MgSO$_4$, and the solvent was removed by distillation under reduced pressure to obtain a crude product. The obtained crude product was purified by silica gel column chromatography (eluent: hexane/dichloromethane=1/4) to obtain Intermediate Compound E (amount: 56 g, yield: 76%). The objective was analyzed by FAB-MS, and as a result, the mass number of Intermediate Compound E was 375.

(Synthesis of Intermediate Compound F)

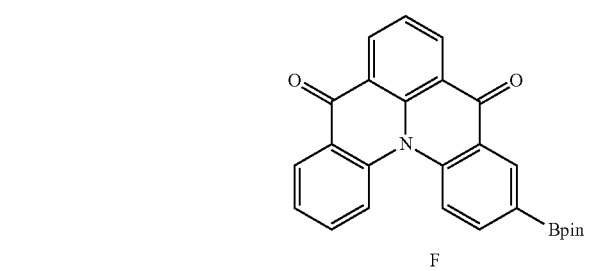

In an Ar atmosphere, in a 2000 mL three-neck flask, Intermediate Compound E (38 g), bis(pinacolato)diboron (32 g), [1,1'-bis(diphenylphosphino)ferrocene]dichloropalladium dichloromethane adduct (10 g), and potassium acetate (24.5 g) were dissolved in 1,4-dioxane (650 mL) and stirred at 90° C. for 6 hours. The reaction solution was cooled to room temperature and water was added thereto, and CH$_2$Cl$_2$ was added thereto to extract an organic layer. The separated organic layer was dried over MgSO$_4$, and the solvent was removed by distillation under reduced pressure. The obtained crude product was purified by silica gel column chromatography (eluent: hexane/dichloromethane=1/4) to obtain Intermediate Compound F (amount: 36 g, yield: 86%). The objective was analyzed by FAB-MS, and as a result, the mass number of Intermediate Compound F was 423.

(Synthesis of Compound 10)

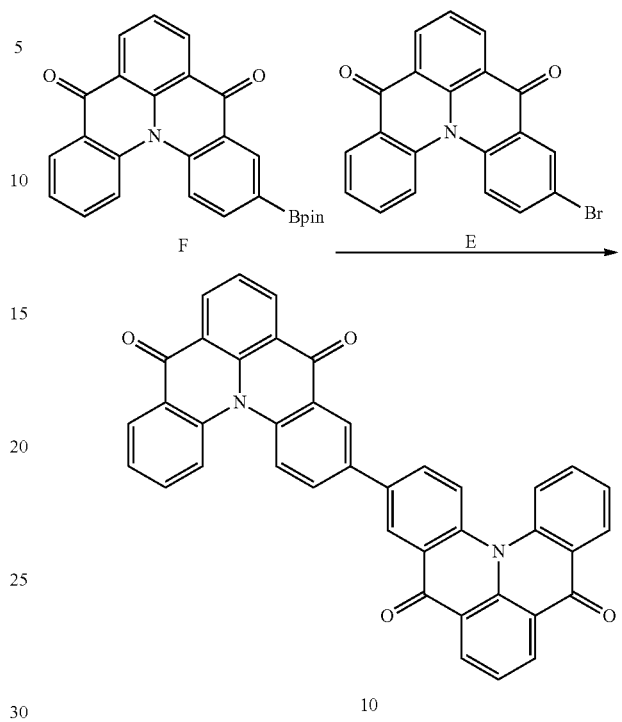

In an Ar atmosphere, in a 2000 mL three-neck flask, Intermediate Compound E (37 g), Intermediate Compound F (43 g), Pd(OAc)$_2$ (1.9 g), 2-dicyclohexylphosphino-2',6'-dimethoxybiphenyl (SPhos, 7.1 g), and K$_3$PO$_4$ (73 g) were dissolved in toluene/EtOH/water (10:1:2, 1,000 mL) which was degassed, and stirred at 80° C. for 10 hours. The reaction solution was cooled to room temperature and water was added thereto, and CH$_2$Cl$_2$ was added thereto to extract an organic layer. The separated organic layer was dried over MgSO$_4$, and the solvent was removed by distillation under reduced pressure. The obtained crude product was purified by silica gel column chromatography (eluent: hexane/dichloromethane=1/6) to obtain Compound 10 (amount: 43 g, yield: 73%). Compound 10 was analyzed by FAB-MS, and as a result, the mass number thereof was 592.

(2) Synthesis of Compound 13

Fused polycyclic compound 13 according to an example may be synthesized by, for example, the reaction below.

(Synthesis of Compound 13)

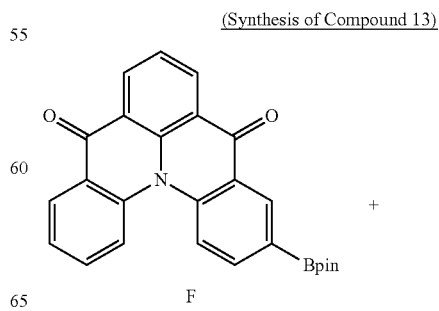

-continued

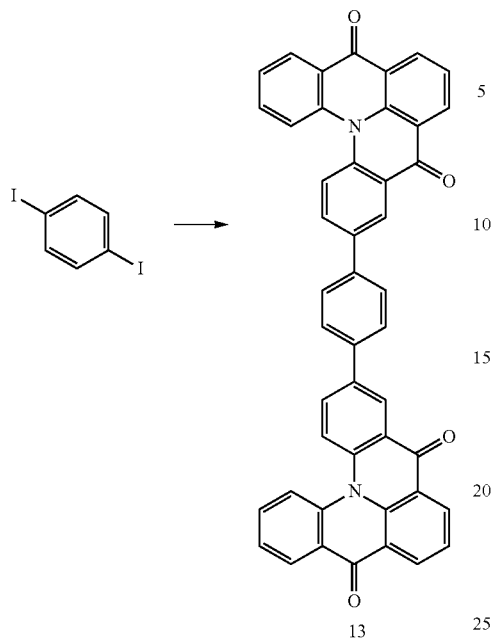

13

In an Ar atmosphere, in a 2000 mL three-neck flask, $C_6H_4$-1,4-$I_2$ (16 g), Intermediate Compound F (45 g), Pd(OAc)$_2$ (1.9 g), SPhos (7.1 g), and K$_3$PO$_4$ (73 g) were dissolved in toluene/EtOH/water (10:1:2, 800 mL) which was degassed, and stirred at 80° C. for 10 hours. The reaction solution was cooled to room temperature and water was added thereto, and CH$_2$Cl$_2$ was added thereto to extract an organic layer. The separated organic layer was dried over MgSO$_4$, and the solvent was removed by distillation under reduced pressure. The obtained crude product was purified by silica gel column chromatography (eluent: dichloromethane) to obtain Compound 13 (amount: 44 g, yield: 68%). Compound 13 was analyzed by FAB-MS, and as a result, the mass number thereof was 668.

(3) Synthesis of Compound 14

Fused polycyclic compound 14 according to an example may be synthesized by, for example, the reaction below.

(Synthesis of Compound 14)

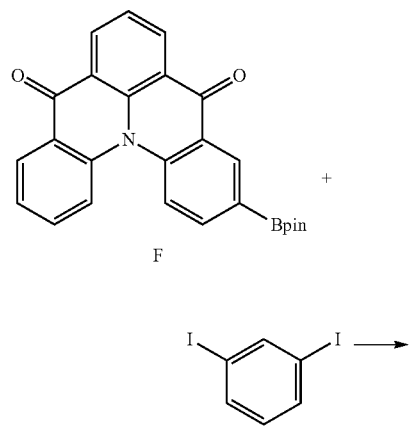

-continued

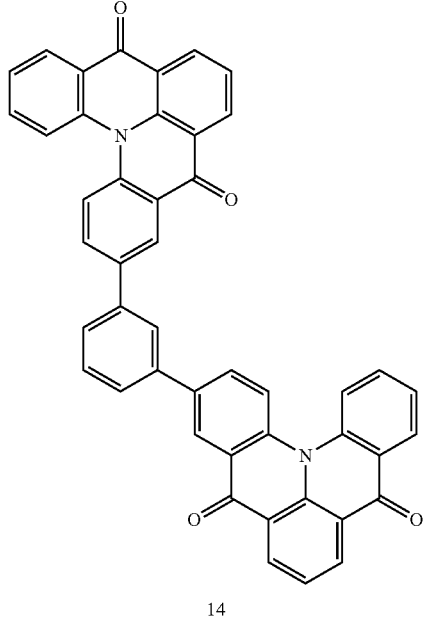

14

Compound 14 was synthesized by using $C_6H_4$-1,3-$I_2$ (16 g) instead of $C_6H_4$-1,4-$I_2$ (16 g) in the synthesis method of Compound 13 (amount: 45 g, yield: 70%). Compound 14 was analyzed by FAB-MS, and as a result, the mass number thereof was 668.

(4) Synthesis of Compound 15

Fused polycyclic compound 15 according to an example may be synthesized by, for example, the reaction below.

(Synthesis of Compound 15)

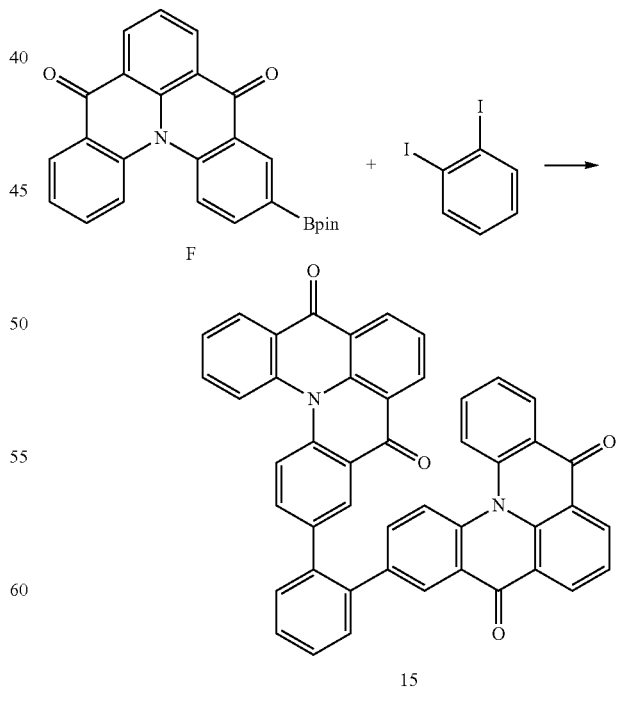

15

Compound 15 was synthesized by using $C_6H_4$-1,2-$I_2$ (16 g) instead of $C_6H_4$-1,4-$I_2$ (16 g) in the synthesis method of Compound 13 (amount: 45 g, yield: 70%). Compound 15 was analyzed by FAB-MS, and as a result, the mass number thereof was 668.

(5) Synthesis of Compound 31

Fused polycyclic compound 31 according to an example may be synthesized by, for example, the reaction below.

(Synthesis of Compound 31)

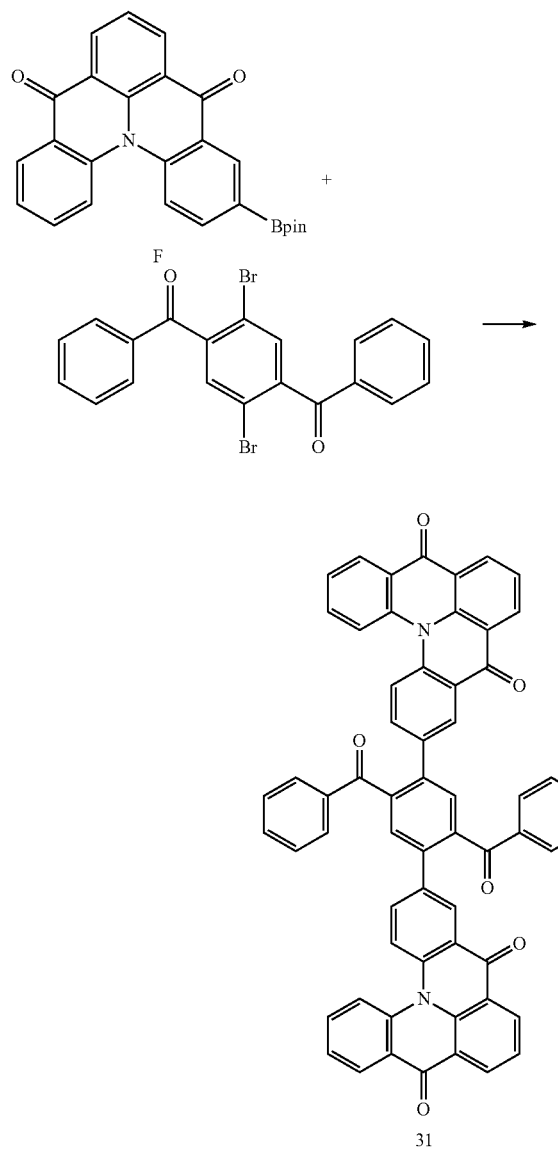

31

$C_6H_2$-1,4-$Br_2$-2,5-$(C(=O)Me)_2$ was synthesized by a method described in the non-patent document, Journal of Physical Chemistry C (2016), 120(21), 11631-11639. Compound 31 was synthesized by using $C_6H_2$-1,4-$Br_2$-2,5-$(C(=O)Me)_2$ (16 g) instead of $C_6H_4$-1,4-$I_2$ (16 g) in the synthesis method of Compound 13 (amount: 7 g, yield: 15%). Compound 31 was analyzed by FAB-MS, and as a result, the mass number thereof was 876.

(6) Synthesis of Compound 64

Fused polycyclic compound 64 according to an example may be synthesized by, for example, the reaction below.

(Synthesis of Compound 64)

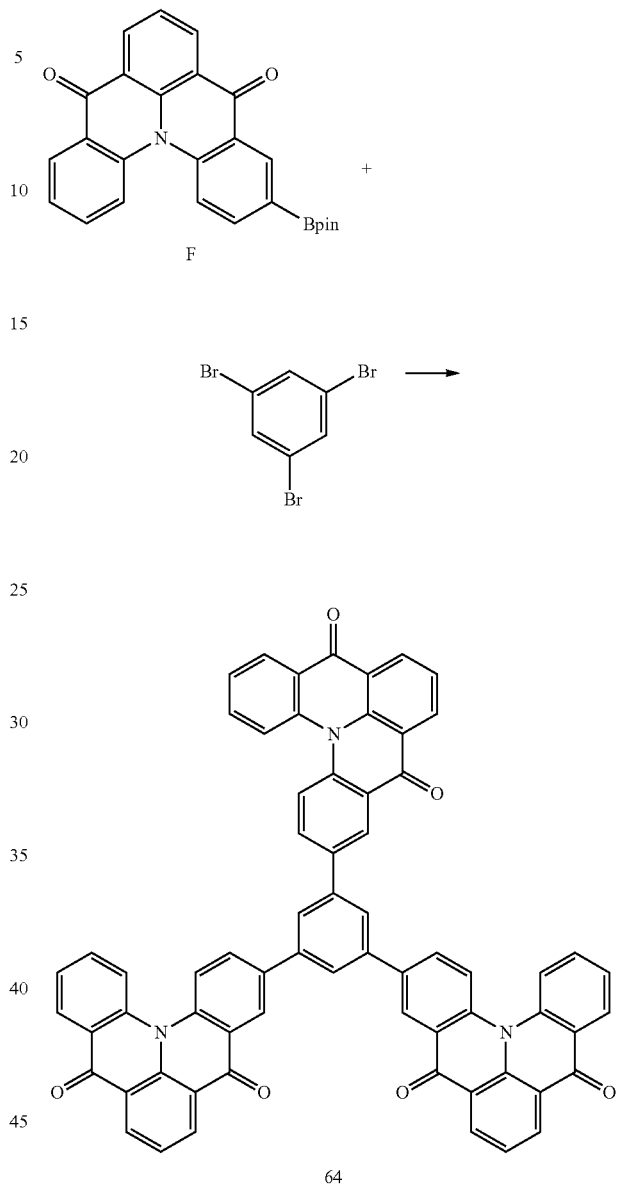

64

In an Ar atmosphere, in a 2000 mL three-neck flask, $C_6H_3$-1,3,5-$Br_3$ (10 g), Intermediate Compound F (45 g), Pd(OAc)$_2$ (1.9 g), SPhos (7.1 g), and $K_3PO_4$ (73 g) were dissolved in toluene/EtOH/water (10:1:2, 800 mL) which was degassed, and stirred under reflux for 12 hours. The reaction solution was cooled to room temperature and water was added thereto, and $CH_2Cl_2$ was added thereto to extract an organic layer. The separated organic layer was dried over $MgSO_4$, and the solvent was removed by distillation under reduced pressure. The obtained crude product was purified by silica gel column chromatography (eluent: dichloromethane) to obtain Compound 64 (amount: 2.4 g, yield: 8%). Compound 64 was analyzed by FAB-MS, and as a result, the mass number thereof was 963.

(7) Synthesis of Compound 91

Fused polycyclic compound 91 according to an example may be synthesized by, for example, the reaction below.

(Synthesis of Compound 91)

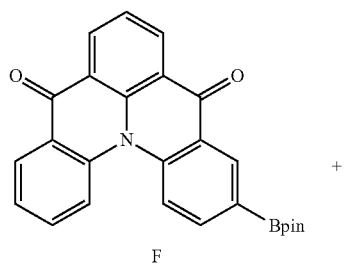

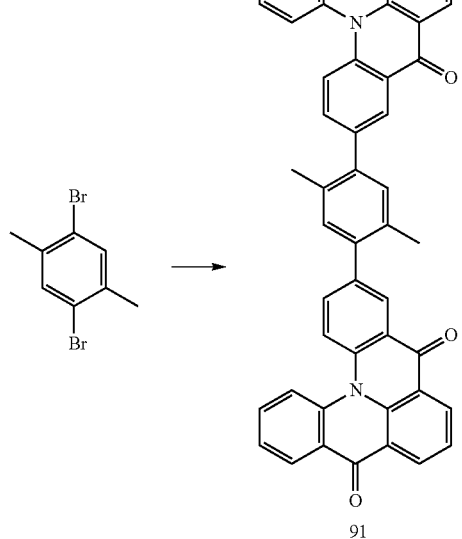

$C_6H_2$-1,4-$Br_2$-2,5-$Me_2$ was synthesized by a method described in the non-patent document, Journal of Physical Chemistry C (2016), 120(21), 11631-11639. Compound 91 was synthesized by using $C_6H_2$-1,4-$Br_2$-2,5-$Me_2$ (13 g) instead of $C_6H_4$-1,4-$I_2$ (16 g) in the synthesis method of Compound 13 (amount: 17 g, yield: 50%). Compound 91 was analyzed by FAB-MS, and as a result, the mass number thereof was 696.

(8) Synthesis of Comparative Example Compound X-5

Comparative Example Compound X-5, which will be described below, may be synthesized by the reaction below.

(Synthesis of Compound X-5)

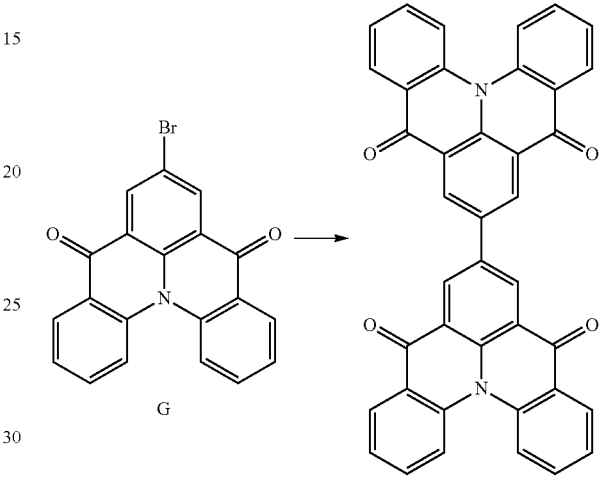

Intermediate Compound G was synthesized by a method described in the patent document, Liao, Liangsheng; China, CN109456326 A. In an Ar atmosphere, in a 1000 mL three-neck flask, Intermediate Compound G (3.8 g), Pd(OAc)$_2$ (43 mg), P($C_6H_4$-2-Me)$_3$ (69 mg), Cs$_2$CO$_3$ (3.3 g), and hydroquinone (59 mg) were dissolved in dimethylacetamide (DMA, 50 mL) which was degassed, and stirred under reflux for 10 hours. The reaction solution was cooled to room temperature and water was added thereto, and CH$_2$Cl$_2$ was added thereto to extract an organic layer. The separated organic layer was dried over MgSO$_4$, and the solvent was removed by distillation under reduced pressure. The obtained crude product was purified by silica gel column chromatography (eluent: dichloromethane/hexane=1/1) to obtain Comparative Example Compound X-5 (amount: 2.0 g, yield: 30%). Comparative Example Compound X-5 was analyzed by FAB-MS, and as a result, the mass number thereof was 592.

2. Manufacture and Evaluation of Organic Electroluminescence Device Including Fused Polycyclic Compound (Manufacture of Organic Electroluminescence Device)

Compounds 10, 13, 14, 15, 31, 64 and 91 as described above were used as a dopant material of the emission layer to manufacture the organic electroluminescence devices of Examples 1 to 7, respectively.

[Example Compounds]
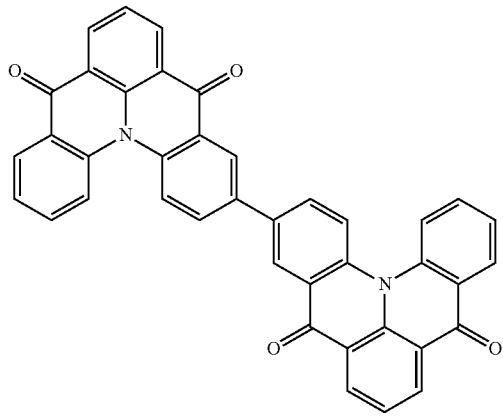
10
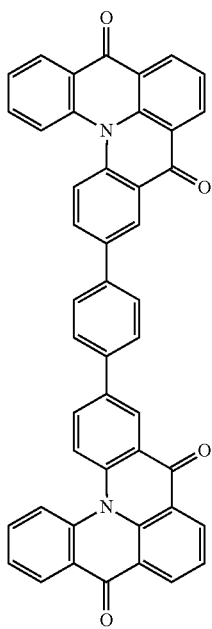
13
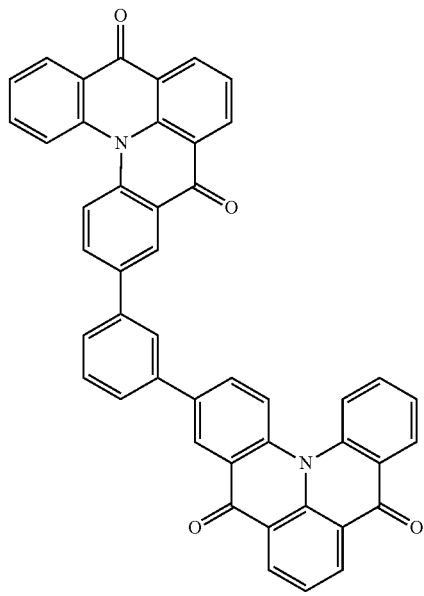
14
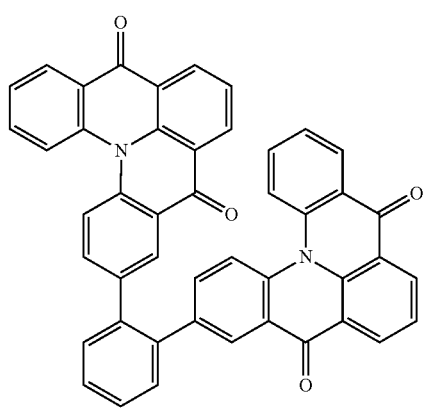
15
31

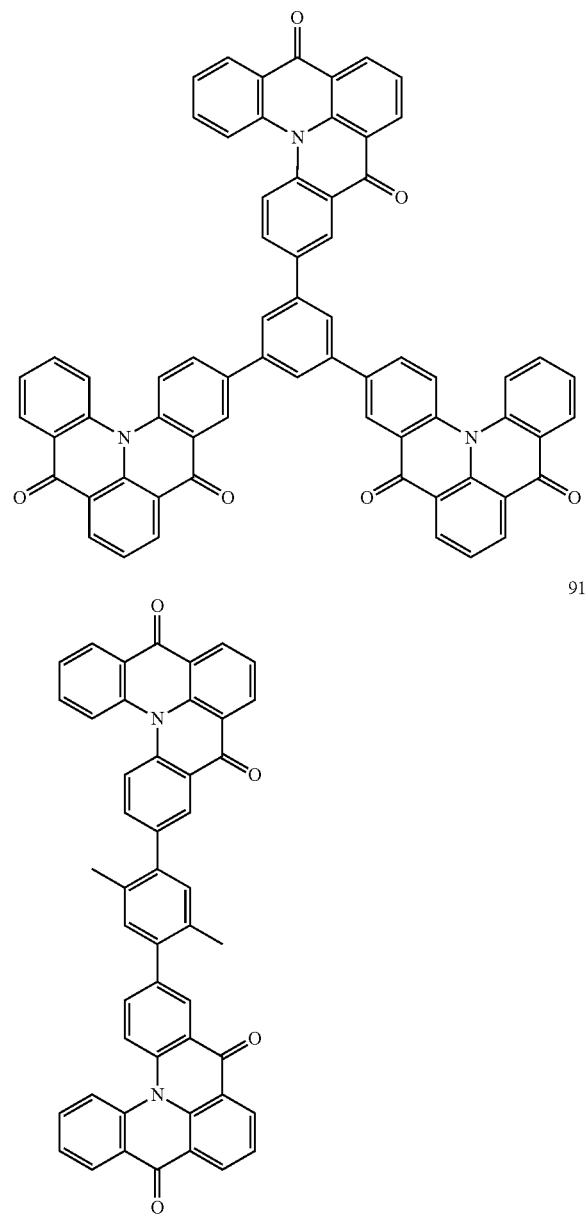
Comparative Example Compounds X-1 to X-7 below were used to manufacture devices of Comparative Examples.
[Comparative Example Compounds]
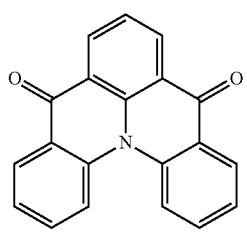
X-1
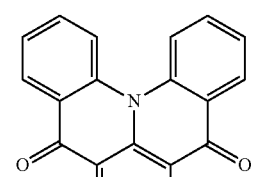
X-2
X-3
X-4
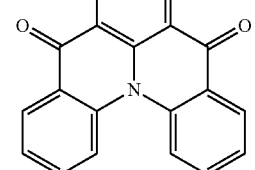
X-5

-continued

X-6
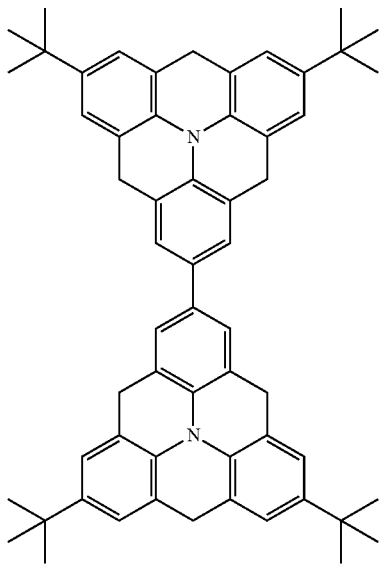

X-7
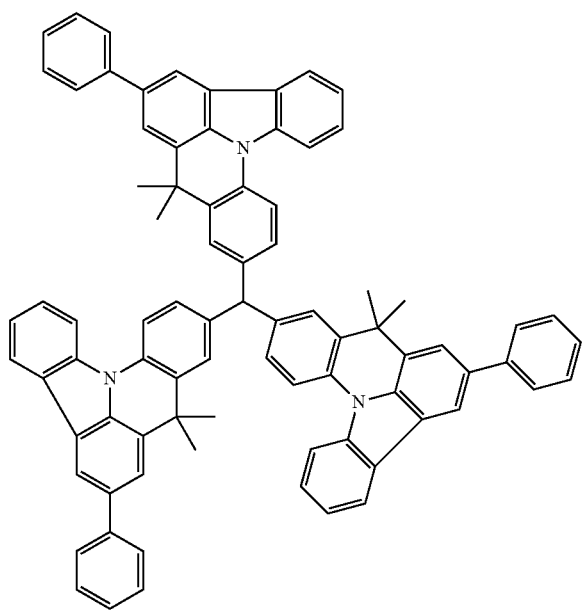

The organic electroluminescence device of an example including the fused polycyclic compound of an example in the emission layer was manufactured as follows. Examples 1 to 7 correspond to the organic electroluminescence devices manufactured by using Compounds 10, 13, 14, 15, 31, 64, and 91 as described above as a luminescent material, respectively. Comparative Examples 1 to 7 correspond to the organic electroluminescence devices manufactured by using Comparative Example Compounds X-1 to X-7 as a luminescent material, respectively.

A 150 nm-thick first electrode was formed with ITO, a 10 nm-thick hole injection layer was formed of 1,4,5,8,9,11-hexaazatriphenylenehexacarbonitrile (HAT-CN), a 80 nm-thick first hole transport layer was formed of N,N'-di(1-naphthyl)-N,N-diphenyl-(1,1'-biphenyl)-4,4'-diamine (α-NPD), a 5 nm-thick second hole transport layer was formed of 1,3-bis(N-carbazolyl)benzene (mCP), a 20 nm-thick emission layer was formed by doping 1% of Example Compounds or Comparative Example Compounds to 3,3'-bis(N-carbazolyl)-1,1'-biphenyl (mCBP), a 30 nm-thick electron transport layer was formed of 1,3,5-tris(N-phenyl-benzimidazole-2-yl)benzene (TPBi), a 0.5 nm-thick electron injection layer was formed of LiF, and a 100 nm-thick second electrode was formed of Al. Each layer was formed by a deposition method in a vacuum atmosphere.

Compounds used for manufacturing the organic electroluminescence devices of Examples and Comparative Examples are disclosed below. The compounds below include some commercial products, and commercial products were subjected to sublimation purification and used to manufacture the devices.

HAT-CN
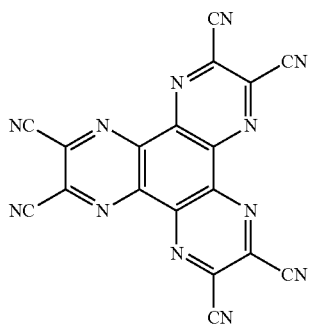

α-NPD
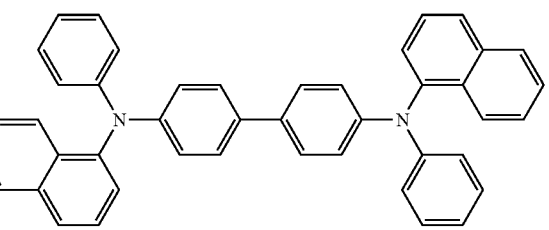

mCP
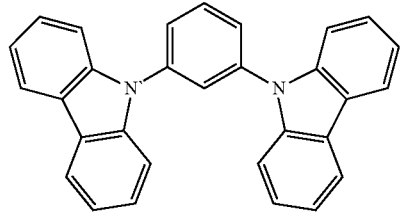

mCBP
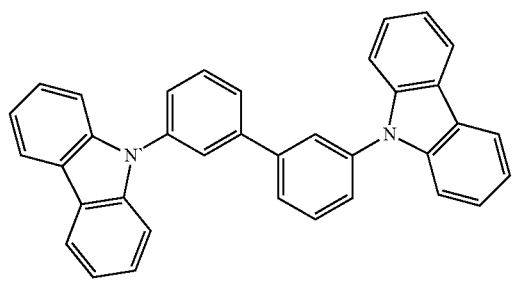

-continued

TPBi

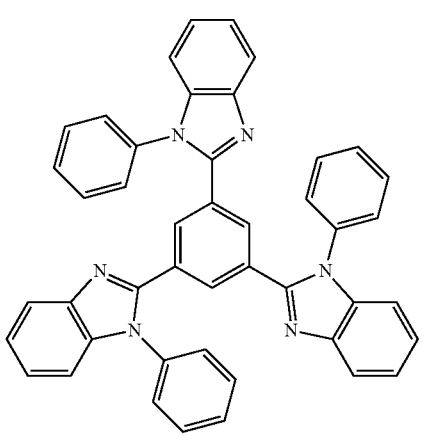

(Experimental Example)

Efficiency of the organic electroluminescence devices manufactured with Example Compounds 10, 13, 14, 15, 31, 64, and 91, and Comparative Example Compounds X-1 to X-7 as described above was evaluated. The evaluation results are shown in Table 1 below. In evaluation of the devices, the maximum emission wavelength in the emission spectrum is expressed in $\lambda_{max}$, the maximum value of the external quantum efficiency in $EQE_{MAX}$, and the value of the external quantum efficiency at 1000 cd/m² in $EQE_{1000\ nit}$.

TABLE 1

| Device manufacturing examples | Dopant compound | $\lambda_{max}$ (nm) | $EQE_{max}$ (%) | $EQE_{1000\ nit}$ (%) |
| --- | --- | --- | --- | --- |
| Example 1 | Compound 10 | 463 | 18 | 15 |
| Example 2 | Compound 13 | 461 | 19 | 16 |
| Example 3 | Compound 14 | 452 | 20 | 16 |
| Example 4 | Compound 15 | 468 | 20 | 16 |
| Example 5 | Compound 31 | 462 | 19 | 15 |
| Example 6 | Compound 64 | 472 | 21 | 17 |
| Example 7 | Compound 97 | 459 | 18 | 16 |
| Comparative Example 1 | Comparative Example Compound X-1 | 460 | 14 | 11 |
| Comparative Example 2 | Comparative Example Compound X-2 | 461 | 17 | 10 |
| Comparative Example 3 | Comparative Example Compound X-3 | 461 | 15 | 4 |
| Comparative Example 4 | Comparative Example Compound X-4 | 462 | 16 | 3 |
| Comparative Example 5 | Comparative Example Compound X-5 | 481 | 10 | 2 |
| Comparative Example 6 | Comparative Example Compound X-6 | 667 | 2 | 1 |
| Comparative Example 7 | Comparative Example Compound X-7 | 651 | 2 | 1 |

Referring to the results of Table 1, it may be seen that Examples of the organic luminescence devices using the fused polycyclic compounds according to embodiments luminescent materials exhibit all improved luminous efficiency while maintaining emission wavelength of blue light compared to Comparative Examples.

Example Compounds have quinolinoacridinedione or quinolinoacridinedione derivative structures in a molecule to form an expanded conjugation structure, thereby stabilizing the structure of the polycyclic aromatic ring and increasing a multiple resonance phenomenon to facilitate reverse intersystem crossing. When the compounds of Examples are used as thermally activated delayed fluorescence dopants, a halfwidth and wavelength range are suitable for a blue luminescent material and luminous efficiency is improved. In particular, it may be seen that Example 6 including, as an emitting dopant, Compound 64 containing three quinolinoacridinedione or quinolinoacridinedione derivative structures has more improved efficiency than other Examples. The organic electroluminescence device of an example includes the fused polycyclic compound of an example as a dopant of a thermally activated delayed fluorescence (TADF) organic electroluminescence device, and thus may achieve high device efficiency in a blue wavelength region, for example, a deep blue wavelength region.

It may be confirmed that Comparative Example Compounds X-1 to X-4 included in Comparative Examples 1 to 4 have a quinolinoacridinedione structure, but include only one quinolinoacridinedione structure, and thus have reduced luminous efficiency compared to Examples. It may be confirmed that Comparative Example Compounds X-2 to X-4 included in Comparative Examples 2 to 4 have a quinolinoacridinedione structure to which a phenyl group or an acridine group is connected, but this does not improve luminous efficiency as much as that in Examples.

It may be confirmed that Comparative Example Compounds X-5 included in Comparative Example 5 has two quinolinoacridinedione structures, but two quinolinoacridinedione structures are symmetrically connected to each other and the dipoles in the molecule cancel out due to the symmetrical structure of quinolinoacridinediones, and thus when Comparative Example Compound X-5 is applied to the device, the luminous efficiency is reduced.

It may be confirmed that Comparative Example Compounds X-6 and X-7 included in Comparative Examples 6 and 7 have different light emitting wavelength ranges not to thereby emit blue light, and thus when Comparative Example Compounds X-6 and X-7 are applied to the emission layer of the blue light emitting device, the luminous efficiency is reduced.

The organic electroluminescence device of an embodiment may exhibit improved device characteristics of high efficiency.

The fused polycyclic compounds of an embodiment may be included in the emission layer of the organic electroluminescence device to contribute to high efficiency of the organic electroluminescence device.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. An organic electroluminescence device comprising:
a first electrode;
a second electrode facing the first electrode; and a plurality of organic layers disposed between the first electrode and the second electrode, wherein at least one of the organic layers comprises a fused polycyclic compound, and the fused polycyclic compound is represented by Formula 1:

A-L-(-B)$_n$ [Formula 1]

wherein in Formula 1,

L is a direct linkage, O, S, —S=O, —Si(R$_a$)(R$_b$), —N(R$_c$), P(R$_d$), B(R$_e$), N=N, C=C, C=O, C(=O)O, OC(=O)O, C=S, P=O, P=S, N, P, B, a substituted or unsubstituted alkyl linking group having 1 to 30 carbon atoms, a substituted or unsubstituted alkenyl linking group having 2 to 30 carbon atoms, a substituted or unsubstituted alkynyl linking group having 3 to 30 carbon atoms, a substituted or unsubstituted aryl linking group having 6 to 60 ring-forming carbon atoms, or a substituted or unsubstituted heteroaryl linking group having 2 to 60 ring-forming carbon atoms, R$_a$ to R$_e$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, n is an integer from 1 to 3, A is a group represented by Formula 2, and B is a group represented by Formula 3,

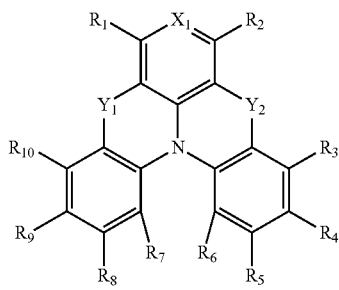

[Formula 2]

wherein in Formula 2,

X$_1$ is N or C(R$_{11}$),

Y$_1$ and Y$_2$ are each independently C=O, C=S, S=O, SO$_2$, C=C(R$_f$)(R$_g$), P=O, or P=S, R$_1$ to R$_{11}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, except that one of R$_1$ to R$_{10}$ is a binding site to L in Formula 1, and R$_f$ and R$_g$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring,

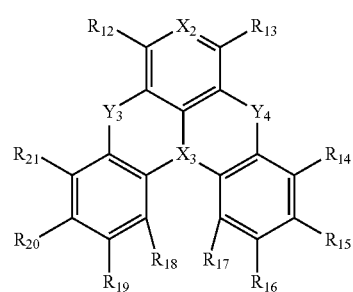

[Formula 3]

wherein in Formula 3,

X$_2$ is N or C(R$_{22}$),

X$_3$ is N, B, or P,

Y$_3$ and Y$_4$ are each independently C=O, C=S, S=O, SO$_2$, C=C(R$_h$)(R$_i$), P=O, P=S, N(R$_j$), or B(R$_k$), R$_{12}$ to R$_{22}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, except that one of R$_{12}$ to R$_{22}$ is a binding site to L in Formula 1, and R$_h$ to R$_k$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, and provided that when n is 1 in Formula 1, when X$_1$ is CR$_{11}$, and Y$_1$ and Y$_2$ are C=O in Formula 2, and when X$_2$ is CR$_{22}$, X$_3$ is N, and Y$_3$ and Y$_4$ are C=O in Formula 3, then L is not a substituted or unsubstituted alkenyl linking group.

2. The organic electroluminescence device of claim 1, wherein the organic layers comprise:
a hole transport region disposed on the first electrode;
an emission layer disposed on the hole transport region; and
an electron transport region disposed on the emission layer, and the emission layer comprises the fused polycyclic compound.

3. The organic electroluminescence device of claim 2, wherein the emission layer emits delayed fluorescence.

4. The organic electroluminescence device of claim 2, wherein
the emission layer is a delayed fluorescence emission layer containing a host and a dopant, and
the dopant comprises the fused polycyclic compound.

5. The organic electroluminescence device of claim 1, wherein in Formula 1, A and B have a same structure.

6. The organic electroluminescence device of claim 1, wherein in Formula 1,
n is 2 or 3, and
a plurality of B(s) have a same structure as each other.

7. The organic electroluminescence device of claim 1, wherein the fused polycyclic compound represented by Formula 1 is represented by Formula 4:

[Formula 4]

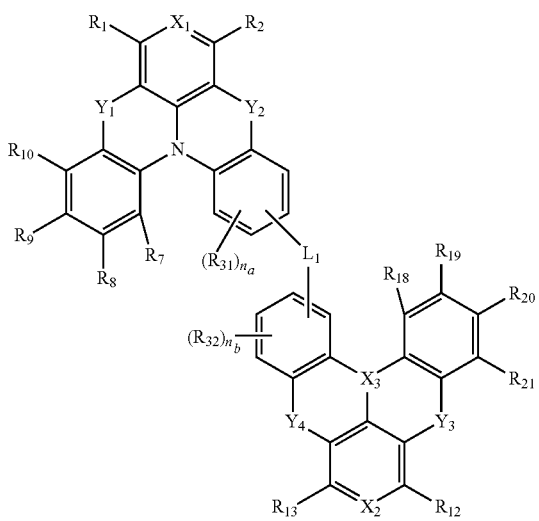

wherein in Formula 4,
$L_1$ is a direct linkage, O, S, S=O, $Si(R_a)(R_b)$, $N(R_c)$, $P(R_d)$, $B(R_e)$, N=N, C=C, C=O, C(=O)O, OC(=O)O, C=S, P=O, or P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 2 to 30 carbon atoms, a substituted or unsubstituted arylene group having 6 to 60 ring-forming carbon atoms, or a substituted or unsubstituted heteroarylene linking group having 2 to 60 ring-forming carbon atoms,
$R_{31}$ and $R_{32}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring,
$n_a$ and $n_b$ are each independently an integer from 0 to 3, and
$X_1, X_2, X_3, Y_1, Y_2, Y_3, Y_4, R_1, R_2, R_7$ to $R_{13}, R_{18}$ to $R_{22}$, and $R_a$ to $R_k$ are the same as defined in connection with Formula 2 and Formula 3.

8. The organic electroluminescence device of claim 7, wherein the fused polycyclic compound represented by Formula 4 is represented by one of Formula 4-1 to Formula 4-3:

[Formula 4-1]

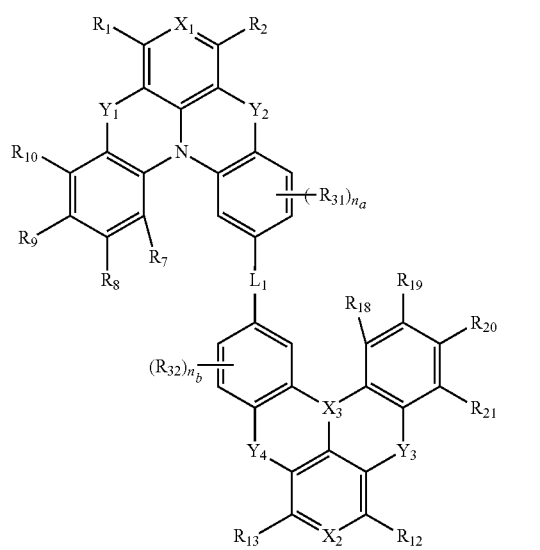

[Formula 4-2]

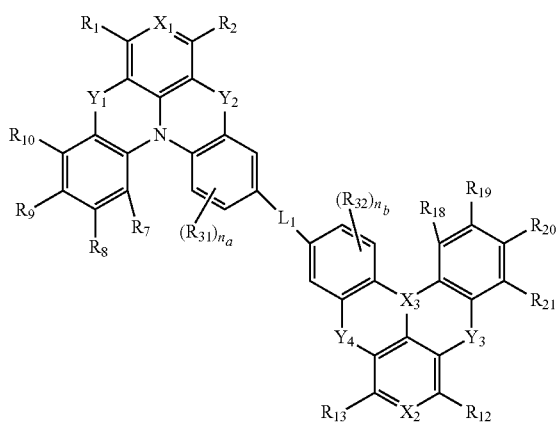

-continued

[Formula 4-3]

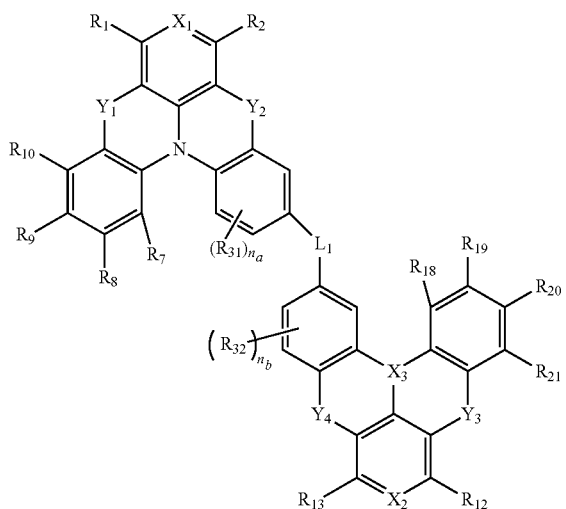

wherein in Formula 4-1 to Formula 4-3,
X$_1$, X$_2$, X$_3$, Y$_1$, Y$_2$, Y$_3$, Y$_4$, R$_1$, R$_2$, R$_7$ to R$_{13}$, R$_{18}$ to R$_{22}$, R$_a$ to R$_k$, L$_1$, R$_{31}$, R$_{32}$, n$_a$, and n$_b$ are the same as defined in connection with Formula 2, Formula 3, and Formula 4.

9. The organic electroluminescence device of claim 1, wherein the fused polycyclic compound represented by Formula 1 is represented by Formula 5:

[Formula 5]

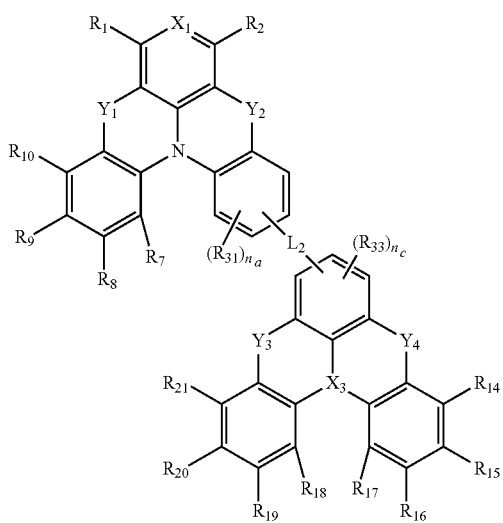

wherein in Formula 5,
L$_2$ is a direct linkage, O, S, S=O, Si(R$_a$)(R$_b$), N(R$_c$), P(R$_d$), B(R$_e$), N=N, C=C, C=O, C(=O)O, OC(=O)O, C=S, P=O, or P=S, a substituted or unsubstituted divalent alkyl group having 1 to 30 carbon atoms, a substituted or unsubstituted divalent alkenyl group having 2 to 30 carbon atoms, a substituted or unsubstituted divalent alkynyl group having 2 to 30 carbon atoms, a substituted or unsubstituted arylene group having 6 to 60 ring-forming carbon atoms, or a substituted or unsubstituted heteroarylene linking group having 2 to 60 ring-forming carbon atoms, R$_{31}$ and R$_{33}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, n$_a$ is an integer from 0 to 3,
n$_c$ is an integer from 0 to 2, and
X$_1$, X$_2$, X$_3$, Y$_1$, Y$_2$, Y$_3$, Y$_4$, R$_1$, R$_2$, R$_7$ to R$_{11}$, R$_{14}$ to R$_{21}$, and R$_a$ to R$_k$ are the same as defined in connection with Formula 2 and Formula 3.

10. The organic electroluminescence device of claim 9, wherein the fused polycyclic compound represented by Formula 5 is represented by one of Formula 5-1 to Formula 5-3:

[Formula 5-1]

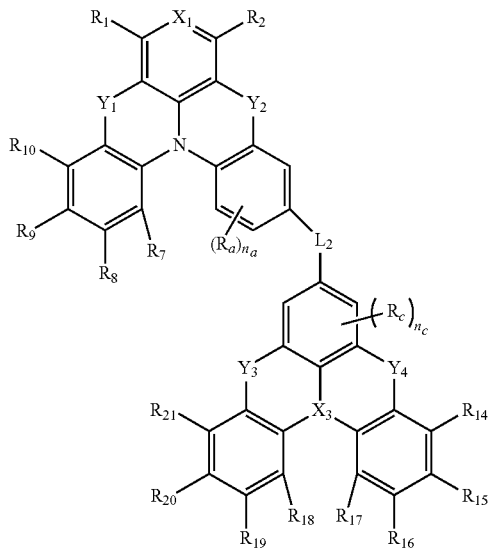

[Formula 5-2]

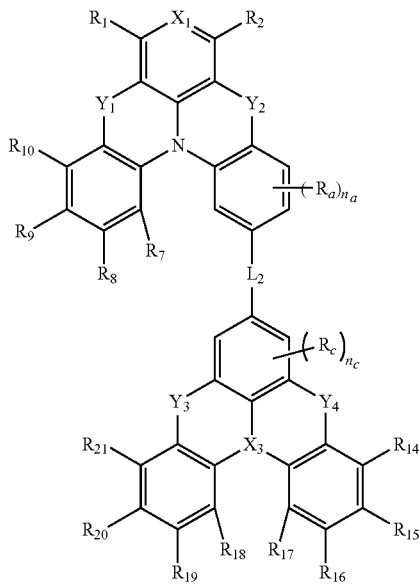

[Formula 5-3]

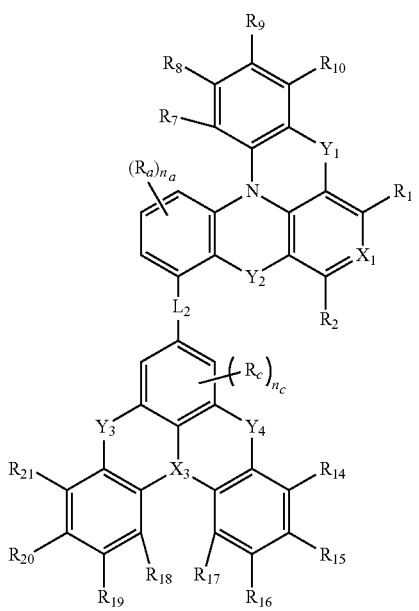

wherein in Formula 5-1 to Formula 5-3, $X_1$, $X_2$, $X_3$, $Y_1$, $Y_2$, $Y_3$, $Y_4$, $R_1$, $R_2$, $R_7$ to $R_{11}$, $R_{14}$ to $R_{21}$, $R_a$ to $R_k$, $L_1$, $R_{31}$, $R_{33}$, $n_a$ and $n_c$ are the same as defined in connection with Formula 2, Formula 3, and Formula 5.

11. The organic electroluminescence device of claim 1, wherein the fused polycyclic compound represented by Formula 1 is represented by Formula 6:

[Formula 6]

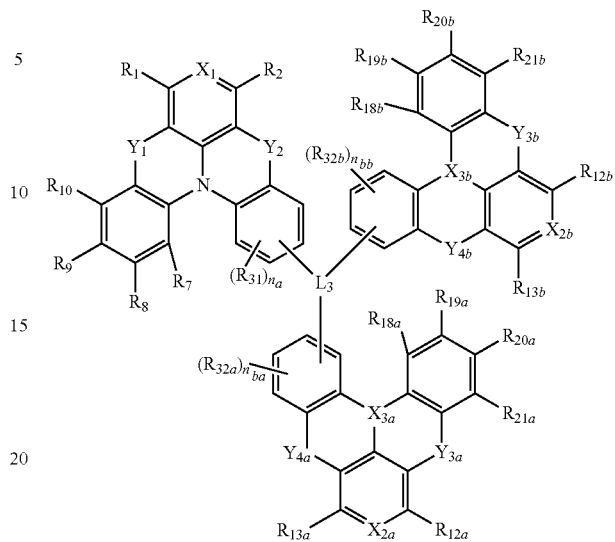

wherein in Formula 6, $L_3$ is N, P, B, a substituted or unsubstituted trivalent alkyl group having 1 to 30 carbon atoms, a substituted or unsubstituted trivalent alkenyl group having 2 to 30 carbon atoms, a substituted or unsubstituted trivalent alkynyl group having 3 to 30 carbon atoms, a substituted or unsubstituted trivalent aryl group having 6 to 60 ring-forming carbon atoms, or a substituted or unsubstituted trivalent heteroaryl group having 2 to 60 ring-forming carbon atoms, $X_2a$ and $X_2b$ are each independently N or $C(R_{22})$, $X_{3a}$ and $X_{3b}$ are each independently N, B, or P, $Y_{3a}$, $Y_{3b}$, $Y_{4a}$, and $Y_{4b}$ are each independently C=O, C=S, S=O, $SO_2$, $C≡C(R_h)(R_i)$, P=O, P=S, $N(R_j)$, or $B(R_k)$, $R_{12a}$, $R_{13a}$, $R_{18a}$ to $R_{21a}$, $R_{12b}$, $R_{13b}$, $R_{18b}$ to $R_{21b}$, $R_{31}$, $R_{32a}$, and $R_{32b}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, $n_a$, $n_{ba}$, and $n_{bb}$ are each independently an integer from 0 to 3, and $X_1$, $Y_1$, $Y_2$, $R_1$, $R_2$, $R_7$ to $R_{11}$, $R_{22}$, and $R_a$ to $R_k$ are the same as defined in connection with Formula 2 and Formula 3.

12. The organic electroluminescence device of claim 11, wherein the fused polycyclic compound represented by Formula 6 is represented by Formula 6-1:

[Formula 6-1]

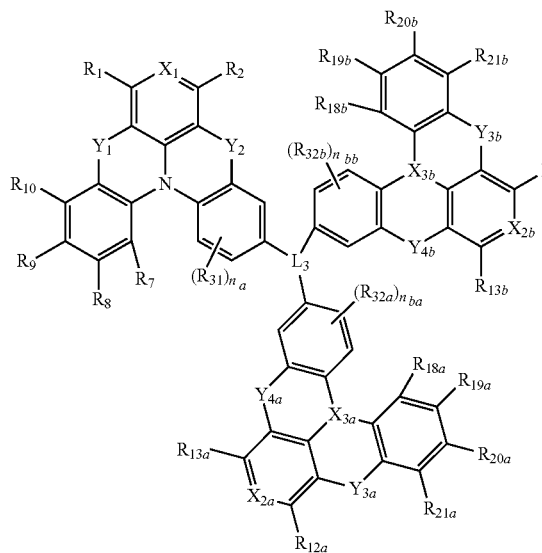

wherein in Formula 6-1, $X_1$, $Y_1$, $Y_2$, $R_1$, $R_2$, $R_7$ to $R_{11}$, $R_{22}$, $R_a$ to $R_k$, $L_3$, $X_{2a}$, $X_{2b}$, $X_{3a}$, $X_{3b}$, $Y_{3a}$, $Y_{3b}$, $Y_{4a}$, $Y_{4b}$, $R_{12a}$, $R_{13a}$, $R_{18a}$ to $R_{21a}$, $R_{12b}$, $R_{13b}$, $R_{18b}$ to $R_{21b}$, $R_{31}$, $R_{32a}$, $R_{32b}$, $n_a$, $n_{ba}$, and $n_{bb}$ are the same as defined in connection with Formula 2, Formula 3, and Formula 6.

13. The organic electroluminescence device of claim 1, wherein the fused polycyclic compound represented by Formula 1 is represented by Formula 7:

[Formula 7]

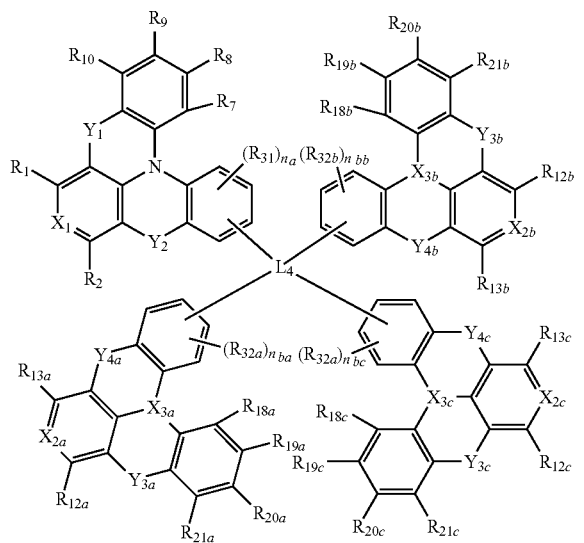

wherein in Formula 7, $L_4$ is a substituted or unsubstituted tetravalent alkyl group having 1 to 30 carbon atoms, a substituted or unsubstituted tetravalent alkenyl group having 2 to 30 carbon atoms, a substituted or unsubstituted tetravalent alkynyl group having 3 to 30 carbon atoms, a substituted or unsubstituted tetravalent aryl group having 6 to 60 ring-forming carbon atoms, or a substituted or unsubstituted tetravalent heteroaryl group having 2 to 60 ring-forming carbon atoms, $X_{2a}$ to $X_{2c}$ are each independently N or $C(R_{22})$, $X_{3a}$ to $X_{3c}$ are each independently N, B, or P, $Y_{3a}$ to $Y_{3c}$, and $Y_{4a}$ to $Y_{4c}$ are each independently C=O, C=S, S—O, $SO_2$, $C\equiv C(R_h)(R_i)$, P=O, P=S, $N(R_j)$, or $B(R_k)$, $R_{12a}$, $R_{13a}$, $R_{18a}$ to $R_{21a}$, $R_{12b}$, $R_{13b}$, $R_{18b}$ to $R_{21b}$, $R_{12c}$, $R_{13c}$, $R_{18c}$ to $R_{21c}$, $R_{31}$, and $R_{32a}$ to $R_{32c}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, $n_a$ and $n_{ba}$ to $n_{bc}$ are each independently an integer from 0 to 3, and $X_1$, $Y_1$, $Y_2$, $R_1$, $R_2$, $R_7$ to $R_{11}$, $R_{22}$, and $R_a$ to $R_k$ are the same as defined in connection with Formula 2 and Formula 3.

14. The organic electroluminescence device of claim 13, wherein the fused polycyclic compound represented by Formula 7 is represented by Formula 7-1:

[Formula 7-1]

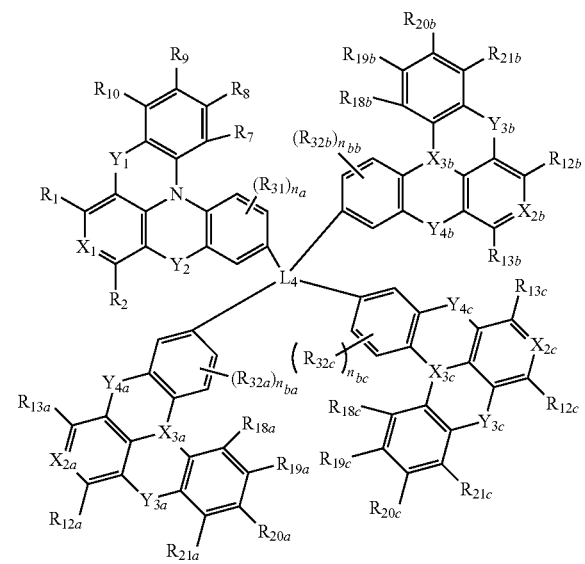

wherein in Formula 7-1, $X_1$, $Y_1$, $Y_2$, $R_1$, $R_2$, $R_7$ to $R_{11}$, $R_{22}$, $R_a$ to $R_k$, $L_4$, $X_2a$ to $X_2c$, $X_{3a}$ to $X_{3c}$, $Y_{3a}$ to $Y_{3c}$, $Y_{4a}$ to $Y_{4c}$, $R_{12a}$, $R_{13a}$, $R_{18a}$ to $R_{21a}$, $R_{12b}$, $R_{13b}$, $R_{18b}$ to $R_{21b}$, $R_{12c}$, $R_{13c}$, $R_{18c}$ to $R_{21c}$, $R_{31}$, $R_{32a}$ to $R_{32c}$, $n_a$, and $n_{ba}$ to $n_{bc}$ are the same as defined in connection with Formula 2, Formula 3, and Formula 7.

15. The organic electroluminescence device of claim 1, wherein in Formula 2, $Y_1$ and $Y_2$ are each independently C=O or C=S.

16. The organic electroluminescence device of claim 1, wherein in Formula 3, X₃ is N, and in Formula 2 and Formula 3, X₁ is the same as X₂, Y₁ is the same as Y₃, and Y₂ is the same as Y₄.

17. The organic electroluminescence device of claim 1, further comprising a capping layer disposed on the second electrode, wherein the capping layer has a refractive index equal to or greater than about 1.6.

18. An organic electroluminescence device comprising:

a first electrode;

a second electrode facing the first electrode; and a plurality of organic layers disposed between the first electrode and the second electrode, wherein at least one of the organic layers comprises a fused polycyclic compound, and the fused polycyclic compound comprises at least one compound selected from Compound Group 1:

[Compound Group 1]

1

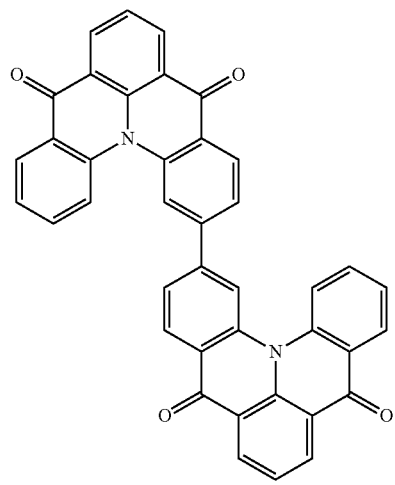

2

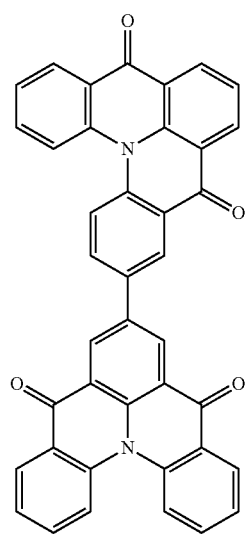

3

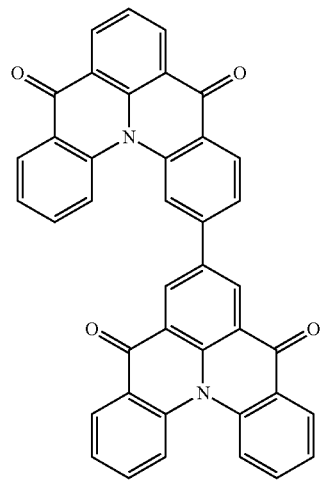

4

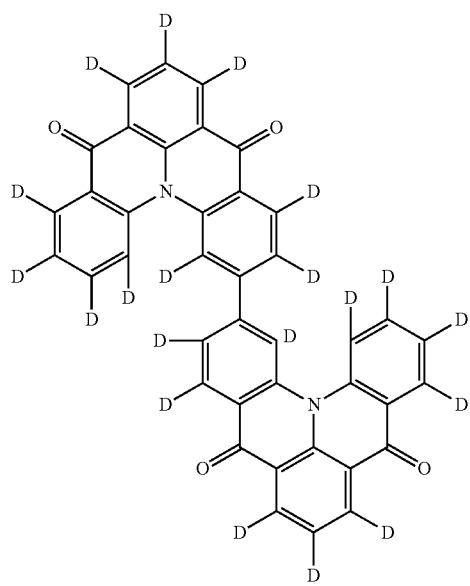

5

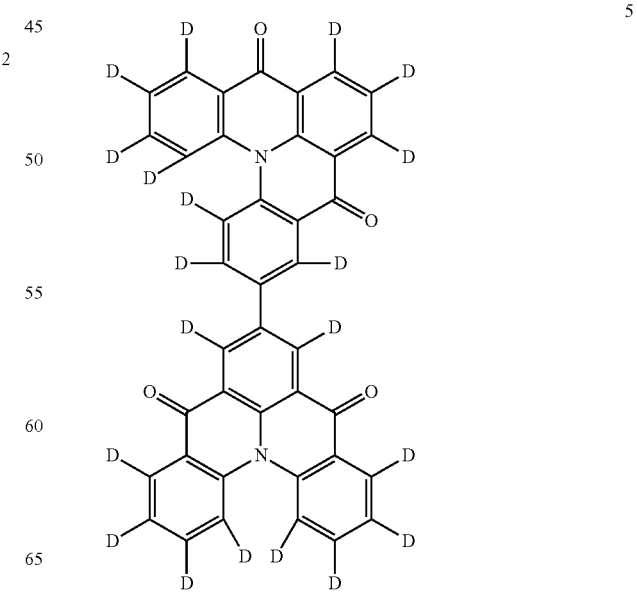

149
-continued
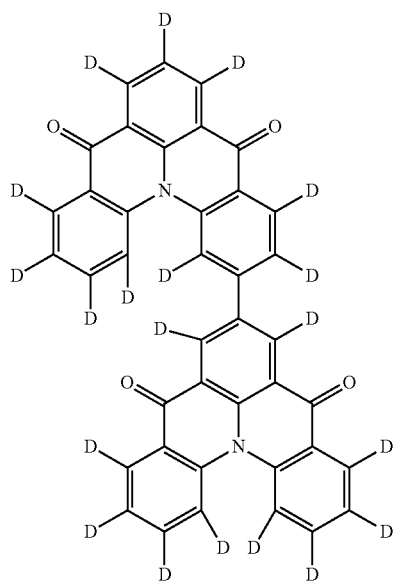
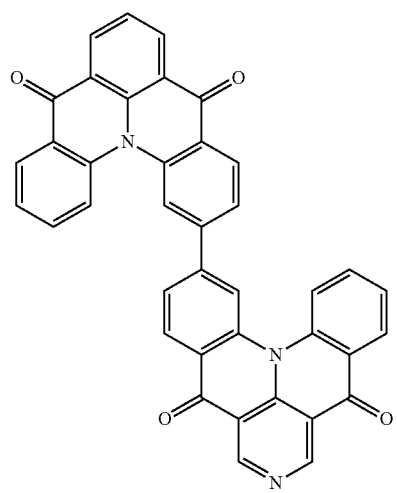
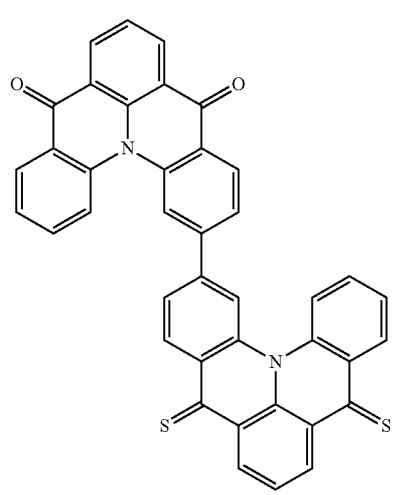
150
-continued
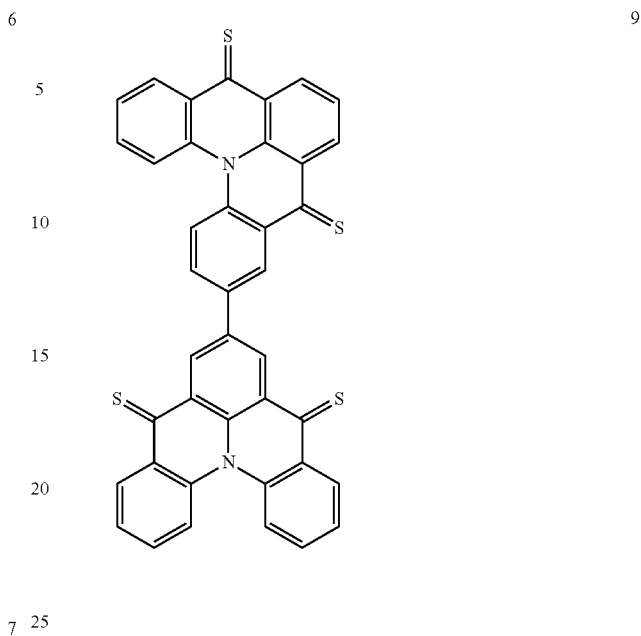
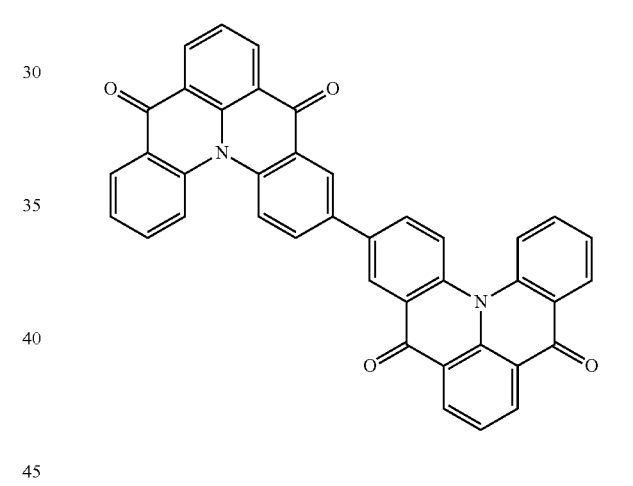
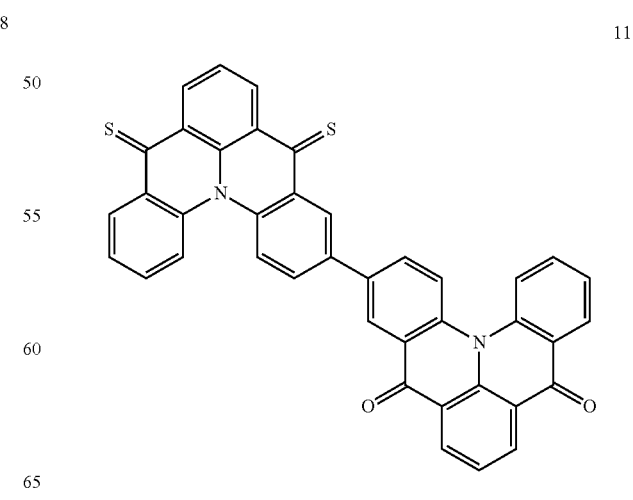

12
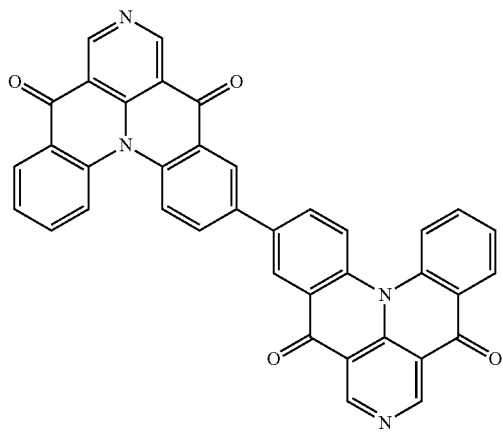
13
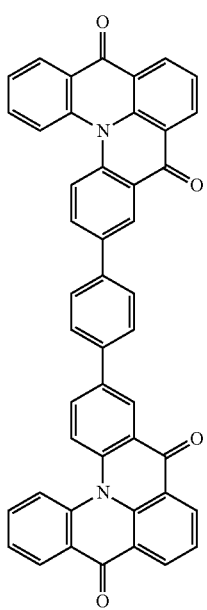
14
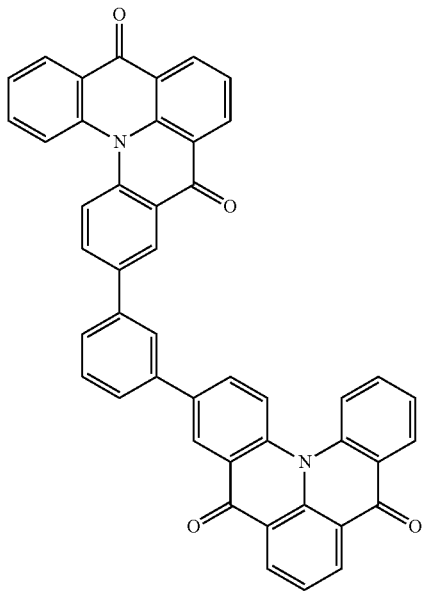
15
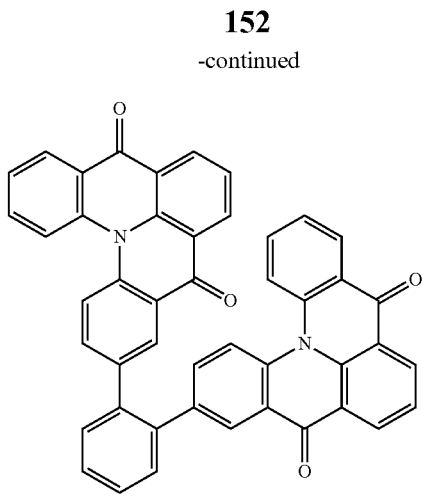
16
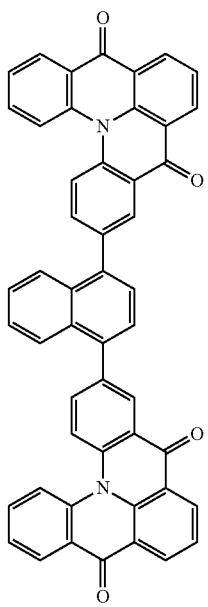
17
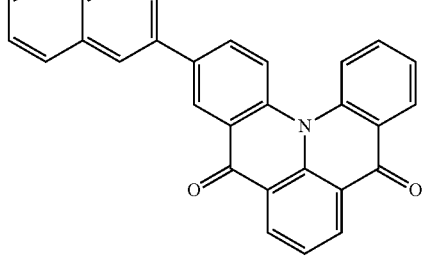

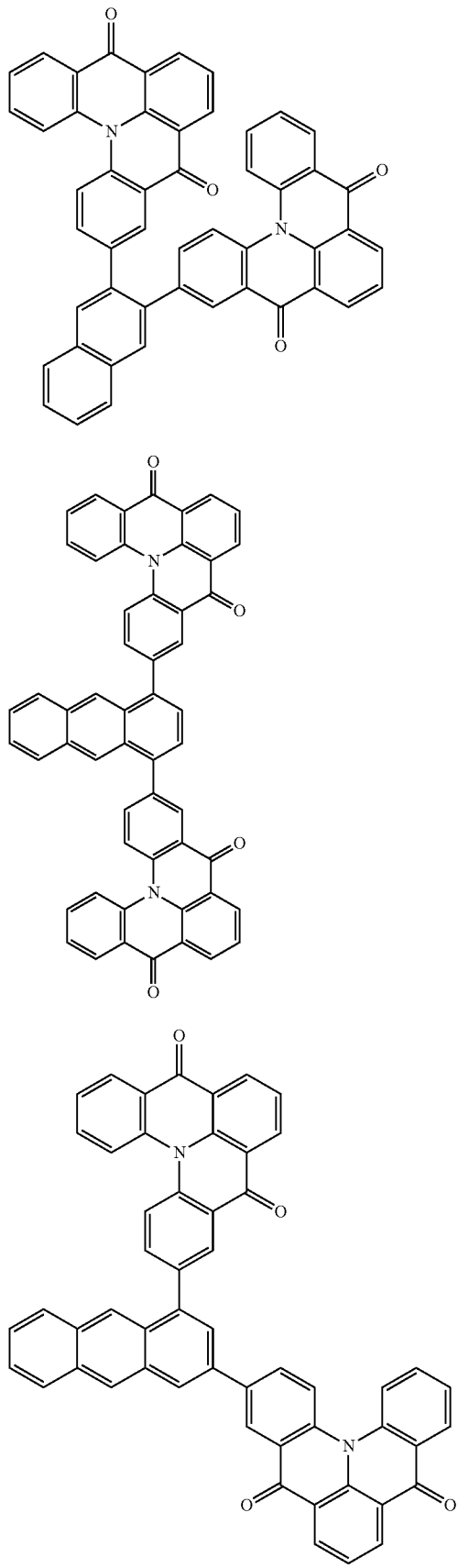

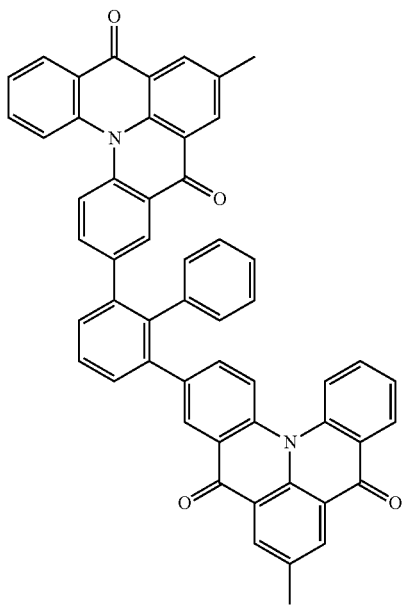
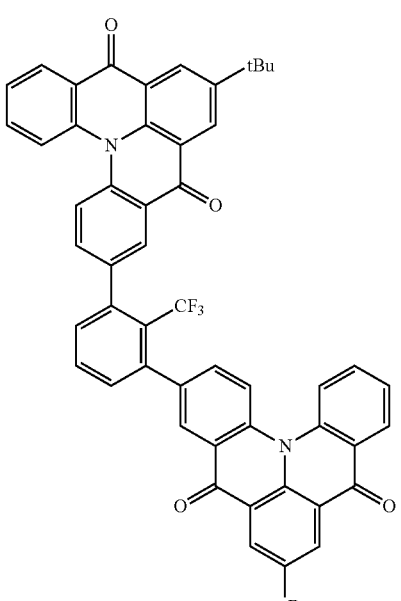
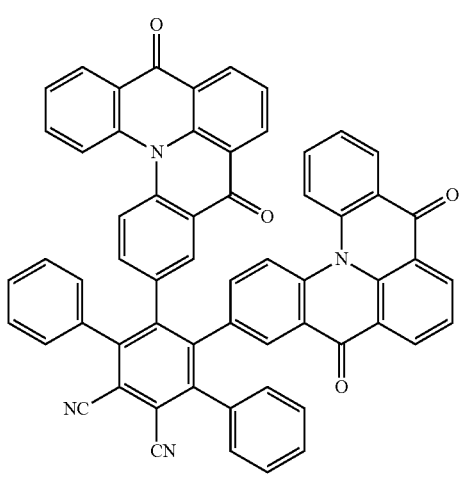

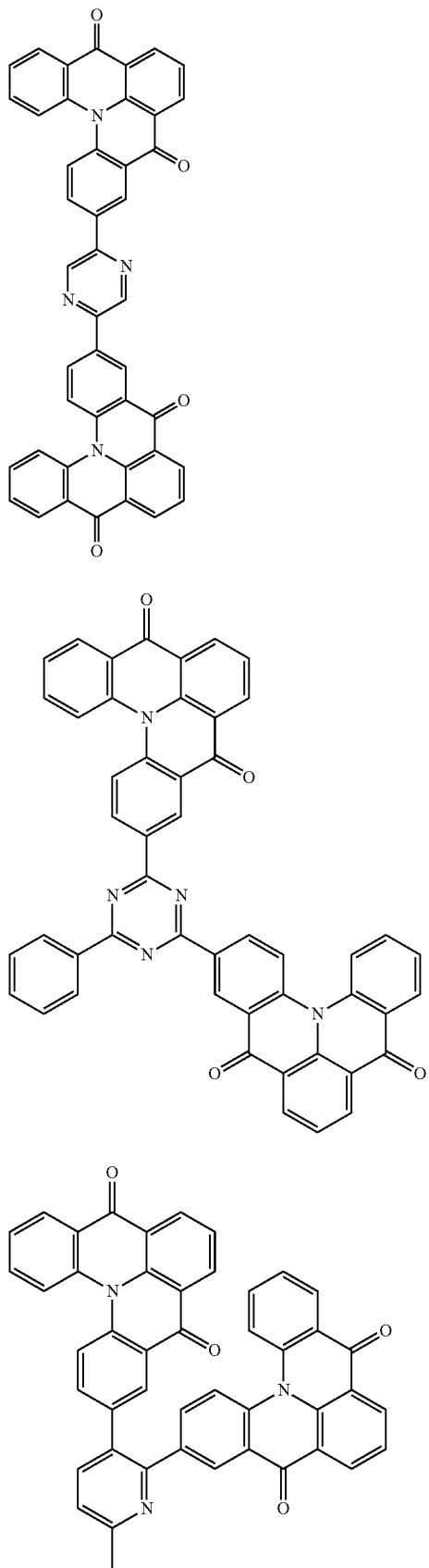
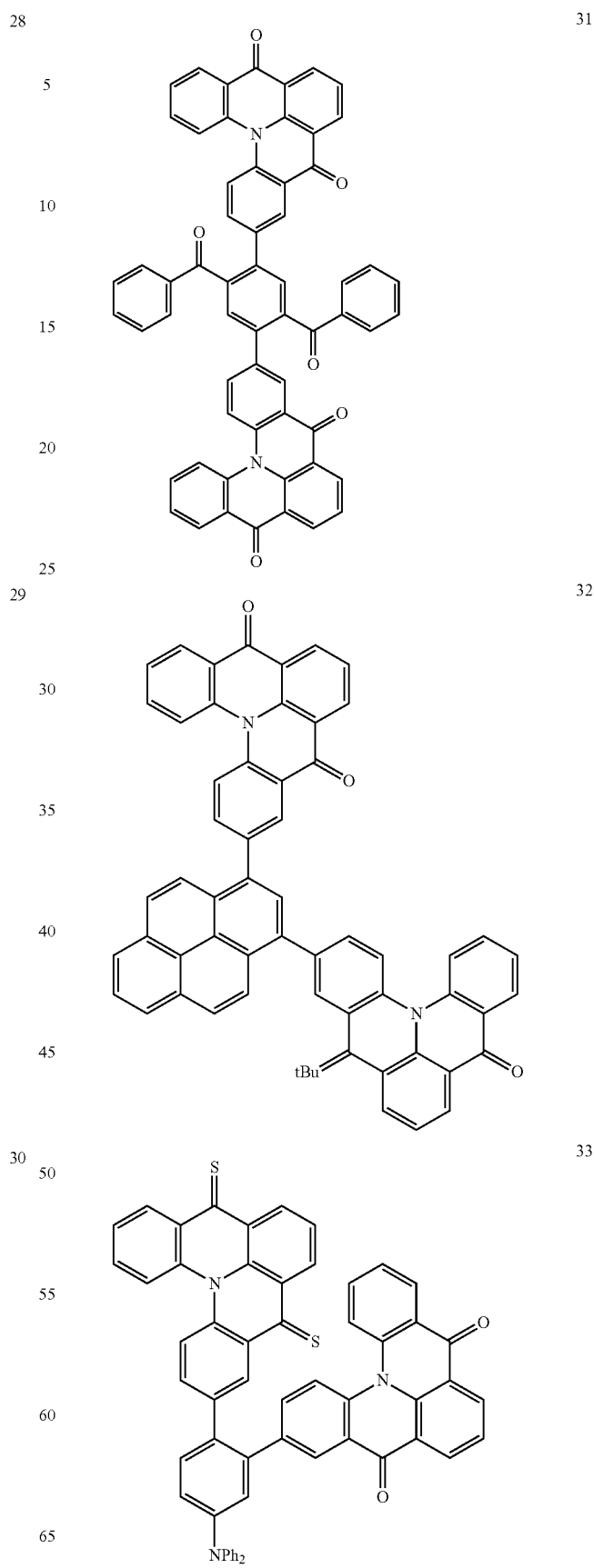

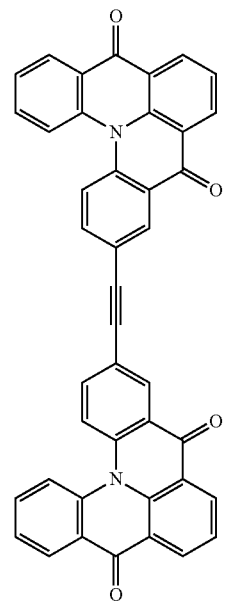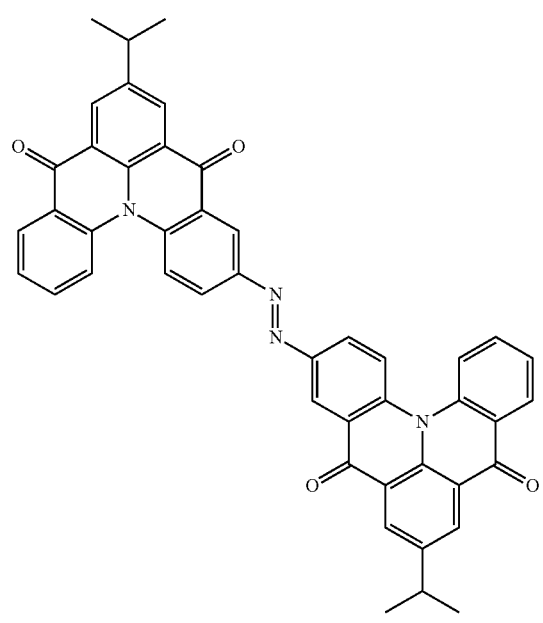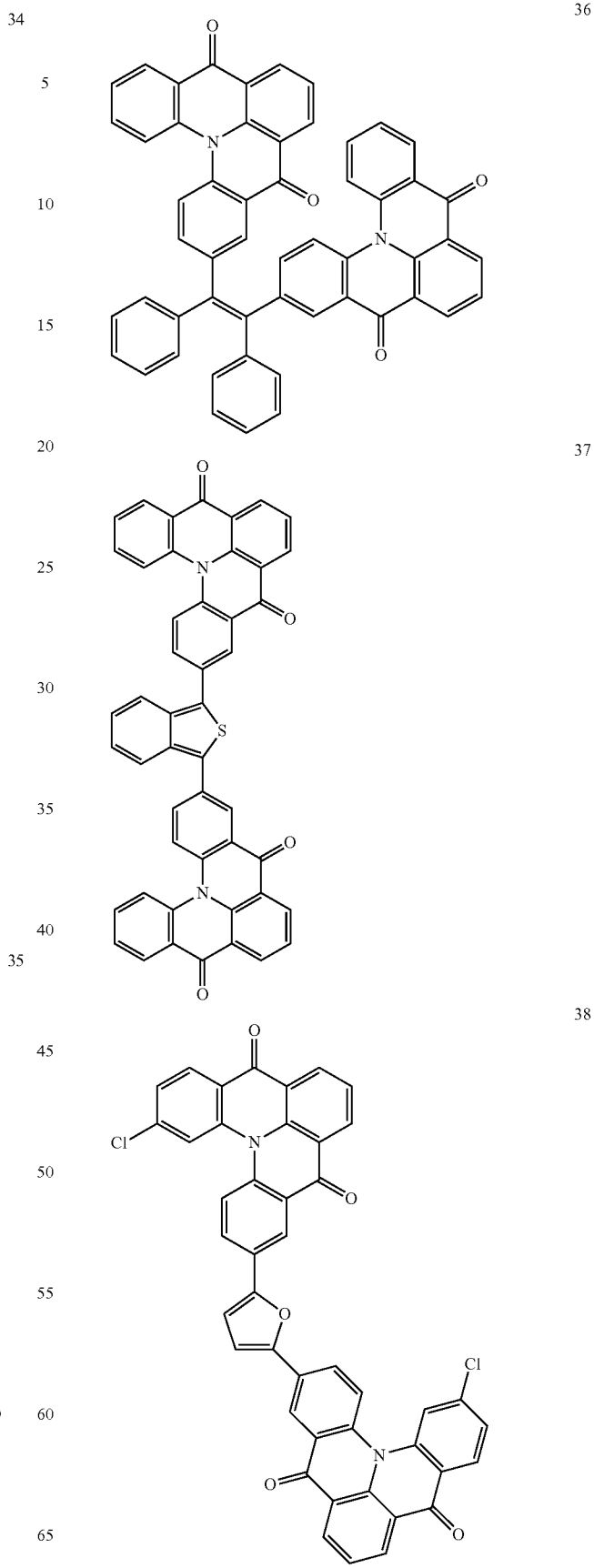

39
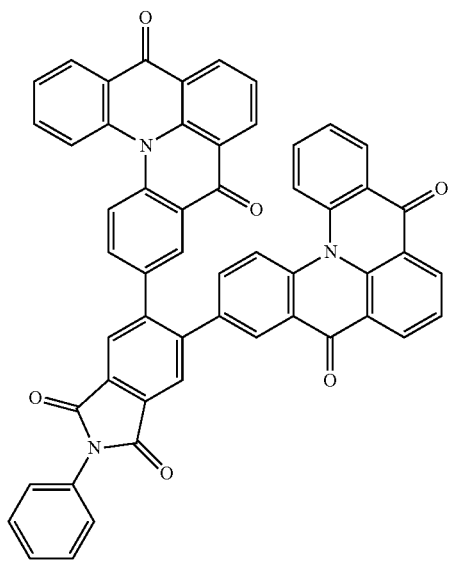
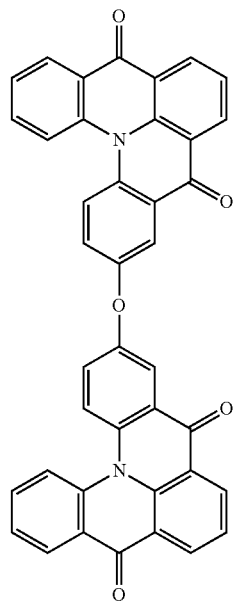
41
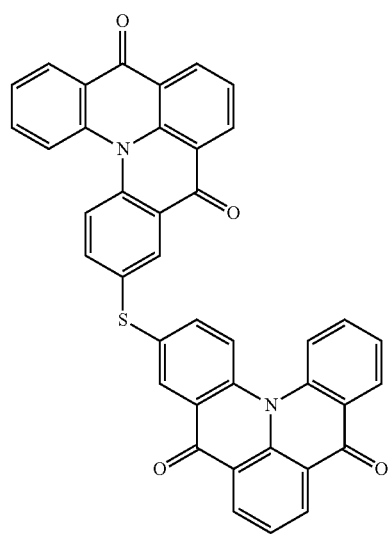
42
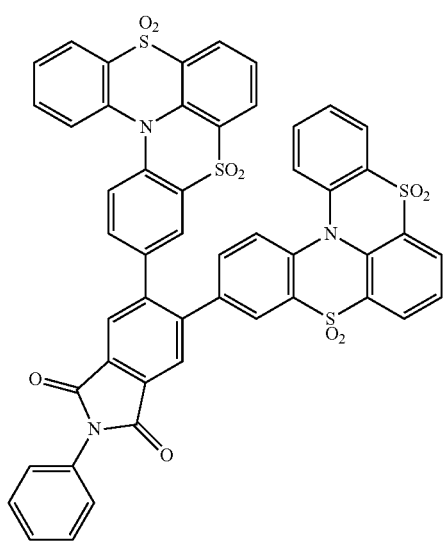
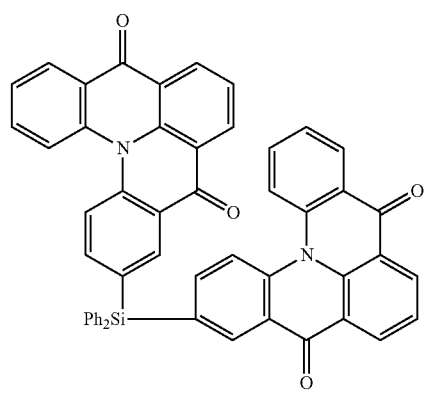
43

163
-continued
44
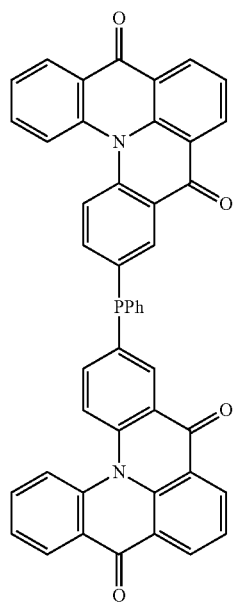
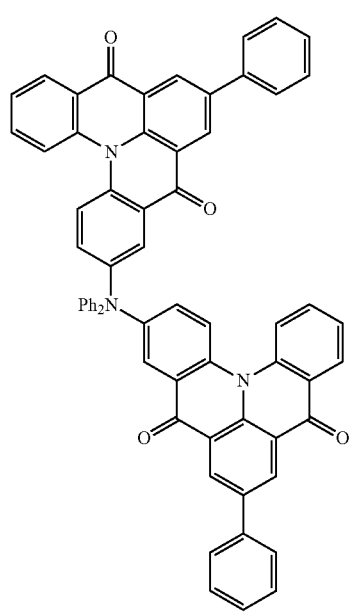
164
-continued
46
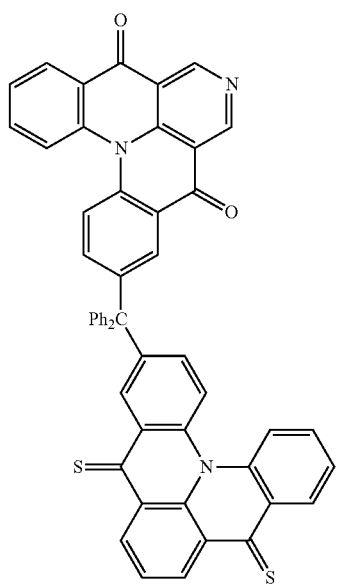
47
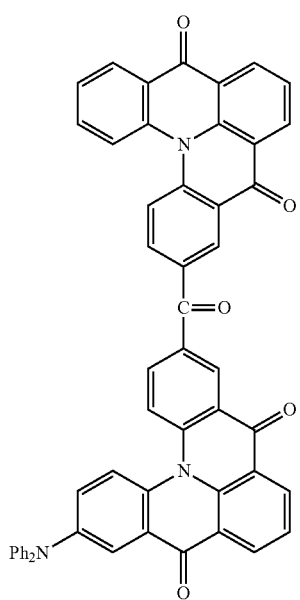

48
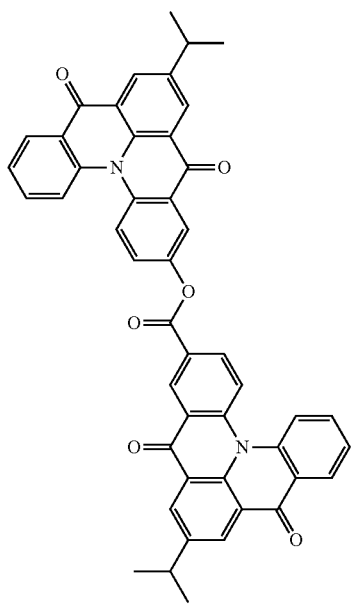
49
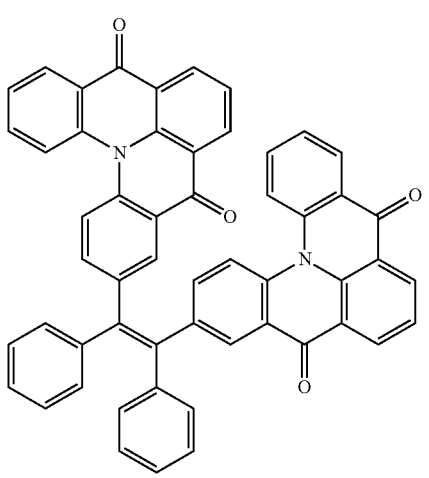
50
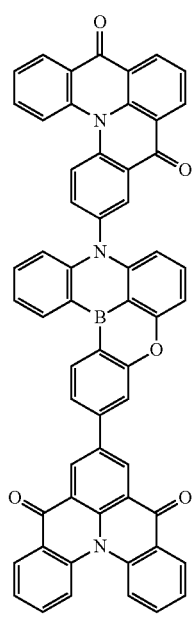
51
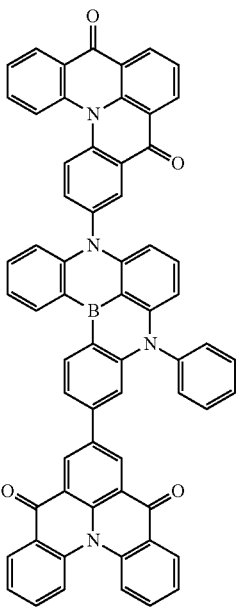
52
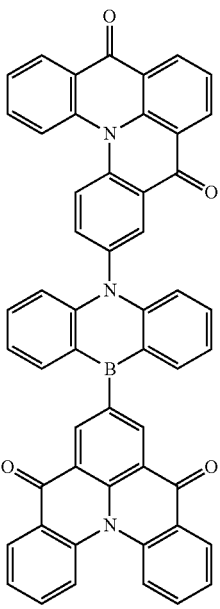

53
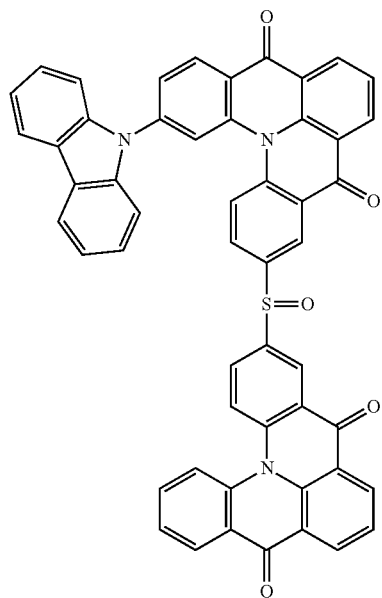
54
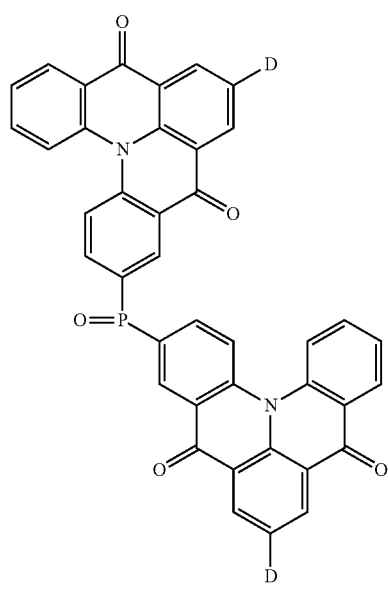
55
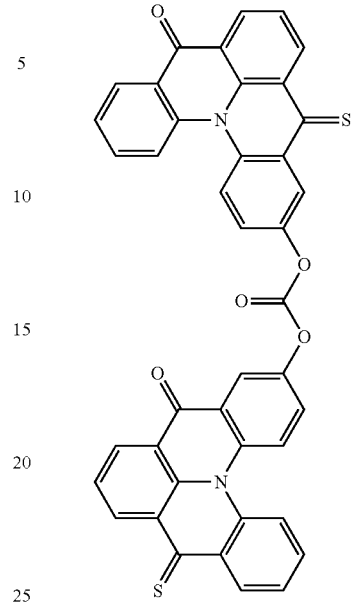
56
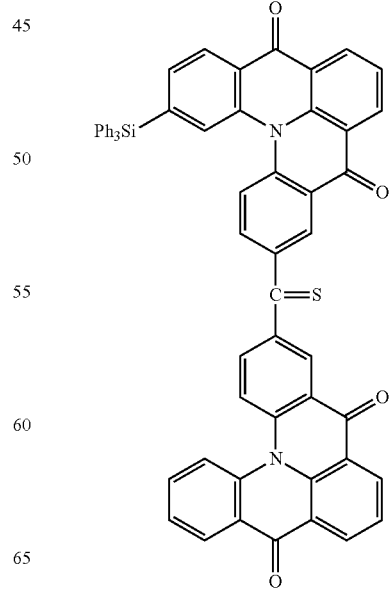

169
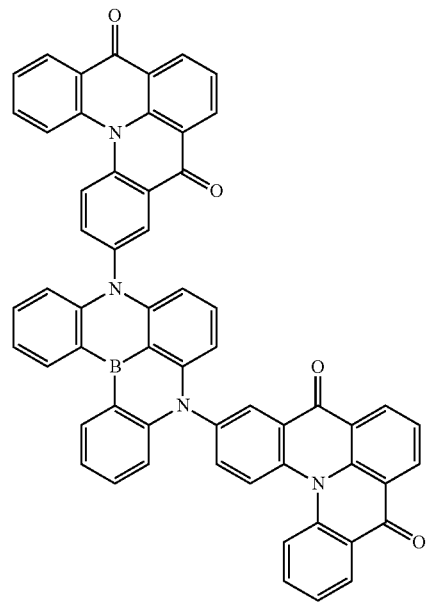
170
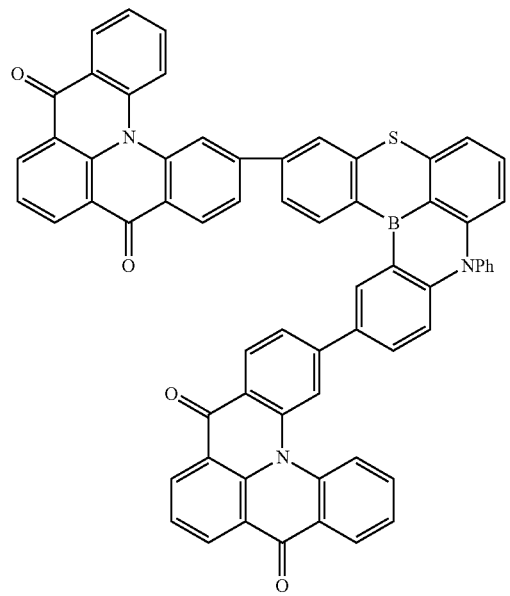
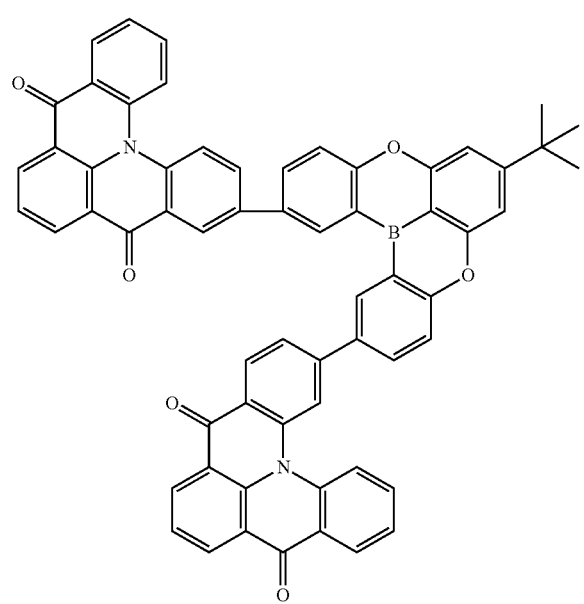
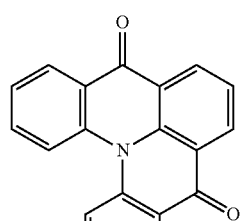
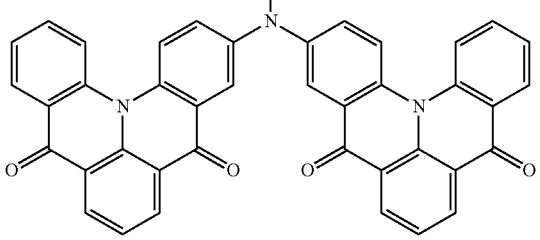

61
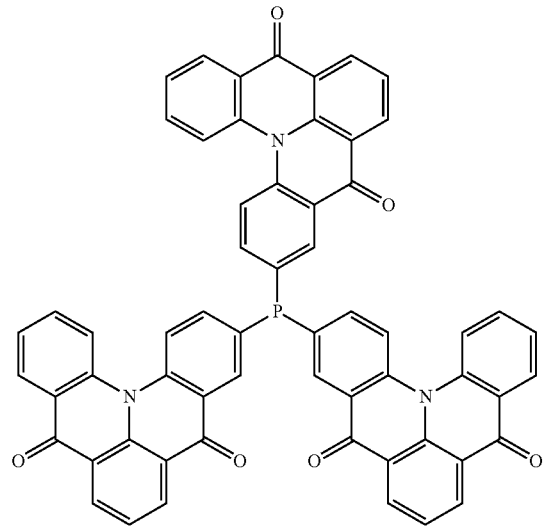
62
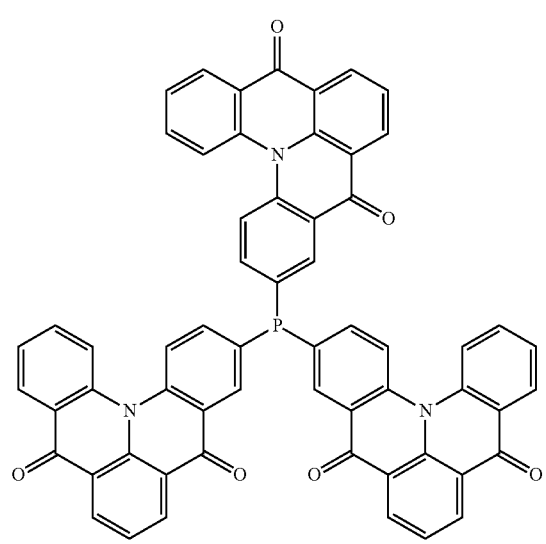
63
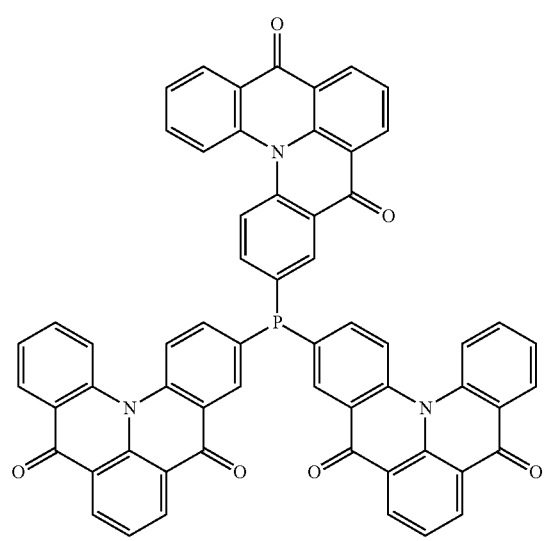
64
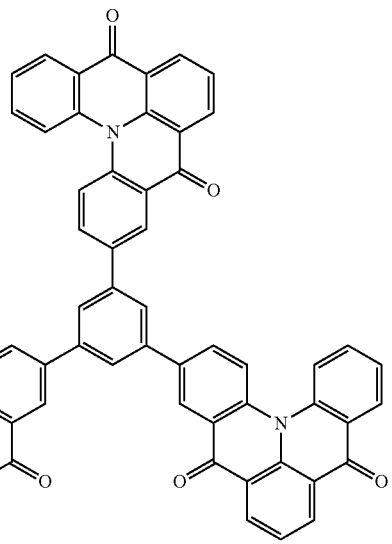
65
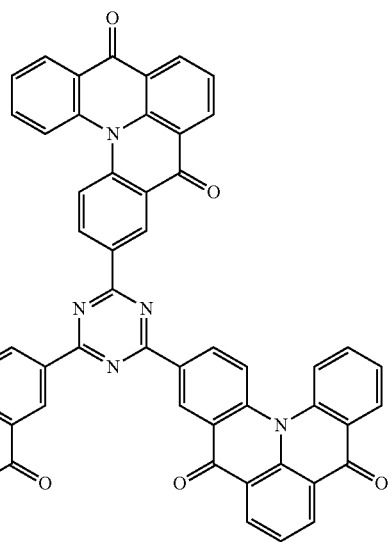

66
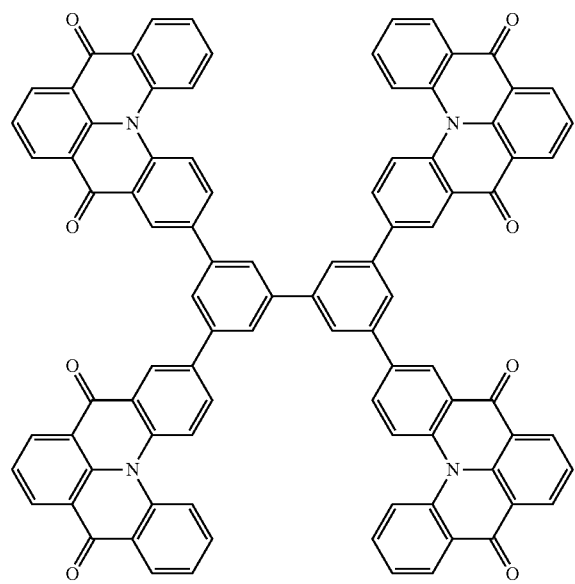
67
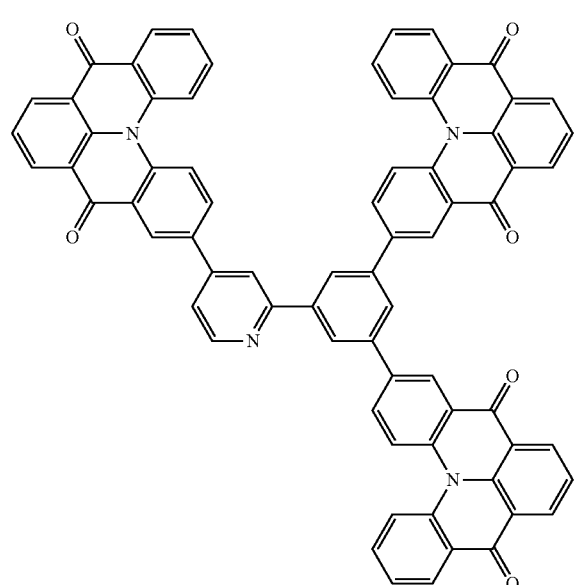
68
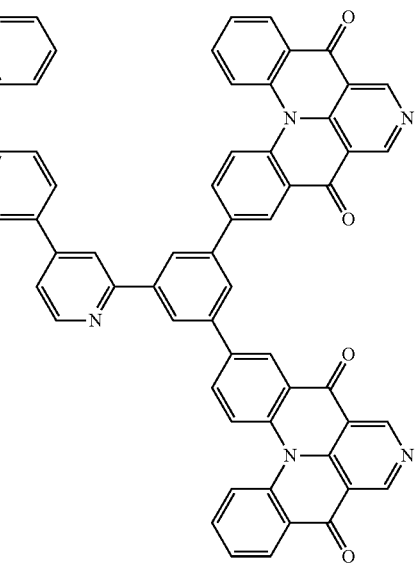
69
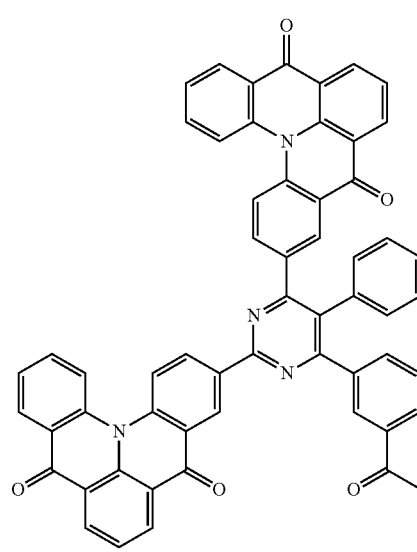
70
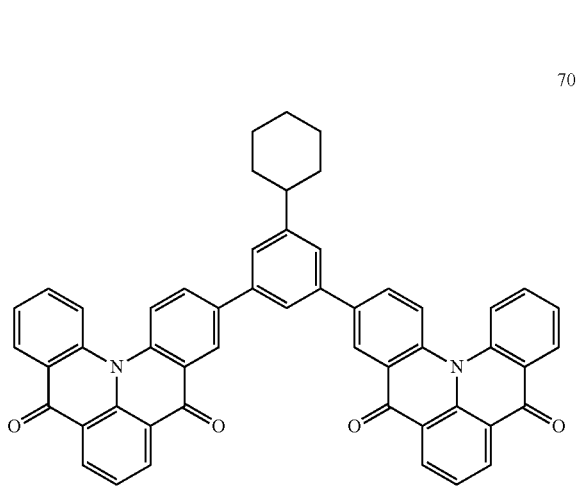

-continued
71
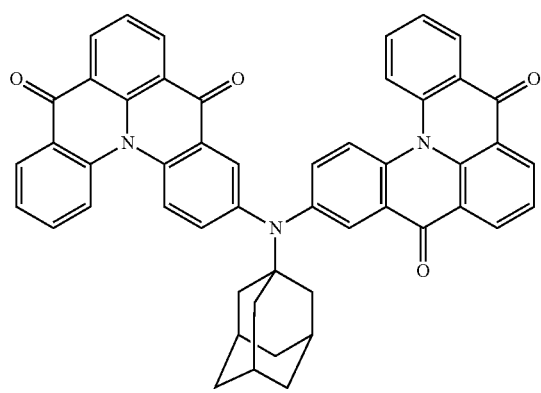
72
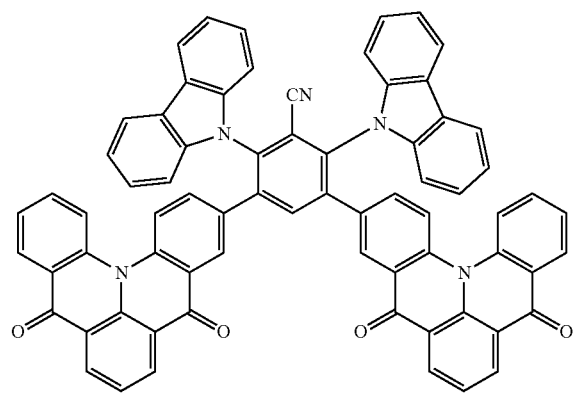
73
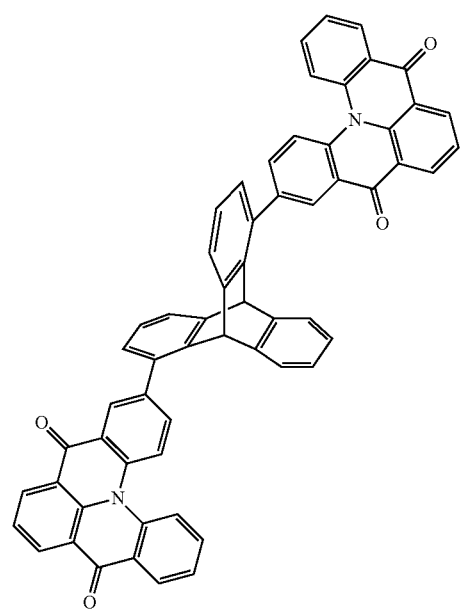
-continued
74
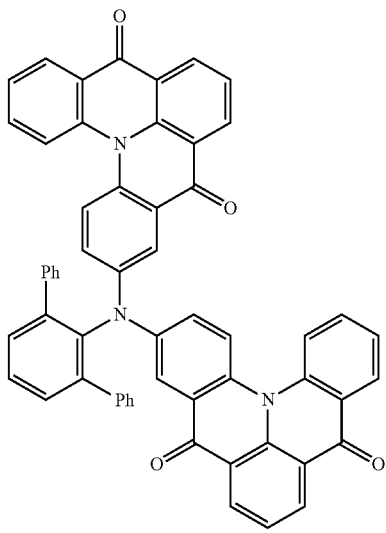
75
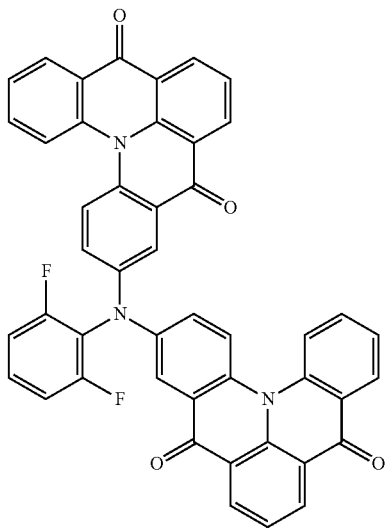
76
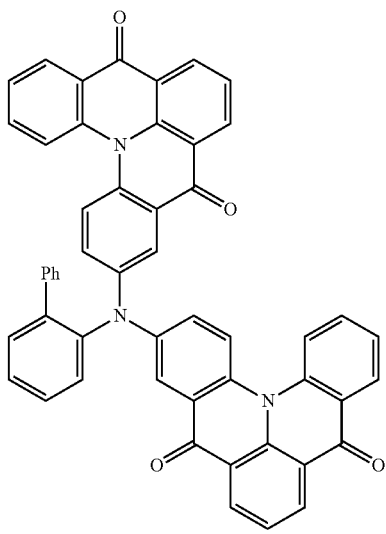

77
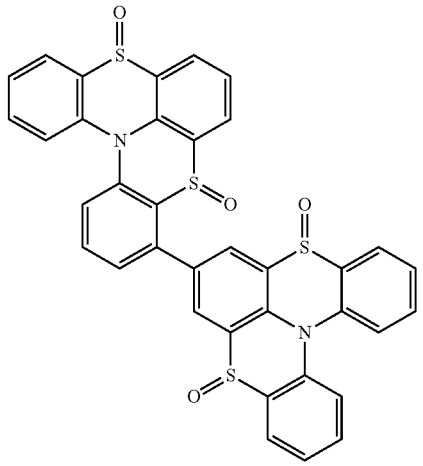
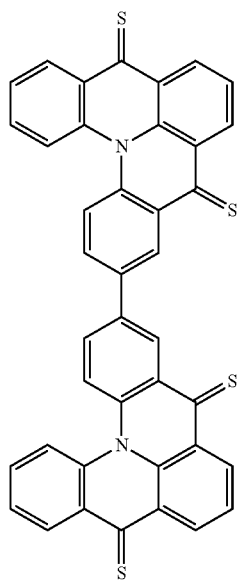
78
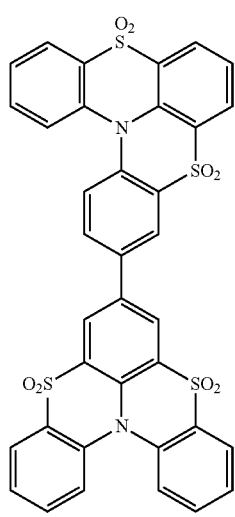
81
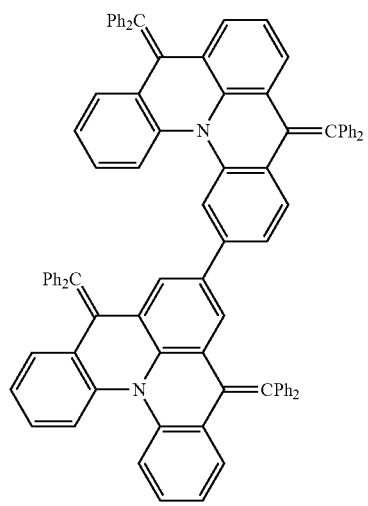
79
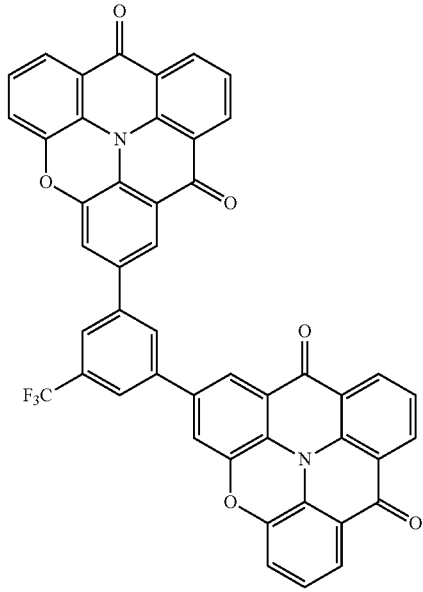
82

83
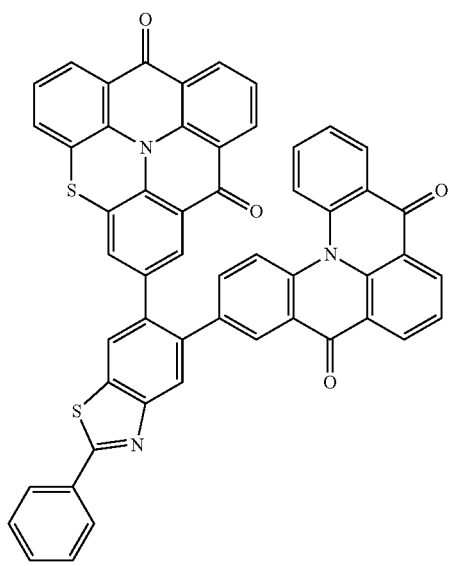
85
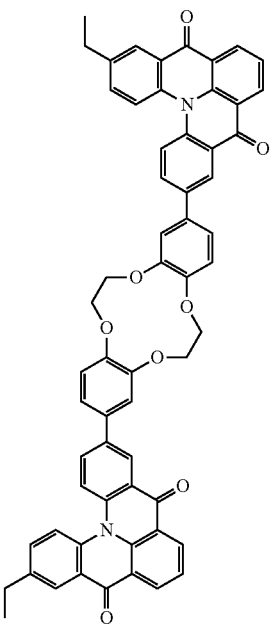
84
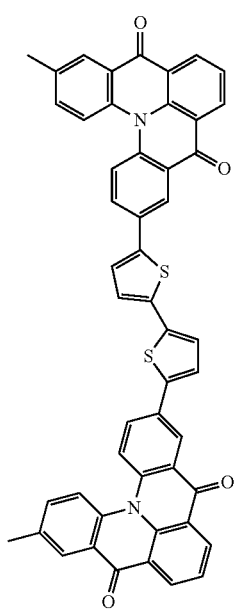
86
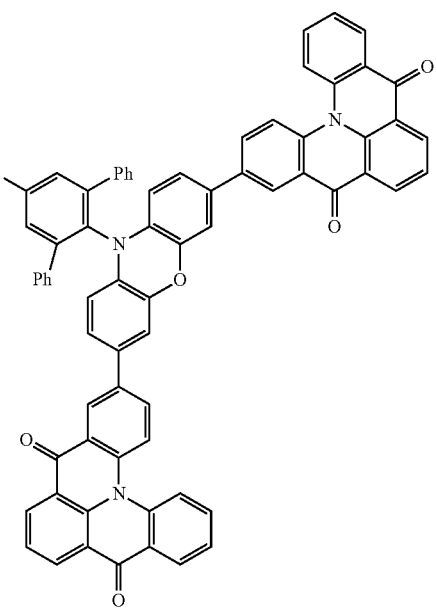

181
-continued
87
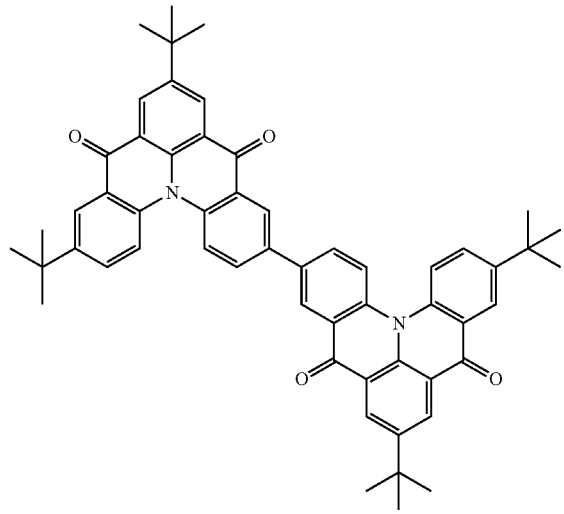
88
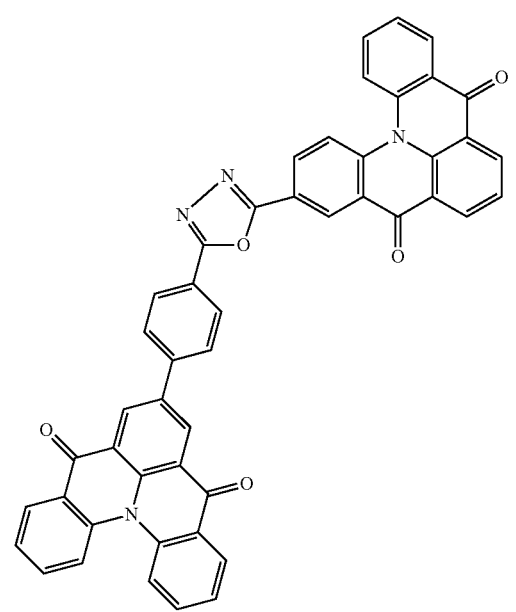
89
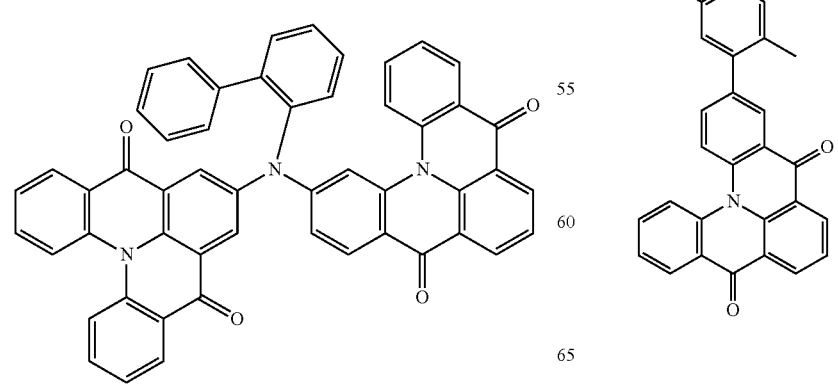
182
-continued
90
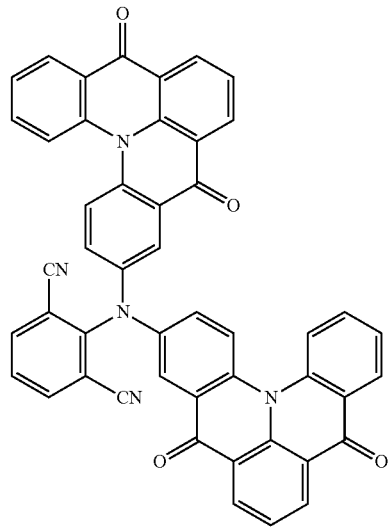
91
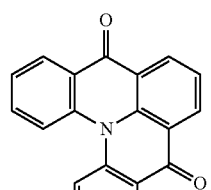

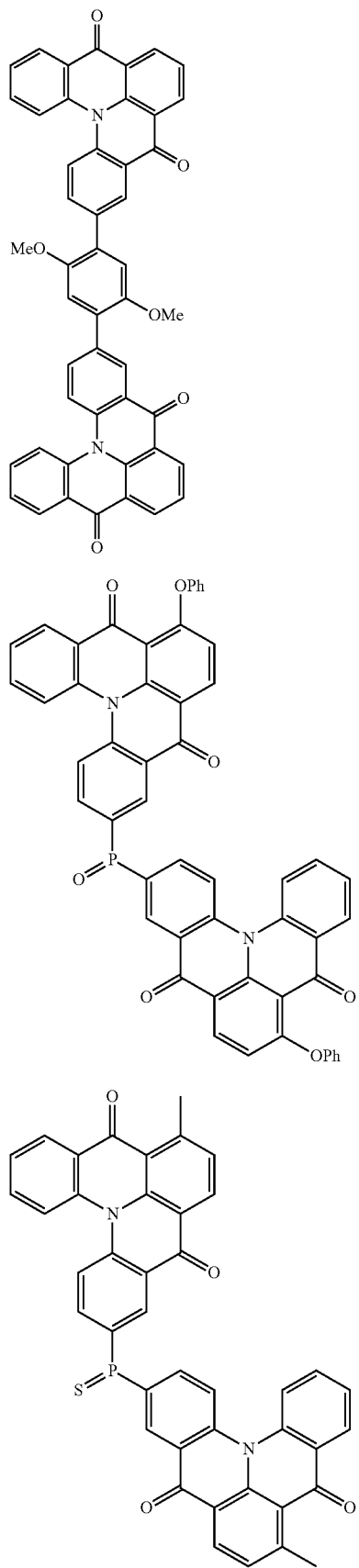
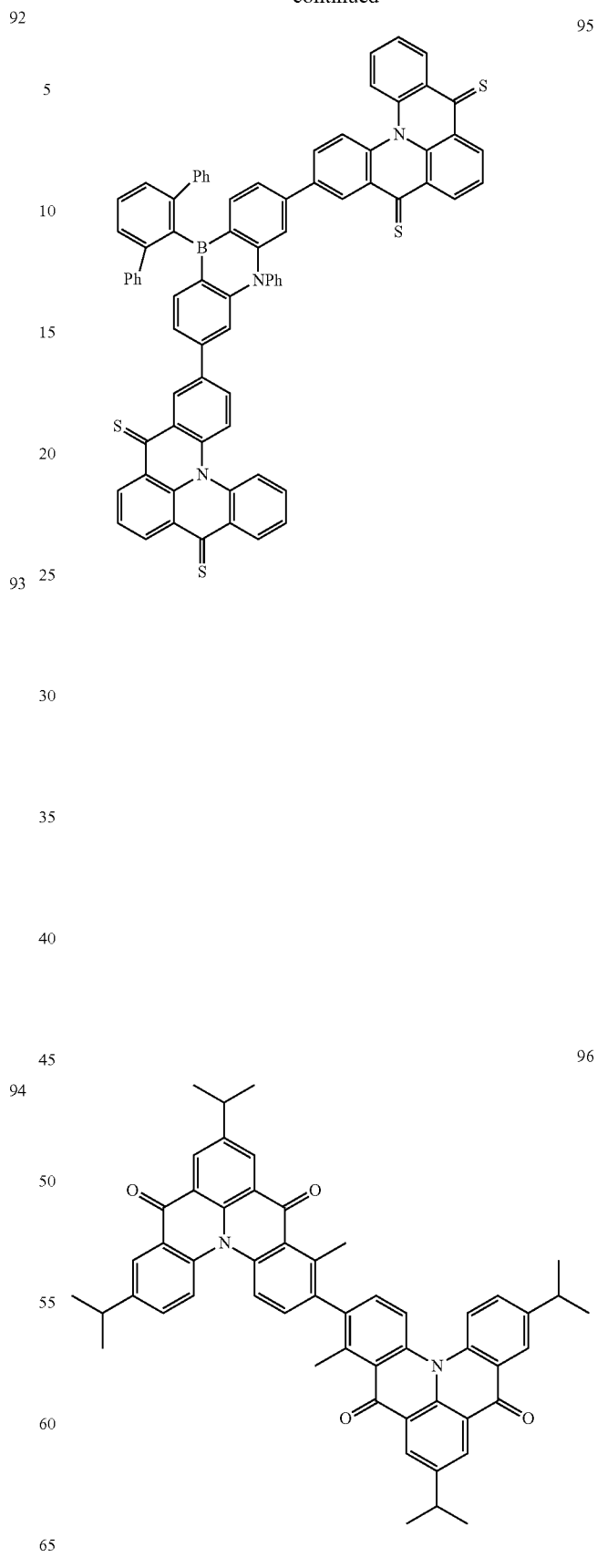

97
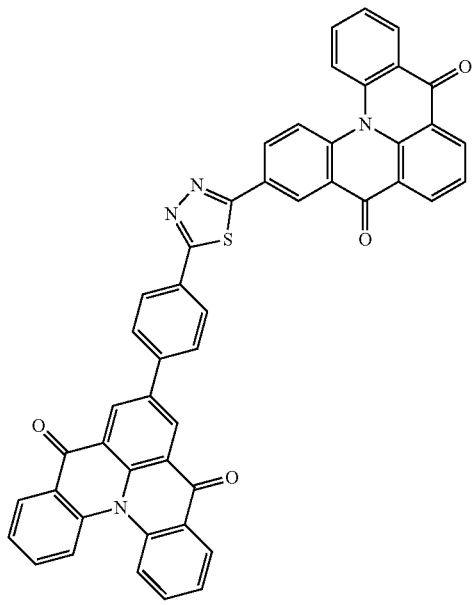
98
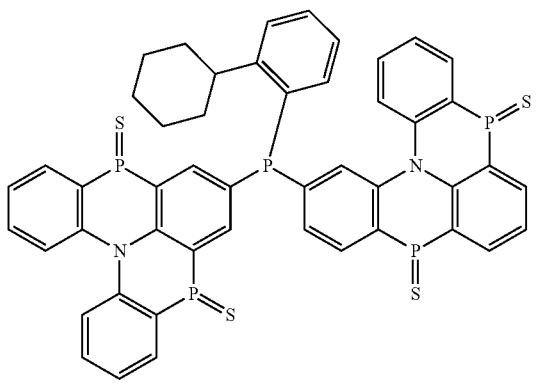
99
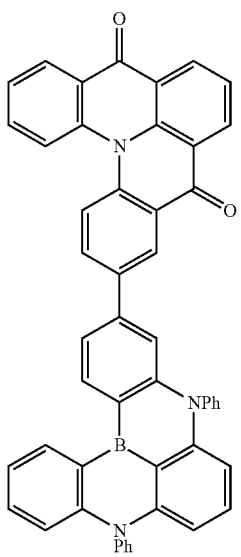
100
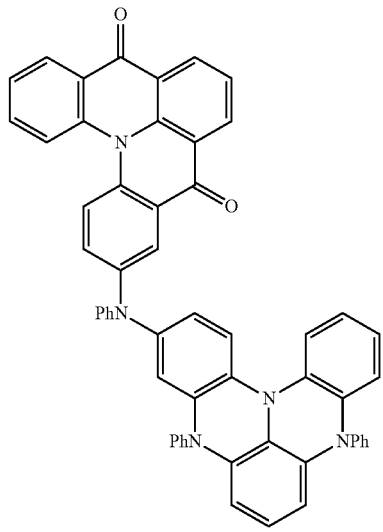
101
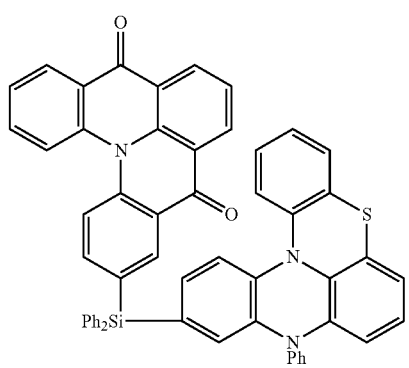
102
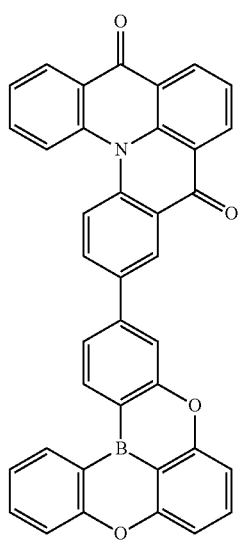

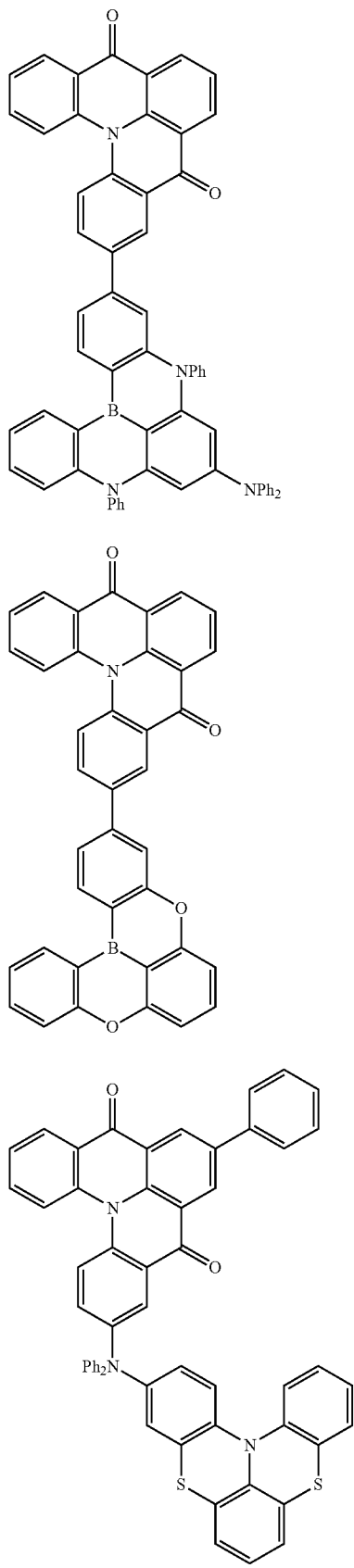
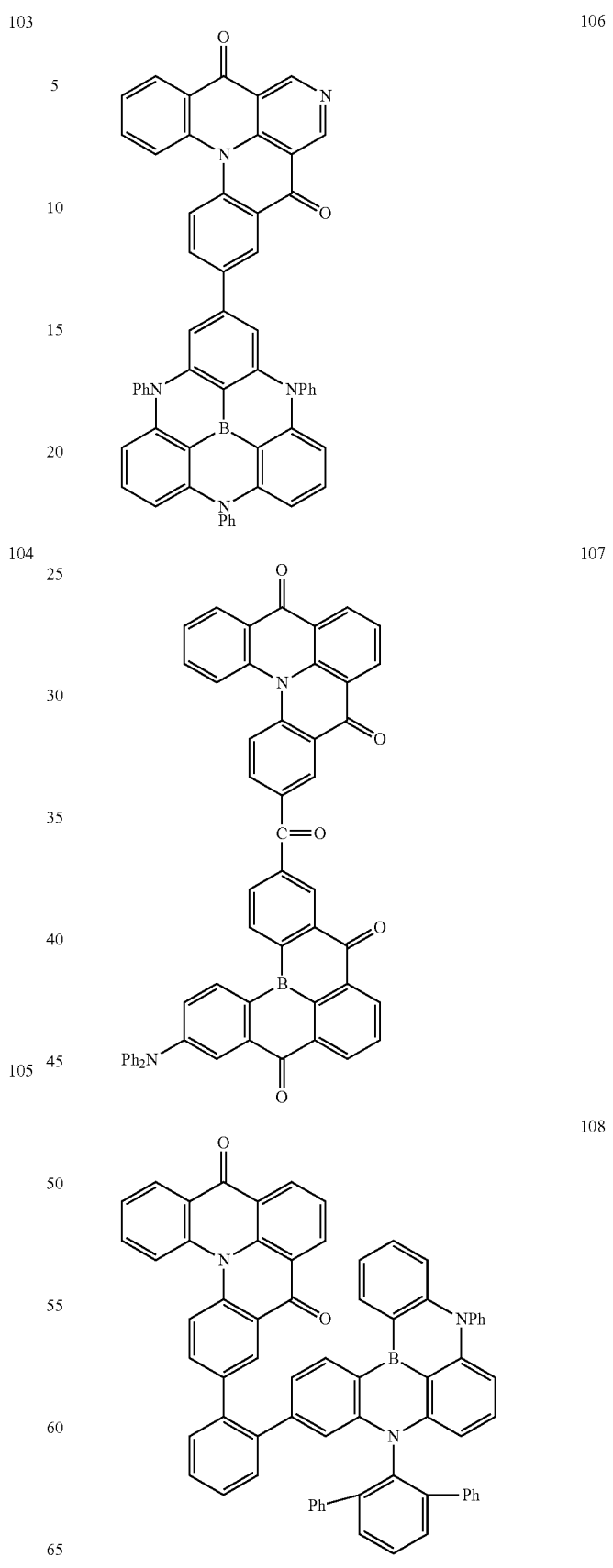

189
-continued
109
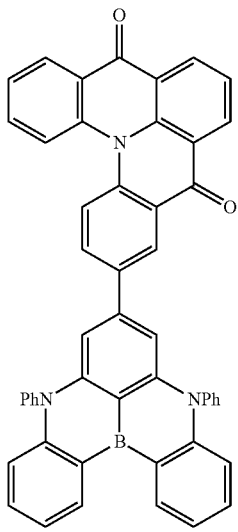
110
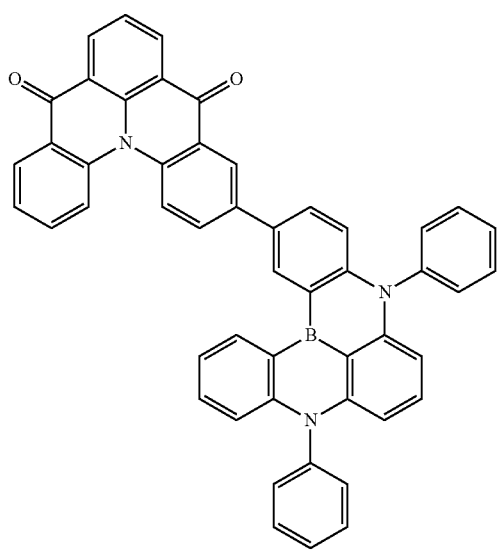
111
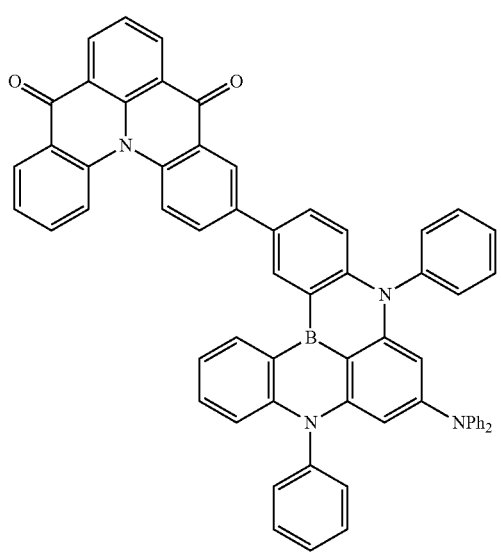
190
-continued
112
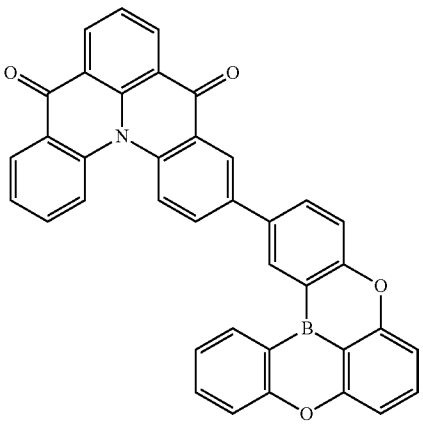
113
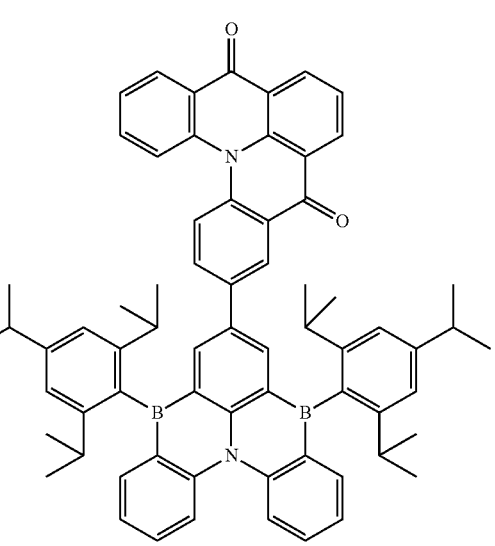
114
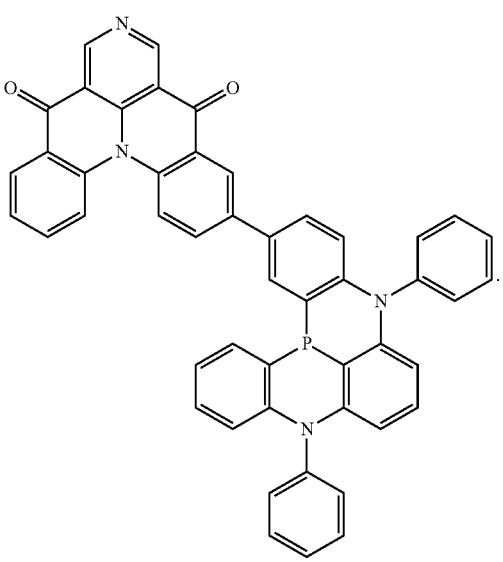
19. An organic electroluminescence device comprising:
a first electrode;
a second electrode facing the first electrode; and an emission layer disposed between the first electrode and the second electrode, wherein the emission layer comprises a host and a delayed fluorescence dopant, and the delayed fluorescence dopant comprises a fused polycyclic compound represented by Formula 1:

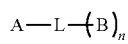
[Formula 1]

wherein in Formula 1,

L is a direct linkage, O, S, S=O, $Si(R_a)(R_b)$, $N(R_c)$, $P(R_d)$, $B(R_e)$, N=N, C≡C, C=O, C(=O)O, OC(=O)O, C=S, P=O, P=S, N, P, B, a substituted or unsubstituted alkyl linking group having 1 to 30 carbon atoms, a substituted or unsubstituted alkenyl linking group having 2 to 30 carbon atoms, a substituted or unsubstituted alkynyl linking group having 3 to 30 carbon atoms, a substituted or unsubstituted aryl linking group having 6 to 60 ring-forming carbon atoms, or a substituted or unsubstituted heteroaryl linking group having 2 to 60 ring-forming carbon atoms, $R_a$ to $R_e$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, n is an integer from 1 to 3, A is a group represented by Formula 2, and B is a group represented by Formula 3,

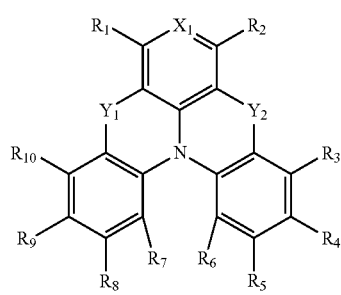
[Formula 2]

wherein in Formula 2, $X_1$ is N or $C(R_{11})$, $Y_1$ and $Y_2$ are each independently C=O, C=S, S=O, $SO_2$, $C=C(R_f)(R_g)$, P=O, or P=S, $R_1$ to $R_{11}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, except that one of $R_1$ to $R_{10}$ is a binding site to L in Formula 1, and $R_f$ and $R_g$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring,

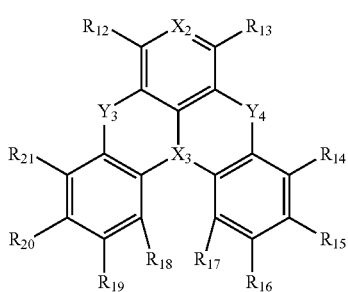
[Formula 3]

wherein in Formula 3, $X_2$ is N or $C(R_{22})$, $X_3$ is N, B, or P, $Y_3$ and $Y_4$ are each independently C=O, C=S, S=O, $SO_2$, $C=C(R_h)(R_i)$, P=O, P=S, $N(R_j)$, or $B(R_k)$, $R_{12}$ to $R_{22}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, except that one of $R_{12}$ to $R_{22}$ is a binding site to L in Formula 1, $R_h$ to $R_k$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group having 2 to 30 carbon atoms, a substituted or unsubstituted aryl group having 6 to 60 ring-forming carbon atoms, or a substituted or unsubstituted heteroaryl group having 2 to 60 ring-forming carbon atoms, or bonded to an adjacent group to form a ring, and provided that when n is 1 in Formula 1, when $X_1$ is $CR_{11}$, and $Y_1$ and $Y_2$ are C=O in Formula 2, and when $X_2$ is $CR_{22}$, $X_3$ is N, and $Y_3$ and $Y_4$ are C=O in Formula 3, then L is not a substituted or unsubstituted alkenyl linking group.

20. The organic electroluminescence device of claim 19, wherein the host comprises a compound represented by Formula E-2a or Formula E-2b:

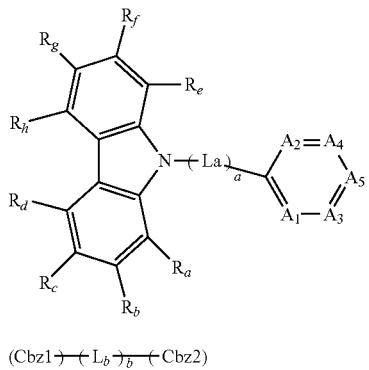

[Formula E-2a]

(Cbz1)─(L$_b$)$_b$─(Cbz2)   [Formula E-2b]

wherein in Formula E-2a,
a is an integer from 0 to 10, and
L$_a$ is a direct linkage, a substituted or unsubstituted arylene group having 6 to 30 ring-forming carbon atoms, or a substituted or unsubstituted heteroarylene group having 2 to 30 ring-forming carbon atoms, A$_1$ to A$_5$ are each independently N or C(R$_i$), R$_a$ to R$_i$ are each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or bonded to an adjacent group to form a ring, and two or three of A$_1$ to A$_5$ are N, and the remainder of A$_1$ to A$_5$ are C(R$_i$), and wherein in Formula E-2b, Cbz1 and Cbz2 are each independently an unsubstituted carbazole group, or a carbazole group substituted with an aryl group having 6 to 30 ring-forming carbon atoms, L$_b$ is a direct linkage, a substituted or unsubstituted arylene group having 6 to 30 ring-forming carbon atoms, or a substituted or unsubstituted heteroarylene group having 2 to 30 ring-forming carbon atoms, and b is an integer from 0 to 10.

* * * * *